(12) United States Patent
Wada et al.

(10) Patent No.: US 10,329,318 B2
(45) Date of Patent: *Jun. 25, 2019

(54) METHOD FOR THE SYNTHESIS OF PHOSPHORUS ATOM MODIFIED NUCLEIC ACIDS

(71) Applicant: WAVE LIFE SCIENCES LTD., Singapore (SG)

(72) Inventors: Takeshi Wada, Kashiwa (JP); Mamoru Shimizu, Uruma (JP)

(73) Assignee: WAVE LIFE SCIENCES LTD., Singapore (SG)

( * ) Notice: Subject to any disclaimer, the term of this patent is extended or adjusted under 35 U.S.C. 154(b) by 0 days.

This patent is subject to a terminal disclaimer.

(21) Appl. No.: 15/608,123

(22) Filed: May 30, 2017

(65) Prior Publication Data

US 2018/0111958 A1    Apr. 26, 2018

Related U.S. Application Data

(62) Division of application No. 15/167,583, filed on May 27, 2016, now Pat. No. 9,695,211, which is a division of application No. 13/131,591, filed as application No. PCT/IB2009/007923 on Dec. 2, 2009, now Pat. No. 9,394,333.

(60) Provisional application No. 61/119,245, filed on Dec. 2, 2008.

(51) Int. Cl.
| | |
|---|---|
| C07H 21/00 | (2006.01) |
| C07H 21/02 | (2006.01) |
| C07H 21/04 | (2006.01) |
| C07H 1/00 | (2006.01) |

(52) U.S. Cl.
CPC .............. *C07H 21/00* (2013.01); *C07H 1/00* (2013.01)

(58) Field of Classification Search
CPC ................................................... C07H 21/00
USPC ....................................... 536/23.1, 24.3, 25.3
See application file for complete search history.

(56) References Cited

U.S. PATENT DOCUMENTS

| | | |
|---|---|---|
| 2,878,264 A | 3/1959 | Lunsford |
| 3,135,766 A | 6/1964 | Gould |
| 3,484,473 A | 12/1969 | Buckman et al. |
| 3,687,808 A | 8/1972 | Merigan et al. |
| 3,745,162 A | 7/1973 | Helsley |
| 4,022,791 A | 5/1977 | Welch, Jr. |
| 4,113,869 A | 9/1978 | Gardner |
| 4,415,732 A | 11/1983 | Caruthers et al. |
| 4,458,066 A | 7/1984 | Caruthers et al. |
| 4,500,707 A | 2/1985 | Caruthers et al. |
| 4,542,142 A | 9/1985 | Martel et al. |
| 4,659,774 A | 4/1987 | Webb et al. |
| 4,663,328 A | 5/1987 | Lafon |
| 4,668,777 A | 5/1987 | Caruthers et al. |
| 4,725,677 A | 2/1988 | Koster et al. |
| 4,735,949 A | 4/1988 | Domagala et al. |
| 4,840,956 A | 6/1989 | Domagala et al. |
| 4,845,205 A | 7/1989 | Huynh Dinh et al. |
| 4,923,901 A | 5/1990 | Koester et al. |
| 4,943,629 A | 7/1990 | DeVries et al. |
| 4,945,158 A | 7/1990 | DeVries et al. |
| 4,973,679 A | 11/1990 | Caruthers et al. |
| 4,981,957 A | 1/1991 | Lebleu et al. |
| 5,047,524 A | 9/1991 | Andrus et al. |
| 5,118,800 A | 6/1992 | Smith et al. |
| 5,130,302 A | 7/1992 | Spielvogel et al. |
| 5,132,418 A | 7/1992 | Caruthers et al. |
| 5,134,066 A | 7/1992 | Rogers et al. |
| 5,138,045 A | 8/1992 | Cook et al. |
| 5,141,813 A | 8/1992 | Nelson |
| 5,151,510 A | 9/1992 | Stec et al. |
| 5,175,273 A | 12/1992 | Bischofberger et al. |
| 5,200,553 A | 4/1993 | Nudelman et al. |
| 5,212,295 A | 5/1993 | Cook |
| 5,223,618 A | 6/1993 | Cook et al. |
| 5,262,530 A | 11/1993 | Andrus et al. |
| 5,292,875 A | 3/1994 | Stec et al. |
| 5,319,080 A | 6/1994 | Leumann |
| 5,359,044 A | 10/1994 | Cook et al. |
| 5,367,066 A | 11/1994 | Urdea et al. |
| 5,378,825 A | 1/1995 | Cook et al. |
| 5,386,023 A | 1/1995 | Sanghvi et al. |
| 5,432,272 A | 7/1995 | Benner |
| 5,457,187 A | 10/1995 | Gmeiner et al. |
| 5,457,191 A | 10/1995 | Cook et al. |

(Continued)

FOREIGN PATENT DOCUMENTS

| | | |
|---|---|---|
| CN | 102675386 A | 9/2012 |
| DE | 1144279 B | 2/1963 |

(Continued)

OTHER PUBLICATIONS

Aaronson, J.G. et al., Rapid HATU-Mediated Solution Phase siRNA Conjugation, Bioconjugate. Chem., 22: 1723-1728 (2011).
Aartsma-Rus, A. et al., Antisense-Induced Multiexon Skipping for Duchenne Muscular Dystrophy Makes More Sense, Am. J. Hum. Genet., 74:83-92 (2004).
Aartsma-Rus, A. et al., Targeted exon skipping as a potential gene correction therapy for Duchenne muscular dystrophy, Neuromuscular Disorders, 12: S71-S77 (2002).
Aartsma-Rus, A. et al., Therapeutic antisense-induced exon skipping in cultured muscle cells from six different DMD patients, Human Molecular Genetics, 12(8):907-914 (2003).
Adams, S.P. et al., Hindered dialkylamino nucleoside phosphite reagents in the synthesis of two DNA 51-mers, Journal of the American Chemical Society, 105(3): 661-663 (1983).

(Continued)

*Primary Examiner* — Jezia Riley
(74) *Attorney, Agent, or Firm* — Choate, Hall & Stewart LLP; Brenda Herschbach Jarrell; Xiaodong Li

(57) ABSTRACT

Described herein are methods of syntheses of phosphorous atom-modified nucleic acids comprising chiral X-phosphonate moieties. The methods described herein provide backbone-modified nucleic acids in high diasteteomeric purity via an asymmetric reaction of an achiral molecule comprising a chemically stable H-phophonate moiety with a nucleoside/nucleotide.

17 Claims, 58 Drawing Sheets

(56) References Cited

U.S. PATENT DOCUMENTS

| | | |
|---|---|---|
| 5,459,255 A | 10/1995 | Cook et al. |
| 5,484,908 A | 1/1996 | Froehler et al. |
| 5,489,677 A | 2/1996 | Sanghvi et al. |
| 5,502,177 A | 3/1996 | Matteucci et al. |
| 5,506,212 A | 4/1996 | Hoke et al. |
| 5,512,668 A | 4/1996 | Stec et al. |
| 5,521,302 A | 5/1996 | Cook |
| 5,525,711 A | 6/1996 | Hawkins et al. |
| 5,541,307 A | 7/1996 | Cook et al. |
| 5,552,540 A | 9/1996 | Haralambidis |
| 5,565,488 A | 10/1996 | Braunlich et al. |
| 5,576,302 A | 11/1996 | Cook et al. |
| 5,587,361 A | 12/1996 | Cook et al. |
| 5,587,469 A | 12/1996 | Cook et al. |
| 5,594,121 A | 1/1997 | Froehler et al. |
| 5,596,091 A | 1/1997 | Switzer |
| 5,599,797 A | 2/1997 | Cook et al. |
| 5,602,240 A | 2/1997 | De Mesmaeker et al. |
| 5,607,923 A | 3/1997 | Cook et al. |
| 5,608,046 A | 3/1997 | Cook et al. |
| 5,610,289 A | 3/1997 | Cook et al. |
| 5,614,617 A | 3/1997 | Cook et al. |
| 5,618,704 A | 4/1997 | Sanghvi et al. |
| 5,620,963 A | 4/1997 | Cook et al. |
| 5,622,989 A | 4/1997 | Br aunlich et al. |
| 5,623,070 A | 4/1997 | Cook et al. |
| 5,635,488 A | 6/1997 | Cook et al. |
| 5,643,889 A | 7/1997 | Suhadolnik et al. |
| 5,643,989 A | 7/1997 | Van De Grampel et al. |
| 5,646,267 A | 7/1997 | Stec et al. |
| 5,654,284 A | 8/1997 | Cook et al. |
| 5,661,134 A | 8/1997 | Cook et al. |
| 5,677,437 A | 10/1997 | Teng et al. |
| 5,681,940 A | 10/1997 | Wang et al. |
| 5,681,941 A | 10/1997 | Cook et al. |
| 5,688,941 A | 11/1997 | Cook et al. |
| 5,708,161 A | 1/1998 | Reese |
| 5,712,378 A | 1/1998 | Wang |
| 5,734,041 A | 3/1998 | Just et al. |
| 5,750,692 A | 5/1998 | Cook et al. |
| 5,777,092 A | 7/1998 | Cook et al. |
| 5,783,682 A | 7/1998 | Cook et al. |
| 5,792,844 A | 8/1998 | Sanghvi et al. |
| 5,795,765 A | 8/1998 | Izu et al. |
| 5,808,023 A | 9/1998 | Sanghvi et al. |
| 5,824,503 A | 10/1998 | Kurome et al. |
| 5,834,607 A | 11/1998 | Manoharan et al. |
| 5,846,466 A | 12/1998 | Abe et al. |
| 5,851,840 A | 12/1998 | Sluka et al. |
| 5,852,188 A | 12/1998 | Cook |
| 5,856,465 A | 1/1999 | Stec et al. |
| 5,883,237 A | 3/1999 | Stec et al. |
| 5,892,024 A | 4/1999 | Chaturvedula et al. |
| 5,898,031 A | 4/1999 | Crooke |
| 5,908,772 A | 6/1999 | Mitta et al. |
| 5,914,396 A | 6/1999 | Cook et al. |
| 5,932,450 A | 8/1999 | Dattagupta et al. |
| 5,936,080 A | 8/1999 | Stec et al. |
| 5,965,721 A | 10/1999 | Cook et al. |
| 5,969,118 A | 10/1999 | Sanghvi et al. |
| 5,976,855 A | 11/1999 | Svendsen et al. |
| 5,998,148 A | 12/1999 | Bennett et al. |
| 5,998,602 A | 12/1999 | Torrence et al. |
| 5,998,603 A | 12/1999 | Cook et al. |
| 6,004,813 A | 12/1999 | Serlupi-Crescenzi et al. |
| 6,005,107 A | 12/1999 | Nguyen-Ba et al. |
| 6,015,886 A | 1/2000 | Dale et al. |
| 6,015,887 A | 1/2000 | Teng |
| 6,017,700 A | 1/2000 | Horn et al. |
| 6,025,482 A | 2/2000 | Cook et al. |
| 6,031,092 A | 2/2000 | Just et al. |
| 6,056,973 A | 5/2000 | Allen et al. |
| 6,057,371 A | 5/2000 | Glennon |
| 6,066,500 A | 5/2000 | Bennett et al. |
| 6,080,543 A | 6/2000 | Engel et al. |
| 6,087,482 A | 7/2000 | Teng et al. |
| 6,107,094 A | 8/2000 | Crooke |
| 6,121,433 A | 9/2000 | Cook et al. |
| 6,124,445 A | 9/2000 | Imbach et al. |
| 6,127,540 A | 10/2000 | Nguyen-Ba et al. |
| 6,133,438 A | 10/2000 | Cook et al. |
| 6,140,096 A | 10/2000 | Kofod et al. |
| 6,146,829 A | 11/2000 | Cook et al. |
| 6,147,200 A | 11/2000 | Manoharan et al. |
| 6,159,728 A | 12/2000 | Stockley et al. |
| 6,160,109 A | 12/2000 | Just et al. |
| 6,166,197 A | 12/2000 | Cook et al. |
| 6,172,209 B1 | 1/2001 | Manoharan et al. |
| 6,191,266 B1 | 2/2001 | Wang |
| 6,194,576 B1 | 2/2001 | Nguyen-Ba et al. |
| 6,207,646 B1 | 3/2001 | Krieg et al. |
| 6,214,551 B1 | 4/2001 | Sanghvi et al. |
| 6,214,805 B1 | 4/2001 | Torrence et al. |
| 6,222,025 B1 | 4/2001 | Cook et al. |
| 6,232,463 B1 | 5/2001 | Cook et al. |
| 6,235,887 B1 | 5/2001 | Froehler et al. |
| 6,239,116 B1 | 5/2001 | Krieg et al. |
| 6,239,265 B1 | 5/2001 | Cook |
| 6,242,589 B1 | 6/2001 | Cook et al. |
| 6,248,519 B1 | 6/2001 | Engel et al. |
| 6,265,172 B1 | 7/2001 | St. Clair et al. |
| 6,270,968 B1 | 8/2001 | Dalbøge et al. |
| 6,271,004 B1 | 8/2001 | Warthoe |
| 6,271,357 B1 | 8/2001 | Cook et al. |
| 6,300,069 B1 | 10/2001 | Missel et al. |
| 6,306,627 B1 | 10/2001 | Decker |
| 6,316,024 B1 | 11/2001 | Allen et al. |
| 6,316,626 B1 | 11/2001 | Swayze et al. |
| 6,320,040 B1 | 11/2001 | Cook et al. |
| 6,322,985 B1 | 11/2001 | Kashi et al. |
| 6,326,199 B1 | 12/2001 | Cook et al. |
| 6,339,066 B1 | 1/2002 | Bennett et al. |
| 6,344,356 B1 | 2/2002 | Stemmer |
| 6,369,209 B1 | 4/2002 | Manoharan et al. |
| 6,369,237 B1 | 4/2002 | Verdine et al. |
| 6,372,492 B1 | 4/2002 | Bennett et al. |
| 6,380,368 B1 | 4/2002 | Froehler et al. |
| 6,383,808 B1 | 5/2002 | Monia et al. |
| 6,407,223 B1 | 6/2002 | Stec et al. |
| 6,440,739 B1 | 8/2002 | Bennett et al. |
| 6,440,943 B1 | 8/2002 | Cook et al. |
| 6,444,656 B1 | 9/2002 | Nguyen-Ba et al. |
| 6,451,524 B1 | 9/2002 | Ecker |
| 6,455,308 B1 | 9/2002 | Freier |
| 6,468,983 B2 | 10/2002 | Silverman et al. |
| 6,495,677 B1 | 12/2002 | Ramasamy et al. |
| 6,500,945 B2 | 12/2002 | Cook |
| 6,506,594 B1 | 1/2003 | Barany et al. |
| 6,506,894 B1 | 1/2003 | Reese et al. |
| 6,528,262 B1 | 3/2003 | Gilad et al. |
| 6,528,640 B1 | 3/2003 | Beigelman et al. |
| 6,538,126 B1 | 3/2003 | Cho et al. |
| 6,559,279 B1 | 5/2003 | Manoharan et al. |
| 6,562,960 B1 | 5/2003 | Baxter et al. |
| 6,582,936 B1 | 6/2003 | Serafini et al. |
| 6,608,186 B1 | 8/2003 | Miculka et al. |
| 6,610,837 B1 | 8/2003 | Guzaev et al. |
| 6,613,873 B1 | 9/2003 | Buchardt et al. |
| 6,617,438 B1 | 9/2003 | Beigelman et al. |
| 6,632,600 B1 | 10/2003 | Short |
| 6,639,022 B2 | 10/2003 | Michels et al. |
| 6,639,062 B2 | 10/2003 | Manoharan et al. |
| 6,649,750 B1 | 11/2003 | Capaldi et al. |
| 6,670,461 B1 | 12/2003 | Wengel et al. |
| 6,682,889 B1 | 1/2004 | Wang et al. |
| 6,699,979 B2 | 3/2004 | Cook |
| 6,737,520 B2 | 5/2004 | Manoharan et al. |
| 6,762,281 B2 | 7/2004 | Manoharan et al. |
| 6,767,739 B2 | 7/2004 | Crooke et al. |
| 6,809,195 B1 | 10/2004 | Sanghvi et al. |
| 6,811,975 B2 | 11/2004 | Cook et al. |
| 6,815,542 B2 | 11/2004 | Hong et al. |
| 6,861,518 B2 | 3/2005 | Just et al. |
| 6,867,294 B1 | 3/2005 | Sanghvi et al. |

(56) References Cited

U.S. PATENT DOCUMENTS

| | | |
|---|---|---|
| 6,900,301 B2 | 5/2005 | Cook et al. |
| 6,933,146 B2 | 8/2005 | Helliwell et al. |
| 6,933,288 B2 | 8/2005 | Migawa et al. |
| 6,936,432 B2 | 8/2005 | Gopalan et al. |
| 6,943,240 B2 | 9/2005 | Bauer et al. |
| 6,949,520 B1 | 9/2005 | Hartmann et al. |
| 6,977,245 B2 | 12/2005 | Klinman et al. |
| 6,995,259 B1 | 2/2006 | Vargeese et al. |
| 7,015,315 B1 | 3/2006 | Cook et al. |
| 7,018,793 B1 | 3/2006 | Short |
| 7,019,127 B2 | 3/2006 | Reese et al. |
| 7,022,833 B2 | 4/2006 | Reese |
| 7,030,230 B2 | 4/2006 | Ross et al. |
| 7,045,610 B2 | 5/2006 | Dempcy et al. |
| 7,049,122 B2 | 5/2006 | Chang et al. |
| 7,067,497 B2 | 6/2006 | Hanecak et al. |
| 7,101,993 B1 | 9/2006 | Cook et al. |
| 7,119,184 B2 | 10/2006 | Manoharan et al. |
| RE39,464 E | 1/2007 | Cook et al. |
| 7,160,920 B2 | 1/2007 | Garvey et al. |
| 7,205,399 B1 | 4/2007 | Vargeese et al. |
| 7,214,491 B2 | 5/2007 | Yadav et al. |
| 7,227,014 B2 | 6/2007 | Crooke et al. |
| 7,238,795 B2 | 7/2007 | Seela et al. |
| 7,247,621 B2 | 7/2007 | Hong et al. |
| 7,259,150 B2 | 8/2007 | Crooke et al. |
| 7,264,932 B2 | 9/2007 | Latham et al. |
| 7,268,119 B2 | 9/2007 | Cook et al. |
| 7,271,156 B2 | 9/2007 | Krieg et al. |
| 7,285,658 B2 | 10/2007 | Cook et al. |
| 7,288,376 B2 | 10/2007 | Sarma et al. |
| 7,303,895 B1 | 12/2007 | O'Regan et al. |
| 7,304,081 B2 | 12/2007 | Yao et al. |
| 7,354,909 B2 | 4/2008 | Klinman et al. |
| 7,381,527 B2 | 6/2008 | Sarma et al. |
| 7,399,845 B2 | 7/2008 | Seth et al. |
| 7,407,943 B2 | 8/2008 | Crooke et al. |
| 7,407,965 B2 | 8/2008 | Chen et al. |
| 7,410,975 B2 | 8/2008 | Lipford et al. |
| 7,414,116 B2 | 8/2008 | Milton et al. |
| 7,425,545 B2 | 9/2008 | Crooke et al. |
| 7,427,672 B2 | 9/2008 | Imanishi et al. |
| 7,429,565 B2 | 9/2008 | Boojamra et al. |
| 7,432,249 B2 | 10/2008 | Crooke |
| 7,432,250 B2 | 10/2008 | Crooke |
| 7,432,261 B2 | 10/2008 | Cannizzaro et al. |
| 7,452,901 B2 | 11/2008 | Boojamra et al. |
| 7,470,724 B2 | 12/2008 | Cannizzaro et al. |
| 7,495,088 B1 | 2/2009 | Brakel et al. |
| 7,501,091 B2 | 3/2009 | Munoz et al. |
| 7,507,808 B2 | 3/2009 | Dobie |
| 7,507,811 B2 | 3/2009 | Khvorova et al. |
| 7,511,131 B2 | 3/2009 | Crooke et al. |
| 7,517,520 B2 | 4/2009 | Manolova et al. |
| 7,534,879 B2 | 5/2009 | van Deutekom |
| 7,537,767 B2 | 5/2009 | Bachmann et al. |
| 7,547,684 B2 | 6/2009 | Seth et al. |
| 7,585,847 B2 | 9/2009 | Bratzler et al. |
| 7,598,031 B2 | 10/2009 | Liew |
| 7,598,227 B2 | 10/2009 | Crooke et al. |
| 7,598,230 B2 | 10/2009 | Cook et al. |
| 7,608,594 B2 | 10/2009 | Blagg et al. |
| 7,622,451 B2 | 11/2009 | Blagg et al. |
| 7,629,321 B2 | 12/2009 | Crooke |
| 7,645,747 B2 | 1/2010 | Boojamra et al. |
| 7,662,558 B2 | 2/2010 | Liew |
| 7,666,854 B2 | 2/2010 | Seth et al. |
| 7,666,888 B2 | 2/2010 | Bartberger et al. |
| 7,683,036 B2 | 3/2010 | Esau et al. |
| 7,695,902 B2 | 4/2010 | Crooke |
| 7,696,345 B2 | 4/2010 | Allerson et al. |
| 7,713,941 B2 | 5/2010 | Cook et al. |
| 7,718,623 B2 | 5/2010 | Kitagawa et al. |
| 7,723,508 B2 | 5/2010 | Crooke et al. |
| 7,732,590 B2 | 6/2010 | Bhanot et al. |
| 7,732,660 B2 | 6/2010 | Helliwell et al. |
| 7,741,305 B2 | 6/2010 | Crooke et al. |
| 7,741,457 B2 | 6/2010 | Seth et al. |
| 7,749,700 B2 | 7/2010 | Baird et al. |
| 7,750,131 B2 | 7/2010 | Seth et al. |
| 7,750,141 B2 | 7/2010 | Crooke et al. |
| 7,750,731 B2 | 7/2010 | Poulsen et al. |
| 7,759,318 B1 | 7/2010 | Perera et al. |
| 7,776,344 B2 | 8/2010 | Hartmann et al. |
| 7,776,874 B2 | 8/2010 | Yao et al. |
| 7,777,023 B2 | 8/2010 | Vargeese et al. |
| 7,803,930 B2 | 9/2010 | Crooke et al. |
| 7,807,653 B2 | 10/2010 | Cook et al. |
| 7,807,816 B2 | 10/2010 | Wilton et al. |
| 7,811,998 B2 | 10/2010 | Blagg et al. |
| 7,812,003 B2 | 10/2010 | Safe et al. |
| 7,838,287 B2 | 11/2010 | Goldsmith et al. |
| 7,863,252 B2 | 1/2011 | Crooke et al. |
| 7,884,086 B2 | 2/2011 | Bennett et al. |
| 7,884,117 B2 | 2/2011 | Zhang et al. |
| 7,888,324 B2 | 2/2011 | Crooke et al. |
| 7,893,039 B2 | 2/2011 | Swayze et al. |
| 7,919,472 B2 | 4/2011 | Monia et al. |
| 7,947,658 B2 | 5/2011 | Aronin et al. |
| 7,951,934 B2 | 5/2011 | Freier |
| 7,960,353 B2 | 6/2011 | Blagg |
| 7,960,541 B2 | 6/2011 | Wilton et al. |
| 7,973,015 B2 | 7/2011 | van Ommen et al. |
| 8,003,619 B2 | 8/2011 | Hartmann et al. |
| 8,008,011 B2 | 8/2011 | Schmutz et al. |
| 8,008,459 B2 | 8/2011 | Goldsmith et al. |
| 8,022,083 B2 | 9/2011 | Boojamra et al. |
| 8,039,235 B2 | 10/2011 | Lin et al. |
| 8,057,997 B2 | 11/2011 | Seela et al. |
| 8,058,288 B2 | 11/2011 | Yao et al. |
| 8,067,173 B2 | 11/2011 | Liew |
| 8,076,303 B2 | 12/2011 | Iyer et al. |
| 8,084,437 B2 | 12/2011 | Freier et al. |
| 8,084,600 B2 | 12/2011 | Natt et al. |
| 8,088,582 B2 | 1/2012 | Sampath et al. |
| 8,093,222 B2 | 1/2012 | Freier et al. |
| 8,093,225 B2 | 1/2012 | Mamet |
| 8,101,348 B2 | 1/2012 | Tuschl et al. |
| 8,101,358 B2 | 1/2012 | Liew |
| 8,101,585 B2 | 1/2012 | Yu et al. |
| 8,101,743 B2 | 1/2012 | Brown-Driver et al. |
| 8,106,025 B2 | 1/2012 | Bennett et al. |
| 8,110,358 B2 | 2/2012 | Liew |
| 8,110,558 B2 | 2/2012 | Bennett et al. |
| 8,114,597 B2 | 2/2012 | Liew |
| 8,124,745 B2 | 2/2012 | Allerson et al. |
| 8,133,674 B2 | 3/2012 | Liew |
| 8,133,675 B2 | 3/2012 | Liew |
| 8,133,876 B2 | 3/2012 | Bennett et al. |
| 8,138,328 B2 | 3/2012 | Crooke et al. |
| 8,143,230 B2 | 3/2012 | Bhanot et al. |
| 8,148,072 B2 | 4/2012 | Liew |
| 8,158,598 B2 | 4/2012 | Bhanot et al. |
| 8,163,707 B2 | 4/2012 | Qiu et al. |
| 8,178,506 B2 | 5/2012 | Lollo et al. |
| 8,188,059 B2 | 5/2012 | Bhanot et al. |
| 8,206,923 B2 | 6/2012 | Garza Gonzalez et al. |
| 8,207,263 B2 | 6/2012 | Popot et al. |
| 8,212,011 B2 | 7/2012 | Blagg |
| 8,212,012 B2 | 7/2012 | Blagg |
| 8,226,759 B2 | 7/2012 | Shin et al. |
| 8,232,384 B2 | 7/2012 | Wilton et al. |
| 8,257,922 B2 | 9/2012 | Liew |
| 8,258,289 B2 | 9/2012 | Bhanot et al. |
| 8,361,977 B2 | 1/2013 | Baker et al. |
| 8,383,660 B2 | 2/2013 | Chang et al. |
| 8,410,070 B2 | 4/2013 | Miller et al. |
| 8,415,465 B2 | 4/2013 | Freier |
| 8,431,693 B2 | 4/2013 | Manoharan et al. |
| 8,450,474 B2 | 5/2013 | Wilton et al. |
| 8,455,634 B2 | 6/2013 | Wilton et al. |
| 8,455,635 B2 | 6/2013 | Wilton et al. |
| 8,455,636 B2 | 6/2013 | Wilton et al. |
| 8,470,987 B2 | 6/2013 | Wada et al. |

(56) References Cited

U.S. PATENT DOCUMENTS

| | | |
|---|---|---|
| 8,476,423 B2 | 7/2013 | Wilton et al. |
| 8,481,710 B2 | 7/2013 | Davidson et al. |
| 8,486,907 B2 | 7/2013 | Wilton et al. |
| 8,501,414 B2 | 8/2013 | Danzer et al. |
| 8,524,880 B2 | 9/2013 | Wilton et al. |
| 8,557,549 B2 | 10/2013 | Chang et al. |
| 8,557,844 B2 | 10/2013 | Platt et al. |
| 8,592,566 B2 | 11/2013 | Iwamura et al. |
| 8,632,963 B2 | 1/2014 | Shah et al. |
| 8,633,206 B2 | 1/2014 | Promo et al. |
| 8,647,742 B2 | 2/2014 | Dendukuri et al. |
| 8,648,186 B2 | 2/2014 | Monteleone |
| 8,653,254 B2 | 2/2014 | Umemoto et al. |
| 8,669,058 B2 | 3/2014 | Liew |
| 8,674,044 B2 | 3/2014 | Popot et al. |
| 8,679,750 B2 | 3/2014 | Hayden et al. |
| 8,680,063 B2 | 3/2014 | Aronin et al. |
| 8,729,036 B2 | 5/2014 | Zamore et al. |
| 8,735,417 B2 | 5/2014 | Altman et al. |
| 8,750,507 B2 | 6/2014 | Roosta et al. |
| 8,754,107 B2 | 6/2014 | George et al. |
| 8,759,507 B2 | 6/2014 | Van Deutekom |
| 8,802,659 B2 | 8/2014 | Thomas et al. |
| 8,809,516 B2 | 8/2014 | Manoharan et al. |
| 8,822,671 B2 | 9/2014 | Shimizu et al. |
| 8,859,755 B2 | 10/2014 | Wada et al. |
| 8,865,146 B2 | 10/2014 | Fukuhara et al. |
| 8,871,785 B2 | 10/2014 | Boojamra et al. |
| 8,877,435 B2 | 11/2014 | Helliwell et al. |
| 8,883,752 B2 | 11/2014 | Swayze et al. |
| 8,883,969 B2 | 11/2014 | Ide et al. |
| 8,927,513 B2 | 1/2015 | Manoharan et al. |
| 8,952,145 B2 | 2/2015 | Freier |
| 8,957,040 B2 | 2/2015 | Bennett et al. |
| 8,957,042 B2 | 2/2015 | Safe et al. |
| 8,975,389 B2 | 3/2015 | Manoharan et al. |
| 8,980,853 B2 | 3/2015 | Bennett et al. |
| 8,987,222 B2 | 3/2015 | Aronin et al. |
| 8,987,435 B2 | 3/2015 | Swayze et al. |
| 8,993,738 B2 | 3/2015 | Prakash et al. |
| 9,006,198 B2 | 4/2015 | Bennett et al. |
| 9,018,368 B2 | 4/2015 | Wilton et al. |
| 9,024,007 B2 | 5/2015 | Wilton et al. |
| 9,035,040 B2 | 5/2015 | Wilton et al. |
| 9,040,674 B2 | 5/2015 | Benson et al. |
| 9,057,066 B2 | 6/2015 | Hung et al. |
| 9,120,774 B2 | 9/2015 | Blagg et al. |
| 9,121,020 B2 | 9/2015 | Feinstein et al. |
| 9,126,927 B2 | 9/2015 | Yao et al. |
| 9,127,033 B2 | 9/2015 | Prakash et al. |
| 9,127,123 B2 | 9/2015 | Livingston et al. |
| 9,132,289 B2 | 9/2015 | Kawai |
| 9,139,604 B2 | 9/2015 | Boojamra et al. |
| 9,175,286 B2 | 11/2015 | Wilton et al. |
| 9,186,367 B2 | 11/2015 | Thomas et al. |
| 9,249,416 B2 | 2/2016 | Wilton et al. |
| 9,260,716 B2 | 2/2016 | Davidson et al. |
| 9,273,315 B2 | 3/2016 | Hung et al. |
| 9,284,344 B2 | 3/2016 | Kim et al. |
| 9,308,252 B2 | 4/2016 | Suckow et al. |
| 9,321,799 B2 | 4/2016 | Prakash et al. |
| 9,353,372 B2 | 5/2016 | Freier |
| 9,382,540 B2 | 7/2016 | Prakash et al. |
| 9,382,575 B2 | 7/2016 | Eom et al. |
| 9,394,333 B2 * | 7/2016 | Wada ................ C07H 1/00 |
| 9,422,555 B2 | 8/2016 | Wilton et al. |
| 9,428,541 B2 | 8/2016 | Platt et al. |
| 9,441,229 B2 | 9/2016 | Wilton et al. |
| 9,447,415 B2 | 9/2016 | Wilton et al. |
| 9,453,228 B2 | 9/2016 | Kandimalla et al. |
| 9,476,044 B2 | 10/2016 | Tuschl et al. |
| 9,480,740 B2 | 11/2016 | Reed et al. |
| 9,481,704 B2 | 11/2016 | Clarke |
| 9,572,824 B2 | 2/2017 | Thomas et al. |
| 9,598,458 B2 | 3/2017 | Shimizu et al. |
| 9,605,019 B2 | 3/2017 | Verdine et al. |
| 9,605,262 B2 | 3/2017 | Wilton et al. |
| 9,605,263 B2 | 3/2017 | Rigo |
| 9,611,472 B2 | 4/2017 | Zamore et al. |
| 9,617,547 B2 | 4/2017 | Gemba |
| 9,695,211 B2 * | 7/2017 | Wada ................ C07H 21/00 |
| 9,725,474 B2 | 8/2017 | Murata et al. |
| 9,738,895 B2 | 8/2017 | Swayze et al. |
| 9,744,183 B2 | 8/2017 | Verdine et al. |
| 9,809,616 B2 | 11/2017 | Amblard et al. |
| 9,827,258 B2 | 11/2017 | Thomas et al. |
| 9,885,082 B2 | 2/2018 | Hrdlicka |
| 9,896,688 B2 | 2/2018 | Chang et al. |
| 2001/0055761 A1 | 12/2001 | Kanemoto et al. |
| 2002/0013792 A1 | 1/2002 | Imielinski et al. |
| 2002/0082227 A1 | 6/2002 | Henry |
| 2002/0137921 A1 | 9/2002 | Cook |
| 2002/0183502 A1 | 12/2002 | Mesmaeker et al. |
| 2003/0045705 A1 | 3/2003 | Cook et al. |
| 2003/0049662 A1 | 3/2003 | Monia et al. |
| 2003/0050261 A1 | 3/2003 | Krieg et al. |
| 2003/0159938 A1 | 8/2003 | Hradil |
| 2003/0198982 A1 | 10/2003 | Seela et al. |
| 2003/0232978 A1 | 12/2003 | Seeberger et al. |
| 2003/0235845 A1 | 12/2003 | van Ommen et al. |
| 2004/0002596 A1 | 1/2004 | Hong et al. |
| 2004/0023901 A1 | 2/2004 | Cook et al. |
| 2004/0023921 A1 | 2/2004 | Hong et al. |
| 2004/0059104 A1 | 3/2004 | Cook et al. |
| 2004/0063647 A1 | 4/2004 | Johnson |
| 2004/0149587 A1 | 8/2004 | Hradil |
| 2004/0203145 A1 | 10/2004 | Zamore et al. |
| 2004/0213780 A1 | 10/2004 | Krainc |
| 2005/0042646 A1 | 2/2005 | Davidson et al. |
| 2005/0059619 A1 | 3/2005 | Krieg et al. |
| 2005/0096284 A1 | 5/2005 | McSwiggen |
| 2005/0159375 A1 | 7/2005 | Srivastava et al. |
| 2005/0169888 A1 | 8/2005 | Hartmann et al. |
| 2005/0176045 A1 | 8/2005 | Fedorov et al. |
| 2005/0203044 A1 | 9/2005 | Zinnen |
| 2005/0215513 A1 | 9/2005 | Boojamra et al. |
| 2005/0227947 A1 | 10/2005 | Chen et al. |
| 2005/0239102 A1 | 10/2005 | Verdine et al. |
| 2005/0261237 A1 | 11/2005 | Boojamra et al. |
| 2005/0277133 A1 | 12/2005 | McSwiggen |
| 2005/0277609 A1 | 12/2005 | Krieg et al. |
| 2006/0003962 A1 | 1/2006 | Ahluwalia et al. |
| 2006/0035858 A1 | 2/2006 | Geary et al. |
| 2006/0035866 A1 | 2/2006 | Cannizzaro et al. |
| 2006/0041115 A1 | 2/2006 | Ravikumar |
| 2006/0063730 A1 | 3/2006 | Monia et al. |
| 2006/0079478 A1 | 4/2006 | Boojamra et al. |
| 2006/0099616 A1 | 5/2006 | van Ommen et al. |
| 2006/0147952 A1 | 7/2006 | van Ommen et al. |
| 2006/0166910 A1 | 7/2006 | Tuschl et al. |
| 2006/0199776 A1 | 9/2006 | Blagg et al. |
| 2006/0199788 A1 | 9/2006 | Cannizzaro et al. |
| 2006/0211644 A1 | 9/2006 | Krieg et al. |
| 2006/0257912 A1 | 11/2006 | Kaemmerer et al. |
| 2006/0264404 A1 | 11/2006 | Boojamra et al. |
| 2007/0027116 A1 | 2/2007 | Cho et al. |
| 2007/0099851 A1 | 5/2007 | Linn |
| 2007/0099860 A1 | 5/2007 | Sah et al. |
| 2007/0123484 A1 | 5/2007 | Bhat et al. |
| 2007/0135363 A1 | 6/2007 | Cook et al. |
| 2007/0149462 A1 | 6/2007 | Iyer et al. |
| 2007/0161547 A1 | 7/2007 | Bhat et al. |
| 2007/0161590 A1 | 7/2007 | Van Bilsen et al. |
| 2007/0196852 A1 | 8/2007 | Heindl et al. |
| 2007/0249589 A1 | 10/2007 | Aebi et al. |
| 2007/0259832 A1 | 11/2007 | Cook et al. |
| 2007/0265224 A1 | 11/2007 | Cook et al. |
| 2007/0270452 A1 | 11/2007 | Blagg et al. |
| 2007/0282097 A1 | 12/2007 | Ohgi et al. |
| 2007/0287831 A1 | 12/2007 | Seth et al. |
| 2007/0299027 A1 | 12/2007 | Hung et al. |
| 2008/0015158 A1 | 1/2008 | Ichiro et al. |
| 2008/0015162 A1 | 1/2008 | Bhanot et al. |
| 2008/0039418 A1 | 2/2008 | Freier |

(56) References Cited

U.S. PATENT DOCUMENTS

| | | |
|---|---|---|
| 2008/0045473 A1 | 2/2008 | Uhlmann et al. |
| 2008/0064867 A1 | 3/2008 | Leuck et al. |
| 2008/0119426 A1 | 5/2008 | Dale |
| 2008/0200409 A1 | 8/2008 | Wilson et al. |
| 2008/0200423 A1 | 8/2008 | Cook et al. |
| 2008/0209581 A1 | 8/2008 | van Ommen et al. |
| 2008/0221055 A1 | 9/2008 | Sah et al. |
| 2008/0221303 A1 | 9/2008 | Katzhendler et al. |
| 2008/0249291 A1 | 10/2008 | Kwon et al. |
| 2008/0274989 A1 | 11/2008 | Davidson et al. |
| 2009/0012120 A1 | 1/2009 | Borhan et al. |
| 2009/0023675 A1 | 1/2009 | McSwiggen et al. |
| 2009/0053148 A1 | 2/2009 | Kandimalla et al. |
| 2009/0053205 A1 | 2/2009 | Kandimalla et al. |
| 2009/0060898 A1 | 3/2009 | Kandimalla et al. |
| 2009/0062224 A1 | 3/2009 | Kim et al. |
| 2009/0076246 A1 | 3/2009 | van Deutekom |
| 2009/0093425 A1 | 4/2009 | Dowdy et al. |
| 2009/0131372 A1 | 5/2009 | Chen et al. |
| 2009/0162316 A1 | 6/2009 | Verdine et al. |
| 2009/0163709 A1 | 6/2009 | Blagg |
| 2009/0186410 A1 | 7/2009 | Aronin et al. |
| 2009/0187014 A1 | 7/2009 | Blagg |
| 2009/0227543 A1 | 9/2009 | Cannizzaro et al. |
| 2009/0228998 A1 | 9/2009 | van Ommen et al. |
| 2009/0247488 A1 | 10/2009 | Cannizzaro et al. |
| 2009/0263413 A1 | 10/2009 | Iwamura et al. |
| 2009/0275535 A1 | 11/2009 | Boojamra et al. |
| 2009/0306176 A1 | 12/2009 | Schlingensiepen et al. |
| 2010/0008937 A1 | 1/2010 | Peer et al. |
| 2010/0008981 A1 | 1/2010 | Kaemmerer et al. |
| 2010/0022467 A1 | 1/2010 | Boojamra et al. |
| 2010/0022620 A1 | 1/2010 | Crispin et al. |
| 2010/0038543 A1 | 2/2010 | Toda et al. |
| 2010/0048882 A1 | 2/2010 | Blagg et al. |
| 2010/0069472 A1 | 3/2010 | Hung et al. |
| 2010/0074889 A1 | 3/2010 | Qiu et al. |
| 2010/0105630 A1 | 4/2010 | Blagg |
| 2010/0120900 A1 | 5/2010 | van Bilsen et al. |
| 2010/0186626 A1 | 7/2010 | Shin et al. |
| 2010/0203002 A1 | 8/2010 | Fukuhara et al. |
| 2010/0204162 A1 | 8/2010 | Platt et al. |
| 2010/0215642 A1 | 8/2010 | Lan et al. |
| 2010/0273999 A1 | 10/2010 | Jung et al. |
| 2010/0299768 A1 | 11/2010 | Perrin et al. |
| 2010/0311684 A1 | 12/2010 | Cook et al. |
| 2010/0325746 A9 | 12/2010 | Kaemmerer et al. |
| 2011/0009477 A1 | 1/2011 | Yu et al. |
| 2011/0015253 A1 | 1/2011 | Wilton et al. |
| 2011/0015258 A1 | 1/2011 | Wilton et al. |
| 2011/0021365 A1 | 1/2011 | Seela et al. |
| 2011/0039334 A1 | 2/2011 | Bennett et al. |
| 2011/0046203 A1 | 2/2011 | Wilton et al. |
| 2011/0071101 A1 | 3/2011 | Boojamra et al. |
| 2011/0105587 A1 | 5/2011 | Fishcher et al. |
| 2011/0111491 A1 | 5/2011 | Davidson et al. |
| 2011/0136765 A1 | 6/2011 | Promo et al. |
| 2011/0178284 A1 | 7/2011 | Wada et al. |
| 2011/0201599 A1 | 8/2011 | Bahceci et al. |
| 2011/0212520 A1 | 9/2011 | Davidson et al. |
| 2011/0213010 A1 | 9/2011 | Hayden et al. |
| 2011/0257251 A1 | 10/2011 | Gude-Rodriguez et al. |
| 2011/0263686 A1 | 10/2011 | Wilton et al. |
| 2011/0269814 A1 | 11/2011 | Manoharan et al. |
| 2011/0269821 A1 | 11/2011 | Swayze et al. |
| 2011/0288053 A1 | 11/2011 | Boojamra et al. |
| 2011/0294124 A1 | 12/2011 | Wada et al. |
| 2011/0294869 A1 | 12/2011 | Petersen |
| 2011/0306652 A1 | 12/2011 | Freier |
| 2011/0312086 A1 | 12/2011 | Van Deutekom |
| 2012/0022144 A1 | 1/2012 | Wilton et al. |
| 2012/0022145 A1 | 1/2012 | Wilton et al. |
| 2012/0029057 A1 | 2/2012 | Wilton et al. |
| 2012/0029058 A1 | 2/2012 | Wilton et al. |
| 2012/0029059 A1 | 2/2012 | Wilton et al. |
| 2012/0029060 A1 | 2/2012 | Wilton et al. |
| 2012/0041050 A1 | 2/2012 | Wilton et al. |
| 2012/0059045 A1 | 3/2012 | Prakash et al. |
| 2012/0064137 A1 | 3/2012 | Kawai |
| 2012/0095076 A1 | 4/2012 | Sah et al. |
| 2012/0108800 A1 | 5/2012 | Murata et al. |
| 2012/0136039 A1 | 5/2012 | Aronin et al. |
| 2012/0156138 A1 | 6/2012 | Smith |
| 2012/0157511 A1 | 6/2012 | Manoharan et al. |
| 2012/0190649 A1 | 7/2012 | Thomas et al. |
| 2012/0208864 A1 | 8/2012 | Bhanot et al. |
| 2012/0214865 A1 | 8/2012 | Bennett et al. |
| 2012/0216823 A1 | 8/2012 | Fukuhara et al. |
| 2012/0246747 A1 | 9/2012 | Tuschl et al. |
| 2012/0252745 A1 | 10/2012 | Blagg et al. |
| 2012/0252879 A1 | 10/2012 | Hung et al. |
| 2012/0276037 A1 | 11/2012 | Suzuki et al. |
| 2012/0308609 A1 | 12/2012 | Gibbon et al. |
| 2012/0316224 A1 | 12/2012 | Verdine et al. |
| 2013/0005794 A1 | 1/2013 | Kaemmerer et al. |
| 2013/0046008 A1 | 2/2013 | Bennett et al. |
| 2013/0072671 A1 | 3/2013 | Van Deutekom |
| 2013/0084576 A1 | 4/2013 | Prakash et al. |
| 2013/0116310 A1 | 5/2013 | Wilton et al. |
| 2013/0116420 A1 | 5/2013 | Prakash et al. |
| 2013/0156845 A1 | 6/2013 | Manoharan et al. |
| 2013/0178612 A1 | 7/2013 | Wada et al. |
| 2013/0184450 A1 | 7/2013 | Wada et al. |
| 2013/0189782 A1 | 7/2013 | Hung et al. |
| 2013/0197061 A1 | 8/2013 | Hohjoh et al. |
| 2013/0217755 A1 | 8/2013 | Wilton et al. |
| 2013/0236536 A1 | 9/2013 | Phiasivongsa et al. |
| 2013/0243725 A1 | 9/2013 | Clarke |
| 2013/0253033 A1 | 9/2013 | Wilton et al. |
| 2013/0253178 A1 | 9/2013 | Shimizu et al. |
| 2013/0253180 A1 | 9/2013 | Wilton et al. |
| 2013/0274313 A1 | 10/2013 | Wilton et al. |
| 2013/0281684 A1 | 10/2013 | Freier |
| 2013/0302806 A1 | 11/2013 | Van Deutekom |
| 2013/0316969 A1 | 11/2013 | Boojamra et al. |
| 2013/0323836 A1 | 12/2013 | Manoharan et al. |
| 2013/0331438 A1 | 12/2013 | Wilton et al. |
| 2014/0080769 A1 | 3/2014 | Platt et al. |
| 2014/0080896 A1 | 3/2014 | Nelson et al. |
| 2014/0080898 A1 | 3/2014 | Wilton et al. |
| 2014/0107330 A1 | 4/2014 | Freier et al. |
| 2014/0120088 A1 | 5/2014 | Carpentier |
| 2014/0142160 A1 | 5/2014 | Lee et al. |
| 2014/0155587 A1 | 6/2014 | Wilton et al. |
| 2014/0163213 A1 | 6/2014 | Debelak et al. |
| 2014/0194610 A1 | 7/2014 | Verdine et al. |
| 2014/0213635 A1 | 7/2014 | Van Deutekom |
| 2014/0220573 A1 | 8/2014 | Hrdlicka |
| 2014/0221395 A1 | 8/2014 | Dhanoa |
| 2014/0235566 A1 | 8/2014 | Amblard et al. |
| 2014/0243515 A1 | 8/2014 | Wilton et al. |
| 2014/0243516 A1 | 8/2014 | Wilton et al. |
| 2014/0255936 A1 | 9/2014 | Rademakers et al. |
| 2014/0256578 A1 | 9/2014 | Hayden et al. |
| 2014/0275212 A1 | 9/2014 | van Deutekom |
| 2014/0303238 A1 | 10/2014 | Linsley et al. |
| 2014/0309190 A1 | 10/2014 | Thomas et al. |
| 2014/0309283 A1 | 10/2014 | Wilton et al. |
| 2014/0309284 A1 | 10/2014 | Wilton et al. |
| 2014/0309285 A1 | 10/2014 | Wilton et al. |
| 2014/0316121 A1 | 10/2014 | Prakash et al. |
| 2014/0323707 A1 | 10/2014 | Seth et al. |
| 2014/0350076 A1 | 11/2014 | van Deutekom |
| 2014/0357698 A1 | 12/2014 | Van Deutekom et al. |
| 2014/0357855 A1 | 12/2014 | Van Deutekom et al. |
| 2014/0373188 A1 | 12/2014 | Zamore et al. |
| 2014/0378527 A1 | 12/2014 | van Deutekom |
| 2015/0025039 A1 | 1/2015 | Boojamra et al. |
| 2015/0051389 A1 | 2/2015 | Seth et al. |
| 2015/0057330 A1 | 2/2015 | Wilton et al. |
| 2015/0080457 A1 | 3/2015 | Manoharan et al. |
| 2015/0080563 A2 | 3/2015 | van Deutekom |
| 2015/0096064 A1 | 4/2015 | Tuschl et al. |
| 2015/0126725 A1 | 5/2015 | Swayze et al. |

(56) References Cited

U.S. PATENT DOCUMENTS

| | | |
|---|---|---|
| 2015/0148404 A1 | 5/2015 | de Visser et al. |
| 2015/0159163 A1 | 6/2015 | Prakash et al. |
| 2015/0166999 A1 | 6/2015 | Gemba |
| 2015/0167006 A1 | 6/2015 | Swayze et al. |
| 2015/0197540 A1 | 7/2015 | Shimizu et al. |
| 2015/0211006 A1 | 7/2015 | Butler et al. |
| 2015/0218559 A1 | 8/2015 | Van Deutekom et al. |
| 2015/0259679 A1 | 9/2015 | Bennett et al. |
| 2015/0267197 A1 | 9/2015 | Bennett et al. |
| 2015/0275208 A1 | 10/2015 | Oestergaard et al. |
| 2015/0291636 A1 | 10/2015 | Atamanyuk et al. |
| 2015/0292015 A1 | 10/2015 | Bennett et al. |
| 2015/0307877 A1 | 10/2015 | Freier |
| 2015/0315594 A1 | 11/2015 | Prakash et al. |
| 2015/0322434 A1 | 11/2015 | van Deutekom |
| 2015/0329859 A1 | 11/2015 | Bennett et al. |
| 2015/0335708 A1 | 11/2015 | Froelich et al. |
| 2015/0353931 A1 | 12/2015 | Wilton et al. |
| 2015/0361424 A1 | 12/2015 | van Deutekom |
| 2015/0376615 A1 | 12/2015 | Wilton et al. |
| 2015/0376616 A1 | 12/2015 | Wilton et al. |
| 2015/0376624 A1 | 12/2015 | Gryaznov et al. |
| 2015/0376625 A1 | 12/2015 | Oestergaard et al. |
| 2016/0002281 A1 | 1/2016 | Mayes et al. |
| 2016/0002631 A1 | 1/2016 | Wilton et al. |
| 2016/0002632 A1 | 1/2016 | Wilton et al. |
| 2016/0002635 A1 | 1/2016 | Wilton et al. |
| 2016/0017327 A1 | 1/2016 | Rudnicki et al. |
| 2016/0024496 A1 | 1/2016 | Bennett et al. |
| 2016/0040161 A1 | 2/2016 | Packard et al. |
| 2016/0046939 A1 | 2/2016 | Prakash et al. |
| 2016/0050929 A1 | 2/2016 | Benfatti et al. |
| 2016/0050930 A1 | 2/2016 | Benfatti et al. |
| 2016/0053256 A1 | 2/2016 | Hung et al. |
| 2016/0068837 A1 | 3/2016 | Chang et al. |
| 2016/0076033 A1 | 3/2016 | Torii et al. |
| 2016/0108396 A1 | 4/2016 | Jensen et al. |
| 2016/0122761 A1 | 5/2016 | Prakash et al. |
| 2016/0128928 A1 | 5/2016 | Fukuhara et al. |
| 2016/0129023 A1 | 5/2016 | Thomas et al. |
| 2016/0138022 A1 | 5/2016 | Kandimalla et al. |
| 2016/0159846 A1 | 6/2016 | Prakash et al. |
| 2016/0168570 A1 | 6/2016 | Van Deutekom et al. |
| 2016/0186175 A1 | 6/2016 | Seth et al. |
| 2016/0186178 A1 | 6/2016 | Radovic-Moreno et al. |
| 2016/0186185 A1 | 6/2016 | Prakash et al. |
| 2016/0194349 A1 | 7/2016 | Prakash et al. |
| 2016/0194636 A1 | 7/2016 | Van Deutekom et al. |
| 2016/0214974 A1 | 7/2016 | Schaetzer et al. |
| 2016/0230172 A1 | 8/2016 | Rigo |
| 2016/0237108 A1 | 8/2016 | Fraley et al. |
| 2016/0237432 A1 | 8/2016 | Bennett et al. |
| 2016/0251653 A1 | 9/2016 | Davidson et al. |
| 2016/0251655 A1 | 9/2016 | Freier et al. |
| 2016/0251658 A1 | 9/2016 | Van Deutekom et al. |
| 2016/0264964 A1 | 9/2016 | Cancilla et al. |
| 2016/0312217 A1 | 10/2016 | Hung et al. |
| 2016/0331835 A1 | 11/2016 | Gemba et al. |
| 2016/0331836 A1 | 11/2016 | Gemba et al. |
| 2016/0333349 A1 | 11/2016 | Gemba et al. |
| 2016/0347780 A1 | 12/2016 | Wada et al. |
| 2016/0347784 A1 | 12/2016 | Verdine et al. |
| 2016/0355810 A1 | 12/2016 | Van Deutekom |
| 2016/0369273 A1 | 12/2016 | Freier |
| 2017/0009233 A1 | 1/2017 | Wilton et al. |
| 2017/0009234 A1 | 1/2017 | Wilton et al. |
| 2017/0029445 A1 | 2/2017 | Shimizu et al. |
| 2017/0029457 A1 | 2/2017 | Verdine et al. |
| 2017/0037399 A1 | 2/2017 | Meena et al. |
| 2017/0044526 A1 | 2/2017 | Wan et al. |
| 2017/0067050 A1 | 3/2017 | Tuschl et al. |
| 2017/0114086 A1 | 4/2017 | Clarke |
| 2017/0114340 A1 | 4/2017 | Mueller et al. |
| 2017/0130224 A1 | 5/2017 | Oestergaard et al. |
| 2017/0197903 A1 | 7/2017 | Hoashi |
| 2017/0239280 A1 | 8/2017 | Thomas et al. |
| 2017/0275621 A1 | 9/2017 | Butler et al. |
| 2017/0327824 A1 | 11/2017 | Oestergaard et al. |
| 2017/0349897 A1 | 12/2017 | Rigo |

FOREIGN PATENT DOCUMENTS

| | | |
|---|---|---|
| DE | 01934150 A1 | 1/1970 |
| EP | 0 002 322 A2 | 6/1979 |
| EP | 192521 A1 | 8/1986 |
| EP | 269258 A2 | 6/1988 |
| EP | 0506242 A1 | 9/1992 |
| EP | 0531447 A1 | 3/1993 |
| EP | 0604409 A1 | 7/1994 |
| EP | 0655088 A1 | 5/1995 |
| EP | 0779893 A2 | 6/1997 |
| EP | 0831854 A1 | 4/1998 |
| EP | 0973945 A1 | 1/2000 |
| EP | 1097162 A2 | 5/2001 |
| EP | 1100807 A1 | 5/2001 |
| EP | 1185305 | 3/2002 |
| EP | 1244682 A1 | 10/2002 |
| EP | 1311526 A1 | 5/2003 |
| EP | 1418179 A2 | 5/2004 |
| EP | 1499627 A2 | 1/2005 |
| EP | 1539188 A2 | 6/2005 |
| EP | 1556077 A2 | 7/2005 |
| EP | 1560840 A2 | 8/2005 |
| EP | 1562971 A2 | 8/2005 |
| EP | 1670810 A2 | 6/2006 |
| EP | 1670896 A2 | 6/2006 |
| EP | 1795536 A1 | 6/2007 |
| EP | 1957507 A2 | 8/2008 |
| EP | 1984381 A2 | 10/2008 |
| EP | 2021472 A2 | 2/2009 |
| EP | 2062980 A2 | 5/2009 |
| EP | 2066684 A2 | 6/2009 |
| EP | 2149571 A1 | 2/2010 |
| EP | 2161038 A1 | 3/2010 |
| EP | 2170917 A2 | 4/2010 |
| EP | 2173760 A2 | 4/2010 |
| EP | 2176280 A2 | 4/2010 |
| EP | 2282744 A1 | 2/2011 |
| EP | 2285819 A1 | 2/2011 |
| EP | 2316967 A1 | 5/2011 |
| EP | 2360166 A1 | 8/2011 |
| EP | 1 866 319 B1 | 11/2011 |
| EP | 2399588 A1 | 12/2011 |
| EP | 2422819 A2 | 2/2012 |
| EP | 2428227 A1 | 3/2012 |
| EP | 2458005 A1 | 5/2012 |
| EP | 2462153 A2 | 6/2012 |
| EP | 2479182 A1 | 7/2012 |
| EP | 1606407 B1 | 12/2013 |
| EP | 14193887.8 | 11/2014 |
| EP | 14198167.0 | 12/2014 |
| EP | 15182401.8 | 8/2015 |
| EP | 15191074.2 | 10/2015 |
| EP | 15191075.9 | 10/2015 |
| EP | 15191076.7 | 10/2015 |
| EP | 2982758 A1 | 2/2016 |
| EP | 2125852 B1 | 4/2016 |
| EP | 2370451 B1 | 11/2016 |
| EP | 2 534 262 B1 | 12/2016 |
| GB | 1448437 A | 9/1976 |
| GB | 2016273 A | 9/1979 |
| JP | H03-074398 A | 3/1991 |
| JP | 3072345 B1 | 7/2000 |
| JP | 2003/238586 A | 8/2003 |
| JP | 2009-190983 A | 8/2009 |
| JP | 4348044 B2 | 10/2009 |
| JP | 04348077 B2 | 10/2009 |
| JP | 2011/088935 A | 5/2011 |
| WO | WO-91/10671 A1 | 7/1991 |
| WO | WO-91/16331 A1 | 10/1991 |
| WO | WO-91/17755 A1 | 11/1991 |
| WO | WO-92/03452 A1 | 3/1992 |
| WO | WO-92/20822 A1 | 11/1992 |
| WO | WO-92/20823 A1 | 11/1992 |

(56) References Cited

FOREIGN PATENT DOCUMENTS

| | | |
|---|---|---|
| WO | WO-93/08296 A1 | 4/1993 |
| WO | WO-94/17093 A1 | 8/1994 |
| WO | WO-94/22886 A1 | 10/1994 |
| WO | WO-94/22888 A1 | 10/1994 |
| WO | WO-94/22890 A1 | 10/1994 |
| WO | WO-96/02555 A1 | 2/1996 |
| WO | WO-96/07392 A2 | 3/1996 |
| WO | WO-96/14329 A1 | 5/1996 |
| WO | WO-96/19572 A1 | 6/1996 |
| WO | WO-96/36627 A1 | 11/1996 |
| WO | WO-96/37504 A1 | 11/1996 |
| WO | WO-96/39413 A1 | 12/1996 |
| WO | WO-97/06183 A1 | 2/1997 |
| WO | WO-97/09443 A1 | 3/1997 |
| WO | WO-97/14710 A1 | 4/1997 |
| WO | WO-97/47637 A1 | 12/1997 |
| WO | WO-98/02582 A2 | 1/1998 |
| WO | WO-98/03542 A1 | 1/1998 |
| WO | WO-98/07734 A1 | 2/1998 |
| WO | WO-98/016535 A1 | 4/1998 |
| WO | WO-98/18810 A1 | 5/1998 |
| WO | WO-98/39334 A1 | 9/1998 |
| WO | WO-98/46794 A1 | 10/1998 |
| WO | WO-98/53801 A1 | 12/1998 |
| WO | WO-99/00377 A1 | 1/1999 |
| WO | WO-99/05160 A2 | 2/1999 |
| WO | WO-99/12034 A1 | 3/1999 |
| WO | WO-99/56755 A1 | 11/1999 |
| WO | WO-99/58118 A2 | 11/1999 |
| WO | WO-00/00499 A1 | 1/2000 |
| WO | WO-00/04034 A2 | 1/2000 |
| WO | WO-00/06588 A1 | 2/2000 |
| WO | WO-00/09159 A1 | 2/2000 |
| WO | WO-00/23444 A1 | 4/2000 |
| WO | WO-00/31110 A1 | 6/2000 |
| WO | WO-00/37658 A2 | 6/2000 |
| WO | WO-00/55179 A1 | 9/2000 |
| WO | WO-00/58329 A1 | 10/2000 |
| WO | WO-00/76554 A1 | 12/2000 |
| WO | wo-01/02415 A1 | 1/2001 |
| WO | WO-01/022990 A2 | 4/2001 |
| WO | WO-01/27126 A1 | 4/2001 |
| WO | WO-01/40515 A1 | 6/2001 |
| WO | WO-01/49701 A1 | 7/2001 |
| WO | WO-01/64702 A1 | 9/2001 |
| WO | WO-2001/068663 A1 | 9/2001 |
| WO | WO-01/81303 A1 | 11/2001 |
| WO | WO-01/85751 A1 | 11/2001 |
| WO | WO-01/88198 A1 | 11/2001 |
| WO | WO-02/12263 A1 | 2/2002 |
| WO | WO-02/14340 A1 | 2/2002 |
| WO | WO-02/15410 A2 | 2/2002 |
| WO | WO-02/20544 A1 | 3/2002 |
| WO | WO-02/22635 A1 | 3/2002 |
| WO | WO-02/24906 A1 | 3/2002 |
| WO | WO-02/32450 A2 | 4/2002 |
| WO | WO-02/57425 A2 | 7/2002 |
| WO | WO-2002/051716 A1 | 7/2002 |
| WO | WO-02/97134 A2 | 12/2002 |
| WO | WO-02/099317 A1 | 12/2002 |
| WO | WO-03/002065 A2 | 1/2003 |
| WO | WO-03/004602 A2 | 1/2003 |
| WO | WO-03/011887 A2 | 2/2003 |
| WO | WO-03/012057 A2 | 2/2003 |
| WO | WO-03/014306 A2 | 2/2003 |
| WO | WO-03/014307 A2 | 2/2003 |
| WO | WO-03/018600 A2 | 3/2003 |
| WO | WO-03/066633 A1 | 8/2003 |
| WO | WO-2003/071001 A1 | 8/2003 |
| WO | WO-2003/072757 A2 | 9/2003 |
| WO | WO-2003/073989 A2 | 9/2003 |
| WO | WO-03/097662 A1 | 11/2003 |
| WO | WO-03/099840 A1 | 12/2003 |
| WO | WO-03/100017 A2 | 12/2003 |
| WO | WO-03/106477 A1 | 12/2003 |
| WO | WO-2004/000351 A1 | 12/2003 |
| WO | WO-2004/003228 A1 | 1/2004 |
| WO | WO-2004/007718 A2 | 1/2004 |
| WO | WO-2004/014312 A2 | 2/2004 |
| WO | WO-2004/014933 A1 | 2/2004 |
| WO | WO-2004/016805 A2 | 2/2004 |
| WO | WO-2004010956 A2 | 2/2004 |
| WO | WO-2004/024919 A1 | 3/2004 |
| WO | WO-2004/039829 A2 | 5/2004 |
| WO | WO-2004041889 A2 | 5/2004 |
| WO | WO-2004044134 A2 | 5/2004 |
| WO | WO-2004044136 A2 | 5/2004 |
| WO | WO-2004044141 A2 | 5/2004 |
| WO | WO-2004044181 A2 | 5/2004 |
| WO | WO-2004/048522 A2 | 6/2004 |
| WO | WO-2004055162 A2 | 7/2004 |
| WO | WO-2004/080466 A1 | 9/2004 |
| WO | WO-2004/083432 A1 | 9/2004 |
| WO | WO-2004/083446 A2 | 9/2004 |
| WO | WO-2004/085454 A1 | 10/2004 |
| WO | WO-2004/096233 A2 | 11/2004 |
| WO | WO-2004/096235 A2 | 11/2004 |
| WO | WO-2004/096286 A2 | 11/2004 |
| WO | WO-2004093783 A2 | 11/2004 |
| WO | WO-2005/002626 A1 | 1/2005 |
| WO | WO-2005000201 A2 | 1/2005 |
| WO | WO-2005005599 A2 | 1/2005 |
| WO | WO-2005/014609 A2 | 2/2005 |
| WO | WO-2005013901 A2 | 2/2005 |
| WO | WO-2005/019236 A1 | 3/2005 |
| WO | WO-2005/019237 A1 | 3/2005 |
| WO | WO-2005/021568 A2 | 3/2005 |
| WO | WO-2005/023828 A1 | 3/2005 |
| WO | WO-2005/028494 A1 | 3/2005 |
| WO | WO-2005019418 A2 | 3/2005 |
| WO | WO-2005023825 A2 | 3/2005 |
| WO | WO-2005023995 A2 | 3/2005 |
| WO | WO-2005/039630 A2 | 5/2005 |
| WO | WO-2005/042018 A2 | 5/2005 |
| WO | WO-2005/042716 A2 | 5/2005 |
| WO | WO-2005040180 A2 | 5/2005 |
| WO | WO-2005063976 A2 | 7/2005 |
| WO | WO-2005/070859 A1 | 8/2005 |
| WO | WO-2005/085272 A1 | 9/2005 |
| WO | WO-2005/092909 A1 | 10/2005 |
| WO | WO-2006/000057 A1 | 1/2006 |
| WO | WO-2006020676 A2 | 2/2006 |
| WO | WO-2006/022323 A1 | 3/2006 |
| WO | WO-2006/029258 A2 | 3/2006 |
| WO | WO-2006/031267 A2 | 3/2006 |
| WO | WO-2006031461 A2 | 3/2006 |
| WO | WO-2006044531 A2 | 4/2006 |
| WO | WO-2006/049454 A1 | 5/2006 |
| WO | WO-2006/050501 A2 | 5/2006 |
| WO | WO-2006/053861 A1 | 5/2006 |
| WO | WO-2006/065751 A2 | 6/2006 |
| WO | WO-2006/066260 A2 | 6/2006 |
| WO | WO-2006/070284 A1 | 7/2006 |
| WO | WO-2006/080596 A1 | 8/2006 |
| WO | WO-2006/091915 A2 | 8/2006 |
| WO | WO-2006/117400 A2 | 11/2006 |
| WO | WO-2006/121960 A2 | 11/2006 |
| WO | WO-2007/002904 A2 | 1/2007 |
| WO | WO-2007/005941 A2 | 1/2007 |
| WO | WO-2007027775 A2 | 3/2007 |
| WO | WO-2007/041045 A2 | 4/2007 |
| WO | WO-2007/051045 A2 | 5/2007 |
| WO | WO-2007/059041 A2 | 5/2007 |
| WO | WO-2007/064291 A1 | 6/2007 |
| WO | WO-2007/070598 A2 | 6/2007 |
| WO | WO-2007064954 A2 | 6/2007 |
| WO | WO-2007/089584 A2 | 8/2007 |
| WO | WO-2007/089611 A2 | 8/2007 |
| WO | WO-2007/090071 A2 | 8/2007 |
| WO | WO-2007/095316 A2 | 8/2007 |
| WO | WO-2007131232 A2 | 11/2007 |
| WO | WO-2007131237 A2 | 11/2007 |
| WO | WO-2007131238 A2 | 11/2007 |
| WO | WO-2007134014 A2 | 11/2007 |

(56) References Cited

FOREIGN PATENT DOCUMENTS

| | | |
|---|---|---|
| WO | WO-2007136988 A2 | 11/2007 |
| WO | WO-2007143315 A2 | 12/2007 |
| WO | WO-2007143316 A2 | 12/2007 |
| WO | WO-2007143317 A2 | 12/2007 |
| WO | WO-2007146511 A2 | 12/2007 |
| WO | WO-2008/005562 A2 | 1/2008 |
| WO | WO-2008/008476 A2 | 1/2008 |
| WO | WO-2008/021136 A2 | 2/2008 |
| WO | WO-2008017081 A1 | 2/2008 |
| WO | WO-2008/049085 A1 | 4/2008 |
| WO | WO-2008/051763 A1 | 5/2008 |
| WO | WO-2008/068638 A2 | 6/2008 |
| WO | WO-2008/073959 A2 | 6/2008 |
| WO | WO-2008066776 A2 | 6/2008 |
| WO | WO-2008/098104 A1 | 8/2008 |
| WO | WO-2008118883 A1 | 10/2008 |
| WO | WO-2008139262 A2 | 11/2008 |
| WO | WO-2008/148801 A2 | 12/2008 |
| WO | WO-2008/151833 A2 | 12/2008 |
| WO | WO-2009/001097 A2 | 12/2008 |
| WO | WO-2009/007855 A2 | 1/2009 |
| WO | WO-2009/014237 A2 | 1/2009 |
| WO | WO-2009046141 A2 | 4/2009 |
| WO | WO-2009/086264 A1 | 7/2009 |
| WO | WO-2009/089659 A1 | 7/2009 |
| WO | WO-2009/098197 A1 | 8/2009 |
| WO | WO-2009117589 A1 | 9/2009 |
| WO | WO-2009124238 A1 | 10/2009 |
| WO | WO-2009/135322 A1 | 11/2009 |
| WO | WO-2009143387 A2 | 11/2009 |
| WO | WO-2009143390 A2 | 11/2009 |
| WO | WO-2009143391 A2 | 11/2009 |
| WO | WO-2009143463 A2 | 11/2009 |
| WO | WO-2009/146123 A2 | 12/2009 |
| WO | WO-2009148605 A2 | 12/2009 |
| WO | WO-2010/003133 A2 | 1/2010 |
| WO | WO-2010/030858 A1 | 3/2010 |
| WO | WO-2010/039543 A2 | 4/2010 |
| WO | WO-2010/042636 A2 | 4/2010 |
| WO | WO-2010/048549 A2 | 4/2010 |
| WO | WO-2010/048585 A2 | 4/2010 |
| WO | WO-2010036696 A1 | 4/2010 |
| WO | WO-2010036698 A1 | 4/2010 |
| WO | WO-2010048552 A2 | 4/2010 |
| WO | WO-2010/064146 A2 | 6/2010 |
| WO | WO-2010/072831 A1 | 7/2010 |
| WO | WO-2010080953 A1 | 7/2010 |
| WO | WO-2010/096650 A1 | 8/2010 |
| WO | WO-2010091301 A1 | 8/2010 |
| WO | WO-2010107838 A1 | 9/2010 |
| WO | WO-2010/113937 A1 | 10/2010 |
| WO | WO-2010/118263 A1 | 10/2010 |
| WO | WO-2010120262 A1 | 10/2010 |
| WO | WO-2010/129853 A2 | 11/2010 |
| WO | WO-2010/141471 A2 | 12/2010 |
| WO | WO-2010/146784 A1 | 12/2010 |
| WO | WO-2010/150789 A1 | 12/2010 |
| WO | WO-2011/005761 A1 | 1/2011 |
| WO | WO-2011/005764 A1 | 1/2011 |
| WO | WO-2011/005860 A2 | 1/2011 |
| WO | WO-2011/010706 A1 | 1/2011 |
| WO | WO-2011/015572 A1 | 2/2011 |
| WO | WO-2011/015573 A1 | 2/2011 |
| WO | WO-2011/017521 A2 | 2/2011 |
| WO | WO-2011/017561 A1 | 2/2011 |
| WO | WO-2011/034072 A1 | 3/2011 |
| WO | WO-2011038288 A1 | 3/2011 |
| WO | WO-2011/045702 A2 | 4/2011 |
| WO | WO-2011/062210 A1 | 5/2011 |
| WO | WO-2011/064974 A1 | 6/2011 |
| WO | WO-2011085271 A2 | 7/2011 |
| WO | WO-2011/097643 A1 | 8/2011 |
| WO | WO-2011/097644 A2 | 8/2011 |
| WO | WO-2011/108682 A1 | 9/2011 |
| WO | WO-2011/133871 A2 | 10/2011 |
| WO | WO-2011127175 A1 | 10/2011 |
| WO | WO-2011127307 A1 | 10/2011 |
| WO | WO-2011/139699 A2 | 11/2011 |
| WO | WO-2011/139911 A2 | 11/2011 |
| WO | WO-2011135396 A1 | 11/2011 |
| WO | WO-2012/030683 A2 | 3/2012 |
| WO | WO-2012/073857 A1 | 6/2012 |
| WO | WO-2012092367 A1 | 7/2012 |
| WO | WO-2012109395 A1 | 8/2012 |
| WO | WO-2012/151324 A1 | 11/2012 |
| WO | WO-2013/012758 A1 | 1/2013 |
| WO | WO-2013/013068 A2 | 1/2013 |
| WO | WO-2013/022984 A1 | 2/2013 |
| WO | WO-2013/022990 A1 | 2/2013 |
| WO | WO-2013022966 A1 | 2/2013 |
| WO | WO-2013022967 A1 | 2/2013 |
| WO | WO-2013/033223 A1 | 3/2013 |
| WO | WO-2013030588 A1 | 3/2013 |
| WO | WO-2013/138236 A1 | 9/2013 |
| WO | WO-2014/010250 A1 | 1/2014 |
| WO | WO-2014/010718 A1 | 1/2014 |
| WO | WO-2014/012081 A2 | 1/2014 |
| WO | WO-2014/025805 A1 | 2/2014 |
| WO | WO-2014/028739 A1 | 2/2014 |
| WO | WO-2014/059356 A2 | 4/2014 |
| WO | WO-2014062686 A1 | 4/2014 |
| WO | WO-2014062691 A2 | 4/2014 |
| WO | WO-2014062736 A1 | 4/2014 |
| WO | WO-2014/067904 A1 | 5/2014 |
| WO | WO-2014/069520 A1 | 5/2014 |
| WO | WO-2014/076195 A1 | 5/2014 |
| WO | WO-2014/076196 A1 | 5/2014 |
| WO | WO-2014/080004 A1 | 5/2014 |
| WO | WO-2014070771 A1 | 5/2014 |
| WO | WO-2014/099941 A1 | 6/2014 |
| WO | WO-2014/118267 A1 | 8/2014 |
| WO | WO-2014/118272 A1 | 8/2014 |
| WO | WO-2014/130607 A1 | 8/2014 |
| WO | WO-2014/154486 A1 | 10/2014 |
| WO | WO-2014/154488 A1 | 10/2014 |
| WO | WO-2014/179626 A2 | 11/2014 |
| WO | WO-2014/188001 A1 | 11/2014 |
| WO | WO-2014/205451 A2 | 12/2014 |
| WO | WO-2014/207232 A1 | 12/2014 |
| WO | WO-2015/010135 A2 | 1/2015 |
| WO | WO-2015/017675 A2 | 2/2015 |
| WO | WO-2015/032617 A1 | 3/2015 |
| WO | WO-2015/051169 A2 | 4/2015 |
| WO | WO-2015/051214 A1 | 4/2015 |
| WO | WO-2015/051366 A2 | 4/2015 |
| WO | WO-2015054676 A2 | 4/2015 |
| WO | WO-2015057727 A1 | 4/2015 |
| WO | WO-2015057738 A1 | 4/2015 |
| WO | WO-2015/070212 A1 | 5/2015 |
| WO | WO-2015/071388 A1 | 5/2015 |
| WO | WO-2015/089511 A2 | 6/2015 |
| WO | WO-2015/107425 A2 | 7/2015 |
| WO | WO-2015/108046 A1 | 7/2015 |
| WO | WO-2015/108047 A1 | 7/2015 |
| WO | WO-2015/108048 A1 | 7/2015 |
| WO | WO-2015143078 A1 | 9/2015 |
| WO | WO-2015/168172 A1 | 11/2015 |
| WO | WO-2015/168589 A2 | 11/2015 |
| WO | WO-2015/171932 A1 | 11/2015 |
| WO | WO-2015/179525 A1 | 11/2015 |
| WO | WO-2016/011226 A1 | 1/2016 |
| WO | WO-2016/020399 A1 | 2/2016 |
| WO | WO-2016/021683 A1 | 2/2016 |
| WO | WO-2016/027168 A2 | 2/2016 |
| WO | WO-2016/037191 A1 | 3/2016 |
| WO | WO-2016/079181 A1 | 5/2016 |
| WO | WO-2016/079183 A1 | 5/2016 |
| WO | WO-2016/096938 A1 | 6/2016 |
| WO | WO-2016/102664 A1 | 6/2016 |
| WO | WO-2016112132 A1 | 7/2016 |
| WO | WO-2016/127000 A1 | 8/2016 |
| WO | WO-2016/127002 A1 | 8/2016 |
| WO | WO-2016/130589 A2 | 8/2016 |
| WO | WO-2016/130806 A2 | 8/2016 |

(56) References Cited

FOREIGN PATENT DOCUMENTS

| WO | WO-2016/138017 A1 | 9/2016 |
|---|---|---|
| WO | WO-2016/141236 A1 | 9/2016 |
| WO | WO-2016/145142 A1 | 9/2016 |
| WO | WO-2016/154096 A1 | 9/2016 |
| WO | WO-2016/161374 A1 | 10/2016 |
| WO | WO-2016/164896 A2 | 10/2016 |
| WO | WO-2016/167780 A1 | 10/2016 |
| WO | WO-2016168592 A2 | 10/2016 |
| WO | WO-2016/209862 A1 | 12/2016 |
| WO | WO-2017/004261 A1 | 1/2017 |
| WO | WO-2017/011276 A1 | 1/2017 |
| WO | WO-2017/011286 A1 | 1/2017 |
| WO | WO-2017/015109 A1 | 1/2017 |
| WO | WO-2017/015555 A1 | 1/2017 |
| WO | WO-2017/015575 A1 | 1/2017 |
| WO | WO-2017/019660 A1 | 2/2017 |
| WO | WO-2017/023660 A1 | 2/2017 |
| WO | WO-2017/032726 A1 | 3/2017 |
| WO | WO-2017/035340 A1 | 3/2017 |
| WO | WO-2017/040078 A1 | 3/2017 |
| WO | WO-2017/055423 A1 | 4/2017 |
| WO | WO-2017/059411 A1 | 4/2017 |
| WO | WO-2017/059446 A1 | 4/2017 |
| WO | WO-2017/062862 A2 | 4/2017 |
| WO | WO-2017/067970 A1 | 4/2017 |
| WO | WO-2017/068087 A1 | 4/2017 |
| WO | WO-2017/079291 A1 | 5/2017 |
| WO | WO-2017/081223 A1 | 5/2017 |
| WO | WO-2017/157672 A1 | 9/2017 |
| WO | WO-2017/157899 A1 | 9/2017 |
| WO | WO-2017/160741 A1 | 9/2017 |
| WO | WO-2017/165489 A1 | 9/2017 |
| WO | WO-2017/178656 A1 | 10/2017 |
| WO | WO-2017180835 A1 | 10/2017 |
| WO | WO-2017/192679 A1 | 11/2017 |
| WO | WO-2017/194498 A1 | 11/2017 |
| WO | WO-2017/194664 A1 | 11/2017 |
| WO | WO-2017/198775 A1 | 11/2017 |
| WO | WO-2017/210647 A1 | 12/2017 |
| WO | WO-2017/221883 A1 | 12/2017 |
| WO | WO-2018/022473 A1 | 2/2018 |
| WO | WO-2018/067973 A1 | 4/2018 |

OTHER PUBLICATIONS

Adarsh, et al., Organelle Specific Targeted Drug Delivery—A Review, International Journal of Research in Pharmaceutical and Biomedical Sciences, 2(3): 895-912 (2011).

Ager, D.J. The Peterson olefination reaction, Organic Reactions, 38:1-223 (2004).

Agrawal, S. and Kandimalla, E.R., Antisense and/or Immunostimulatory Oligonucleotide THerapeutics, Current Cancer Drug Targets, Bentham Science, 1(3): 1 page URL: <http:www.eurekaselect.com/65087/article> [Retrieved Apr. 3, 2016].

Agrawal, S. and Tang, J.Y., GEM 91—an antisense oligonucleotide phosphorothioate as a therapeutic agent for AIDS, Antisense Research and Development, 2(4):261-266 (1992).

Agrawal, S. et al., Mixed-backbone oligonucleotides as second generation antisense oligonucleotides: In vitro and in vivo studies, Proc. Natl. Acad. Sci. USA, 94: 2620-2625 (1997).

Aldaye, F.A. et al., Assembling materials with DNA as the guide, Science, 321(5897): 1795-1799 (2008).

Aldrich Chemical Co. Catalog, 2007-2008 Issue, only p. 1719 supplied: see first full entry at col. 1 (S-methyl methanethiosulfonate), Milwaukee, WI.

Almer et al., Synthesis of Stereochemically Homogeneous Oligoribonucleoside All-Rp-Phosphorothioates by Combining H-Phosphonate Chemistry and Enzymatic Digestion, J. Chem. Soc., Chem. Commun., 1459-1460 (1994).

Almer, et al. A New Approach to Stereospecific Synthesis of P-chiral Phosphorothioates. Preparation of Diastereomeric Dithymidyl-(3'-5') Phosphorothioates, Chem. Commun., (3): 290-1 (2004).

Almer, et al. Solid Support Synthesis of all-Rp-oligo(ribonucleoside phosphorothioate)s, Nucleic Acids Research 24(19): 3811-3820 (1996).

Almer, H. et al., Synthesis of Diribonucleoside Phosphorothioates via Sterospecific Sulfurization of H-Phosphonate Diesters, J. Org. Chem., 57(23): 6163-6169 (1992).

ALS Association, The ALS Association and the Packard Center Partner to Develop Animal Model Systems for Most Common Cause of Familial ALS, 4 pages (Mar. 1, 2012). URL: http://www.alsa.org/news/archive/new-animal-model-systems.html [Retrieved Dec. 14, 2017].

Altschul, S.F. et al., Basic local alignment search tool, Journal of Molecular Biology, 215(3):403-410 (1990).

Altschul, S.F. et al., Gapped BLAST and PSI-BLAST: a new generation of protein database search programs, Nucleic Acids Research, 25(17):3389-3402 (1997).

Alul, R.H. et al., Oxalyl-CPG: a labile support for synthesis of sensitive oligonucleotide, Nucleic Acids Research, 19(7):1527-1532 (1991).

Alvarez, K. et al., Photocleavable Protecting Groups as Nucleobase Protections Allowed the Solid-Phase Synthesis of Base-Sensitive SATE-Prooligonucleotides, Journal of Organic Chemistry, 64(17): 6319-6328(1999).

Amarzguioui et al., Tolerance for mutations and chemical modifications in a siRNA, Nucleic Acids Research 31(2): 589-595 (2003).

Anthony, K. et al., Exon Skipping Quantification by Quantitative Reverse-Transcription Polymerase Chain Reaction in Duchenne Muscular Dystrophy Patients Treated with the Antisense Oligomer Eteplirsen, Human Gene Therapy Methods, 23: 336-345 (2012).

Arai, K. et al., Synthesis and properties of novel 2'-O-alkoxymethyl-modified nucleic acids, Bioorganic & Medicinal Chemistry Letters, 21(21): 6285-6287 (2011).

Aristarkhova, L.N. et al., Investigation in the field of thiosulfonic acids. 28. alkyl esters of cyclopentane- and cyclohexanethiosulfonic acids, Journal of Organic Chemistry of the USSR, 6: 2454-2458 (1970).

Athyros, V.G. et al., Antisense technology for the prevention or the treatment of cardiovascular disease: the next blockbuster?, Expert Opin. Investig. Drugs, 17(7): 969-72 (2008).

Ausin, C. et al., Assesment of heat-sensitive thiophosphate protecting groups in the development of thermolytic DNA oligonucleotide prodrugs, Tetrahedron, 66(1):68-79 (2010).

Bachelin et al., Structure of a Stereoregular Phosphorothioate DNA/RNA duplex, Nat. Struct. Biol., 5(4): 271-276 (1998).

Baek, M-S. et al., In Vitro Metabolic Stabilities and Metabolism of 2'-O-(Methoxyethyl) Partially Modified Phosphorothioate Antisense Oligonucleotides in Preincubated Rat or Human Whole Liver Homogenates, Oligonucleotides, 20(6): 309-316 (2010).

Ballas, Z.K. et al., Induction of NK Activity in Murine and Human Cells by CpG Motifs in Oligodeoxynucleotides and Bacterial DNA, J. Immunoll., 57: 1840-1845 (1996).

Barber, I. et al., The Prooligonucleotides Approach I: Esterase-Mediated Reversibility of Dithymidine S-Alkyl Phosphorothiolates to Dithymidine Phosphorothioates, Bioorganic and Medicinal Chemistry Letters, 5(6):563-568 (1995).

Barber, I. et al., The Prooligonucleotides Approach II: Synthesis and stability studies of chimeric oligonucleotide models, Bioorganic and Medicinal Chemistry Letters, 5(14):1441-1444 (1995).

Barnes, P.J. and Peterson, S. Efficacy and Safety of Inhaled Corticosteroids in Asthma, Am. Rev. Respir. Dis., 148: Sl-S26 (1993).

Bartz, H. et al., Poly-guanosine strings improve cellular uptake and stimulatory activity of phosphodiester CpG oligonucleotides in human leukocytes, Vaccine, 23: 148-155 (2004).

Battistini et al., Stereoselective Synthesis of Cyclic Dinucloetide Phosphorothioates, Tetrahedron, 49(5): 1115-1132 (1993).

Bayever, E. et al., Systematic administration of a phosphorothioate oligonucleotide with a sequence complementary to p53 for acute myelogenous leukemia and myelodysplastic syndrome: intial results of a phase I trial, Antisense Research Development, 3(4):383-390 (1993).

(56) References Cited

OTHER PUBLICATIONS

Beal, P.A. et al., Second Structural Motif for Recognition of DNA by Oligonucleotide-Directed Triple-Helix Formation, Science, 251: 1360-1363 (1991).
Beaucage, S.L. and Iyer, R.P., Advances in the Synthesis of Oligonucleotides by the Phosphoramidite Approach, Tetrahedron, 48(12):2223-2311 (1992).
Benner, S.A. and Sismour, A.M., Synthetic biology, Nature Reviews Genetics, 6(7):533-543 (2005).
Berge, S.M. et al., Pharmaceutical salts, J. Pharm. Sci., 66(1):1-19 (1997).
Besch, R. et al, Specific Inhibition of ICAM-1 Expression Mediated by Gene Targeting with Triplex-forming Oligonucleotides, J. Biol. Chem., 277(26): 32473-32479 (2002).
Birts, C.N. et a., Transcription of Click-Linked DNA un Human Cells, Angew. Chem. Int. Ed., 53:2362-2365 (2014).
Bisbal, C. and Silverman, R.H., Diverse functions of RNase L and implication in pathology, Biochimie, 89(6-7):789-798 (2007).
Blade, H. et al., Modular Synthesis of Constrained Ethyl (cEt) Purine and Pyrimidine Nucleosides, J. Org. Chem., 80: 5337-5343 (2015).
Block, E. et al., Allium Chemistry: Synthesis and Sigmatropic Rearrangements of Alk(en)yl 1-Propenyl Disulfide S-Oxides from Cut Onion and Garlic, Journal of the Ameican Chemical Society, 118(12): 2799-2810 (1996).
Block, S.S. and Weidner, J.P, Vibrational Behavior and Structure of Disulfide Dioxides (Thiolsulfonates), Applied spectroscopy, 20(2): 73-79 (1966).
Bobkov, G.V. et al., Phosphoramidite building blocks for efficient incorporation of 2'-O-aminoethoxy(and propoxy)methyl nucleosides into oligonucleotides, Tetrahedron, 64: 6238-6251 (2008).
Bock, L.C. et al., Selections of single-stranded DNA molecules that bind and inhibit human thrombin, Nature, 355: 564-566 (1992).
Boczkowska, M. et al., Stereodefined Phosphorothioate Analogues of DNA: Relative Thermodynamic Stability of the Model PS-DNA/DNA and PS-DNA/RNA complexes, Biochemistry, 41: 12483-12487 (2002).
Bode, C. et al. CpG DNA as a vaccine adjuvant, Expert Rev. Vaccines, 10(4): 499-511 (2011).
Bodor, N. et al., A convenient synthesis of (acyloxy)alkyl .alpha.-ethers of phenols, The Journal of Organic Chemistry, 48(26):5280-5284 (1983).
Bohringer, M. et al., Why Pentose and not Hexose Nucleic Acids? Part II: Oligonucleotides of 2'3'-dideoxy-β-d-glucopyranosyl ('homo-DNA') production, Helvetica Chimica Acta, 75:1416-1477 (1992).
Bologna, J. et al., Uptake and Quantification of Intracellular Concentration of Lipophilic Pro-Oligonucleotides in HeLa Cells, Antisense and Nucleic Acid Drug Development, 12(1):33-41 (2002).
Bonora, G.M. et al., Large scale, liquid phase synthesis of oligonucleotides by the phosphoramidite approach, Nucleic Acids Research, 21(5): 1213-1217 (1993).
Boudreau, R.L. et al., Nonallele-specific silencing of mutant and wild type huntingtin demonstrates therapeutic efficacy in Huntington's disease mice, 17(6): 1053-1063 (2009).
Braasch et al., RNA Interference in Mammalian Cells by Chemically-Modified RNA, Biochemistry 42(26): 7967-7975 (2003).
Brill, W. et al., Thioalkylation of Nucleoside-H-Phosphonates and Its Application to Solid Phase Synthesis of Oligonucleotides, Tetrahedron Letters, 36(5):703-706 (1995).
Brooks, P.C. et al., Insulin-like Growth Factor Receptor Cooperates with Integrin avβ5 to Promote Tumor Cell Dissemination in Vivo, The Journal of Clinical Investigation, 99(6):1390-1398 (1997).
Brown, J.W.S. and Simpson, C.G., Splice Site Selection in Plant Pre-mRNA Splicing, Ann. Rev. Plant Physiol. Plant Mol. Biol., 49: 77-95 (1998).
Bumcrot, D et al., RNAi therapeutics: a potential new class of pharmaceutical drugs, Nat. Chem. Biol., 2: 711-9 (2006).
Bundgaard, H., (C) Means to Enhance Penetration. (1) Prodrugs as a means to improve the delivery of peptide drugs, Advanced Drug Delivery Reviews, 8:1-38 (1992).
Bundgaard, H., Design and Application of Prodrugs, A Textbook of Drug Design and Development, Edited by Krogsgaard-Larsen, P. and Bundgaard, H., Chapter 5: 113-191 (1991).
Bundgaard, H., Design of Prodrugs, Elsevier, 7-9 and 21-24 (Chapter 1) (1985).
Bunnell. B.A. et al., Targeted Delivery of Antisense Oligonucleotides by Molecular Conjugates, Somatic Cell and Molecular Genetics, 18(6):559-569 (1992).
Burgers et al., Absolute configuration of the diastereomers of adenosine 5'-O-(1-thiaotriphosphate): Consequences for the stereochemistry of polymerization by DNA-dependent RNA polymerase from *Escherichia coli*, Proceedings of the National Academy of Sciences of the United States of America 75(10): 4798-4800 (1978).
Burgers, P. M. J. et al., Stereochemistry of Hydrolysis by Snake Venom Phosphodiesterase, J. Biol. Chem., 254(16): 7476-7478 (1979).
Burgers, P.M.J. and Eckstein, F., A Study of the Mechanism of DNA Polymerase I from *Escherichia coli* with Diastereomeric Phosphorothioate Analogs of Deoxyadenosine Triphosphate, J. Biol. Chem., 254(15): 6889-6893 (1979).
Burgers, P.M.J. and Eckstein, F., Diastereomers of 5'-O-adenosyl 3'-O-uridyl phosphorothioate: chemical synthesis and enzymatic properties, Biochemistry, 18: 592-596 (1979).
Campbell, J. et al., Hybrid polymer/MOF membranes for Organic Solvent Nanofiltration (OSN): Chemical modification and the quest for perfection, Journal of Membrane Science, 503: 166-176 (2016).
Cankurtaran, E.S. et al., Clinical Experience with Risperidone and Memantine in the Treatment of Huntington's Disease, Journal of the National Medical Association, 98(8): 1353-1355 (2006).
Carbone, G.M. et al., Selective inhibition of transcription of the Ets2 gene in prostate cancer cells by a triplex-forming oligonucleotide, Nucl. Acid. Res., 31: 833-843 (2003).
Carrillo, H., and Lipman, D.J., The multiple sequence alignment problem in biology, SIAM J. Appl. Math., 48:1073-1082 (1988).
CAS Registry No. 1225524-67-3; STN Entry Date May 28, 2010; α-[(2-methylphenyl)methyl]-2-Pyrrolidinemethanol.
CAS Registry No. 1225524-68-4; STN Entry Date May 28, 2010; α-[(4-methylphenyl)methyl]-2-Pyrrolidinemethanol.
CAS Registry No. 1225545-00-5; STN Entry Date May 28, 2010; α-[(2,4,6-trimethylphenyl)methyl]-2-Pyrrolidinemethanol.
CAS Registry No. 1225554-20-0; STN Entry Date May 28, 2010; α-[(4-ethylphenyl)methyl]-2-Pyrrolidinemethanol.
CAS Registry No. 1225594-74-0; STN Entry Date May 28, 2010; α-[(2-chloro-6-fluorophenyl)methyl]-2-Pyrrolidinemethanol.
CAS Registry No. 1225682-42-7; STN Entry Date May 30, 2010; α-[(4-chlorophenyl)methyl]-2-Pyrrolidinemethanol.
CAS Registry No. 1226037-41-7; STN Entry Date May 30, 2010; α-[(3-chlorophenyl)methyl]-2-Pyrrolidinemethanol.
CAS Registry No. 1226118-97-3; STN Entry Date May 30, 2010; α-[(3-bromophenyl)methyl]-2-Pyrrolidinemethanol.
CAS Registry No. 1226119-02-3; STN Entry Date May 30, 2010; α-[(4-bromophenyl)methyl]-2-Pyrrolidinemethanol.
CAS Registry No. 1226146-65-1; STN Entry Date May 30, 2010; α-[(2,4-dimethylphenyl)methyl]-2-Pyrrolidinemethanol.
CAS Registry No. 1226160-20-8; STN Entry Date May 30, 2010; α-[(2,5-dimethylphenyl)methyl]-2-Pyrrolidinemethanol.
CAS Registry No. 1226178-36-4; STN Entry Date May 30, 2010; α-[(2-fluorophenyl)methyl]-2-Pyrrolidinemethanol.
CAS Registry No. 1226188-06-2; STN Entry Date May 30, 2010; α-[[4-(1-methylethyl)phenyl]methyl]- 2-Pyrrolidinemethanol.
CAS Registry No. 1226204-20-1; STN Entry Date May 30, 2010; α-[(3-methylphenyl)methyl]-2-Pyrrolidinemethanol.
CAS Registry No. 1226231-44-2; STN Entry Date May 30, 2010; α-[(2-chlorophenyl)methyl]-2-Pyrrolidinemethanol.
CAS Registry No. 1226352-28-8; STN Entry Date May 30, 2010; α-[(2,4-dichlorophenyl)methyl]-2-Pyrrolidinemethanol.
CAS Registry No. 1226352-38-0; STN Entry Date May 30, 2010; α-[(3,4-dichlorophenyl)methyl]-2-Pyrrolidinemethanol.
CAS Registry No. 1226413-27-9; STN Entry Date May 30, 2010; a-(phenylmethyl)- 2-Pyrrolidinemethanol.
CAS Registry No. 1226419-15-3; STN Entry Date May 30, 2010; α-[(4-fluorophenyl)methyl]-2-Pyrrolidinemethanol.

(56) References Cited

OTHER PUBLICATIONS

CAS Registry No. 1263282-82-1 ; STN Entry Date Feb. 21, 2011; (S)-[(diphenyl)methyl]-2-Pyrrolidinemethanol.
CAS RN 78-96-6, Entered STN: Nov. 16, 1984.
Chak, L-L, and Okamura, K., Argonaute-dependent small RNAs derived from single-stranded, non-structured precursors, Frontiers in Genetics, 5(172): 1-15 (2014).
Chan, J.H.P. et al., Antisense Oligonucleotides: From Design to Therapeutic Application, Clinical and Experimental Pharmacology and Physiology, 33: 544-540 (2006).
Chang, W. et al., Systematic chemical modifications of single stranded siRNAs significantly improved CTNNB1 mRNA silencing, Bioorg. Med. Chem. Lett., 1-5 (2016), http://dx.doi.org/10.1016/j.bmcl.2016.07.064.
Chappell, C. et al., Involvement of human polynucleotide kinase in double-strand break repair by non-homologous end joining, The EMBO Journal, 21(11): 2827-2832 (2002).
Chatgilialoglu, C. and Snieckus, V., Chemical Synthesis: Gnosis to Prognosis, Kluwer Academic, 293-340 (1996).
Check, E., RNA interference: hitting the on switch, Nature, 448(7156): 855-858 (2007).
Cheloufi, S. et al., A Dicer-independent miRNA biogenesis pathway that requires Ago catalysis, Nature, 465(7298): 584-589 (2010).
Chen, B. and Bartlett, M., A One-Step Solid Phase Extraction Method for Bioanalysis of a Phosphorothioate Oligonucleotide and Its 3' n-1 Metabolite from Rat Plasma by uHPLC-MS/MS, The AAPS Journal, 14(4): 772-780 (2012).
Chiu, Y. and Rana, T.M., siRNA function in RNAi: A chemical modification analysis, RNA, 9(9):1034-1048 (2003).
Chmielewski, M.K. and Markiewicz, W.T., Novel Method of Synthesis of 5"-Phosphate 2'-O-ribosyl-ribonucleosides and Their 3'-Phosphoramidites, Molecules, 18:14780-14796 (2013).
Cieslak, J. et al., 31P NMR Study of the Desulfurization of Oligonucleoside Phosphorothioates Effected by "Aged" Trichloroacetic Acid Solutions, J. Org. Chem., 70: 3303-3306 (2005).
Cieslak, J. et al., Thermolytic 4-methylthio-1-butyl group for phosphate/thiophosphate protection in solid-phase synthesis of DNA oligonucleotides, Journal of Organic Chemistry, 69(7):2509-2515 (2004).
Clark, J.H, Flouride IOn as a Base in Organic Synthesis, Chemical Reviews, 1980 American Chemical Society 80(5): 429-452 (1980).
Communication Relating to the Results of the Partial International Search of PCT/IB2015/000395, Annex to Form PCT/ISA/206, 3 pages (dated Aug. 24, 2015).
Conway, N., The introduction of reporter groups at multiple and/or specific sites in DNA containing phosphorothioate diesters, Nucleic Acids Research, 43-44 (1989).
Cooney, M., et al., Site-Specific Oligonucleotide Binding Represses Transcription of the Human c-myc Gene in Vitro, Science, 241: 456-459 (1988).
Cosstick, R. and Eckstein, F., Synthesis of d(GC) and d(CG) Octamers Containing Alternating Phosphorothioate Linkages: Effect of the Phosphorothioate Group on the B-Z Transition, Biochemistry, 24: 3630-3638 (1985).
Coughlin, J.E. et al., Orally bioavailable anti-HBV dinucleotide acyloxyalkyl prodrugs, Bioorganic and Medicinal Chemistry Letters, 20(5):1783-1786 (2010).
Cox, J.R. and Ramsay, O.B., Mechanisms of Nucleophilic Substitution in Phosphate Esters, Chemical Reviews, 64(4): 317-352, (1964).
Crary, S.M. et al., Specific phosphorothioate substitutions probe the active site of Bacilus subtilis ribonuclease P, RNA, 8:933-947 (2002).
Crooke, S.T. and Geary, R.S. Clinical pharmacological properties of mipomersen (Kynamro), a second generation antisense inhibitor of apolipoprotein B, Br. J. Clin. Pharmacol., 76: 269-276 (2012).
Crooke, S.T., Antisense Strategies, Current Molecular Medicine, 4: 465-487 (2004).
Crooke, S.T., Molecular mechanisms of action of antisense drugs, Biochemica et Biophysica Acta, 1489: 31-44 (1999).
Crooke, S.T., Progress in Antisense Technology , Annu. Rev. Med., 55: 61-95 (2004).
Cullen, K.A. et al., Ambulatory surgery in the United States, 2006, National Health Statistics Reports, 11: 1-28 (Jan. 28, 2009—Revised Sep. 4, 2009).
Current Protocols in Nucleic Acid Chemistry, Edited by Beaucage, S.L. et al., Chapter 2: Protection of Nucleosides for Oligonucleotide Synthesis, 2.0.1.-2.16.31 (2012).
Davis, B.G. et al., Altering the specificity of subtilisn bacillus lentus through the introduction of positive charge at single amino acid sites, Bioorganic & Medicinal Chemistry, 7(11): 2303-2311 (1999).
De Koning, M.G. et al., Simple and Efficient Solution-Phase Synthesis of Oligonucleotides Using Extractive Work-Up, Organic Process Research & Developmen, 10: 1238-1245 (2006).
DeJesus-Hernandez, M. et al., Expanded GGGGCC hexanucleotide repeat in non-coding region of C9ORF72 causes chromosome 9p-linked frontotemporal dementia and amyotrophic lateral sclerosis, Neuron, 72(2): 245-256 (2011).
Deleavey, G.F. and Damha, M.J., Designing chemically modified oligonucleotides for targeted gene silencing. Chem. Biol., 19: 937-54 (2012).
Dellinger, D.J. et al., Streamlined Process for the Chemical Synthesis of RNA Using 2'-O-Thionocarbamate-Protected Nucleoside Phosphoramidites in the Solid Phase, J. Am. Chem. Soc., 133: 11540-11556 (2011).
Devereux, J. et al., A comprehensive set of sequence analysis programs for the VAX, Nucleic Acids Research, 12(1):387-395 (1984).
Dias, N. and Stein, C.A., Antisense Oligonucleotides: Basic Concepts and Mechanisms, Molecular Cancer Therapeutics, 1: 347-355 (2002).
Dietz, G.P.H. et al., Delivery of bioactive molecules into the cell: the Trojan horse approach, Molecular and Cellular Neuroscience, 27(2): 85-131 (2004).
Dikfidan, A. et al., RNA Specificity and Regulation of Catalysis in the Eukaryotic Polynucleotide Kinase Clp1, Molecular Cell, 54: 975-986 (2014).
Djukanovic, R. et al., Mucosal Inflammation in Asthma, Am. Rev. Respir. Dis., 142: 434-457 (1990).
Documents submitted to and/or received from the United States Securities and Exchange Commission; downloaded from EDGAR (Feb. 2, 2015 to Dec. 10, 2015).
Documents submitted to and/or received from the United States Securities and Exchange Commission; downloaded from EDGAR (Dec. 17, 2015 to Oct. 4, 2016).
Documents submitted to and/or received from the United States Securities and Exchange Commission; downloaded from EDGAR (Nov. 9, 2016 to May 10, 2017).
Donnelly, C.J. et al., M1415. Development of C9orf72 ALS Biomarkers and Therapeutics, Annals of Neurology, 72 (suppl 16): S67-S68 (2012).
Donnelly, C.J. et al., RNA Toxicity from the ALS/FTD C9ORF72 Expansion Is Mitigated by antisense Intervention, Neuron, 80:415-428 (2013).
Dorman et al., Synthesis of Oligodeoxynucleotides and Oligodeoxynucleotide Analogs using Phosphoramidite Intermediates, Tetrahedron, 40(1):95-102 (1984).
Dua, P. et al., Patents on SELEX and therapeutic aptamers, Recent Patents on DNA & Gene Sequences, 2(3):172-186 (2008).
Eaton, W.A. et al., Submillisecond kinetics of protein folding, Curr. Opin. Chem. Biol., 1:10-14 (1997).
Eckstein, F. et al., Stereochemistry of polymerization by DNA-dependent RNA-polymerase from *Escherichia coli*: an investigation with a diastereomeric ATP-analogue, Proc. Natl. Acad. Sci. USA, 73: 2987-90 (1976).
Eckstein, F. Phosphorothioates, Essential Components of Therapeutic Oligonucleotides, Nucleic Acid Therapeutics, 24(6): 374-387 (2014).
Eckstein, F., Oligonucleotides and Analogues A Practical Approach, IRL Press, (Jan. 24, 1991).

(56) References Cited

OTHER PUBLICATIONS

Efimov, V.A. et al., Rapid synthesis of long-chain deoxyribooligonucleotides by the N-methylimidazolide phosphotriester method, Nucleic Acids Research, 11(23): 8369-8387 (1983).
Egholm, M. et al., PNA hybridizes to complementary oligonucleotides obeying the Watson-Crick hydrogen-bonding rules, Nature, 365, 566-568 (1993).
Egli, M. et al., Crystal structure of homo-DNA and nature's choice of pentose over hexose in the genetic system, Journal of the American Chemical Society, 128(33):10847-56 (2006).
Egli, M. et al., Probing the Influence of Stereoelectronic Effects on the Biophysical Properties of Oligonucleotides: Comprehensive Analysis of the RNA Affinity, Nuclease Resistance, and Crystal Structure of Ten 2'-0-Ribonucleic Acid Modifications, Biochemistry, 44: 9045-9057 (2005).
El Harchaoui, K. et al., Current and future pharmacologic options for the management of patients unable to achieve low-density lipoprotein-cholesterol goals with statins, Am. J. Cardiovasc. Drugs, 8(4): 233-242 (2008).
El-Sagheer, A.H. and Brown, T., Efficient RNA synthesis by in vitro transcription of a triazole-modified DNA template, Chem. Commun., 47(44):12057-12058 (2011).
El-Sagheer, A.H. and Brown, T., New strategy for the synthesis of chemically modified RNA constructs exemplified by hairpin and hammerhead ribozymes, PNAS, 107(35):15329-15334 (2010).
El-Sagheer, A.H. et al., Biocompatible artificial DNA linker that is read through by DNA polymerases and is functional in *Escherichia coli*, PNAS, 108(28):11338-11343 (2011).
Elbashir, S.M. et al., Duplexes of 21-nucleotide RNAs mediate RNA interference in cultured mammalian cells, Nature, 411: 494-498 (2001).
Elbashir, S.M. et al., Functional anatomy of siRNAs for mediating efficient RNAi in *Drosophila melanogaster* embryo lysate, The EMBO Journal, 20(23): 6877-6888 (2001).
Ellington, A.D. and Szostak, J.W., In vitro selection of RNA molecules that bind specific ligands, Nature, 346: 818-822 (1990).
Engelhardt, J.A. et al., Scientific and Regulatory Policy Committee Points-to-consider Paper: Drug-induced Vascular Injury Associated with Nonsmall Molecule Therapeutics in Preclinical Development: Part 2. Antisense Oligonucleotides, Toxicologic Pathology, XX: (Jan. 10, 2015).
Epton, R., Innovation and Perspectives in Solid Phase Synthesis, Peptides, Proteins and Nucleic Acids, 21:157-162 (1994).
Erler, W. et al., Patient Advisory Board Meeting, WAVE Life Sciences, London, 46 pages (Mar. 2, 2017).
Erler, W., Stereopure Exon 51-Skipping Oligonucleotide as a Potential Disease-Modifying Therapy for Duchenne Muscular Dystrophy, WAVE Life Sciences, 10 pages (2017).
Eschenmoser, A. et al., Why pentose- and not hexose-nucleic acids? Introduction to the problem, conformational analysis of oligonucleotide single strands containing 2', 3'-dideoxyglucopyranosyl building blocks ('homo-DNA'), and reflections on the conformation of A- and B-DNA, Helvetica Chimica Acta, 75:218-259 (1992).
Eschenmoser, A., Chemical etiology of nucleic acid structure, Science, 284(5423):2118-24 (1999).
Eschenmoser, A., Towards a Chemical Etiology of the Natural Nucleic Acids' Structure, Chemical Synthesis, Edited by Chatgilialoglu, C. and Snieckus, V., Kluwer Academic Publishers, 293-340 (1996).
Ewles, M. et al, Quantification of oligonucleotides by LC-MS/MS: the challenges of quantifying a phosphorothioate oligonucleotide and multiple metabolites, Bioanalysis, 6(4), 447-464 (2014).
Exiqon, Locked Nucleic Acid (LNA), Custom Oligonucleotides for RNA and DNA Research, 16 pages (Aug. 2009).
Famulok, M. Oligonucleotide aptamers that recognize small molecules, Curr. Opin. Struct. Biol., 9: 324-329 (1999).
Fearon, K. et al., Phosphorothioate oligodeoxynucleotides: large-scale synthesis and analysis, impurity characterization, and the effect of phosphorus stereochemistry, Oligonucleotides asTherapeutic Agents, Ciba Found. Symp. 209: 19-31 (1997).
Fendrich et al., Determination of the Absolute P-configuration of a Phthalidyl∟ Phosphonate Thymidine-Thymidine Dimer, Nucleosides Nucleotides Nucleic Acids., 22(5-8): 1127-1129 (2003).
Ferreira, F. et al., Lewis acid deprotection of silyl-protected oligonucleotides and base-sensitive oligonucleotide analogues, Tetrahedron Letters, 45(33):6287-6290 (2004).
File Registry on STN, RN 18217-60-2, Entered STN: Nov. 16, 1984.
File Registry on STN, RN 871246-91-2, Entered STN: Jan. 5, 2006.
Fire, A. et al., Potent and specific RNA interference by double-stranded RNA in Caenorhadbditis elegans, Nature, 391: 806-811 (1998).
Forster, A.C. and Symons, R.H. Self-cleavage of plus and minus RNAs of a virusoid and a structural model for the active sites, Cell, 49(2): 211-220 (1987).
Forster, A.C. and Symons, R.H. Self-Cleavage of Virusoid RNA is performed by the Proposed 55-Nucleotide Active Site, Cell, 50: 9-16 (1987).
Frank-Kamenetsky, M. et al., Therapeutic RNAi targeting PCSK9 acutely lowers plasma cholesterol in rodents and LDL cholesterol in nonhuman primates. Proc. Natl. Acad. Sci. USA., 105(33): 11915-11920 (2008).
Frazier, K. et al., Potential Mechanisms of vascular toxicity in Monkeys with antisense oligonucleotides, TIDES oligo conference, 1-25 (May 15, 2014).
Frazier, K.S. Antisense Oligonucleotide Therapies: The Promise and the Challenges from a Toxicologic Pathologist's Perspective, Toxicology Pathology, 43: 78-89 (2015).
Frederiksen, J.K. et al., Separation of RNA Phosphorothioate Oligonucleotides by HPLC, Methods of Enzymology, 468:289-309 (2009).
Freier, S.M. et al., Improved free-energy parameters for predictions of RNA duplex stability, Proc. Nat. Acad. Sci. USA, 83: 9373-9377 (1986).
Freschauf, G., Identification of Small Molecule Inhibitors of the Human DNA Repair Enzyme Polynucleotide Kinase/Phosphatase, Master of Science in Experimental Oncology Thesis, University of Alberta, 155 pages (2011).
Froehler, B.C. et al., Synthesis of DNA via deoxynucleoside H-phosphonate intermediates, Nucleic Acids Research, 14(13): 5399-5407 (1986).
Fujii et al., Acylphosphonates. 5.1 A new method for stereospecific generation of phosphorothioate via aroylphosphonate intermediate, Tetrahedron Letters, 27(8): 935-938 (1986).
Fujii et al., Acylphosphonates. 7.1 A New Method for Stereospecific and Stereoselective Generation of Dideoxyribonucleoside Phosphorothioates via the Acylphosphonate Intermediates, Tetrahedron, 43: 3395-3407 (1987).
Gaffney, P.R.J. et al., Liquid-Phase Synthesis of 2'-Methyl-RNA on a Homostar Support through Organic-Solvent Nanofiltration, Chem. Eur. J., 21:1-10 (2015).
Gallier, F. et al., 5',6'-Nucleoside Phosphonate Analogues Architecture: Synthesis and Comparative Evaluation towards Metabolic Enzymes, Chem Med Chem, 6: 1094-1106 (2011).
Ganguly, A.K. et al., Structure of Halomicin B, J.C.S. Chem. Comm., 395-396 (1974).
Garegg, P.J. et al., Nucleoside H-Phosphonates. III. Chemical Synthesis of Oligodeoxyribonucleotides by the Hydrogenphosphonate Approach, Tetrahedron Letters, 27(34): 4051-4054 (1986).
Gauglitz, G.G. et al., Hypertrophic Scarring and Keloids: Pathomechanisms and Current Emerging Treatment Strategies, Mol. Med., 17(1-2): 113-125 (2011).
Giacometti, R.D. et al., Design, synthesis, and duplex-stabilizing properties of conformationally constrained tricyclic analogues of LNA, Org. Biomol. Chem., 14: 2034-2040 (2016).
Gijsen, H.J.M et al., Development of two diastereoselective rougtes towards trans-4-aminomethyl-piperidin-3-o1 building blocks, Tetrahedron 64(10): 2456-2464 (2008).
Goraczmiak, R. et al., Gene silencing by synthetic U1 Adaptors, Nature Biotechnology 27(3): 257-263 (2008).
Gosselin, G. et al., New insights regarding the potential of the pronucleotide approach in antiviral chemotherapy, 43(1):195-208 (1996).

(56) References Cited

OTHER PUBLICATIONS

Gough, G.R. et al., Recovery and recycling of synthetic units in the construction of oligodeoxyribonucleotides on solid supports, Tetrahedron Letters, 22(42): 4177-4180 (1981).
Gould, W.A. et al., Pyrrolidines. IX. 3-Aryl-3-pyrrolidinols, Journal of Medicinal Chemistry, 7(1): 60-67 (1964).
Graham, M.J. et al., Antisense inhibition of proprotein convertase subtilisin/kexin type 9 reduces serum LDL in hyperlipidemic mice, J. Lipid Res., 48(4): 763-767 (2007).
Grajkowski, A. et al., Design and Development of Thermolytic DNA Oligonucleotide Prodrugs, Annals of the New York Academy of Sciences, 1058:26-38 (2005).
Grajkowski, A. et al., Solid-Phase Synthesis of Thermolytic DNA Oligonucleotides Functionalized with a Single 4-Hydroxy-1-butyl or 4-Phosphato-/Thiophosphato-1-butyl Thiophosphate Protecting Group, Journal of Organic Chemistry, 72(3): 805-815 (2007).
Grajkowski, A. et al., Thermolytic CpG-containing DNA oligonucleotides as potential immunotherapeutic prodrugs, Nucleic Acids Research, 33(11):3550-3560 (2005).
Green, L.S. et al., Inhibitory DNA Ligands to Platelet-Derived Growth Factor B-Chain, Biochemistry, 35: 14413-14424 (1996).
Green, L.S. et al., Nuclease-resistant nucleic acid ligands to vascular permeability factor/vascular endothelial growth factor, Chem. Biol., 2(10): 683-695 (1995).
Griffiths-Jones, S. et al., miRBase: microRIVA sequences, targets and gene nomenclature, Nucleic Acids Research, 34 (Database Issue): D140-D144 (2006).
Griffiths-Jones, S. The microRNA Registry, Nucleic Acids Research, 32 (Database Issue): D109-D111 (2004).
Groebke, K. et al., Why pentose and not hexose nucleic acids? Part V. Purine-purine pairing in homo-DNA: guanine, isoguanine, 2,6-diaminopurine and xanthine. Helvetica Chimica Acta. 81: 375-474 (1998).
Gryaznov, S. and, Chen, J.-K., Oligodeoxyribonucleotide N3'4P5' Phosphoramidates: Synthesis and Hybridization Properties, J. Am. Chem. Soc., 116: 3143-3144 (1994).
Gude, L. et al., Mapping Targetable Sites on Human Telomerase RNA Pseudoknot/Template Domain Using 2'-OMe RNA-interacting Polynucleotide (RIPtide) Microarrays, J. Biol. Chem., 287(22): 18843-18853 (2012).
Guerciolini, R., Allele-selective Silencing of Mutant Huntingtin by Stereopure Oligonucleotides, WAVE Life Sciences, Huntington's Disease Society of America, HDSA Presentation 2016 (Jun. 3, 2016).
Guerlavais-Dagland, T et al., Fluoride-labile protecting groups for the synthesis of base-sensitive methyl-SATE oligonucleotide prodrugs, European Journal of Organic Chemistry, 2003(12):2327-2335 (2003).
Guga et al., Oxathiaphospholane Approach to the Synthesis of P-Chiral, Isotopomeric Deoxy(ribonucleoside phosphorothioate)s and Phosphates Labeled with an Oxygen Isotope. Angew Chem., 113(3): 630-633 (2001).
Guga et al., Unusual Thermal Stability of RNA/[RP-PS]-DNA/RNA Triplexes Containing a Homopurine DNA Strand, Biophys J., 92(7): 2507-2515 (2007).
Guga, P. and STEC, W.J., Synthesis of Phosphorothioate Oligonucleotides with Stereodefined Phsphorothioate Linkages, Current Protocols in Nucleic Acid Chemistry, Unit 4.17: 4.17.1-4.17.28 (2003).
Guga, P., P-chiral oligonucleotides in biological recognition processes, Current Topics in Medicinal Chemistry, 7:695-713 (2007).
Guo, M. et al., Solid-phase stereoselective synthesis of 2'-0-methyl-oligo-ribonucleoside phosphorothioates using nucleoside bicyclic oxazaphospholidines, Biorganic & Medicinal Chemistry Letters, 8(18):2539-2544 (1998).
Guzaev, A.P., Reactivity of 3H-1,2,4-dithiazole-3-thiones and 3H-1,2-dithiole-3-thiones as sulfurizing agents for oligonucleotide synthesis, Tetrahedron Letters, 52: 434-437 (2011).
Hacia, J.G. et al., Phosphorothioate oligonucleotide-directed triple helix formation, Biochemistry, 33:5367-5369 (1994).

Hagedorn, P.H. et al., Locked nucleic acid: modality, diversity, and drug discovery, Drug Discovery, (Oct. 1-14, 2017).
Hammond, S.M. and Wood, M.J. Genetic therapies for RNA mis-splicing diseases, Trends Genet., 27: 196-205 (2011).
Hanagata, N., Structure-dependent immunostimulatory effect of CpG oligodeoxynucleoties and their delivery system, Int. J. Nanomedicine, 7: 2181-95 (2012).
Hansen et al., Azaribofuranoside Analogues as Designed Inhibitors of Purine Nucleoside Phosphorylase, Synthesis and Biological Evaluation, Acta Chemis Scandinavica 52: 1214-1222 (1998).
Haringsma, H.J. et al., mRNA knockdown by single strand RNA is improved by chemical modifications, Nucleic Acids Research, 40(9): 4125-4136 (2012).
Harper, S.Q. et al., RNA interference improves motor and neuropathological abnormalities in a Huntington's disease mouse model, Proc. Natl. Acad. Sci. USA, 102(16): 5820-5825 (2005).
Hartmann, B. et al., Sequence effects on energetic and structural properties of phosphorothioate DNA: a molecular modelling study, Nucleic Acids Research, 27(16): 3342-3347 (1999).
Hartmann, G. et al., Delineation of a CpG Phosphorothioate Oligodeoxynucleotide for Activating Primate Immune Responses In Vitro and In Vivo, The Journal of Immunology, 164(3): 1617-1624 (2000).
Hau, P. et al., Results of G004, a phase lib actively controlled clinical trial with the TGF-b2 targeted compound AP 12009 for recurrent anaplastic astrocytoma, Journal of Clinical Oncology, 2006 ASCO Annual Meeting Proceedings (Post-Meeting Edition), 24(18, Jun. 20 Supplement): 1566 (2006).
Hayashi, S. et al., Studies on Antitumor Substances, Chemical & Pharmaceutical Bulletin, 12(11): 1271-1276 (1964).
Heemskerk, H.A. et al., In vivo comparison of 2'-O-methyl phosphorothioate and morpholino antisense oligonucleotides for Duchenne muscular dystrophy exon skipping, The Journal of Gene Medicine, 11:257-266 (2009).
Heger, W. et al., Embryotoxic effects of thalidomide derivatives on the non-human primate *Callithrix jacchus*; 3. Teratogenic potency of the EM 12 enantiomers, Arch. Toxicol., 62: 205-208 (1988).
Hendrix, C. et al., 1',5'-Anhydrohexitol Oligonucleotides: Synthesis, Base Pairing and Recognition by Regular Oligodeoxyribonucleotides and Oligoribonucleotides, Chem. Eur. J., 3(1): 110-120 (1997).
Henry, A.A. and Romesberg, F.E., Beyond A, C, G and T: augmenting nature's alphabet, Current Opinion in Chemical Biology, 7(6): 727-733 (2003).
Henry, S.P. et al., Activation of the Alternative Pathway of Complement by a Phosphorothioate Oligonucleotide: Potential Mechanism of Action, The Journal of Pharmacology and Experimental Therapeutics, 281(2): 810-816 (1997).
Herbert, B-S. et al., Nonradioactive detection of telomerase activity using the telomeric repeat amplification protocol, Nat. Protoc., 1(3): 1583-1590 (2006).
Herdewijn, Oligonucleotide Synthesis, Methods in Molecular Biology, 288: 1-435 (2005).
Heuberger, B.D. and Switzer, C., A Pre-RNA Candidate Revisited: Both Enantiomers of Flexible Nucleoside Triphosphates are DNA Polymerase Substrates, Journal of the American Chemical Society, 130(2):412-413 (2008).
Higuchi, T. et al., Pro-drugs as Novel Delivery Systems, ACS Symposium Series, 14 (1975).
Hirama, T. et al., PCR-Based Rapid Identification System Using Bridged Nucleic Acids for Detection of Clarithromycin-Resistant *Mycobacterium avium*-M. intracellulare Complex Isolates, Journal of Clinical Microbiology, 54(3): 699-704 (2016).
Hirao, I., Unnatural base pair systems for DNA/RNA-based biotechnology, Current Opinion in Chemical Biology,10:622-627 (2006).
Hirose, M. et al., MDM4 expression as an indicator of TP53 reactivation by combined targeting of MDM2 and MDM4 in cancer cells without TP53 mutation, Oncoscience, 1(12): (2014).
Hohjoh, H., Disease-Causing Allele-Specific Silencing by RNA Interference, Pharmaceuticals, 6: 522-535 (2013).
Hu, J. et al., Allele-Selective Inhibition of Huntingtin Expression by Switching to an miRNA-like RNAi Mechanism, Chemistry & Biology 17: 1183-1188 (2010).

(56) References Cited

OTHER PUBLICATIONS

Hu, J. et al., Exploring the Effect of Sequence Length and Composition on Allele-Selective Inhibition of Human Huntingtin Expression by Single-Stranded Silencing RNAs, Nucleic Acid Therapeutics, 24(3): 199-209 (2014).

Hu, J. et al., Recognition of c9orf72 Mutant RNA by Single-Stranded Silencing RNAs, Nucleic Acid Therapeutics, 8 (2016). Supplementary Figure, 1 page.

Hunziker, J. et al., Why Pentose-And Not Hexose-Nucleic Acids? Part III. Oligo(2′,3′-dideoxy-β-D-glucopyranosyl)nucleotides. ('Homo-DNA'): Base-Pairing Properties, Helvetica Chimica Acta, 76(1):259-352 (1993).

Hyrup., B. and Nielsen, P.E., Peptide Nucleic Acids (PNA): Synthesis, Properties and Potential Applications, Bioorg. Med. Chem., 4(1): 5-23 (1996).

Inagawa, T. et al., Inhibition of human immunodeficiency virus type 1 replication by P-stereodefined oligo(nucleoside phosphorothioate)s in a long-term infection model, FEBS Letters, 528(1-3): 48-52 (2002).

International Preliminary Report on Patentability for PCT/JP2010/065900, 6 pages (dated Mar. 29, 2012).

International Preliminary Report on Patentability for PCT/JP2010/065900, English Translation, 7 pages (dated Apr. 19, 2012).

International Preliminary Report on Patentability for PCT/JP2011/055018, English Translation, 5 pages (dated Oct. 11, 2012).

International Preliminary Report on Patentability for PCT/JP2011/071559, English Translation, 7 pages (dated Apr. 25, 2014).

International Preliminary Report on Patentability for PCT/JP2013/004303, 7 pages (dated Jan. 13, 2015).

International Preliminary Report on Patentability for PCT/JP2013/069107, English Translation, 10 pages (dated Jan. 15, 2015).

International Search Report for PCT/IB2009/007923, 4 pages (dated Sep. 6, 2010).

International Search Report for PCT/IB2015/000395, 7 pages (dated Oct. 30, 2015).

International Search Report for PCT/JP2010/065900, 1 page (dated Sep. 15, 2010).

International Search Report for PCT/JP2011/055018, 2 pages (dated Mar. 29, 2011).

International Search Report for PCT/JP2011/071559, 3 pages (dated Dec. 20, 2011).

International Search Report for PCT/JP2011/077313, 2 pages (dated Jan. 10, 2012).

International Search Report for PCT/JP2013/004303, 3 pages (dated Aug. 13, 2013).

International Search Report for PCT/JP2013/069107, 2 pages (dated Oct. 1, 2013).

International Search Report for PCT/JP2015/050714, and English Translation, 8 pages (dated Apr. 21, 2015).

International Search Report for PCT/JP2015/050716 and English Translation, 8 pages (dated Apr. 21, 2015).

International Search Report for PCT/JP2015/050718 and English Translation, 8 pages (dated Apr. 21, 2015).

International Search Report for PCT/US2010/041068, 1 page (dated Sep. 1, 2010).

International Search Report for PCT/US2011/064287, 2 pages (dated Apr. 12, 2012).

International Search Report for PCT/US2012/046805, 2 pages (dated Sep. 19, 2012).

International Search Report for PCT/US2013/050407, 5 pages (dated Jan. 9, 2014).

International Search Report for PCT/US2016/043542, 6 pages (dated Dec. 28, 2016).

International Search Report for PCT/US2016/043598, 4 pages (dated Nov. 28, 2016).

International Search Report for PCT/US2016/056123, 5 pages (dated Mar. 17, 2017).

International Search Report for PCT/US2017/022135, 3 pages (dated Jun. 6, 2017).

International Search Report for PCT/US2017/030753, 6 pages (dated Sep. 26, 2017).

International Search Report for PCT/US2017/030777, 5 pages (dated Oct. 2, 2017).

International Search Report for PCT/US2017/035837, 4 pages (dated Aug. 24, 2017).

International Search Report for PCT/US2017/043431, ISA/US, 5 pages (dated Dec. 21, 2017).

International Search Report for PCT/US2017/045218, 3 pages (dated Sep. 27, 2017).

International Search Report for PCT/US2017/055601, ISR/US, 6 pages (dated Feb. 15, 2018).

International Search Report for PCT/US2017/062996, 4 pages (dated Mar. 9, 2018).

Ionis Pharmaceuticals, Inc., Ionis Pharmaceuticals Licenses IONIS-HTT Rx to Partner Following Successful Phase 1/2a Study in Patients with Huntington's Disease, Press Release, 2 pages (Dec. 11, 2017).

Isis Pharmaceuticals, Inc. 2014 Annual Report, Improving Patients' Lives by Treating Disease Through Targeting RNA, 192 pages (2014).

*Isis Pharmaceuticals, Inc.* v. *Santaris Pharma A/S Corp.*, Order Denying Defendants' Motion for Summary Judgment Without Prejudice, Case No. 11cv02214 BTM (KSC), United States District Court, S.D. California, 5 pages (Sep. 19, 2012).

Isis Pharmaceuticals, Intellectual Property: Capturing Value From Innovation, Isis' Annual Meeting of Stockholders and Open House, Intellectual Property Poster, 1 page (2011). Received from Internet <http://www.isispharm.com/Site_Gfx/pdf/11-AnMtg_IntellectualProperty_TAB.pdf>.

Isis Pharmaceuticals, Intellectual Property: Capturing Value From Innovation, Isis' Annual Meeting of Stockholders and Open House, Intellectual Poperty Poster, 1 page (2012). Received from Internet <http://ww.isispharm.com/Site_Gfx/pdf/2012_Annual_Meeting_IP_Poster.pdf>.

Iwamoto et al., Stereocontrolled Synthesis of H-phosphonate DNA, Nucleic Acids Symposium Series, (50):159-60 (2006).

Iwamoto, N. et al., Control of phosphorothioate stereochemistry substantially increases the efficacy of antisense oligonucleotides, Nature Biotechnology, Life Sciences Reporting Summary, 6 pages (2017).

Iwamoto, N. et al., Control of phosphorothioate stereochemistry substantially increases the efficacy of antisense oligonucleotides, Nature Biotechnology, pp. 1-9 (2017).

Iwamoto, N. et al., Control of phosphorothioate stereochemistry substantially increases the efficacy of antisense oligonucleotides, Nature Biotechnology, Supplementary Methods, Supplementary Tables 1-4, and Supplementary Note, 23 pages (2017).

Iwamoto, N. et al., Control of phosphorothioate stereochemistry substantially increases the efficacy of antisense oligonucleotides, Nature Biotechnology, Supplementary Text and Figures 1-9, 13 pages (2017).

Iwamoto, N. et al., Control of phosphorothioate stereochemistry substantially increases the efficacy of antisense oligonucleotides, Nature Biotechnology, with Supplemental Data, 19 pages (2017).

Iwamoto, N. et al., Optimization of Therapeutic Phosphorothioate Oligonucleotides by P-Chirality Control, WAVE Life Sciences, PSJ Congress: The Pharmaceutical Society of Japan, (Mar. 25, 2015-Mar. 28, 2016).

Iwamoto, N. et al., Stereocontrolled solid-phase synthesis of oligonucleoside H-phosphonates by an oxazaphospholidine approach, Angewandte Chemie International Edition, 48(3):496-499 (2009).

Iyer, R.P. et al., A novel nucleoside phosphoramidite synthon derived from 1R, 2S-ephedrine, Tetrahedron Asymmetry 6(5):1051-1054 (1995).

Iyer, R.P. et al., Acyloxyaryl prodrugs of oligonucleoside phosphorothioates, Bioorganic and Medicinal Chemistry Letters, 6(16):1917-1922 (1996).

Iyer, R.P. et al., Bioreversible oligonucleotide conjugates by site-specific derivatization, Bioorganic and Medicinal Chemistry Letters, 7:871-876 (1997).

(56) References Cited

OTHER PUBLICATIONS

Iyer, R.P. et al., Stereospecific Bio-Reversibility of Dinucleoside S-Alkyl Phosphorothiolates to Dinucleoside Phosphorothioates, Bioorganic & Medicinal Chemistry Letter, 4(20):2471-2476 (1994).
Iyer, R.P., et al., 3H-1,2-Benzodithiole-3-one 1,1-Dioxide as an Improved Sulfurizing Reagent in the Solid-Phase Synthesis of Oligodeoxyribonucleoside Phosphorothioates, Journal of the American Chemical Society, 112(3):1253-1254 (1990).
Iyer, R.P., et al., Prodrugs of Oligonucletides: The Acyloxyalkyl Esters of Oligodeoxyribonucleoside Phosphorothioates, Bioorganic Chemistry, 23:1-21 (1995).
Iyer, R.P., et al., Solid-phase stereoselective synthesis of oligonucleoside phosphorothioates: The nucleoside bicyclic oxazaphospholidines as novel synthons, Tetrahedron Letters, 39:2491-2494 (1998).
Jahns, H., et al., Stereochemical bias introduced during RNA synthesis modulates the activity of phosphorothioate siRNAs, Nat. Commun., 6: 6317 (2015).
Jepsen, J.S. et al., LNA-Antisense Rivals Sirna for Gene Silencing, Current Opinion In Drug Discovery and Development, 7(2): 188-194 (2004).
Jepsen, J.S. et al., Locked Nucleic Acid: A Potent Nucleic Acid Analog in Therapeutics and Biotechnology, Oligonucleotides,14: 130-146 (2004).
Jiang, J. et al., Allele-Specific Silencing of Mutant Myh6 Transcripts in Mice Suppresses Hypertrophic Cardiomyopathy, Science, 342: 111-114 (2013).
Jin et al., A Stereoselective Synthesis of Dinucleotide Boranophosphate, Using Chiral Indole-Oxazaphosphorine Intermediates, Tetrahedron Letters, 39: 6433-6436 (1998).
Jin et al., Stereoselective Synthesis of Dithymidine Phosphorothioates Using Xylose Derivatives as Chiral Auxiliaries, J. Org. Chem., 63(11): 3647-3654 (1998).
Johansson et al., Studies towards synthesis of dinucleoside arylphosphonates with metal complexing properties, Nucleosides Nucleotides & Nucleic Acids, 22(5-8): 1459-61 (2003).
Johansson et al., Synthesis of dinucleoside pyridylphosphonates involving palladium(o)-catalysed phosphorus-carbon bond formation as a key step, Chem. Commun., 2564-2565 (2001).
Johansson et al., The case for configurational stability of H-phosphonate diesters in the presence of diazabicyclo[5.4.0]undec-7-ene (DBU), Bioorg Med Chem., 9(9): 2315-22 (2001).
Jones, R.J. et al., Synthesis and binding properties of pyrimidine oligodeoxynucleoside analogs containing neutral phosphodiester replacements: The Formacetal and 3'-Thioformacetal Internucleoside Linkages, J. Org. Chem., 58: 2983-2991 (1993).
Jopling, C.L. et al., Modulation of Hepatitis C Vicus RNA Abundance by a Liver-Specific MicroRNA, Science, 309: 1577-1581 (2005).
Joyce, G.F. et al., The case for an ancestral genetic system involving simple analogues of the nucleotide, Proceedings of the National Academy of Sciences, 84:4398-4402 (1987).
Joyce, G.F. The antiquity of RNA-based evolution, Nature, 418(6894): 214-221 (2002).
Kakeya, N. et al., Studies on Prodrugs of Cephalosporins. I. Synthesis and Biological Properties of Glycyloxybenzoyloxymethyl and Glycylaminobenzoyloxymethyl Esters of 7-[2-(2-Aminothiazol-4-yl)-(Z)-2-methoxyiminoacetamido]-3-methyl-3-cephem-4-carboxylic Acid, Chem. Pharm. Bull., 32(2): 692-698 (1984).
Kamada, A.K. et al., Issues in the Use of Inhaled Glucocorticoids, Am. J. Respir. Crit. Care. Med., 153: 1739-1748 (1996).
Karwowski, B. et al., Stereocontrolled Synthesis of LNA Dinucleoside Phosphorothioate by the Oxathiaphospholane Approach, Bioorganic & Medicinal Chemistry Letters, 11: 1001-1003 (2001).
Kashida, H. et al., Acyclic artificial nucleic acids with phosphodiester bonds exhibit unique functions, Polymer Journal, (Jan. 6, 2016).
Kaur, H. et al., Activation of natural killer-like YT-INDY cells by oligodeoxynucleotides and binding by homologous pattern recognition proteins, Scandinavian Journal of Immunology, 62: 361-370 (2005).

Kawasaki, A et. al., Uniformly Modified 2'-Deoxy-2'-fluoro Phosphorothioate Oligonucleotides as Nuclease-Resistant Antisense Compounds with High Affinity and Specificity for RNA Targets, J. Med. Chem., 36: 831-841 (1993).
Kay, C. et al., Huntingtin Haplotypes Provide Prioritized Target Panels for Allele-Specific Silencing in Huntington Disease Patients of European Ancestry, Molecular Therapy, Accepted Article Preview Online (Jul. 23, 2015).
Kay, C. et al., Huntingtin Haplotypes Provide Prioritized Target Panels for Allele-specific Silencing in Huntington Disease Patients of European Ancestry, The American Society of Gene & Cell Therapy, (Jan. 13, 2015).
Kay, C. et al., Personalized gene silencing therapeutics for Huntington disease, Clinical Genetics, (Jan. 8, 2014).
Kers et al., A new type of nucleotide analogue with 4-pyridylphosphonate internucleotide linkage, Tetrahedron Letters, 40(22): 4263-4266 (1999).
Kihara, M et al., New norepinephrine potentiators: synthesis and structure-actvity relastionships of a series of 4-phenyl-1,2,3,4-tetrahydroisoquinolin-4-ols, Chemical & Pharmaceutical Bulletin 42(1): 67-73 (1994).
Kim, D. et al., Immunostimulation and anti-DNA antibody production by backbone modified CpG-DNA, Biochemical and Biophysical Research Communications, 379(2): 362-367 (2009).
Kim, M., Beta conformation of polyglutamine track revealed by a crystal structure of Huntingtin N-terminal region with insertion of three histidine residues, Prion, 7(3): 221-228 (2013).
Kim, N.W. et al., Specific Association of Human Telomerase Activity with Immortal Cells and Cancer, Science, 226: 2011-2015 (1994).
Kim, S-H. and Cech, T.R., Three-dimensional model of the active site of the selfsplicing rRNA precursor of Tetrahymena, Proc. Natl. Acad. Sci. U S A., 84(24): 8788-8792 (1987).
Kim, S-K. et al., Bridged Nucleic Acids (BNAs) as Molecular Tools, J Biochem Mol Biol Res., 1(3): 67-71 (2015).
Kim, S. et al., Liquid-Phase RNA Synthesis by Using Alkyl-Chain-Soluble Support, Chem. Eur. J., 19: 8615-8620 (2013).
Kiviniemi, A. et al., Solid-Supported 2'-O-Glycoconjugation of Oligonucleotides by Azidation and Click Reactions, Bioconjugate Chemistry, 22(6): 1249-1255 (2011).
Klose, J. et al., Preparation of 2-(2-Cyanoethyl)-sulfanyl-1H-isoindole-1,3-(2H)-dione and related sulfur transfer reagents, Tetrahedron, 53(42):14411-14416 (1997).
Koch, T., A New Dimension in LNA Therapeutics, Roche Innovation Center, Copenhagen, Denmark, Presentation, 39 pages (May 3, 2017).
Koizumi, M. et al., Triplex formation with 2'-O,4'-C-ethylene-bridged nucleic acids (ENA) having C3'-endo conformation at physiological pH, Nuc. Acids Res., 31(12): 3267-3273 (2003).
Kool, E.T., Replacing the Nucleobases in DNA with Designer Molecules, Accounts of Chemical Research, 35:936-943 (2002).
Kordasiewicz, H.B. et al., Sustained therapeutic reversal of Huntington's disease by transient repression of huntingtin synthesis, Neuron, 74(6): 1031-1044 (2012).
Koseoglu, M. et al., Effects of hemolysis interference on routine biochemistry parameters. Biochemia Medica., 21(1): 79-85 (2011). Retrieved May 18, 2017, URL: <http://www.biochemia-medica.com/2011/21/79>.
Koshkin, A.A. et al., LNA (Locked Nucleic Acids): Synthesis of the Adenine, Cytosine, Guanine, 5-Methylcytosine, Thymine and Uracil Bicyclonucleoside Monomers, Oligomerisation, and Unprecedented Nucleic Acid Recognition, Tetrahedron 54: 3607-3630 (1998).
Kozikowski, A.P. et al., Chemistry of the main group metals: A stereoselective synthesis of allyl vinyl thioethers for the thio-claisen reaction, Journal of Organometallic Chemistry, 164(3): C33-C37 (1979).
Koziolkewicz et al., Stability of Stereoregular Oligo-(nucleoside Phosphorothioate)s in Human Plasma: Diastereoselectiviy of Plasma 3'-Exonuclease, Antisense Nucl. Acid Drug Dev., 7: 43-48 (1997).
Koziolkewicz et al., Stereodifferentiation—the effect of P chirality of oligo(nucleoside phosphorothioates) on the activity of bacterial RNase H, Nucl. Acids Res., 23(24): 5000-5005 (1995).

(56) References Cited

OTHER PUBLICATIONS

Koziolkiewicz, M. et al., Effect of P-chirality of oligo(deoxyribonucleoside phosphorothioate)s) on the activity of terminal deoxyribonucleotidyl transferase, FEBS Letters, 434(1-2): 77-82 (1998).
Kraszewski et al., Studies on Reactions of Nucleoside H-phosphonates with Bifunctional Reagents. Part 1. Reaction with amino alcohols, J. Chem. Soc., Perkin Trans., 1: 1699-1704. (1993).
Kremer, B. et al., A Worldwide Study of the Huntington's Disease Mutation, The New England Journal of Medicine, 330(20): 1401-1406 (1994).
Kretschmer-Kazemi Far, R. And Sczakiel, G., The activity of siRNA in mammalian cells is related to structural target accessibility: a comparison with antisense oligonucleotides, Nucleic Acids Research, 31(15):4417-4424 (2003).
Krieg, A.M. et al., CpG motifs in bacterial DNA trigger direct B-cell activation, Nature, 374: 546-549 (1995).
Krieg, A.M. et al., P-Chirality-Dependent Immune Activiation by Phosphorothioate CpG Oligodeoxynucleotides, Oligonucleotides, 13:491-499 (2003).
Krieg, A.M., Development of TLR9 agonists for cancer therapy, The Journal of Clinical Investigation, 117(5): 1184-1194 (2007).
Krieg, A.M., Therapeutic potential of Toll-like receptor 9 activation, Nature Reviews, 471-484 (2006).
Krishna, H. et al., Alkynyl Phosphonate DNA: A Versatile "Click-"able Backbone for DNA-Based Biological Applications, J. Am. Chem. Soc., 134: 11618?11631 (2012).
Krotz, A.H. et al., Phosphorothioate Oligonucleotides with Low Phosphate Diester Content: Greater than 99.9% Sulfurization Efficiency with "Aged" Solutions of Phenylacetyl Disulfide (PADS), Organic Process Research & Development, 8: 852-858 (2004).
Krueger, A.T. et al., Synthesis and properties of size-expanded DNAs: toward designed, functional genetic systems, Accounts of Chemical Research, 40:141-150 (2007).
Krutzfeldt, J. et al., Silencing of microRNAs in vivo with 'antagomirs', Nature, 438: 685-689 (2005).
Kumar, R. et al., The First Analogues of LNA (Locked Nucleic Acids): Phosphorothioate-LNA and 2'-THIO-LNA, Bioo. Med. Chem. Let., 8: 2219-2222 (1998).
Kungurtsev, V. et al., Solution-Phase Synthesis of Short Oligo-2'-deoxyribonucleotides by Using Clustered Nucleosides as a Soluble Support, Eur. J. Org. Chem., 6687-6693 (2013).
Kuramoto, Y. et al., Mannosylated cationic liposomes/CpG DNA complex for the treatment of hepatic metastasis after intravenous administration in mice, Journal of Pharmaceutical Science, 98(3): 1193-1197 (2009).
Kwon, H-J. et al., NF-kappaB-dependent regulation of tumor necrosis factor-alpha gene expression by CpG-oligodeoxynucleotides, Biochem. Biophys. Res. Commun., 311(1): 129-138 (2003).
Lahiri, N., Shooting The messenger with single-stranded RNA gene silencing, edited by Wild, E., HDBuzz, 7 pages. (Sep. 24, 2012). Retrieved Oct. 7, 2015. URL: http://en.hdbuzz.net/099.
LaPlanche, L.A. et al., Phosphorothioate-modified oligodeoxyribonucleotides. III. NMR and UV spectroscopic studies of the Rp-Rp, Sp-Sp, and Rp-Sp duplexes, [d(GGsAATI'CC)2, derived from diastereomeric 0-ethyl phosphorothioates, Nucleic Acids Research, 14(22): 9081-9093 (1986).
Latimer, L.J.P. et al, Synthetic repeating sequence DNAs containing phosphorothioates: nuclease sensitivity and triplex formation, Nucleic Acids Research, 17(4): 1549-1561 (1989).
Laurent et al., Chiral and steric effects in the efficient binding of alpha-anomeric deoxyoligonucleoside N-alkylphosphoramidates to ssDNA and RNA, Nucleic Acids Res., 27(21): 4151-9 (1999).
Lauritsen, A. et al., Methylphosphonate LNA: A Locked Nucleic Acid with a Methylphosphonate Linkage, Bioo. Med. Chem. Lett., 13: 253-256 (2003).
Lauritsen, A. et al., Oligodeoxynucleotides containing amide-linked LNA-type dinucleotides: synthesis and high-affinity nucleic acid hybridization, Chem. Comm., 5: 530-531 (2002).

Lavergne, T. et al., A Base-Labile Group for 2'-OH Protection of Ribonucleosides: A Major Challenge for RNA Synthesis, Chem. Eur. J, 14, 9135-9138 (2008).
Lee, K-W et al., CG sequence- and phosphorothioate backbone modification-dependent activation of the NF-κB-responsive gene expression by CpG-oligodeoxynucleotides in human RPMI 8226 B cells, Molecular Immonulogy, 41: 955-964 (2004).
Lesnikowski et al., Studies on Stereospecific Formation of P-Chiral Internucleotide Linkage. Synthesis of (RP, RP)- and (SP, SP)-Thymidylyl (3', 5') Thymidylyl (3', 5') Thymidine Di (O,O-Phosphorothioate) Using 2-Nitrobenzyl Group as a New S-Protection, Tetrahedron Letters 30(29) 3821-3824 (1989).
Lesnikowski, Z. J. et al., Octa(thymidine methanephosphonates) of partially defined sterochemistry: synthesis and effect of chirality at phosphorus on binding to pentadecadeoxyriboadenylic acid, Nucleic Acids Research, 18(8): 2109-2115 (1990).
Levin, A.A. et al., Basic Principles of the Pharmacokinetics of Antisense Oligonucleotide Drugs, Antisense Drug Technology: Principles, Strategies, and Applications, Second Edition, Chapter 7: 183-215 (2008).
Leviten, M., Wave's Purity Progress, Biocentury, 1-6 (Sep. 28, 2017).
Li L.C., Small RNA Mediated Gene Activation, RNA and the Regulation of Gene Expression: A Hidden Layer of Complexity, Edited by Kevin V. Morris, Chapter 13, Caister Academic Press (2008).
Li, L-C. et al., Small dsRNAs induce transcriptional activation in human cells, PNAS, 103(46): 17337-17342 (2006).
Li, M. et al., Synthesis and cellular activity of stereochemically-pure 2'-O-(2-methoxyethyl)-phosphorothioate oligonucleotides, Chem. Commun., 53: 541-544 (2017).
Li-Tsang, C.W. et al., Prevalence of hypertrophic scar formation and its characteristics among the Chinese population, Burns, 31: 610-616 (2005).
Liang, X-h. et al., Identification and characterization of intracellular proteins that bind oligonucleotides with phosphorothioate linkages, Nucleic Acids Research, 43(5): 2927-2945, Supplemental Data pp. 1-20 (2015).
Lima, W. et al., Single-Stranded ssRNAi Activate RNAi in Animals, Cell, 150: 883-894 (2012).
Lima, W.F. et al., The influence of antisense oligonucleotide-induced RNA structure on *Escherichia coli* RNase H1 activity, J. Biol. Chem., 272(29):18191-9 (1997).
Lima, W.F., et al., Human RNase H1 discriminates between subtle variations in the structure of the heteroduplex substrate, Mol. Pharmacol., 71: 83-91 (2007).
Limbach, P.A. et al., Summary: the modified nucleosides of RNA, Nucleic Acids Research, 22(12):2183-2196 (1994).
Lin et al., Synthesis and resolution of dinucleotide (TpAZT) phosphoramidates, Synthetic Commun., 33(14): 2553-2562 (2003).
Linton, M.F., et al., Transgenic Mice Expressing High Plasma Concentrations of Human Apolipoproteins B100 and Lipoprotein (a), J. Clin. Invest., 92: 3029-37 (1993).
Liu, J. et al., Modulation of Splicing by Single-Stranded Silencing RNAs, Nucleic Acid Therapeutics, 25(3): 113-120 (2015).
Liu, W. et al., Increased Steady-State Mutant Huntingtin mRNA in Huntington's Disease Brain, Journal of Huntington's Disease 2: 491-500 (2013).
Lopez, C. et al., Inhibition of AAC(6')-lb-Mediated Resistance to Amikacin in Acinetobacter baumannii by an Antisense Peptide-Conjugated 2',4'- Bridged Nucleic Acid-NC-DNA Hybrid Oligomer, Antimicrobial Agents and Chemotherapy, 59(9): 5798-5803 (2015).
Lu, X. et al., Antisense-Mediated Inhibition of Human Immunodeficiency Virus (HIV) Replication by Use of and HIV Type 1-Based Vector Results in Severely Attenuated Mutans Incapable of Developing Resistance, Journal of Virology, 78(13): 7079-7088 (2004).
Lu, Y. and Just, G., Stereoselective synthesis of dithymidine phosphorothioates using d-xylose derived chiral auxiliaries, Tetrahedron, 57(9):1677-1687 (2001).
Lu, Y. et al., Stereoselective Synthesis of R(P)- and S(P)-Dithymidine Phosphorothioates via Chiral Indolooxazaphosphorine Intermediates Derived from Tryptophan This work was financially supported by Natural Science and Engineering Research Council of

(56) References Cited

OTHER PUBLICATIONS

Canada (NSERC). We thank Nadim Saadeh and Dr. Orval Mamer, McGill University biomedical mass spectroscopy unit, for recording mass spectra, Angewandte Chemie International Edition, 39(24):4521-4524 (2000).
Lu, Y., Recent advances in the stereocontrolled synthesis of antisense phosphorothioates, Mini Reviews in Medicinal Chemistry, 6(3): 319-330 (2006).
Machine Translation of JP 2010-265304 (2010). <http://dossier1.ipdl.inpit.go.jp/AIPN/odse_top_dn.ipdl?NOOOO=7400>.
Machytka et al., Extension of the Applicability of &I-Values for the Configurational Assignment of Diastereomeric Phosphate-Modified Dideoxynucleotides, Nucleosides and Nucleotides, 17(12): 2311-2322 (1998).
Machytka et al., Synthesis and NMR characterization of diastereomeric CPSMeG derivatives, Nucleosides Nucleotides Nucleic Acids., 19(5-6): 903-15 (2000).
Madsen, A., Antisense Against C90RF72, MDA/ALS News Magazine, 2 pages (Jul. 1, 2012). URL: http://alsn.mda.org/article/antisense-against-c90rf72 [Retrieved Dec. 14, 2017].
Maher III, L.J., et al., Inhibition of DNA Binding Proteins by Oligonucleotide-Directed Triple Helix Formation, Science, 245: 725-730 (1989).
Mann, M.J. et al., Therapeutic applications of transcription factor decoy oligonucleotides, J. Clin. Invest., 106:1071-1075 (2000).
Mannironi, C. et al., In Vivo Selection of Dopamine RNA Ligands, Biochemistry, 36: 9726-9734 (1997).
Martin, P., A New Access to 2'-O-alkylated Ribonucleosides and Properties of 2'-O-Alkylated Oligoribonucleotides, Helv. Chim. Acta., Abstract Only, 78: 486-504 (1995).
Martin, P., Stereoselective Synthesis of 2'-O-(2-MethoxyethyDribonucleosides: Neighboring-Group Participation of the Methoxyethoxy Group in the Ribosylation Step, Helv. Chim. Acta, 79: 1930-1938 (1996).
Martinez, J. et al., Single-Stranded Antisense siRNAs Guide Target RNA Cleavage in RNAi, Cell, 110: 563-574 (2002).
Martinez-Montero, S. et al., Locked 2'-Deoxy-2',4'-Difluororibo Modified Nucleic Acids: Thermal Stability, Structural Studies, and siRNA Activity, ACS Chem. Biol., 10: 2016-2023 (2015).
Masahiro, T. et al., Nematicidal and antimicrobial constituents from Allium grayi Regel and *Allium fistulosum* L. var. *caespitosum*, Agricultural and Biological Chemistry, 52(9): 2383-2385 (1988).
Matranga, C. et al., Passenger-Strand Cleavage Facilitates Assembly of siRNA into Ago2-Containing RNAi Enzyme Complexes, Cell, 123: 607-620 (2005). Supplemental Data, 6 pages.
Matsui, M. et al., Argonaute 2-dependent Regulation of Gene Expression by Single-stranded miRNA Mimics, Molecular Therapy, 10 pages (2016).
Matsui, M. et al., Transcriptional Silencing by Single-Stranded RNAs Targeting a Noncoding RNA That Overlaps a Gene Promoter, ACS Chem. Biol., 8: 122-126 (2013).
Matsuno, Y. et al., Synthetic Method for Oligonucleotide Block by Using Alkyl-Chain-Soluble Support, Org. Lett., 18: 800-803 (2016).
Matysiak, S et al., Acetals as New 2'-O-Protecting Functions for the Synthesis of the Oligoribonucleotides: Synthesis of Uridine Building Blocks and Evaluatino of Their Relative Acid Stability, Helvetica Chimica Acta 81: 1545-1566 (1998).
Maung, J. et al., Alternatives to 1-H-tetrazole in the preparation of phosphonate diesters and phosphonamidates from phosphonyl dichlorides, Tetrahedron Lett., 45: 6497-6499 (2004).
Mauritz, R.P. et al., Elucidation of the Hydrolytical Properties of α-Hydroxybenzylphosphonates as a New Potential Pro-Oligonucleotide Concept, Nucleosides and Nucleotides, 18(6-7):1417-1418 (1999).
Mauritz, R.P. et al., Synthesis of 3',5'-Dithymidylyl-α-hydroxyphosphonate Dimer Building Blocks for Oligonucleotide Synthesis—A New Pro-oliguncleotide, Nucleosides and Nucleotides, 16(7-9):1209-1212 (1997).

McBride, J.L. et al., Prelinical Safety of RNAi-Mediated HTT Suppression in the Rhesus Macaque as a Potential Therapy for Huntington's Disease, Molecular Therapy, 19:1-11 (2011).
Meade, M.F., et al., Efficient delivery of RNAi prodrugs containing reversible charge-neutralizing phosphotriester backbone modifications, Nat. Biotech., 32: 1256-61 (2014).
Medical News Today, AVI BioPharma Announces FDA Clears IND Applications for Clinical Trials of RNA Therapeutic Agents for Treatment of Ebola and Marburg Viruses, Accessed Apr. 2, 2015, 2 pages (Dec. 30, 2008).
Meena, Control of Human RNase H Mediated Cleavage by Stereopure Phosphorothioate Oligonucleotides, WAVE Life Sciences, TIDES Meeting, 23 pages (May 3-6, 2015).
Meena, Development of Allele Specific Antisense Oligonucleotides, WAVE Life Sciences, ACS Central Regional Meeting (CERM), Covington, KY (May 19, 2016).
Meena, Development of Allele Specific Antisense Oligonucleotides, WAVE Life Sciences, TIDES Meeting (May 11, 2016).
Meena, et al., Discovery and Early Clinical Development of the First Allele-Specific Stereopure ASO Drug Candidate with Disease—Modifying Potential for the Treatment of Huntington's Disease, Wave Life Sciences, Poster, 1 page (2016).
Meena, et al., Therapeutic Implications of Controlling P-Chirality in Phosphorothioate Oligonucleotides, TIDES Poster (May 12-15, 2014).
Meena, et al., Therapeutic Implications of Controlling P-Chirality in Phosphorothioate Oligonucleotides, TIDES, San DIEGO, WAVE Life Sciences, Poster, 1 page (May 3-6, 2014).
Meena, Optimization of Antisense Drugs by P-Stereochemistry Control, Wave Life Sciences, OTS Annual Meeting 2014, Oligonucleotide Therapeutics Society, 13 pages (Oct. 12-14, 2014).
Merki, E. et al., Antisense oligonucleotide directed to human apolipoprotein B-100 reduces lipoprotein(a) levels and oxidized phospholipids on human apolipoprotein B-1 00 particles in lipoprotein(a) transgenic mice, Circulation, 118(7): 743-53 (2008).
Mesmaeker, A.D. Backbone modifications in oligonucleotides and peptide nucleic acid systems, Current Opinion in Structural Biology, 5: 343-355 (1995).
Mesmaeker, A.D. et al. Amides as a New Type of Backbone Modification in Oligonucleotides, Angew. Chem., Int. Ed. Engl., 33: 226-229 (1994).
Methods in Enzymology, Edited by Widder, K. and Green, R., Drug and Enzyme Targeting, Academic Press, 112: 309-396 (1985).
Midturi, J. et al., Spectrum of Pulmonary Toxicity Associated with the Use of Interferon Therapy for Hepatitis C: Case Report and Review of the Literature, Clinical Infectious Diseases, 39(11): 1724-1729 (2004).
Mignet, N. et al., Synthesis and evaluation of glucuronic acid derivatives as alkylating agents for the reversible masking of internucleoside groups of antisense oligonucleotides, Carbohydrate Research, 303:17-24 (1997).
Mignet, N. et al., The Prooligonucleotide Approach. V: Influence of the phosphorus atom environment on the hydrolysis of enzymolabile dinucleoside phosphotriesters, Bioorganic and Medicinal Chemistry Letters, 7(7):851-854 (1997).
Milkowski, J.D. et al., Thiol Protection with the Acetamidomethyl Group: S-Acetamidomethyl-l-cysteine Hydrochloride, Organic Syntheses, 6: 5 (1988).
Misaki, S et al., Dehydration of 2-Trifluoromethyl-3,3,3-Trifluoropropanil with Base, Journal of Flourine Chemistry 24: 531-533 (1984).
Molenkamp, B.G. et al., Local Administration of PF-3512676 CpG-B Instigates Tumor-Specific CD8+ T-Cell Reactivity in Melanoma Patients, Clin. Cancer Res., 14(14): 4532-4542 (2008).
Molina, A.G. et al., Acetylated and Methylated β-Cyclodextrins as Viable Soluble Supports for the Synthesis of Short 2'-Oligodeoxyribonucleotides in Solution, Molecules, 17: 12102-12120 (2012).
Molina, A.G. et al., Assembly of Short Oligoribonucleotides from Commercially Available Building Blocks on a Tetrapodal Soluble Support, Current Organic Synthesis, 12:1-6 (2015).
Molina, A.G. et al., Solution phase synthesis of short oligoribonucleotides on a precipitative tetrapodal support, Beilstein Journal of Organic Chemistry, 10: 2279-2285 (2014).

(56) References Cited

OTHER PUBLICATIONS

Molina, A.G., Synthesis of Short Oligonucleotides on a Soluble Support by the Phosphoramidite Method, University of Turku, 1-66 (2015).
Monteys, A.M. et al., Artificial miRNAs Targeting Mutant Huntingtin Show Preferential Silencing In Vitro and In Vivo, Molecular THerapy—Nucleic Acids, 4: e234 1-11 (2015).
Monteys, A.M. et al., Single nucleotide seed modification restores in vivo tolerability of a toxic artificial miRNA sequence in the mouse brain, Nucleic Acids Res., 42(21): 13315-13327 (2014).
Morales-Rojas, H. and Kool, E.T., A porphyrin C-nucleoside incorporated into DNA, Organic Letters, 4(25):4377-4380 (2002).
Morcos, P.A., Achieving targeted and quantifiable alteration of mRNA splicing with Morpholino oligos, Biochem. Biophys. Res. Commun., 358(2): 521-527 (2007).
Morita, K. et al., 2'-O,4'-C-Ethylene-bridged nucleic acids (ENA) with nuclease-resistance and high affinity for RNA, Nucl. Acids Res., Supp. 1: 241-242 (2001).
Morita, K. et al., 20-O,40-C-Ethylene-Bridged Nucleic Acids (ENA): Highly Nuclease- Resistant and Thermodynamically Stable Oligonucleotides for Antisense Drug, Bioo. Med. Chem. Lett., 12: 73-76 (2002).
Morita, K. et al., Synthesis and properties of 2'-O,4'-C-Ethylene-bridged nucleic acids (ENA) as effective antisense oligonucleotides, Bioorganic & Medicinal Chemistry, 11(10): 2211-2226 (2003).
Morvan, F. et al., Cellular uptake and intracellular quantification of fluorescent labeled T20 Me-SATE prooligonucleotides, Nucleosides Nucleotides Nucleic Acids, 20(4-7):1165-1168 (2001).
Morvan, F. et al., Kinetics study of the biotransformation of an oligonucleotide prodrug in cells extract by matrix-assisted laser desorption/ionization time-of-flight mass spectrometry, Nucleosides, Nucleotides and Nucleic Acids, 20(2-4):1159-1163 (2001).
Morvan, F. et al., The Oligonucleotide Prodrug Approach: The Pro-Oligonucleotides, Pharmaceutical Aspects of Oligonucleotides, 79-97 (2000).
Moser, H. E. et al., Sequence-Specific Cleavage of Double Helical DNA by Triple Helix Formation, Science, 238: 645-650 (1987).
Nawrot et al., DNA Oligonucleotides Containing Stereodefined Phosphorothioate Linkages in Selected Positions, Current Protocols in Nucleic Acid Chemistry, Unit 4.34: 4.34.1-4.34.15 (2009).
Nencka, R. et al., Novel Conformationally Locked Nucleosides and Nucleotides, Collection Symposoim Series, 14: 119-122 (2014).
Nielsen, J. and Caruthers, M.H., Directed Arbuzov-type reactions of 2-cyano-1,1-dimethylethyl deoxynucleoside phosphites, J. Am. Chem. Soc., 110: 6275-6 (1988).
Nielsen, N.M. and Bundgaard, H. Glycolamide Esters as Biolabile Prodrugs of Carboxylic Acid Agents: Synthesis, Stability, Bioconversion, and Physicochemical Properties, Journal of Pharmaceutical Sciences, 77(4): 285-298 (1988).
Nielsen, P.E. and Haaima, G., Peptide nucleic acid (PNA). A DNA mimic with a pseudopeptide backbone, Chem. Soc. Rev., 73-78 (1997).
Nielsen, P.E. et al., Sequence-Selective Recognition of DNA by Strand Displacement with a Thymine-Substituted Polyamide, Science, 254(5037): 1497-1500 (1991).
Nielsen, P.E. et al., Synthesis of 29-O,39-C-linked bicyclic nucleosides and bicyclic Oligonucleotides, J. Chem. Soc. Perkins Trans., 1: 3423-3433 (1997).
Nieuwlandt, D. et al., In Vitro Selection of RNA Ligands to Substance P, Biochemistry, 34: 5651-5659 (1995).
Nilsson et al., Chemical and Stereochemical Aspects of Oxidative Coupling of H-Phosphonate and H-Phosphonothioate Diesters. Reactions with N,N-,N,O and O,O-Binucleophiles, Letters in Organic Chemistry, 2(2): 188-197 (2005).
Nilsson et al., Controlling Stereochemistry During Oxidative Coupling. Preparation of Rp or Sp Phosphoramidates from One P-chiral Precursor, Chem. Commun., (22): 2566-7 (2004).
Nilsson, J. et al., Chemoselectivity in oxidative coupling of bifunctional nucleophiles with dinucleoside H-phosphonate and dinucleoside H-phosphonothioate diesters, Nucleosides, Nucleotides & Nucleic Acids, 22(5-8):1467-1469 (2003).
Nowotny, M. et al., Structure of human RNase H1 complexed with an RNA/DNA hybrid: insight into HIV reverse transcription, Mol Cell, 28(2):264-76 (2007).
Nukaga, Y. et al., Stereocontrolled Solid-Phase Synthesis of Phosphate/Phosphorothioate (PO/PS) Chimeric Oligodeoxyribonucleotides on an Automated Synthesizer Using an Oxazaphospholidine-Phosphoramidite Method, J. Org. Chem., A-J, 10 pages (Publication Date (Web): Mar. 3, 2016).
Nukaga, Y. et al., Stereocontrolled Solid-Phase Synthesis of Phosphorothioate Oligoribonucleotides Using 2'-O-(2-Cyanoethoxymethyl)-nucleoside 3'-O-Oxazaphospholiidine Monomers, Journal of Organic Chemistry, 77(18):7913-7922 (2012).
O'Connell, D. et al., Calcium-dependent oligonucleotide antagonists specific for L-selectin, Proc. Natl. Acad. Sci. USA, 93: 5883-5887 (1996).
Obika et al. Stability and structural features of the duplexes containing nucleoside analogues with a fixed N-type conformation, 2'-O,4'- C-methyleneribonucleosides, Tetrahedron Lett. 39: 5401-5404 (1998).
Obika, S. et al., Synthesis of 2'-O,4'-C-Methyleneuridine and -cytidine. Novel Bicyclic Nucleosides Having a Fixed C a ,-endo Sugar Puckering, Tetrahedron Lett., 38(50): 8735-8 (1997).
Ohgi, T. et al., A New RNA Synthetic Method with a 2'-O-(2-Cyanoethoxymethyl) Protecting Group, Organic Letters, 7(16): 3477-3480 (2005).
Ohkubo et al., Synthesis of oligodeoxyribonucleotides containing hydroxymethylphosphonate bonds in the phosphoramidite method and their hybridization properties, Tetrahedron Letters, 46(51): 8953-8957 (2005).
Oka, N. and Wada, T., Stereocontrolled synthesis of oligonucleotide analogs containing chiral internucleotidic phosphorus atoms, Chemical Society Reviews, 40(12):5829-5843 (2011).
Oka, N. et al., An oxazaphospholidine approach for the stereocontrolled synthesis of oligonucleoside phosphorothioates, Journal of the America Chemical Society, 125(27):8307-8317 (2003).
Oka, N. et al., Diastereocontrolled Synthesis of Dinucleoside Phosphorothioates Using a Novel Class of Activators, Dialkyl(cyanomethyl)ammonium Tetrafluoroborates, Journal of the American Chemical Society, 124(18):4962-4963 (2002).
Oka, N. et al., Solid-Phase Synthesis of Stereoregular Oligodeoxyribonucleoside Phosphorothioates Using Bicyclic Oxazaphospholidine Derivatives as Monomer Units, Journal of the American Chemical Society, 130(47):16031-16037 (2008).
Oka, N. et al., Stereocontrolled synthesis of dinucleoside boranophosphates by an oxazaphospholidine method, Nucleic Acids Symposium Series, (49): 131-132 (2005).
Oka, N. et al., Stereocontrolled synthesis of oligonucleoside phosphorothioates and PO/PS-chimeric oligonucleotides by using oxazaphospholidine derivaties, Nucleic Acids Symposium Series, 52: 335-336 (2008).
Oka, N. et al., Stereocontrolled Synthesis of Oligoribonucleoside Phosphorothioates by an Oxazaphospholidine Approach, Organic Letters, 11(4):967-970 (2009).
Onizuka, K. et al., Short Interfering RNA Guide Strand Modifiers from Computational Screening, J. Am. Chem. Soc., 135: 17069-17077 (2013).
Osawa, T. et al., Synthesis and Properties of the 5-Methyluridine Derivative of 3,4-Dihydro-2H-pyran-Bridged Nucleic Acid (DpNA), J. Org. Chem., 80: 10474-10481 (2015).
Ostergaard, M. et al., Rational design of antisense oligonucleotides targeting single nucleotide polymorphisms for potent and allele selective suppression of mutant Huntingtin in the CNS, Nucleic Acids Research, 41(21), 9634-9650 (2013).
Ostergaard, M.E. et al., Efficient Synthesis and Biological Evaluation of 5?-GaINAc Conjugated Antisense Oligonucleotides, Bioconjugate. Chem., 26: 1452-1455 (2015).
Otting, G. et al., Why Pentose- and Not Hexose-Nucleid Acids? Part IV. 'Homo-DNA': 1H-, 13C-, 31P-, and 15N-NMR-Spectroscopic Investigation of ddGlc(A-A-A-A-A-T-T-T-T-T) in Aqueous Solution, Helvetica Chimica Acta, 76(8):2701-2756 (1993).

(56) References Cited

OTHER PUBLICATIONS

Padmanabhan, S. et al., Anti-HBV nucleotide prodrug analogs: Synthesis, bioreversibility, and cytotoxicity studies, Bioorganic and Medicinal Chemistry Letters, 16(15):1491-1494 (2006).
Pallan, P.S. et al., Structure and nuclease resistance of 20,40-constrained 20-O-methoxyethyl (cMOE) and 20-O-ethyl (cEt) modified DNAs, Chem. Comm., 48: 8195-8197 (2012).
Pan, Q-W. et al., New therapeutic opportunities for Hepatitis C based on small RNA, World J. Gastroenterol., 13(33): 4431-4436 (2007).
Panzara, M. et al., Duchenne Muscular Dystrophy Advisory Board Meeting, WAVE Life Sciences, 70 pages (Mar. 3, 2017).
Parmer, R. et al., 5'-(E)-Vinylphosphonate: A Stable Phosphate Mimic Can Improve the RNAi Activity of siRNA-GalNAc Conjugates, Chem. Bio. Chem., 17: 1-6 (2016).
Parrish et al., Functional Anatomy of a dsRNA Trigger: Differential Requirement for the Two Trigger Strands in RNA Interference, Molecular Cell, 6:1077-1087 (2000).
Patil et al., Syntheses and properties of oligothymidylate analogs containing stereoregulated phosphorothioate and phosphodiester linkages in an alternating manner, Bioorganic & Medicinal Chemistry Letters, 4(22): 2663-2666 (1994).
Pedersen, L. et al, A Kinetic Model Explains Why Shorter and Less Affine Enzyme-recruiting Oligonucleotides Can Be More Potent, Mol Ther Nucleic Acids, 3: e149 1-8 (2014).
Pendergraff, H.M. et al., Single-Stranded Silencing RNAs: Hit Rate and Chemical Modification, Nucleic Acid Therapeutics, 1-7 (2016).
Perrino, E. et al., New sulfurated derivatives of valproic acid with enhanced histone deacetylase inhibitory activity, Bioorganic & Medicinal Chemistry Letters, 18(6): 1893-1897 (2008).
Petersen, M. and Wengel, J., LNA: a versatile tool for therapeutics and genomics, Trends in Biotechnology, 21(2): 74-81 (2003).
Peyrottes, S. et al., SATE pronucleotide approaches: an overview, Mini-Reviews Medicinal Chemistry, 4(4):395-408 (2004).
Pfister, E.L. et al., Five siRNAs targeting three SNPs may provide therapy for three-quarters of Huntington's disease patients, 19(9): 774-778 (2009).
Pharmacology Review(s), Application No. 203568Orig1s000, Center for Drug Evaluation and Research, Food and Drug Administration, Department of Health & Human Services, 2013.
Pitsch, S. et al., Reliable Chemical Synthesis of Oligoribonucleotides (RNA) with 2'-O-[(Triisopropylsilypoxy]methyl(2'-O-tom)-Protected Phosphoramidites, Helvetica Chimica Acta, 84: 3773-3795 (2001).
Poijarvi, P. et al., 2,2-Bis(ethoxycarbonyl)- and 2-(Alkylaminocarbonyl)-2-cyano-Substituted 3-(Pivaloyloxy)propyl Groups as Biodegradable Phosphate Protections of Oligonucleotides, Bioconjugate Chemistry, 16(6):1564-1571 (2005).
Poijarvi, P. et al., The chemical stability of S-(2-acylthioethyl) and S-acyloxymethyl protected thymidylyl-3',5'-thymidine phosphoromonothiolates and their deacylation products in aqueous solution, Nucleosides Nucleotides and Nucleic Acids, 20(1-2):77-91 (2001).
Poijarvi, P. et al., Towards Nucleotide Prodrugs Derived from 2,2-Bis(hydroxymethyl)malonate and Its Congeners: Hydrolytic Cleavage of 2-Cyano-2-(hydroxymethyl)-3-methoxy-3-oxopropyl and 3-(Alkylamino)-2-cyano-2-(hydroxymethyl)-3-oxopropyl Protections from the Internucleosidic Phosphodiester and Phosphorothioate Linkages, Helvetica Chimica Acta, 85(7):1869-1876 (2002).
Poijarvi, P. et al., Towards Oligonucleotide Pro-Drugs: 2,2-Bis(ethoxycarbonyl) and 2-(Alkylaminocarbonyl)-2-cyano Substituted 3-(Pivaloyloxy)Propyl Groups as Biodegradable Protecting Groups for Internucleosidic Phosphoromonothioate Linkages, Letters in Organic Chemistry, 1(2):183-188 (2004).
Poijarvi, P., Prodrug Approaches of Nucleotides and Oligonucleotides, Current Medicinal Chemistry, 13(28):3441-3465 (2006).
Pon, R. T., Solid-Phase Supports for Oligonucleotide Synthesis, Current Protocols in Nucleic Acid Chemistry, 3.1.1-3.1.28 (2000).
Pontarollo, R.A. et al., Monocytes are required for optimum in vitro stimulation of bovine peripheral blood mononuclear cells by non-methylated CpG motifs, Veterinary Immunology and Immunopathology, 84(1-2): 43-59 (2002).
Pontiggia, R. et al., 2-C-Methyluridine modified hammerhead riboxyme against the estrogen receptor, Bioorganic & Medicinal Chemistry Letters, 20: 2806-2808 (2010).
Pontiggia, R. et al., DNAzymes and ribozymes carrying 2'-C-methyl nucleotides, Nucleic Acids Sumposium Series, 52: 521-522 (2008).
Potter et al, Stereospecificity of nucleases towards phosphorothioate-substituted RNA: stereochemistry of transcription by T7 RNA polymerase, Nucleinc Acids Research, 15(10): 4145-4162 (1987).
Potter, B.V.L. et al., Synthesis and Configurational Analysis of Dinucleoside Phosphate Isotopically Chiral at Phosphorus. Stereochmical Course of Penicillium citrum Nuclease P1 Reaction, Biochemistry, 22: 1369-1377 (1983).
Prakash, T.P. et al., 2'-O-[2-(Methylthio )ethyl]-Modified Oligonucleotide: An Analogue of 2'O-[2-(Methoxy)-ethyl]-Modified Oligonucleotide with Improved Protein Binding Properties and High Binding Affinity to Target RNA, Biochemistry, 41: 11642-11648 (2002).
Prakash, T.P. et al., Identification of metabolically stable 5-phosphate analogs that support single-stranded siRNA activity, Nucleic Acids Research, 43(6): 2993-3011 (2015). Supplementary Data, 80 pages.
Prakash, T.P. et al., Lipid Nanoparticles Improve Activity of Single-Stranded siRNA and Gapmer Antisense Oligonucleotides in Animals, ACS Chem. Biol., 5 pages (2013), DOI: 10.1021/cb4001316.
Prakash, T.P. et al., Synergistic effect of phosphorothioate, 50-vinylphosphonate and GalNAc modifications for enhancing activity of synthetic siRNA, Bioorg. Med. Chem. Lett., 26: 2817-2820 (2016).
Prakash, T.P. et al., Targeted delivery of antisense oligonucleotides to hepatocytes using triantennary N-acetyl galactosamine improves potency 10-fold in mice, Nucleic Acids Res., 42(13): 8796-807 (2014).
Prhavc, M. et al., 2'-O-[2-[2-(N,N-Dimethylamino)ethoxy]ethyl] Modified Oligonucleotides: Symbiosis of Charge Interaction Factors and Stereoelectronic Effects, Organic Letters, 5(12): 2017-2020 (2003).
PUBCHEM, Substance Record for SID 174316404, Available Date: Mar. 31, 2014 (retrieved on Feb. 26, 2018). Retrieved from the Internet: <URL: https://pubchem.ncbi.nlm.nih.gov/substance/174316404>.
PUBCHEM, Substance Record for SID 174316700, Available Date: Mar. 31, 2014 (retrieved on Feb. 26, 2018). Retrieved from the Internet: <URL: https://pubchem.ncbi.nlm.nih.gov/substance/174316700>.
PUBCHEM, Substance Record for SID 174316999, Available Date: Mar. 31, 2014 {retrieved on Feb. 26, 2018). Retrieved from the Internet: <URL: https://pubchem.ncbi.nlm.nih.gov/substance/174316999>.
Puri, N. et al, Targeted Gene Knockout by 2'-O-Aminoethyl Modified Triplex Forming Oligonucleotides, J. Biol. Chem., 276: 28991-28998 (2001).
Puri, N. et al., The Synthesis and Reactivity of New 2-(N,N-Diisoprophylamino)-3-Methylsulfonyl-1,3,2-Benzoxazaphospholes. The Utility of the 5-Chloro analogue in the One-Pot Synthesis of Oligothiophosphates: [ApsppA, ApspppA, ppp5'A2'ps5'A, m7GpsppA, Apspppp, Apspp], Tetrahedron 51(10): 2991-3014 (1995).
Pérez, B. et al., Antisense Mediated Splicing Modulation for Inherited Metabolic Diseases: Challenges for Delivery, Nucleic Acid Therapies, 24(1): 48-56 (2014).
Rajwanshi, V.K. et al., LNA stereoisomers: xylo-LNA (b-d-xylo configured locked nucleic acid) and a-l-LNA (a-l-ribo configured locked nucleic acid), Chem. Commun., 1395-1396 (1999).
Ravikumar, V.T. et al., Unylinker: An Efficient and Scaleable Synthesis of Oligonucleotides Utilizing a Universal Linker Molecule: A Novel Approach to Enhance the Purity of Drugs, Org. Process Res. Dev., 12(3): 399-410 (2008).
Ravn, J. et al., Stereodefined LNA Phosphorthioate Oligonucleotides, Roche Pharma Research and Early Development, RTR

(56) References Cited

OTHER PUBLICATIONS

Research, Roche Innovation Center Copenhagen, RNA & Oligonucleotide Therapeutics Meeting, Poster, 1 page (Mar. 29-Apr. 1, 2017).
Reese, C.B. and Yan, H., Solution phase synthesis of ISIS 2922 (Vitravene) by the modified H-phophane approach, J. Chem. Soc., Perkin Trans. I, 2619-2633 (2002).
Regan, J.F. et al., A Rapid Molecular Approach for Chromosomal Phasing, Plos One, 1-15 (2015).
Reither, S. and Jeltsch, A., Specificity of DNA triple helix formation analyzed by a FRET assay, BMC Biochemistry, 3: 9 pages (2002).
Renton, A.E. et al., A Hexanucleotide Repeat Expansion in C9ORF72 Is the Cause of Chromosome 9p21-Linked ALS-FTD, Neuron 72, 257-268 (Oct. 20, 2011).
Revankar, G. R. and Rao, T.S., DNA with Altered Bases, DNA and Aspects of Molecular Biology, Comprehensive Natural Products Chemistry, 7.09: 313-339 (1999).
Robinson, D.S. et al., Predominant TH2-Like Bronchoalveolar T-Lymphocyte Population in Atopic Asthma, The New England Journal of Medicine, 326: 298-304 (1992).
Rossetti, G., Structural aspects of the Huntingtin protein investigated by biocomputing methods, Thesis, RWTH Aachen University, Forschungszentrum Juelich, 173 pages (2011).
Rozners, E. et al., Evaluation of 2'-hydroxyl protection in RNA-synthesis using the H-phosphonate approad, Nucleic Acids Research, 22(1): 94-99 (1994).
Saetrom, P., Predicting the efficacy of short oligonucleotides in antisense and RNAi experiments with boosted genetic programming, Bioinformatics, 20(17): 3055-3063 (2004).
Sakatsume, O. et al., Solid Phase Synthesis of Oligoribonucleotides by the Phosphoramidite Approach Using 2'-O-1-(2-Chloroethoxy)Ethyl Protection, Tetrahedron, 47(41): 8717-8728 (1991).
Saneyoshi, H. et al., A General Method for the Synthesis of 2'-0-Cyanoethylated Oligoribonucleotides Having Promising Hybridization Affinity for DNA and RNA and Enhanced Nuclease Resistance, The Journal of Organic Chemistry, 70(25): 10453-10460 (2005).
Sanhueza, C.A. et al., Efficient Liver Targeting by Polyvalent Display of a Compact Ligand for the Asialoglycoprotein Receptor, J. Am. Chem. Soc., 9 pages (2016).
Schirle, N. T. and Macrae, I.J., The Crystal Structure of Human Argonaute2, Science, 336(6084): 1037-1040 (2012).
Schirle, N.T. et al., Structural analysis of human Argonaute-2 bound to a modified siRNA guide, J. Am. Chem. Soc., 1-6 (2016).
Schirle, N.T. et al., Structural Basis for microRNA Targeting, Science, 346(6209): 608-613 (2014).
Schirle, N.T. et al., Water-mediated recognition of t1-adenosine anchors Argonaute2 to microRNA targets, eLife, 4: e07646 1-16 (2015).
Schmitz, C. et al., Synthesis of P-Stereogenic Phosphoramidite and Phosphorodiamidite Ligands and Their Application in Asymmetric Catalysis, Eur. J. Org. Chem., 6205-6230 (2015).
Schoning, K.-U. et al., Chemical Etiology of Nucleic Acid Structure: The α-Threofuranosyl-(3'- >2') Oligonucleotide System, Science, 290(5495):1347-1351 (2000).
Schultz, C., Prodrugs of Biologically Active Phospate Esters, Bioorganic and Medicinal Chemistry, 11(6):885-898 (2003).
Schultz, R.G. and Gryaznov, S.M., Oligo-24-fluoro-24-deoxynucleotide N34_P54 phosphoramidates: synthesis and properties, Nucleic Acids Res., 24(15): 2966-2973 (1996).
Schulz, W.G. and Cai, S.L., Synthetic Genetics, Chemical and Engineering News, 5 (2012).
Scrimgeour, E.M. Huntington Disease (Chorea) in the Middle East, SQU. Med. J., 9(1): 16-23 (2009).
Seela et al, Diastereomerically pure Rp and Sp dinucleoside H-phosphonates. The stereochemical course of their conversion into P-methylphosphonates, phosphorothioates and [18O] chiral phosphates, Journal of Organic Chemistry, 56(12): 3861-3869 (1991).

Seidman, M.M. And Glazer, P.T. The potential for gene repair via triple helix formation, The Journal of Clinical Investigation, 112(4): 487-494 (2003).
Senn, J.J. et al., Non-CpG-Containing Antisense 2-Methoxyethyl Oligonucleotides Activate a Proinflammatory Response Independent of Toll-Like Receptor 9 or Meyloid Differentiation Factor 88, The Journal of Pharmacology and Experimental Terapeutics, 314: 972-979 (2005).
Sergueeva et al., Synthesis of Dithymidine Boranophosphates via Stereospecific Boronation of H-phosphonate Diesters and Assignment of their Configuration, Tetrahedron Letters, 40: 2041-2044 (1999).
Seth, P., and Olson, R., Nucleic Acid Therapeutics—Making Sense of Antisesnse, 2016 Drug Design and Delivery Symposium, ACS Webinar, 1-36 (Jul. 26, 2016).
Seth, P.P. et al., An Exocyclic Methylene Group Acts as a Bioisostere of the 2'Oxygen Atom in LNA, J. Am. Chem. Soc, 132(42): 14942-14950 (2010).
Seth, P.P. et al., Configuration of the 50-Methyl Group Modulates the Biophysical and Biological Properties of Locked Nucleic Acid (LNA) Oligonucleotides, J. Med. Chem., 53: 8309-8318 (2010).
Seth, P.P. et al., Design, Synthesis and Evaluation of Constrained Methoxyethyl, (cMOE) and Constrained Ethyl (cEt) Nucleoside Analogs, Nucleic Acids Symposium Series, 52(1), 553-554 (2008).
Seth, P.P. et al., Short Antisense Oligonucleotides with Novel 2'-4' Conformationaly Restricted Nucleoside Analogues Show Improved Potency without Increased Toxicity in Animals, J. Med. Chem., 52: 10-13 (2009).
Seth, P.P. et al., Structural requirements for hybridization at the 50-position are different in a-L-LNA as compared to b-D-LNA, Bioo. Med. Chem. Lett., 22: 296-299 (2012).
Seth, P.P. et al., Structure Activity Relationships of α-l-LNA Modified, Phosphorothioate Gapmer Antisense Oligonucleotides in Animals, Mol. Ther-Nuc. Acids., 1: e47 1-8 (2012).
Seth, P.P. et al., Synthesis and Biophysical Evaluation of 2',4'-Constrained 2'O-Methoxyethyl and 2',4'-Constrained 2'O-Ethyl Nucleic Acid Analogues, J. Org. Chem., 75: 1569-1581 (2010).
Sha, S.J. and Boxer, A., Treatment implications of C90RF72, Alzheimer's Research & Therapy, 4(46): 7 pages (2012).
Sharma, V.K. et al. Antisense oligonucleotides: modifications and clinical trials, Med. Chem. Commun., 5: 1454-71 (2014).
She, X. et al., Synergy between Anti-Endoglin (CD105) Monoclonal Antibodies and TGF-β in Suppression of Growth of Human Endothelial Cells, Int. J. Cancer, 108: 251-257 (2004).
Sheehan, J.P. and Phan, T.M. Phosphorothioate Oligonucleotides Inhibit the Intrinsic Tenase Complex by an Allosteric Mechanism, Biochemistry, 40: 4980-4989 (2001).
Shivalingam, A. et al., Molecular Requirements of High-Fidelity Replication-Competent DNA Backbones for Orthogonal Chemical Ligation, J. Am. Chem. Soc., 139(4):1575-1583 (2017).
Sierzchala et al., Oxathiaphospholane Method of Stereocontrolled Synthesis of Diribonucleoside 3', 5'-Phosphorotioates, Journal of Organic Chemistry 61(19): 6713-6716 (1996).
Silverman, R.H., A scientific journey through the 2-5A/RNase L system, Cytokine Growth Factor Reviews, 18(5-6):381-388 (2007).
Simon-Sanchez, J. et al., The clinical and pathological phenotype of C9ORF72 hexanucleotide repeat expansions, Brain, 135: 723-735 (2012).
Singh, P.P. et al., Universality of LNA-mediated high-affinity nucleic acid recognition, Chem. Comm., 1247-1248 (1998).
Singh, S.K. et al., Synthesis of 2'-Amino-LNA: A Novel Conformationally Restricted High-Affinity Oligonucleotide Analogue with a Handle, J. Org. Chem., 63: 10035-10039 (1998).
Singh, S.K. et al., Synthesis of Novel Bicyclo[2.2.1] Ribonucleosides: 2'-Amino- and 2'-Thio-LNA Monomeric Nucleosides, J. Org. Chem., 63: 6078-6179 (1998).
Singhrao, S.K. et al., Increased Complement Biosynthesis by Microglia and Complement Activation on Neurons in Huntington's Disease, Experimental Neurology, 159: 362-376 (1999).
Skotte, N. H. et al., Allele-specific suppression of mutant huntingtin using antisense oligonucleotides: providing a therapeutic option for all Huntington disease patients, PLoS One, 9(9): e107434 1-18 (2014).

(56) References Cited

OTHER PUBLICATIONS

Small, L.D. et al., Comparison of Some Properties of Thiolsulfonates and Thiolsulfinates, Journal of the American Chemical Society, 71(10): 3565-3566 (1949).
Smith, A. et al., The murine haemopexin receptor, Biochem. J., 276: 417-425 (1991).
Sobkowski, et al. Stereochemistry of internucleotide bond formation by the H?phosphonate method. 1. Synthesis and 31P NMR analysis of 16 diribonulceoside (3'-5')-H-phosphonates and the corresponding phosphorothioates, Nucleosides Nucleotides Nucleic Acids, 24(10-12): 1469-84 (2005).
Sobkowski, M. et al., Recent Advances in H-Phosphonate Chemistry. Part 1. H-Phosphonate Esters: Synthesis and Basic Reactions, Top Curr Chem, 361:137-177 (2014).
Sonveaux, E., Protecting Groups in Oligonucleotide Synthesis, Protocols for Oligonucleotide Conjugates, Methods in Molecular Biology, Edited by Agrawal, S., Humana Press, 26:1-71 (1994).
Sorensen, M.D., Functionalized LNA (locked nucleic acid): high-affinity hybridization of oligonucleotides containing N-acylated and N-alkylated 2'-amino-LNA monomers, Chem. Comm., 2130-2131 (2003).
Spinelli, N. et al., Use of Allylic Protecting Groups for the Synthesis of Base-Sensitive Prooligonucleotides, European Journal of Organic Chemistry, 49-56 (2002).
Sproat, B.S., RNA Synthesis Using 2'-O-(Tert-Butyldimethylsilyl) Protection, Methods in Molecular Biology, 288: 17-31 (2005).
Stawinski et al., Nucleoside H-phosphonates. 14. Synthesis of nucleoside phosphoroselenoates and phosphorothioselenoates via stereospecific selenization of the corresponding H-phosphonate and H-phosphonothioate diesters with the aid of new selenium-transfer reagent, 3H-1,2-benzothiaseleno1-3-one, J. Org. Chem., 59(1): 130-136 (1994).
Stawinski et al., Stereospecific oxidation and oxidative coupling of H-phosphonate and H-phosphonothioate diesters, Tetrahedron Letters, 33(22):3185-3188 (1992).
Stawinski, J. and Stromberg, R. Di- and Oligonucleotide Synthesis Using H-Phosphonate Chemistry, Methods in Molecular Biology, 288: 81-100 (2005).
Stawinski, J. and Thelin, M., 3-H-2,1-benzoxathiol-3-one 1-oxide—A New Reagent for Stereospecific Oxidation of Nucleoside H-Phosphonothioate Diesters, Tetrahedron Letters, 33(22): 3189-3192 (1992).
Stawinski, J. and Thelin, M., 3H-1,2-benzothiaseleno1-3-one. A new selenizing reagent for nucleoside H-phosphonate and H-phosphonothioate diesters, Tetrahedron Letters, 33(47): 7255-7258 (1992).
Stec, W.J. and Zon, G., Stereochemical Studies of the Formation of Chiral Internucleotide Linkages by Phosphormadite COupling in the Synthesis of Oligodeocyribonucleotides, Tetrahedron Letters, 25(46): 5279-5282 (1984).
Stec, W.J. et al., Automated Solid-Phase Synthesis, Separation, and Stereochemistry of Phosphorothioate Analogues of Oligodeocyribonucleotides, J. Am. Chem. Soc., 106: 6077-6079 (1984).
Stec, W.J. et al., Deoxyribonucleoside 3'-O-(2-Thio- and 2-Oxo-"spiro"-4,4-pentamethylene-1,3,2-oxathiaphospholane)s:? Monomers for Stereocontrolled Synthesis of Oligo(deoxyribonucleoside phosphorothioate)s and Chimeric PS/PO Oligonucleotides, J. Am. Chem. Soc., 120(29): 7156-7167 (1998).
Stec, W.J. et al., Diastereomers of Nucleoside 3'-O-(2-Thio-1,3,2-oxathia(selena)phospholanes): Building Blocks for Stereocontrolled Synthesis of Oligo(nucleoside phosphorothioate)s, Journal of the American Chemical Society, 117(49):12019-12029 (1995).
Stec, W.J. et al., Novel route to oligo(deoxyribonucleoside phosphorothioates). Stereocontrolled synthesis of P-chiral oligo(deoxyribonucleoside phosphorothioates), Nucleic Acids Research, 19(21):5883-5888 (1991).
Stec, W.J. et al., Stereocontrolled Synthesis of Oligo (nucleoside phosphorothioate)s , Angew. Chem. Int. Ed. Engl., 33:709-722 (1994).

Stec, W.J. et al., Stereodependent inhibition of plasminogen activator inhibitor type 1 by phosphorothioate oligonucleotides: proof of sequence specificity in cell culture and in vivo rat experiments, Antisense Nucleic Acid Drug Dev., 7(6):567-73 (1997).
Stec, W.J. et al., Stereospecific Synthesis of P-Chiral Analogs of Oligonucleotides, Methods in Molecular Biology, 20: 285-313 (1993).
Stec, W.J., Oligo(nucleoside Phosphorothioate)s: The Quest of P-Chirality, in Phosphorus, Sulfur, and Silicon, 177(6): 1775-1778 (2002).
Stein, C.A. and Cheng, Y.C., Antisense oligonucleotides as therapeutic agents—is the bullet really magical?, Science, 261(5124):1004-12 (1993).
Stout, A.K. et al., Inhibition of wound healing in mice by local interferon a/b injection, Int J Exp Pathol, 74 (1): 79-85 (1993).
Sureshbabu, V.V. et al., Synthesis of tetrazole analogues of amino acids using Fmoc chemistry: isolation of amino free tetrazoles and their incorporation into peptides, Tetrahedron Letters, 48(39): 7038-7041 (2007).
Surono, A. et al., Chimeric RNA/Ethylene Bridged Nucleic Acids Promote Dystrophin Expression in Myocytes of Duchenne Muscular Dystrophy by Inducing Skipping of the Nonsense Mutation-Encoding Econ, Human Gene Therapy, 15:749-757 (2004).
Suska, A. et al., Antisense oligonucleotides: Stereocontrolled synthesis of phosphorothioate oligonucleotides, Pure and Applied Chemistry, 65(4):707-714 (1993).
Suter, S.R. et al., Structure-Guided Control of siRNA Off Target Effects, J. Am. Chem. Soc., 1-9 (2016).
Swayze, E.E. and Bhat, B., The medicinal chemistry of oligonucleotides, Crooke, S.T. (ed) Antisense Drug Technology: Principles, Strategies, and Applications, CRC Press, Boca Raton, FL: 143-82 (2007).
Swayze, E.E. et al., Antisense oligonucleotides containing locked nucleic acid improve potency but cause significant hepatotoxicity in animals, Nucleic Acids Research, 35(20: 687-700 (2007).
Takahashi, D. et al., Novel diphenylmethyl-Derived Amide Protecting Group for Efficient Liquid-Phase Peptide Synthesis: AJIPHASE, Org. Lett., 14(17): 4514-4517 (2012).
Takahashi, T. et al., Interactions between the non-seed region of siRNA and RNA-binding RLC/RISC proteins, Ago and TRBP, in mammalian cells, Nucleic Acids Research, 42(8): 5256-5269 (2014).
Takeno, H. et al., Selection of an RNA Molecule that Specifically Inhibits the Protease Activity of Subtilisin, J. Biochem., 125: 1115-1119 (1999).
Takeshima, Y. et al., Oligonucleotides against a splicing enhancer sequence led to dystrophin production in muscle cells from a Duchenne muscular dystrophy patient, Brain & Development, 23:788-790 (2001).
Tam, Journal of Hematotherapy & Stem Cell Research, 12: 467-471 (2003).
Tamura et al., Preparation of Stereoregulated Antisense Oligodeoxyribonucleoside Phosorothioate and Interaction with its Complementary DNA and RNA, Nucleosides & Nucleotides,17(1-3): 269-282 (1998).
Tang, J. et al., Enzymatic Synthesis of Stereoregular (All Rp) Oligonucleotide Phosphorothioate and Its Properties, Nucleosides Nucleotides, 14(3-5):985-990 (1995).
Tawarada, R. et al., Mechanistic studies on oxidative condensation of a thymidine 3'-H-phosphonate derivative with 3'-O-acetylthymidine, Archive for Organic Chemistry, (3):264-273 (2009).
Thayer, J.R. et al., Separation of oligonucleotide phosphorothioate distereoisomers by pellicular anion-exchange chromatography, Journal of Chromatography A, 1218: 802-808 (2011).
Tomoskozi et al., Stereospecific conversion of H-phosphonates into phosphoramidates. The use of vicinal carbon-phosphorus couplings for configurational determination of phosphorus, Tetrahedron, 51(24): 6797-6804 (1995).
Tosquellas, G. et al., First synthesis of alternating Sate-phosphotriester/phosphodiester prooligonucleotides on solid support, Bioorganic and Medicinal Chemistry Letters, 8(20): 2913-2918 (1998).

(56) References Cited

OTHER PUBLICATIONS

Tosquellas, G. et al., Prooligonucleotides exhibit less serum-protein binding than phosphodiester and phosphorothioate oligonucleotides, Nucleosides, Nucleotides and Nucleic Acids, 19(5-6):995-1003 (2000).
Tosquellas, G. et al., The pro-oligonucleotide approach: solid phase synthesis and preliminary evaluation of model pro-dodecathymidylates, Nucleic Acids Research, 26(9):2069-2074 (1998).
Tosquellas, G. et al., The Prooligonucleotide Approach III: Synthesis and bioreversibility of a chimeric phosphorodithioate prooligonucleotide, Bioorganic and Medicinal Chemistry Letters, 6(4):457-462 (1996).
Tosquellas, G. et al., The Prooligonucleotide Approach IV : Synthesis of chimeric prooligonucleotides with 6 enzymolabile masking groups and unexpected desulfurization side reaction, Bioorganic and Medicinal Chemistry Letters, 7(3):263-268 (1997).
Ts'O, P.O. et al., An Approach to Chemotherapy Based on Base Sequence Information and Nucleic Acid Chemistry, Ann. N. Y. Acad. Sci., 507: 220-241 (1988).
Tsai, C.H. et al., Enzymatic synthesis of DNA on glycerol nucleic acid templates without stable duplex formation between product and template, Proceedings of the National Academy of Science, 104(37):14598-14603 (2007).
Tuerk, C. and Gold, L., Systematic Evolution of Ligans by Exponential Enrichment: RNA Ligands to Bacteriophage T4 DNA Polymerase, Science, 249: 505-510 (1990).
Turner, D.H. et al, Improved Parameters for Prediction of RNA Structure, Cold Spring Harbor Symposia on Quantitative Biology, LII: 123-133 (1987).
Turner, D.H. et al., Free Energy Increments for Hydrogen Bonds in Nucleic Acid Base Pairs, J. Am. Chem. Soc., 109: 3783-3785 (1987).
U.S. Food and Drug Administration, Development of New Stereoisomeric Drugs, 8 pages (May 1, 1992). URL: http://www.fda.gov/Drugs/GuidanceComplianceRegulatoryInformation/Guidances/ucm122883.htm [Retrieved Jun. 15, 2016].
Umemoto, T et al., Oligoribonucleotide Synthesis by the use of 1-(2-cyanoethoxy)ethyl (CEE) as a 2'-hydroxy protecting group, Tetrahedron Letters 45: 9529-9531 (2004).
Uphoff, K.W. et al., In vitro selection of aptamers: the death of pure reason, Curr. Opin. Struct. Biol., 6: 281-288 (1996).
Usman, N. et al., Automated Chemical Synthesis of Long Oligoribonucleotides Using 2'-O-Siylylated Ribonucleoside 3'-O-Phosphoramidites on a Controlled-Pore Glass Support, J. Am. Chem. Soc. 109(25): 7845-7854 (1987).
Uznanski, B. et al., Stereochemistry of base-catalyzed ring opening of 1,3,2-oxathiaphospholanes. Absolute configuration of 2-{N-[(Rc)-1-(.alpha.-naphthyl)ethyl]amino}-2-thiono-1,3,2-oxathiaphospholanes and O,S-dimethyl N-[(Rc)-1-(.alpha.-naphthl)ethyl]phosphoramidothioates, Journal of the American Chemical Society, 114(26):10197-10202 (1992).
Van Aerschot, A. et al., 1,5-Anhydrohexitol Nucleic Acids, a New Promising Antisense Construc, Angew. Chem. Int. Ed. Engl., 34: 1338-1339 (1995).
Van Der Veken, P. et al., Irreversible inhibition of dipeptidyl peptidase 8 by dipeptide-derived diaryl phosphonates, Journal of Medicinal Chemistry, 50(23): 5568-5570 (2007).
Van Deutekom, J.C.T. et al., Antisense-induced exon skipping restores dystrophin expression in DMD patient derived muscle cells, Human Molecular Genetics, 10(15):1547-1554 (2001).
Vasquez, K.M. et al., Chromosomal mutations induced by triplex-forming oligonucleotides in mammalian cells, Nucl. Acids Res. 27(4): 1176-1181 (1999).
Vasseur, J-J. et al., Oligonucleosides: Synthesis of a Novel Methylhydroxylamine-Linked Nucleoside Dimer and Its Incorporation into Antisense Sequences, J. Am. Chem. Soc., 114: 4006-4007 (1992).
Veedu, R.N. et al., Novel Applications of Locked Nucleic Acids, Nucleic Acids Symposium Series, 51: 29-30 (2007).
Verhagen et al., A Conformationally locked Aminomethyl C-Glycoside and Studies on Its N-Pyren-1-ylcarbonyl Derivative Inserted into Oligodeoxynucleotides, European Journal of Organic Chemistry, 2538-2548 (2006).
Verma, S. and Eckstein, F., Modified Oligonucleotides: Synthesis and Strategy for Users, Annu. Rev. Biochem., 67: 99-134 (1998).
Vermeulen, A. et al., Double-Stranded Regions Are Essential Design Components of Potent Inhibitors of RISC Function, RNA, 13: 723-730 (2007).
Vives, E. et al., Lipophilic pro-oligonucleotides are rapidly and efficiently internalized in HeLa cells, Nucleic Acids Research, 27(20):4071-4076 (1999).
Vlassov, V.V. et al., Transport of oligonucleotides across natural and model membranes, Biochimica et Biophysica Acta, 1197: 95-108 (1994).
Vu, H. and Hirschbein, B.L., Internucleotide Phosphite Sulfurization With Tetraethylthiuram Disulfide. Phosphorothioate Oligonucleotide Synthesis Via Phosphoramidite Chemistry, Tetrahedron Letters, 32(26):3005-3008 (1991).
Vuyisich, M. and Beal, P.A., Regulation of the RNA-dependent protein kinase by triple helix formation, Nuc, Acids Res., 28(12): 2369-74 (2000).
Wada et al., Stereocontrolled Synthesis of Phosphorothioate RNA by the Oxazaphospholidine Approach, Nucleic Acids Symp. Ser., 48: 57-58 (2004).
Wada, T. et al., Chemical synthesis and properties of stereoregulated phosphorothioate RNAs, Nucleic Acids Symposium Series, 51:119-120 (2007).
Wada, T. et al., Stereocontrolled synthesis of phosphorothioate DNA by an oxazaphospholidine approach, Nucleic Acids Research Supplement, 3:109-110 (2003).
Wada, Takeshi, Chapter I Development of nucleic acid medicines, 3.3 Chemical synthesis of phosphorous atom-modified nucleic acids, CMC Publication., Frontier of Development of Nucleic Acid Medicine: 67-75 (2009).
Wagner, C.R. et al., Pronucleotides: toward the in vivo delivery of antiviral and anticancer nucleotides, Medicinal Research Reviews, 20(6):417-451 (2000).
Walker, J.R. et al., Structure of the Ku heterodimer bound to DNA and its implications for double-strand break repair, Nature, 412: 607-614 (2001).
Wan et al., Synthesis of Second Generation Antisense Oligonucleotides Containing Chiral Phosphorothioate Linkages and Evaluation of their Biophysical Properties and Biological Activity, 10th Annual Meeting of the Oligonucleotide Therapeutics Society, abstract received by Applicant Oct. 7, 2014, poster setup prior to presentation (first known to Applicant late Oct. 12, 2014, PST), poster presentation Oct. 13, 2014.
Wan, W.B. and Seth, P.P., The Medicinal Chemistry of Therapeutic Oligonucleotides, J. Med. Chem., 59: 9645-9667 (2016).
Wan, W.B. et al., Synthesis, biophysical properties and biological activity of second generation antisense oligonucleoties containing chiral phosphorothioate linkages, Nucleic Acid Research, 42: 13456-13468 (2014). Supplementary Information, 14 pages.
Wang H, et al., Therapeutic gene silencing delivered by a chemically modified siRNA against mutant SOD 1 slows ALS progression, The Journal of Biological Chemistry, 283(23):15845-15852 (2008).
Wang, J.-C. et al., A stereoselective synthesis of dinucleotide phosphorothioate triesters through a chiral indol-oxazaphosphorine intermediate, Tetrahedron Letters, 38(5):705-708 (1997).
Wang, Y. et al., Structure of an argonaute silencing complex with a seed-containing guide DNA and target RNA duplex, Nature, 456(7224): 921-926 (2008).
Warby, S.C. et al., CAG expansion in the Huntington disease gene is associated with a specific and targetable predisposing haplogroup, Am. J. Hum. Genet., 84(3): 351-366 (2009).
Watts, J.K. and Corey, D.R., Gene silencing by siRNAs and antisense oligonucleotides in the laboratory and the clinic, J. Pathol. 226(2): 365-79 (2012).
WAVE Life Sciences Press Release, WAVE Life Sciences Added to the Russell 2000® Index, 2 pages (Jun. 27, 2016).

(56) References Cited

OTHER PUBLICATIONS

WAVE Life Sciences Press Release, WAVE Life Sciences Announces Plan to Deliver Six Clinical Programs by 2018, 6 pages (Jan. 29, 2016).
WAVE Life Sciences Press Release, WAVE Life Sciences Announces Pricing of Initial Public Offering, 3 pages (Nov. 11, 2015).
WAVE Life Sciences Press Release, WAVE Life Sciences Appoints Dr. Michael Panzara as Head of Neurology Franchise, 4 pages (Jul. 12, 2016).
WAVE Life Sciences Press Release, WAVE Life Sciences Appoints Keith Regnante as Chief Financial Officer, 4 pages (Aug. 17, 2016).
WAVE Life Sciences Press Release, WAVE Life Sciences Appoints Roberto Guerciolini, M. Senior Vice President and Head of Early Development, 2 pages (Apr. 7, 2015).
WAVE Life Sciences Press Release, WAVE Life Sciences Closed $18 Million Series a Financing to Advance Stereopure Nucleic Acid Therapeutics, 3 pages (Feb. 2, 2015).
WAVE Life Sciences Press Release, WAVE Life Sciences Enters Collaboration with Pfizer to Develop Genetically Targeted Therapies for the Treatment of Metabolic Diseases, 5 pages (May 5, 2016).
WAVE Life Sciences Press Release, WAVE Life Sciences Expands Stereopure Synthetic Chemistry Platform Capabilities, Augments Patent Portfolio with Addition of Single-Stranded RNAi (ssRNAi), 3 pages (Jun. 8, 2015).
WAVE Life Sciences Press Release, WAVE Life Sciences Raises $66 Million in Series B Financing, 3 pages (Aug. 18, 2015).
WAVE Life Sciences Press Release, WAVE Life Sciences Receives Orphan Drug Designation from FDA for its Lead Candidate Designed to Treat Huntington's Disease, 5 pages (Jun. 21, 2016).
WAVE Life Sciences Press Release, WAVE Life Sciences Reports First Quarter 2016 Financial Results and Provides Business Update, 9 pages (May 16, 2016).
WAVE Life Sciences Press Release, WAVE Life Sciences Reports Fourth Quarter and Full Year 2015 Financial Results and Provides Business Update, 10 pages (Mar. 30, 2016).
WAVE Life Sciences Press Release, WAVE Life Sciences Reports Second Quarter 2016 Financial Results and Provides Business Update, 10 pages (Aug. 15, 2016).
WAVE Life Sciences Press Release, WAVE Life Sciences to Advance Next-Generation Nucleic Acid Therapies to Address Unmet Need in Duchenne Muscular Dystrophy, 6 pages (May 9, 2016).
WAVE Life Sciences Press Release, WAVE Life Sciences to Present at the Deutsche Bank 41st Annual Health Care Conference, 2 pages (Apr. 29, 2016).
WAVE Life Sciences Press Release, WAVE Life Sciences to Present at the Jefferies 2016 Healthcare Conference, 2 pages (Jun. 1, 2016).
WAVE Life Sciences Press Release, WAVE Life Sciences to Present at the Jmp Securities Life Sciences Conference, 2 pages (Jun. 15, 2016).
WAVE Life Sciences Press Release, WAVE Life Sciences to Present at the Leerink Partner 5th Annual Global Healthcare Conference, 2 pages (Feb. 3, 2016).
WAVE Life Sciences Press Release, WAVE Life Sciences to Present at the Leerink Partners Rare Disease & Immuno-Oncology Roundtable, 2 pages (Sep. 14, 2016).
WAVE Life Sciences Press Release, WAVE Life Sciences to Present at the SunTrust Robinson Humphrey 2016 Orphan Drug Day Conference, 2 pages (Feb. 16, 2016).
Weidner, J.P. et al., Alkyl and Aryl Thiolsulfonates, Journal of Medicinal Chemistry, 7(5): 671-673 (1964).
Weiner, G. J. et al., Immunostimulatory oligodeoxynucleotides containing the CpG motif are effective as immune adjuvants in tumor antigen immunization, 94(20): 10833-10837 (1997).
Weinfeld, M., et al., Influence of nucleic acid base aromaticity on substrate reactivity with enzymes acting on single-stranded DNA, Nucleic Acids Res., 21(3): 621-626 (1993).
Weiser, T.G., et al., An estimation of the global volume of surgery: a modeling strategy based on available data, Lancet, 372(9633): 139-144 (2008).
Welz et al., 5-(Benzylmercapto)-1H-tetrazole as activator for 2'-O-TBDMS phosphoramidite building blocks in RNA synthesis, Tetrahedron Letters, 43: 795-797 (2002).
Wengel, J., Synthesis of 3'-C- and 4'-C-Branched Oligodeoxynucleotides and the Development of Locked Nucleic Acid (LNA), Ace. Chem. Res., 32: 301-310 (1999).
Whittaker, B. et al., Stereoselective synthesis of highly functionalised P-stereogenic nucleosides via palladium-catalysed P-C cross-coupling reactions, Tetrahedron Letters, 49: 6984-6987 (2008).
Widdison, W. C. et al., Semisynthetic Maytansine analogues for the targeted treatment of cancer, Journal of Medicinal Chemistry, 49(14): 4392-4408 (2006).
Wild, E. et al., Quantification of mutant huntingtin protein in cerebrospinal fluid from Huntington's disease patients, The Journal of Clinical Investigation, 125(5): 1979-1986 (2015).
Wilk, A. and Stec, W.J., Analysis of oligo(deoxynucleoside phosphorothioate)s and their diastereomeric composition, Nucleic Acids Research, 23(3):530-534 (1995).
Wilk, A. et al., Deoxyribonucleoside Cyclic N-Acylphosphoramidites as a New Class of Monomerrs for the Stereocontrolled Synthesisof Oliothymidylyl- and Oligodeoxycytidylyl-Phosphorohioates, Journal of the American Chemical Society, 122(10): 2149-2156 (2000).
Wong, Chui Ming, Synthesis of anisomycin. Part I. The stereospecific synthesis of N-benzoyl-2-(p-methoxybenzyl)-3-hydroxy-4-carboxamido pyrrolidine and the absolute configuration of anisomycin, Canadian journal of Chemistry 46: 1101-1104 (1968).
Woolf, T.M. et al., Specificity of antisense oligonucleotides in vivo, Prov. Natl. Aca. Sci. USA, 89: 7305-7309 (1992).
Wright, P. et al., Large scale synthesis of oligonucleotides via phosphoramidite nucleosides and a high-loaded polystyrene support, Tetrahedron Letters, 34(21):3373-3736 (1993).
Written Opinion for PCT/IB2009/007923, 8 pages (dated Sep. 6, 2010).
Written Opinion for PCT/IB2015/000395, 10 pages (dated Oct. 30, 2015).
Written Opinion for PCT/JP11/55018, 3 pages (dated Mar. 29, 2011).
Written Opinion for PCT/JP11/71559, 6 pages (dated Dec. 20, 2011).
Written Opinion for PCT/JP15/50716 and English Translation, 11 pages (dated Apr. 21, 2015).
Written Opinion for PCT/JP2010/065900, 5 pages (dated Sep. 15, 2010).
Written Opinion for PCT/JP2013/004303, 6 pages (dated Aug. 13, 2013).
Written Opinion for PCT/JP2015/050714, and English Translation, 11 pages (dated Apr. 21, 2015).
Written Opinion for PCT/JP2015/050718 and English Translation, 6 pages ( dated Apr. 21, 2015).
Written Opinion for PCT/US2010/041068, 11 pages, (dated Sep. 1, 2010).
Written Opinion for PCT/US2011/064287, 14 pages (dated Apr. 12, 2012).
Written Opinion for PCT/US2012/046805, 9 pages (dated Sep. 19, 2012).
Written Opinion for PCT/US2013/050407, 12 pages (dated Jan. 9, 2014).
Written Opinion for PCT/US2016/043542, 14 pages (dated Dec. 28, 2016).
Written Opinion for PCT/US2016/043598, 10 pages (dated Nov. 28, 2016).
Written Opinion for PCT/US2016/056123, 15 pages (dated Mar. 17, 2017).
Written Opinion for PCT/US2017/022135, 11 pages (dated Jun. 6, 2017).
Written Opinion for PCT/US2017/030753, 13 pages (dated Sep. 26, 2017).
Written Opinion for PCT/US2017/030777, 10 pages (dated Oct. 2, 2017).
Written Opinion for PCT/US2017/035837, 15 pages (dated Aug. 24, 2017).
Written Opinion for PCT/US2017/043431, ISA/US, 38 pages (dated Dec. 21, 2017).

(56) References Cited

OTHER PUBLICATIONS

Written Opinion for PCT/US2017/045218, 11 pages (dated Sep. 27, 2017).
Written Opinion for PCT/US2017/055601, ISR/US, 16 pages (dated Feb. 15, 2018).
Written Opinion for PCT/US2017/062996, 9 pages (dated Mar. 9, 2018).
Wu, X. et al., Synthesis of 5'-C- and 2'-O-(Bromoalkyl)-Substituted Ribonucleoside Phosphoramidites for the Post-synthetic Functionalization of Oligonucleotides on Solid Support, Helvetica Chimica Acta, 83: 1127-1144 (2000).
Xiang, Y. et al., Effects of RNase L mutations associated with prostate cancer on apoptosis induced by 2',5'-oligoadenylates, Cancer Research, 63(20):6795-6801 (2003).
Xiong, H.Y. et al., The human splicing code reveals new insights into the genetic determinants of disease, Science, 347(6218): 144 1254806-1-1254806-8 (2015).
Xu, D. and Esko, J.D., Demystifying Heparan Sulfate-Protein Interactions, Annu. Rev. Biochem., 83: 129-157 (2014).
Xu, L. et al., Cyclic ADP-ribose analogues containing the methylenebisphosphonate linkage: effect of pyrophosphate modifications on Ca2+ release activity, J. Med. Chem., 48(12): 4177-4181 (2005).
Xu, Y. et al., Functional comparison of single- and double-stranded siRNAs in mammalian cells, Biochemical and Biophysical Research Communications, 316: 680-687 (2004).
Yamada, O. et al., Diastereoselective Synthesis of 3,4-Dimethoxy-7-morphinanone: A Potential Route to Morphine, Organic Letters, 2(18): 2785-2788 (2000).
Yamakage, S-i. et al., 1-(2-Chloroethoxy)Ethyl Group for the Protection of 2'-Hydroxyl Group in the Synthesis of Oligoribonucleotides, Tetrahedron Letters, 30(46): 6361-6364 (1989).
Yamamoto, S. et al., Unique Palindromic Sequences in Synthetic Oligonucleotides are Required to Induce INF and Augment INF-Mediated Natural Killer Activity, J. Immunol., 148(12): 4072-4076 (1992).
Yamato, K. et al., Enhanced specificity of HPV16 E6E7 siRNA by RNA-DNA chimera modification, Cancer Gene Therapy, 18: 587-597 (2011).
Yanai, H. et al., Suppression of immune responses by nonimmunogenic oligodeoxynucleotides with high affinity for high-mobility group box proteins (HMGBs), PNAS Early Edition, 1-6 (2011).
Yasuda, K. et al., CpG motif-independent activation of TLR9 upon endosomal translocation of "natural" phosphodiester DNA, European Journal of Immunology, 431-436 (2006).
Ye, S. et al., An efficient procedure for genotyping single nucleotide polymorphisms, Nucleic Acids Research, 29(17): e88 1-8 (2001).
Yu, D. et al., Accessible 5'-end of CpGcontaining phosphorothioate oligodeoxynucleotides is essential for immunostimulatory activity, Bioorganic & Medicinal Chemistry Letters, 10: 2585-2588 (2000).
Yu, D. et al., Single-Stranded RNAs Use RNAi to Potently and Allele-Selectively Inhibit Mutant Huntingtin Expression, Cell, 150: 895-908 (2012).
Yu, D. et al., Stereo-Enriched Phosphorothioate Oligodeoxynucleotides: Synthesis, Biophysical and Biological Properties, Bioorganic & Medicinal Chemitry, 8: 275-284 (2000).
Yu, R.Z. et al., Cross-species comparison of in vivo PK/PD relationships for second—generation antisense oligonucleotides targeting apolipoprotein B-100, Biochem. Pharmacol., 77: 910-919 (2009).
Yu, S. et al., A One-Pot Formal [4+2] Cycloaddition Approach to Substituted Piperidines, Indolizidines, and Quinolizidines. Total Synthesis of Indolizidine (−)-209I, Journal of Organic Chemicals, 70:7364-7370 (2005).
Zhang, J. et al., Optimization of Exon Skipping Therapies for Duchenne Muscular Dystrophy, WAVE Life Sciences, PPMD: Parent Project Muscular Dystrophy Meeting, Orlando, FL, Poster, 1 page (Jul. 25, 2016).
Zhang, L. et al., A simple glycol nucleic acid, Journal of the American Chemical Society,127(12):4174-4175 (2005).
Zhang, R.S. et al., Synthesis of two mirror image 4-helix junctions derived from glycerol nucleic acid, Journal of the American Chemical Society, 130(18):5846-5847 (2008).
Zhang, Y. et al., Structural Isosteres of Phosphate Groups in the Protein Data Bank, J. Chem. Inf. Model, 1-18 (2017).
Zhang, Y., Investigating phosphate structural replacements through computational and experimental approaches, Academic Dissertain, University of Helsinki, 119 pages (2014).
Zhao, J. et al., Genome-wide Identification of Polycomb-Associated RNAs by RIP-seq, Molecular Cell, 40: 939-953 (2010).
Zhong, Z. et al., WAVE Life Sciences: Developing Stereopure Nucleic Acid Therapies for the Treatment of Genetic Neurological Diseases, World CNS Summit 2017, Boston, MA, WAVE Life Sciences, Poster, 1 page (Feb. 20-22, 2017).
Zlatev et al., Phosphoramidate dinucleosides as hepatitis C virus polymerase inhibitors, J Med Chem., 51(18): 5745-57 (2008).
Zlatev, I. et al., 5'-C-Malonyl RNA: Small Interfering RNAs Modified with 5'-Monophosphate Bioisostere Demonstrate Gene Silencing Activity, ACS Chem. Biol., 8 pages (2015).
Zon, Automated synthesis of phosphorus-sulfur analogs of nucleic acids—25 years on: potential therapeutic agents and proven utility in biotechnology, New J. Chem., 34(5): 795-804 (2010).
Zon, G and STEC, W.J., Phosphorothioate oligonucleotides, Oligonucleotides and Analogues: A Practical Approach, 87-108 (1991).

* cited by examiner $^1$H NMR spectrum of ($S_P$)-4tt (CDCl$_3$)

$^{31}P$ NMR spectrum of $(S_P)$-4tt $(CDCl_3)$

¹H NMR spectrum of (*R*$_P$)-4tt (CDCl₃)

$^{31}$P NMR spectrum of ($R_P$)-4tt (CDCl$_3$)

Crude UPLC® profile of $(S_P)$-5tt

Crude UPLC® profile of (S_P)-5tt using BTC in place of Ph₃PCl₂

Crude UPLC® profile of ($S_P$)-5tt

Crude UPLC® profile of ($S_P$)-5tt using BTC in place of $PH_3PCL_2$

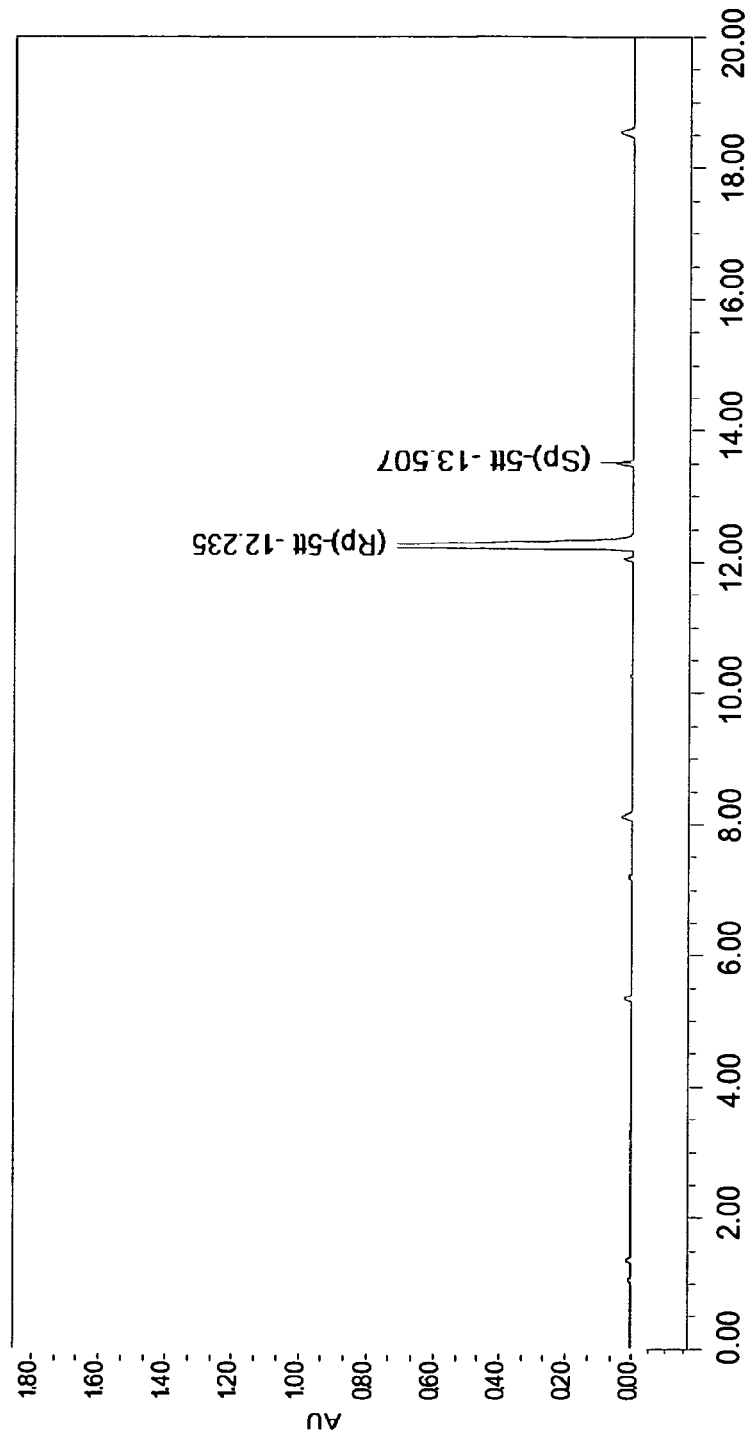

Crude UPLC® profile of ($R_P$)-5tt

Crude UPLC® profile of $(R_P)$-5tt

Crude UPLC® profile of ($S_P$)-5ct

Crude UPLC® profile of ($S_P$)-5ct

Crude UPLC® profile of ($R_P$)-5ct

Crude UPLC® profile of $(R_P)$-5ct

Crude UPLC® profile of ($S_P$)-5at

Crude UPLC® profile of ($R_P$)-5at

Crude UPLC® profile of ($S_P$)-5gt

Crude UPLC® profile of ($R_P$)-5gt

Crude UPLC® profile of ($S_P$)-5tt

Crude UPLC® profile of ($S_P$)-5tt

Crude UPLC® profile of (S$_P$)-5tt

Crude UPLC® profile of ($S_P$)-5tt

Crude UPLC® profile of ($R_P$)-5tt

Crude UPLC® profile of $(R_P)$-5tt

Crude UPLC® profile of (S_P)-5ct

CrudeUPLC® profile of $(R_P)$-5ct

Crude UPLC® profile of ($S_P$)-5at

Crude UPLC® profile of ($S_P$)-5at

Crude UPLC® profile of ($S_P$)-5at

Crude UPLC® profile of ($R_P$)-5at

Crude UPLC® profile of ($R_P$)-5at

Crude UPLC® profile of ($S_P$)-5gt

Crude UPLC® profile of ($R_P$)-5gt

Crude UPLC® profile of ($S_P$)-7tt

Crude UPLC® profile of $(R_P)$-7tt

Crude UPLC® profile of ($S_P$)-8tt

Crude UPLC® profile of ($R_P$)-8tt

Crude UPLC® profile of All-($S_P$)-[$T_{PS}$]$_3$T

MALDI TOF-MS spectrum of All-$(S_P)$-$[T_{PS}]_3$T

Crude UPLC® profile of ($S_P$, $R_P$, $S_P$)-[$T_{PS}$]$_3$T

MALDI TOF-MS spectrum of $(S_P, R_P, S_P)$-$[T_{PS}]_3$T

Crude UPLC® profile of $(R_P, S_P, R_P)$-$[T_{PS}]_3T$

MALDI TOF-MS spectrum of $(R_P, S_P, R_P)\text{-}[T_{PS}]_3T$

Crude UPLC® profile of All-($R_P$)-[$T_{PS}$]$_3$T

MALDI TOF-MS spectrum of All-$(R_P)$-$[T_{PS}]_3$T

Crude UPLC® profile of $(S_P)$-9$u_M$u

MALDI TOF-MS spectrum of $(S_P)$-9$u_M$u

Crude UPLC® profile of $(R_P)$-9$u_M$u

MALDI TOF-MS spectrum of $(R_P)$-$9u_Mu$

Crude UPLC® profile of ($S_P$)-10u$_F$u

MALDI TOF-MS spectrum of $(S_P)$-10$u_F$u

Crude UPLC® profile of $(R_P)$-10u$_F$u

MALDI TOF-MS spectrum of $(R_P)$-10$u_F$u

Crude UPLC® profile of ($S_P$)-11nt

MALDI TOF-MS spectrum of $(S_P)$-11nt

Crude UPLC® profile of $(R_P)$-11nt

MALDI TOF-MS spectrum of $(R_P)$-11nt

METHOD FOR THE SYNTHESIS OF PHOSPHORUS ATOM MODIFIED NUCLEIC ACIDS

FIELD OF THE INVENTION

Described herein are methods of syntheses of phosphorous atom-modified nucleic acids comprising chiral X-phosphonate moieties. The methods described herein provide backbone-modified nucleic acids in high diastereomeric purity via an asymmetric reaction of an achiral molecule comprising a chemically stable H-phosphonate moiety with a nucleoside/nucleotide.

BACKGROUND OF THE INVENTION

Oligonucleotides are useful in therapeutic, diagnostic, research, and new and nanomaterials applications. The use of natural sequences of DNA or RNA is limited by their stability to nucleases. Additionally, in vitro studies have shown that the properties of antisense nucleotides such as binding affinity, sequence specific binding to the complementary RNA, stability to nucleases are affected by the configurations of the phosphorous atoms. Therefore, there is a need in the field for methods to produce oligonucleotides which are stereocontrolled at phosphorus and exhibit desired stability to degradation while retaining affinity for exogenous or endogenous complementary DNA/RNA sequences. There is a need for these compounds to be easily synthesized on solid support or in solution, and to permit a wide range of synthetic modifications on the sugars or nucleobases of the oligonucleotide.

Described herein are stereocontrolled syntheses of phosphorous atom-modified polymeric and oligomeric nucleic acids, which in some embodiments, is performed on solid support.

SUMMARY OF THE INVENTION

In one aspect of the invention, a method for a synthesis of a nucleic acid is provided comprising a chiral X-phosphonate moiety comprising reacting a molecule comprising an achiral H-phosphonate moiety and a nucleoside comprising a 5'-OH moiety to form a condensed intermediate; and converting the condensed intermediate to the nucleic acid comprising a chiral X-phosphonate moiety.

In some embodiments, the method wherein the step of reacting the molecule comprising an achiral H-phosphonate moiety and the nucleoside comprising a 5'-OH moiety to form a condensed intermediate is a one-pot reaction.

In some embodiments, the method provides a nucleic acid comprising a chiral X-phosphonate moiety of Formula 1.

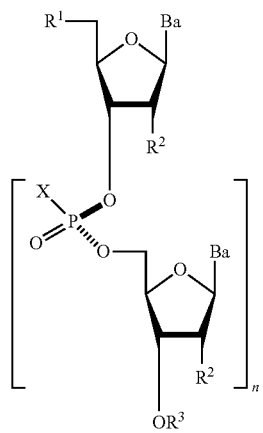

Formula 1

In some embodiments of the compound of Formula 1, $R^1$ is —OH, —SH, —$NR^d R^d$, —$N_3$, halogen, hydrogen, alkyl, alkenyl, alkynyl, alkyl-$Y^1$—, alkenyl-$Y^1$—, alkynyl-$Y^1$—, aryl-$Y^1$—, heteroaryl-$Y^1$—, —$P(O)(R^e)_2$, —$HP(O)(R^e)$, —$OR^a$ or —$SR^c$. $Y^1$ is O, $NR^d$, S, or Se. $R^a$ is a blocking moiety. $R^c$ is a blocking group. Each instance of $R^d$ is independently hydrogen, alkyl, alkenyl, alkynyl, aryl, acyl, substituted silyl, carbamate, —$P(O)(R^e)_2$, or —$HP(O)(R^e)$. Each instance of $R^e$ is independently hydrogen, alkyl, aryl, alkenyl, alkynyl, alkyl-$Y^2$—, alkenyl-$Y^2$—, alkynyl-$Y^2$—, aryl-$Y^2$—, or heteroaryl-$Y^2$—, or a cation which is $Na^{+1}$, $Li^{+1}$, or $K^{+1}$. $Y^2$ is O, $NR^d$, or S. Each instance of $R^2$ is independently hydrogen, —OH, —SH, —$NR^d R^d$, —$N_3$, halogen, alkyl, alkenyl, alkynyl, alkyl-$Y^1$—, alkenyl-$Y^1$—, alkynyl-$Y^1$—, aryl-$Y^1$—, heteroaryl-$Y^1$—, —$OR^b$, or —$SR^c$, wherein $R^b$ is a blocking moiety. Each instance of Ba is independently a blocked or unblocked adenine, cytosine, guanine, thymine, uracil or modified nucleobase. Each instance of X is independently alkyl, alkoxy, aryl, alkylthio, acyl, —$NR^f R^f$, alkenyloxy, alkynyloxy, alkenylthio, alkynylthio, —$S^- Z^+$, —$Se^- Z^+$, or —$BH_3^- Z^+$. Each instance of $R^f$ is independently hydrogen, alkyl, alkenyl, alkynyl, or aryl. $Z^+$ is ammonium ion, alkylammonium ion, heteroaromatic iminium ion, or heterocyclic iminium ion, any of which is primary, secondary, tertiary or quaternary, or Z is a monovalent metal ion. $R^3$ is hydrogen, a blocking group, a linking moiety connected to a solid support or a linking moiety connected to a nucleic acid; and n is an integer of 1 to about 200.

In some embodiments of the method, each X-phosphonate moiety of the compound of Formula 1 is more than 98% diastereomerically pure as determined by $^{31}P$ NMR spectroscopy or reverse-phase HPLC. In some embodiments of the method, each X-phosphonate moiety has a $R_P$ configuration. In other embodiments of the method, each X-phosphonate moiety has a $S_P$ configuration. In other embodiments of the method, each X-phosphonate independently has a $R_P$ configuration or a $S_P$ configuration.

In further embodiments of the method, the molecule comprising an achiral H-phosphonate moiety is a compound of Formula 2.

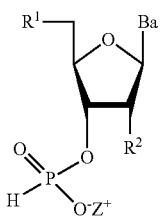

Formula 2

In Formula 2, $R^1$ is $-NR^dR^d$, $-N_3$, halogen, hydrogen, alkyl, alkenyl, alkynyl, alkyl-$Y^1$—, alkenyl-$Y^1$—, alkynyl-$Y^1$—, aryl-$Y^1$—, heteroaryl-$Y^1$—, $-P(O)(R^e)_2$, $-HP(O)(R^e)$, $-OR^a$, or $-SR^c$. $Y^1$ is O, $NR^d$, S, or Se. $R^a$ is a blocking moiety. $R^c$ is a blocking group. Each instance of $R^d$ is independently hydrogen, alkyl, alkenyl, alkynyl, aryl, acyl, substituted silyl, carbamate, $-P(O)(R^e)_2$, or $-HP(O)(R^e)$. Each instance of $R^e$ is independently alkyl, aryl, alkenyl, alkynyl, alkyl-$Y^2$—, alkenyl-$Y^2$—, alkynyl-$Y^2$—, aryl-$Y^2$—, or heteroaryl-$Y^2$—. $Y^2$ is O, $NR^d$, or S. $R^2$ is hydrogen, $-NR^dR^d$, $N_3$, halogen, alkyl, alkenyl, alkynyl, alkyl-$Y^1$—, alkenyl-$Y^1$—, alkynyl-$Y^1$—, aryl-$Y^1$—, heteroaryl-$Y^1$—, $-OR^b$, or $-SR^c$, wherein $R^b$ is a blocking moiety. Ba is a blocked or unblocked adenine, cytosine, guanine, thymine, uracil or modified nucleobase. $Z^+$ is ammonium ion, alkylammonium ion, heteroaromatic iminium ion, or heterocyclic iminium ion, any of which is primary, secondary, tertiary or quaternary, or a monovalent metal ion.

In some embodiments of the method, the method further comprises a chiral reagent. In yet other embodiments of the method, the chiral reagent is a compound of Formula 3.

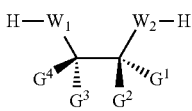

Formula 3

$W_1$ and $W_2$ are independently $-NG^5$-, $-O-$, or $-S-$. $G^1$, $G^2$, $G^3$, $G^4$, and $G^5$ are independently hydrogen, alkyl, aralkyl, cycloalkyl, cycloalkylalkyl, heterocyclyl, hetaryl, or aryl, or two of $G^1$, $G^2$, $G^3$, $G^4$, and $G^5$ are $G^6$ taken together form a saturated, partially unsaturated or unsaturated carbocyclic or heteroatom-containing ring of up to about 20 ring atoms which is monocyclic or polycyclic, fused or unfused, and wherein no more than four of $G^1$, $G^2$, $G^3$, $G^4$, and $G^5$ are $G^6$.

In some embodiments of the method, the nucleoside comprising a 5'-OH moiety is a compound of Formula 4.

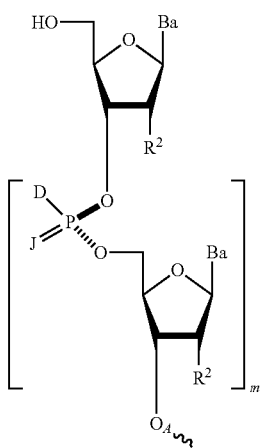

Formula 4

Each instance of $R^2$ is independently hydrogen, $-NR^dR^d$, $N_3$, halogen, alkyl, alkenyl, alkynyl, alkyl-$Y^1$—, alkenyl-$Y^1$—, alkynyl-$Y^1$—, aryl-$Y^1$—, heteroaryl-$Y^1$—, $-OR^b$, or $-SR^c$, wherein $R^b$ is a blocking moiety. $Y^1$ is O, $NR^d$, S, or Se. $R^c$ is a blocking group. Each instance of $R^d$ is independently hydrogen, alkyl, alkenyl, alkynyl, aryl, acyl, substituted silyl, carbamate, $-P(O)(R^e)_2$, or $-HP(O)(R^e)$. Each instance of $R^e$ is independently alkyl, aryl, alkenyl, alkynyl, alkyl-$Y^2$—, alkenyl-$Y^2$—, alkynyl-$Y^2$—, aryl-$Y^2$—, or heteroaryl-$Y^2$—. $Y^2$ is O, $NR^d$, or S. Each instance of Ba is independently a blocked or unblocked adenine, cytosine, guanine, thymine, uracil or modified nucleobase. m is an integer of 0 to n–1. n is an integer of 1 to about 200. $O_A$ is connected to a trityl moiety, a silyl moiety, an acetyl moiety, an acyl moiety, an aryl acyl moiety, a linking moiety connected to a solid support or a linking moiety connected to a nucleic acid. J is O and D is H, or J is S, Se, or $BH_3$ and D is a chiral ligand $C_i$ or a moiety of Formula A.

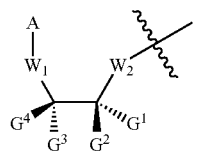

Formula A

In Formula A, $W_1$ and $W_2$ are independently $NHG^5$, OH, or SH. A is hydrogen, acyl, aryl, alkyl, aralkyl, or a silyl moiety. $G^1$, $G^2$, $G^3$, $G^4$, and $G^5$ are independently hydrogen, alkyl, aralkyl, cycloalkyl, cycloalkylalkyl, heterocyclyl, heteroaryl, or aryl, or two of $G^1$, $G^2$, $G^3$, $G^4$, and $G^5$ are $G^6$ which taken together form a saturated, partially unsaturated or unsaturated carbocyclic or heteroatom-containing ring of up to about 20 ring atoms which is monocyclic or polycyclic, fused or unfused and wherein no more than four of $G^1$, $G^2$, $G^3$, $G^4$, and $G^5$ are $G^6$.

In yet other embodiments of the method, the method further comprises providing a condensing reagent $C_R$ whereby the molecule comprising an achiral H-phosphonate moiety is activated to react with the chiral reagent to form a chiral intermediate.

In further embodiments of the method, the condensing reagent $C_R$ is $Ar_3PL_2$, $(ArO)_3PL_2$,

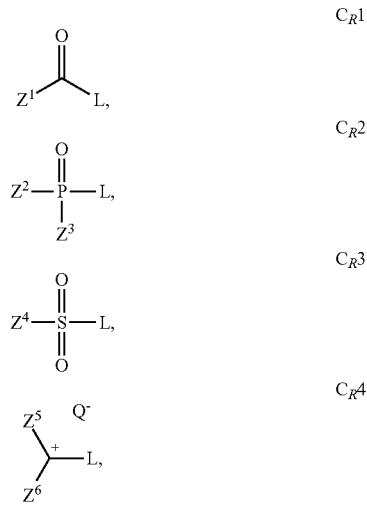

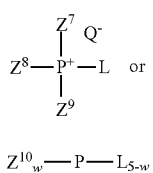
$C_R5$ or $Z^{10}{}_w-P-L_{5-w}$   $C_R6$ $Z^1$, $Z^2$, $Z^3$, $Z^4$, $Z^5$, $Z^6$, $Z^7$, $Z^8$, $Z^9$ and $Z^{10}$ are independently alkyl, aminoalkyl, cycloalkyl, heterocyclic, cycloalkylalkyl, heterocycloalkyl, aryl, heteroaryl, alkyloxy, aryloxy, or heteroaryloxy, or wherein any of $Z^2$ and $Z^3$, $Z^5$ and $Z^6$, $Z^7$ and $Z^8$, $Z^8$ and $Z^9$, $Z^9$ and $Z^7$, or $Z^7$ and $Z^8$ and $Z^9$ are taken together to form a 3 to 20 membered alicyclic or heterocyclic ring. $Q^-$ is a counter anion, L is a leaving group, and w is an integer of 0 to 3. Ar is aryl, heteroaryl, and/or one of Ar group is attached to the polymer support. In some embodiments of the method, the counter ion of the condensing reagent $C_R$ is $Cl^-$, $Br^-$, $BF_4^-$, $PF_6^-$, $TfO^-$, $Tf_2N^-$, $AsF_6^-$, $ClO_4^-$, or $SbF_6^-$, wherein Tf is $CF_3SO_2$. In other embodiments of the method, the leaving group of the condensing reagent $C_R$ is F, Cl, Br, I, 3-nitro-1,2,4-triazole, imidazole, alkyltriazole, tetrazole, pentafluorobenzene, or 1-hydroxybenzotriazole.

In some embodiments of the method, the condensing reagent is phosgene, trichloromethyl chloroformate, bis(trichloromethyl)carbonate (BTC), oxalyl chloride, $Ph_3PCl_2$, $(PhO)_3PCl_2$, N,N'-bis(2-oxo-3-oxazolidinyl)phosphinic chloride (BopCl), 1,3-dimethyl-2-(3-nitro-1,2,4-triazol-1-yl)-2-pyrrolidin-1-yl-1,3,2-diazaphospholidinium hexafluorophosphate (MNTP), or 3-nitro-1,2,4-triazol-1-yl-tris(pyrrolidin-1-yl)phosphonium hexafluorophosphate (PyNTP).

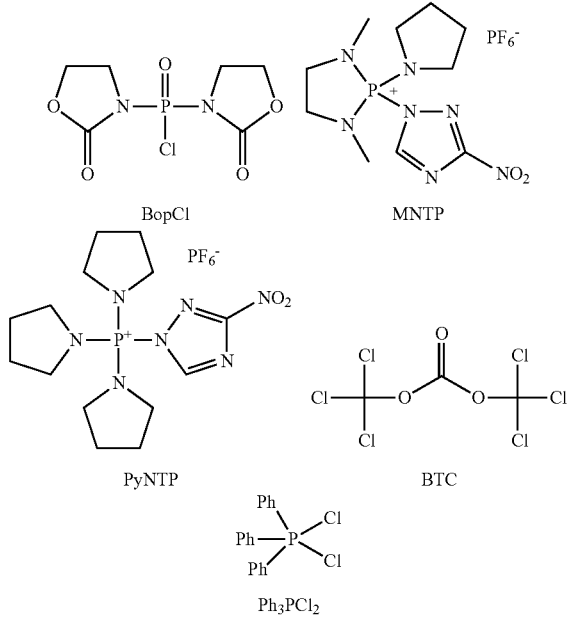

In a further embodiment of the method, the method further comprises providing an activating reagent $A_R$. In one embodiment, the activating reagent $A_R$ is

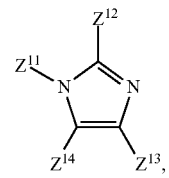
$A_R1$

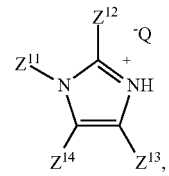
$A_R2$

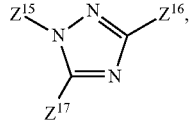
$A_R3$

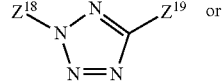  or
$A_R4$

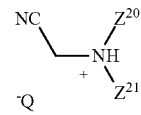
$A_R5$ wherein $Z^{11}$, $Z^{12}$, $Z^{13}$, $Z^{14}$, $Z^{15}$, $Z^{16}$, $Z^{17}$, $Z^{18}$, $Z^{19}$, $Z^{20}$, and $Z^{21}$ are independently hydrogen, alkyl, aminoalkyl, cycloalkyl, heterocyclic, cycloalkylalkyl, heterocycloalkyl, aryl, heteroaryl, alkyloxy, aryloxy, or heteroaryloxy, or wherein any of $Z^{11}$ and $Z^{12}$, $Z^{11}$ and $Z^{13}$, $Z^{11}$ and $Z^{14}$, $Z^{12}$ and $Z^{13}$, $Z^{12}$ and $Z^{14}$, $Z^{13}$ and $Z^{14}$, $Z^{15}$ and $Z^{16}$, $Z^{15}$ and $Z^{17}$, $Z^{16}$ and $Z^{17}$, $Z^{18}$ and $Z^{19}$, or $Z^{20}$ and $Z^{21}$ are taken together to form a 3 to 20 membered alicyclic or heterocyclic ring, or to form 5 or 20 membered aromatic irng; and $Q^-$ is a counter ion. In an embodiment, the counter ion of the activating reagent $A_R$ is $Cl^-$, $Br^-$, $BF_4^-$, $PF_6^-$, $TfO^-$, $Tf_2N^-$, $AsF_6^-$, $ClO_4^-$, or $SbF_6^-$, wherein Tf is $CF_3SO_2$. In one embodiment, the activating reagent $A_R$ is imidazole, 4,5-dicyanoimidazole (DCI), 4,5-dichloroimidazole, 1-phenylimidazolium triflate (PhIMT), benzimidazolium triflate (BIT), benztriazole, 3-nitro-1,2,4-triazole (NT), tetrazole, 5-ethylthiotetrazole, 5-(4-nitrophenyl)tetrazole, N-cyanomethylpyrrolidinium triflate (CMPT), N-cyanomethylpiperidinium triflate, N-cyanomethyldimethylammonium triflate. In another embodiment, the activating reagent $A_R$ is 4,5-dicyanoimidazole (DCI), 1-phenylimidazolium triflate (PhIMT), benzimidazolium triflate (BIT), 3-nitro-1,2,4-triazole (NT), tetrazole, or N-cyanomethylpyrrolidinium triflate (CMPT).

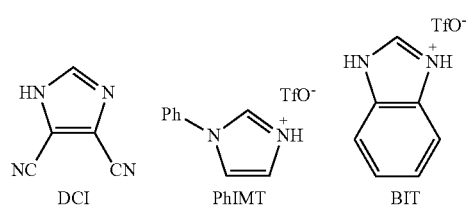

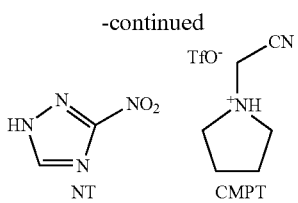

In an embodiment, the activating reagent $A_R$ is N-cyanomethylpyrrolidinium triflate (CMPT).

In some embodiments of the method, the reaction is performed in an aprotic organic solvent. In other embodiments of the method, the solvent is acetonitrile, pyridine, tetrahydrofuran, or dichloromethane. In other embodiments of the method, when the aprotic organic solvent is not basic, a base is present in the reacting step. In some embodiments of the method, the base is pyridine, quinoline, or N,N-dimethylaniline. In some embodiments of the method, the base is

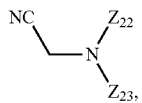

wherein $Z^{22}$ and $Z^{23}$ are independently alkyl, aminoalkyl, cycloalkyl, heterocyclic, cycloalkylalkyl, heterocycloalkyl, aryl, heteroaryl, alkyloxy, aryloxy, or heteroaryloxy, or wherein any of $Z^{22}$ and $Z^{23}$ are taken together to form a 3 to 10 membered alicyclic or heterocyclic ring. In some embodiments of the method, the base is N-cyanomethylpyrrolidine. In some embodiments of the method, the aprotic organic solvent is anhydrous. In other embodiments of the method, the anhydrous aprotic organic solvent is freshly distilled. In yet other embodiments of the method, the freshly distilled anhydrous aprotic organic solvent is pyridine. In another embodiment of the method, the freshly distilled anhydrous aprotic organic solvent is acetonitrile.

In some embodiments of the method, the step of converting the condensed intermediate to a compound of Formula 1 comprises: modifying the condensed intermediate to produce a compound of Formula 5.

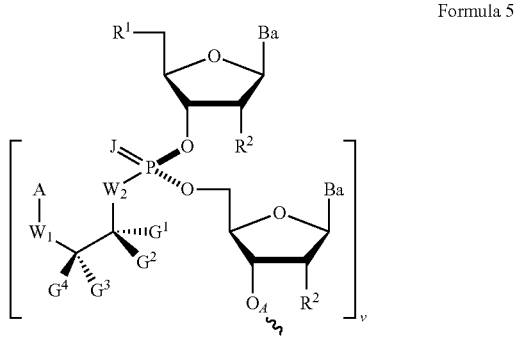

Formula 5

In Formula 5, $R^1$ is $-NR^dR^d$, $-N_3$, halogen, hydrogen, alkyl, alkenyl, alkynyl, alkyl-$Y^1$—, alkenyl-$Y^1$—, alkynyl-$Y^1$—, aryl-$Y^1$—, heteroaryl-$Y^1$—, $-P(O)(R^e)_2$, $-HP(O)(R^e)$, $-OR^a$, or $-SR^c$. $Y^1$ is O, $NR^d$, S, or Se. $R^a$ is a blocking moiety. $R^c$ is a blocking group. Each instance of $R^d$ is independently hydrogen, alkyl, alkenyl, alkynyl, aryl, acyl, substituted silyl, carbamate, $-P(O)(R^e)_2$, or $-HP(O)(R^e)$. Each instance of $R^e$ is independently alkyl, aryl, alkenyl, alkynyl, alkyl-$Y^2$—, alkenyl-$Y^2$—, alkynyl-$Y^2$—, aryl-$Y^2$—, or heteroaryl-$Y^2$—. $Y^2$ is O, $NR^d$, or S. Each instance of $R^2$ is independently hydrogen, $-NR^dR^d$, $N_3$, halogen, alkyl, alkenyl, alkynyl, alkyl-$Y^1$—, alkenyl-$Y^1$—, alkynyl-$Y^1$—, aryl-$Y^1$—, heteroaryl-$Y^1$—, $-OR^b$, or $-SR^c$, wherein $R^b$ is a blocking moiety. Each instance of Ba is independently a blocked or unblocked adenine, cytosine, guanine, thymine, uracil, or modified nucleobase. Each instance of J is S, Se, or $BH_3$. v is an integer of 1. $O_A$ is connected to a linking moiety connected to a solid support or a linking moiety connected to a nucleic acid. A is an acyl, aryl, alkyl, aralkyl, or silyl moiety. $G^1$, $G^2$, $G^3$, $G^4$, and $G^5$ are independently hydrogen, alkyl, aralkyl, cycloalkyl, cycloalkylalkyl, heterocyclyl, heteroaryl, or aryl, or two of $G^1$, $G^2$, $G^3$, $G^4$, and $G^5$ are $G^6$ which taken together form a saturated, partially unsaturated or unsaturated carbocyclic or heteroatom-containing ring of up to about 20 ring atoms which is monocyclic or polycyclic, fused or unfused and wherein no more than four of $G^1$, $G^2$, $G^3$, $G^4$, and $G^5$ are $G^6$.

In some embodiments of the method, the step of converting the condensed intermediate to a compound of Formula 1 comprises: capping the condensed intermediate and modifying the capped condensed intermediate to produce a compound of Formula 5.

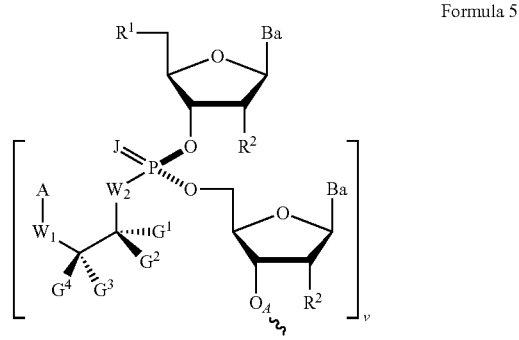

Formula 5

In Formula 5, $R^1$ is $-NR^dR^d$, $-N_3$, halogen, hydrogen, alkyl, alkenyl, alkynyl, alkyl-$Y^1$—, alkenyl-$Y^1$—, alkynyl-$Y^1$—, aryl-$Y^1$—, heteroaryl-$Y^1$—, $-P(O)(R^e)_2$, $-HP(O)(R^e)$, $-OR^a$, or $-SR^c$. $Y^1$ is O, $NR^d$, S, or Se. $R^a$ is a blocking moiety. $R^c$ is a blocking group. Each instance of $R^d$ is independently hydrogen, alkyl, alkenyl, alkynyl, aryl, acyl, substituted silyl, carbamate, $-P(O)(R^e)_2$, or $-HP(O)(R^e)$. Each instance of $R^e$ is independently alkyl, aryl, alkenyl, alkynyl, alkyl-$Y^2$—, alkenyl-$Y^2$—, alkynyl-$Y^2$—, aryl-$Y^2$—, or heteroaryl-$Y^2$—. $Y^2$ is O, $NR^d$, or S. Each instance of $R^2$ is independently hydrogen, $-NR^dR^d$, $N_3$, halogen, alkyl, alkenyl, alkynyl, alkyl-$Y^1$—, alkenyl-$Y^1$—, alkynyl-$Y^1$—, aryl-$Y^1$—, heteroaryl-$Y^1$—, $-OR^b$, or $-SR^e$, wherein $R^b$ is a blocking moiety. Each instance of Ba is independently a blocked or unblocked adenine, cytosine, guanine, thymine, uracil, or modified nucleobase. Each instance of J is S, Se, or $BH_3$. v is an integer of 2 to n−1. $O_A$ is connected to a linking moiety connected to a solid support or a linking moiety connected to a nucleic acid. A is an acyl, aryl, alkyl, aralkyl, or silyl moiety. $G^1$, $G^2$, $G^3$, $G^4$, and $G^5$ are independently hydrogen, alkyl, aralkyl, cycloalkyl, cycloalkylalkyl, heterocyclyl, heteroaryl, or aryl, or two of $G^1$, $G^2$, $G^3$, $G^4$, and $G^5$ are $G^6$ which taken together form a saturated, partially unsaturated or unsaturated carbocyclic or heteroatom-containing ring of up to about 20 ring atoms which is monocyclic or polycyclic, fused or unfused and wherein no more than four of $G^1$, $G^2$, $G^3$, $G^4$, and $G^5$ are $G^6$.

In some embodiments of the method, the method further comprises the steps of: (a) deblocking $R^1$ of the compound of Formula 5 to produce a compound of Formula 4 wherein m is at least 1, J is S, Se, or $BH_3$ and D is a moiety of Formula A; (b) reacting the compound of Formula 4 using the method of claim 10 wherein the step of converting the condensed intermediate comprises capping the condensed intermediate and modifying the capped condensed intermediate to produce a compound of Formula 5 wherein v is greater than 2 and less than about 200; and (c) optionally repeating steps (a) and (b) to form a compound of Formula 5 wherein v is greater than 3 and less than about 200.

In other embodiments of the method, the method further comprises the step of converting the compound of Formula 5 to the compound of Formula 1 wherein each Ba moiety is unblocked. $R^1$ is —OH, —SH, —$NR^dR^d$, —$N_3$, halogen, hydrogen, alkyl, alkenyl, alkynyl, alkyl-$Y^1$—, alkenyl-$Y^1$—, alkynyl-$Y^1$—, aryl-$Y^1$—, heteroaryl-$Y^1$—, —$P(O)(R^e)_2$, —$HP(O)(R^e)$, —$OR^a$ or —$SR^e$. $Y^1$ is O, $NR^d$, S, or Se. $R^a$ is a blocking moiety. $R^c$ is a blocking group. Each instance of $R^d$ is independently hydrogen, alkyl, alkenyl, alkynyl, aryl, acyl, substituted silyl, carbamate, —$P(O)(R^e)_2$, or —$HP(O)(R^e)$. Each instance of $R^e$ is independently hydrogen, alkyl, aryl, alkenyl, alkynyl, alkyl-$Y^2$—, alkenyl-$Y^2$—, alkynyl-$Y^2$—, or heteroaryl-$Y^2$—, or a cation which is $Na^{+1}$, $Li^{+1}$, or $K^{+1}$. $Y^2$ is O, $NR^d$, or S. Each instance of $R^2$ is independently hydrogen, —OH, —SH, —$NR^dR^d$, —$N_3$, halogen, alkyl, alkenyl, alkynyl, alkyl-$Y^1$—, alkenyl-$Y^1$—, alkynyl-$Y^1$—, aryl-$Y^1$—, heteroaryl-$Y^1$—, —$OR^b$, or —$SR^c$, wherein $R^b$ is a blocking moiety. $R^3$ is H. Each instance of X is independently —$S^-Z^+$, —$Se^-Z^+$, or —$BH_3^-Z^+$. $Z^+$ is ammonium ion, alkylammonium ion, heteroaromatic iminium ion, or heterocyclic iminium ion, any of which is primary, secondary, tertiary or quaternary, or Z is a monovalent metal ion.

In some embodiments of the method, the step of converting the condensed intermediate to a compound of Formula 1 comprises acidifying the condensed intermediate to produce a compound of Formula 4, wherein m is at least one, J is O, and D is H. In some embodiments of the method, the condensed intermediate comprises a moiety of Formula A'.

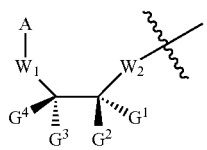

Formula A'

A is hydrogen and $G^1$ and $G^2$ are independently alkyl, aralkyl, cycloalkyl, cycloalkylalkyl, heteroaryl, or aryl and $G^3$, $G^4$, and $G^5$ are independently hydrogen, alkyl, aralkyl, cycloalkyl, cycloalkylalkyl, heterocyclyl, heteroaryl, or aryl, or two of $G^1$, $G^2$, $G^3$, $G^4$, and $G^5$ are $G^6$ which taken together form a saturated, partially unsaturated or unsaturated carbocyclic or heteroatom-containing ring of up to about 20 ring atoms which is monocyclic or polycyclic, fused or unfused and wherein no more than four of $G^1$, $G^2$, $G^3$, $G^4$, and $G^5$ are $G^6$.

In some embodiments of the method, the method further comprises: (a) reacting the compound of Formula 4 wherein m is at least one, J is O, and D is H, using the method of claim 10 wherein the step of converting the condensed intermediate to a compound of Formula 1 comprises acidifying the condensed intermediate to produce a compound of Formula 4 wherein m is at least 2 and less than about 200; J is O, and D is H, and (b) optionally repeating step (a) to produce a compound of Formula 4 wherein m is greater than 2 and less than about 200.

In some embodiments of the method, the acidifying comprises adding an amount of a Brønsted or Lewis acid effective to convert the condensed intermediate into the compound of Formula 4 without removing purine or pyrimidine moieties from the condensed intermediate. In other embodiments of the method, the acidifying comprises adding 1% trifluoroacetic acid in an organic solvent, 3% dichloroacetic acid in an organic solvent, or 3% trichloroacetic acid in an organic solvent. In yet other embodiments of the method, the acidifying further comprises adding a cation scavenger. In some embodiments of the method, the cation scavenger is triethylsilane or triisopropylsilane.

In some embodiments of the method, the step of converting the condensed intermediate to a compound of Formula 1 further comprises deblocking $R^1$ prior to the step of acidifying the condensed intermediate.

In other embodiments of the method, the method further comprises the step of modifying the compound of Formula 4 to introduce an X moiety thereby producing a compound of Formula 1 wherein $R^3$ is a blocking group or a linking moiety connected to a solid support.

In yet other embodiments of the method, the method further comprises treating an X-modified compound to produce a compound of Formula 1 wherein $R^1$ is —OH, —SH, —$NR^dR^d$, —$N_3$, halogen, hydrogen, alkyl, alkenyl, alkynyl, alkyl-$Y^1$—, alkenyl-$Y^1$—, alkynyl-$Y^1$—, aryl-$Y^1$—, heteroaryl-$Y^1$—, —$P(O)(R^e)_2$, —$HP(O)(R^e)$, —$OR^a$ or —$SR^c$. $Y^1$ is O, $NR^d$, S, or Se. $R^a$ is a blocking moiety. $R^e$ is a blocking group. Each instance of $R^d$ is independently hydrogen, alkyl, alkenyl, alkynyl, aryl, acyl, substituted silyl, carbamate, —$P(O)(R^e)_2$, or —$HP(O)(R^e)$. Each instance of $R^e$ is independently hydrogen, alkyl, aryl, alkenyl, alkynyl, alkyl-$Y^2$—, alkenyl-$Y^2$—, alkynyl-$Y^2$—, aryl-$Y^2$—, or heteroaryl-$Y^2$—, or a cation which is $Na^{+1}$, $Li^{+1}$, or $K^{+1}$. $Y^2$ is O, $NR^d$, or S. Each instance of $R^2$ is independently hydrogen, —OH, —SH, —$NR^dR^d$, —$N_3$, halogen, alkyl, alkenyl, alkynyl, alkyl-$Y^1$—, alkenyl-$Y^1$—, alkynyl-$Y^1$—, aryl-$Y^1$—, heteroaryl-$Y^1$—, —$OR^b$, or —$SR^c$, wherein $R^b$ is a blocking moiety. Each Ba moiety is unblocked. $R^3$ is H. Each instance of X is independently alkyl, alkoxy, aryl, alkylthio, acyl, —$NR^fR^f$, alkenyloxy, alkynyloxy, alkenylthio, alkynylthio, —$S^-Z^+$, —$Se^-Z^+$, or —$BH_3^-Z^+$. Each instance of $R^f$ is independently hydrogen, alkyl, alkenyl, alkynyl, or aryl. $Z^+$ is ammonium ion, alkylammonium ion, heteroaromatic iminium ion, or heterocyclic iminium ion, any of which is primary, secondary, tertiary or quaternary, or Z is a monovalent metal ion. n is greater than 1 and less than about 200.

In some embodiments of the method, the modifying step is performed using a boronating agent, a sulfur electrophile, or a selenium electrophile.

In some embodiments of the method, the sulfur electrophile is a compound having one of the following formulas:

$$S_8 \qquad \text{(Formula B)},$$

$$Z^{24}\text{—S—S—}Z^{25},$$

or $$Z^{24}\text{—S—X—}Z^{25}.$$

$Z^{24}$ and $Z^{25}$ are independently alkyl, aminoalkyl, cycloalkyl, heterocyclic, cycloalkylalkyl, heterocycloalkyl, aryl, heteroaryl, alkyloxy, aryloxy, heteroaryloxy, acyl, amide, imide, or thiocarbonyl, or $Z^{24}$ and $Z^{25}$ are taken together to form a 3 to 8 membered alicyclic or heterocyclic ring, which may be substituted or unsubstituted; X is $SO_2$, O, or $NR^f$; and $R^f$ is hydrogen, alkyl, alkenyl, alkynyl, or aryl.

In some embodiments of the method, the sulfur electrophile is a compound of Formula B, C, D, E, or F:

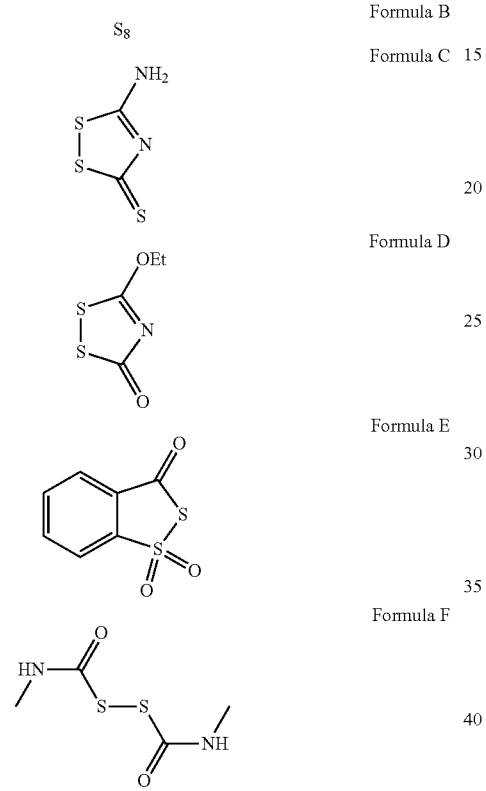

In some embodiments of the method, the selenium electrophile is a compound having one of the following formulas:

Se            (Formula G), $Z^{26}$—Se—Se—$Z^{27}$, or $Z^{26}$—Se—X—$Z^{27}$ $Z^{26}$ and $Z^{27}$ are independently alkyl, aminoalkyl, cycloalkyl, heterocyclic, cycloalkylalkyl, heterocycloalkyl, aryl, heteroaryl, alkyloxy, aryloxy, heteroaryloxy, acyl, amide, imide, or thiocarbonyl, or $Z^{26}$ and $Z^{27}$ are taken together to form a 3 to 8 membered alicyclic or heterocyclic ring, which may be substituted or unsubstituted; X is $SO_2$, S, O, or $NR^f$; and $R^f$ is hydrogen, alkyl, alkenyl, alkynyl, or aryl.

In some embodiments of the method, the selenium electrophile is a compound of Formula G, H, I, J, K, or L.

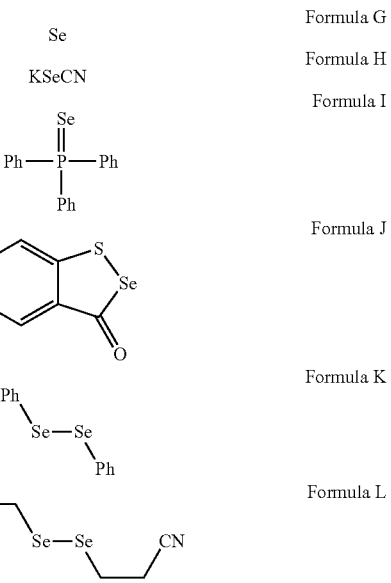

In some embodiments of the method, the boronating agent is borane-N,N-diisopropylethylamine ($BH_3$.DIPEA), borane-pyridine ($BH_3$.Py), borane-2-chloropyridine ($BH_3$.CPy), borane-aniline ($BH_3$.An), borane-tetrahydrofurane ($BH_3$.THF), or borane-dimethylsulfide ($BH_3$.$Me_2$S).

In some embodiments of the method, the modifying step is performed using a silylating reagent followed by a sulfur electrophile, a selenium electrophile, a boronating agent, an alkylating agent, an aldehyde, or an acylating agent.

In some embodiments of the method, the silylating reagent is chlorotrimethylsilane (TMS-Cl), triisopropylsilylchloride (TIPS-Cl), t-butyldimethylsilylchloride (TBDMS-Cl), t-butyldiphenylsilylchloride (TBDPS-Cl), 1,1,1,3,3,3-hexamethyldisilazane (HMDS), N-trimethylsilyldimethylamine (TMSDMA), N-trimethylsilyldiethylamine (TMSDEA), N-trimethylsilylacetamide (TMSA), N,O-bis(trimethylsilyl)acetamide (BSA), or N,O-bis(trimethylsilyl)trifluoroacetamide (BSTFA).

In some embodiments of the method, the sulfur electrophile is a compound having one of the following formulas: $S_8$ (Formula B), $Z^{24}$—S—S—$Z^{25}$, or $Z^{24}$—S—X—$Z^{25}$, wherein $Z^{24}$ and $Z^{25}$ are independently alkyl, aminoalkyl, cycloalkyl, heterocyclic, cycloalkylalkyl, heterocycloalkyl, aryl, heteroaryl, alkyloxy, aryloxy, heteroaryloxy, acyl, amide, imide, or thiocarbonyl, or $Z^{24}$ and $Z^{25}$ are taken together to form a 3 to 8 membered alicyclic or heterocyclic ring, which may be substituted or unsubstituted; X is $SO_2$, O, or $NR^f$; and $R^f$ is hydrogen, alkyl, alkenyl, alkynyl, or aryl.

In some embodiments of the method, the sulfur electrophile is a compound of Formula B, C, D, E, or F:

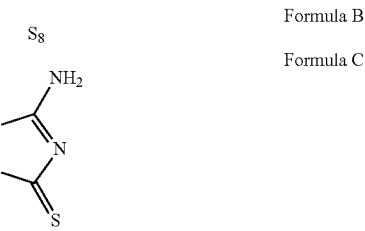

-continued

Formula D
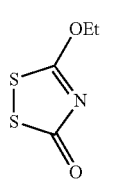

Formula E
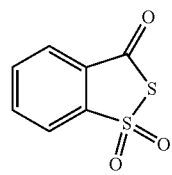

Formula F
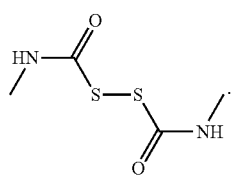

In some embodiments of the method, the selenium electrophile is a compound having one of the following formulas: Se (Formula G), $Z^{26}$—Se—Se—$Z^{27}$, or $Z^{26}$—Se—X—$Z^{27}$, wherein $Z^{26}$ and $Z^{27}$ are independently alkyl, aminoalkyl, cycloalkyl, heterocyclic, cycloalkylalkyl, heterocycloalkyl, aryl, heteroaryl, alkyloxy, aryloxy, heteroaryloxy, acyl, amide, imide, or thiocarbonyl, or $Z^{26}$ and $Z^{27}$ are taken together to form a 3 to 8 membered alicyclic or heterocyclic ring, which may be substituted or unsubstituted; X is $SO_2$, S, O, or $NR^f$; and $R^f$ is hydrogen, alkyl, alkenyl, alkynyl, or aryl.

In some embodiments of the method, the selenium electrophile is a compound of Formula G, H, I, J, K, or L:

Formula G
Se

Formula H
KSeCN

Formula I
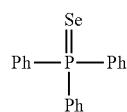

Formula J
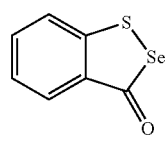

Formula K
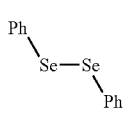

Formula L
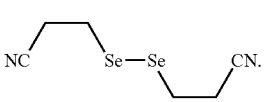

In some embodiments of the method, the boronating agent is borane-N,N-diisopropylethylamine ($BH_3$.DIPEA), borane-pyridine ($BH_3$.Py), borane-2-chloropyridine ($BH_3$.CPy), borane-aniline ($BH_3$.An), borane-tetrahydrofurane ($BH_3$.THF), or borane-dimethylsulfide ($BH_3$.Me$_2$S).

In some embodiments of the method, the alkylating agent is an alkyl halide, alkenyl halide, alkynyl halide, alkyl sulfonate, alkenyl sulfonate, or alkynyl sulfonate. In other embodiments of the method, the aldehyde is (para)-formaldehyde, alkyl aldehyde, alkenyl aldehyde, alkynyl aldehyde, or aryl aldehyde.

In some embodiments of the method, the acylating agent is a compound of Formula M or N.

Formula M
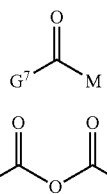

Formula N
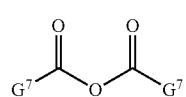

$G^7$ is alkyl, cycloalkyl, heterocyclic, cycloalkylalkyl, heterocycloalkyl, aryl, heteroaryl, alkyloxy, aryloxy, or heteroaryloxy; and M is F, Cl, Br, I, 3-nitro-1,2,4-triazole, imidazole, alkyltriazole, tetrazole, pentafluorobenzene, or 1-hydroxybenzotriazole.

In some embodiments of the method, the modifying step is performed by reacting with a halogenating reagent followed by reacting with a nucleophile. In some embodiments of the method, the halogenating reagent is $CCl_4$, $CBr_4$, $Cl_2$, $Br_2$, $I_2$, sulfuryl chloride ($SO_2Cl_2$), phosgene, bis(trichloromethyl)carbonate (BTC), sulfur monochloride, sulfur dichloride, chloramine, $CuCl_2$, N-chlorosuccinimide (NCS), $CI_4$, N-bromosuccinimide (NBS), or N-iodosuccinimide (NIS). In other embodiments of the method, the nucleophile is $NR'R'H$, $R'OH$, or $R'SH$, wherein $R'$ is hydrogen, alkyl, alkenyl, alkynyl, or aryl, and at least one of $R'$ of $NR'R'H$ is not hydrogen.

In some embodiments of the method, the chiral reagent is the compound of Formula 3 wherein $W_1$ is $NHG^5$ and $W_2$ is OH. In some embodiments of the method, the chiral reagent is Formula O or Formula P.

Formula O
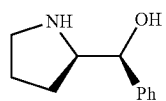

Formula P
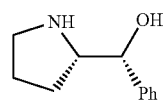

In some embodiments of the method, the chiral reagent is Formula Q or Formula R.

Formula Q
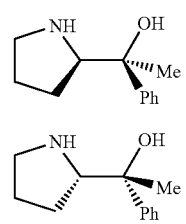

Formula R
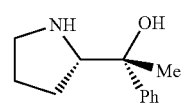

In some embodiments of the method, $R^a$ is substituted or unsubstituted trityl or substituted silyl. In other embodiments of the method, wherein $R^a$ is substituted or unsubstituted trityl or substituted silyl. In other embodiments of the method, $R^b$ is substituted or unsubstituted trityl, substituted silyl, acetyl, acyl, or substituted methyl ether.

In some embodiments of the method, $R^3$ is a blocking group which is substituted trityl, acyl, substituted silyl, or substituted benzyl. In other embodiments of the method, $R^3$ is a linking moiety connected to a solid support.

In some embodiments of the method, the blocking group of the Ba moiety is a benzyl, acyl, formyl, dialkylformamidinyl, isobutyryl, phenoxyacetyl, or trityl moiety, any of which may be unsubstituted or substituted. In some embodiments of the method, $R^1$ is —$N_3$, —$NR^dR^d$, alkynyloxy, or —OH. In some embodiments of the method, $R^1$ is —$N_3$, —$NR^dR^d$, alkynyloxy, or —OH. In other embodiments of the method, $R^2$ is —$NR^dR^d$, alkyl, alkenyl, alkynyl, alkyl-$Y^1$—, alkenyl-$Y^1$—, alkynyl-$Y^1$—, aryl-$Y^1$—, or heteroaryl-$Y^1$—, and is substituted with fluorescent or biomolecule binding moieties. In yet other embodiments of the method, $R^2$ is —$NR^dR^d$, alkyl, alkenyl, alkynyl, alkyl-$Y^1$—, alkenyl-$Y^1$—, alkynyl-$Y^1$—, aryl-$Y^1$—, or heteroaryl-$Y^1$—, and is substituted with fluorescent or biomolecule binding moieties.

In some embodiments of the method, the substituent on $R^2$ is a fluorescent moiety. In other embodiments of the method, the substituent on $R^2$ is biotin or avidin. In yet other embodiments of the method, the substituent on $R^2$ is a fluorescent moiety. In some embodiments of the method, the substituent on $R^2$ is biotin or avidin. In other embodiments of the method, $R^2$ is —OH, —$N_3$, hydrogen, halogen, alkoxy, or alkynyloxy. In yet other embodiments of the method, $R^2$ is —OH, —$N_3$, hydrogen, halogen, alkoxy, or alkynyloxy.

In some embodiments of the method, Ba is 5-bromouracil, 5-iodouracil, or 2,6-diaminopurine. In other embodiments of the method, Ba is modified by substitution with a fluorescent or biomolecule binding moiety. In yet other embodiments of the method, Ba is modified by substitution with a fluorescent or biomolecule binding moiety. In some embodiments of the method, the substituent on Ba is a fluorescent moiety. In other embodiments of the method, the substituent on Ba is biotin or avidin. In yet other embodiments of the method, the substituent on Ba is a fluorescent moiety. In some embodiments of the method, the substituent on Ba is biotin or avidin.

In some embodiments of the method, Z is pyridinium ion, triethylammonium ion, N,N-diisopropylethylammonium ion, 1,8-diazabicyclo[5.4.0]undec-7-enium ion, sodium ion, or potassium ion. In other embodiments of the method, Z is pyridinium ion, triethylammonium ion, N,N-diisopropylethylammonium ion, 1,8-diazabicyclo[5.4.0]undec-7-enium ion, sodium ion, or potassium ion. In some embodiments of the method, X is alkyl, alkoxy, —$NR^fR^f$, —$S^-Z^+$, or —$BH_3^-Z^+$. In other embodiments of the method, X is alkyl, alkoxy, —$NR^fR^f$, —$S^-Z^+$, or —$BH_3^-Z^+$.

In an embodiment of the method, the sulfur electrophile is Formula F, Formula E or Formula B. In some embodiments of the method, the sulfur electrophile is Formula F, Formula E or Formula B. In other embodiments of the method, the selenium electrophile is Formula G or Formula L. In yet other embodiments of the method, the selenium electrophile is Formula G or Formula L. In some embodiments of the method, the boronating agent is borane-N,N-diisopropylethylamine ($BH_3$.DIPEA), borane-2-chloropyridine ($BH_3$.CPy), borane-tetrahydrofurane ($BH_3$.THF), or borane-dimethylsulfide ($BH_3$.$Me_2$S). In other embodiments of the method, the halogenating agent is $CCl_4$, $CBr_4$, $Cl_2$, sulfuryl chloride ($SO_2Cl_2$), or N-chlorosuccinimide (NCS). In yet other embodiments of the method, the condensing reagent is bis(trichloromethyl)carbonate (BTC), $Ph_3PCl_2$, or N,N'-bis(2-oxo-3-oxazolidinyl)phosphinic chloride (BopCl).

In another aspect of the invention, a method is provided of identifying or detecting a target molecule in a sample, the method comprising: contacting a sample suspected of containing a target molecule with a nucleic acid sensor molecule of Formula 1, synthesized according to the methods of the invention, wherein a change in a signal generated by a signal generating unit indicates the presence of said target in said sample. The nucleic acid sensor molecule binds specifically with the target molecule. In some embodiments there is a plurality of nucleic acid sensor molecules. In some embodiments, the plurality of nucleic acid sensor molecules comprises nucleic acid sensor molecules which bind specifically to differing target molecules. In some instances, the method further comprises quantifying the change in signal generated by the signal generating unit to quantify the amount of target molecule in the sample. The signal generating unit detects any sort of signal, including but not limited to fluorescence, surface plasmon resonance, fluorescence quenching, chemiluminescence, interferometry, or refractive index detection.

The sample to be detected is an environmental sample, biohazard material, organic sample, drug, toxin, flavor, fragrance, or biological sample. The biological sample is a cell, cell extract, cell lysate, tissue, tissue extract, bodily fluid, serum, blood or blood product. In some embodiments of the method, the presence of the target molecule indicates the presence of a pathological condition. In some embodiments of the method, the presence of the target molecule indicates the presence of a desirable molecule.

In another aspect of the invention, a method is provided of amplifying desired regions of nucleic acid from a nucleic acid template comprising: (a) providing a plurality of first PCR primers having a region of fixed nucleotide sequence complementary to a consensus sequence of interest; (b) providing a plurality of second PCR primers, (c) amplifying the nucleic acid template via the PCR using the plurality of first PCR primers and the plurality of second PCR primers under conditions wherein a subset of the plurality of first primers binds to the consensus sequence of interest substantially wherever it occurs in the template, and a subset of the plurality of second primers binds to the template at locations removed from the first primers such that nucleic acid regions flanked by the first primer and the second primer are specifically amplified, and wherein the plurality of first PCR primers and/or the plurality of second PCT primers are nucleic acid molecules of Formula 1 which are produced according to the methods of the invention.

In some embodiments, the template is genomic DNA. In some embodiments, the template is eukaryotic genomic DNA. In some embodiments, the template is human genomic DNA. In some embodiments, the template is prokaryotic DNA. In some embodiments, the template is DNA which is a cloned genomic DNA, a subgenomic region of DNA, a chromosome, or a subchromosomal region. In some embodiments, the template is RNA.

INCORPORATION BY REFERENCE

All publications and patent applications disclosed herein in this specification are herein incorporated by reference in their entirety to the same extent as if each individual publication or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

Definitions

Figure 1:
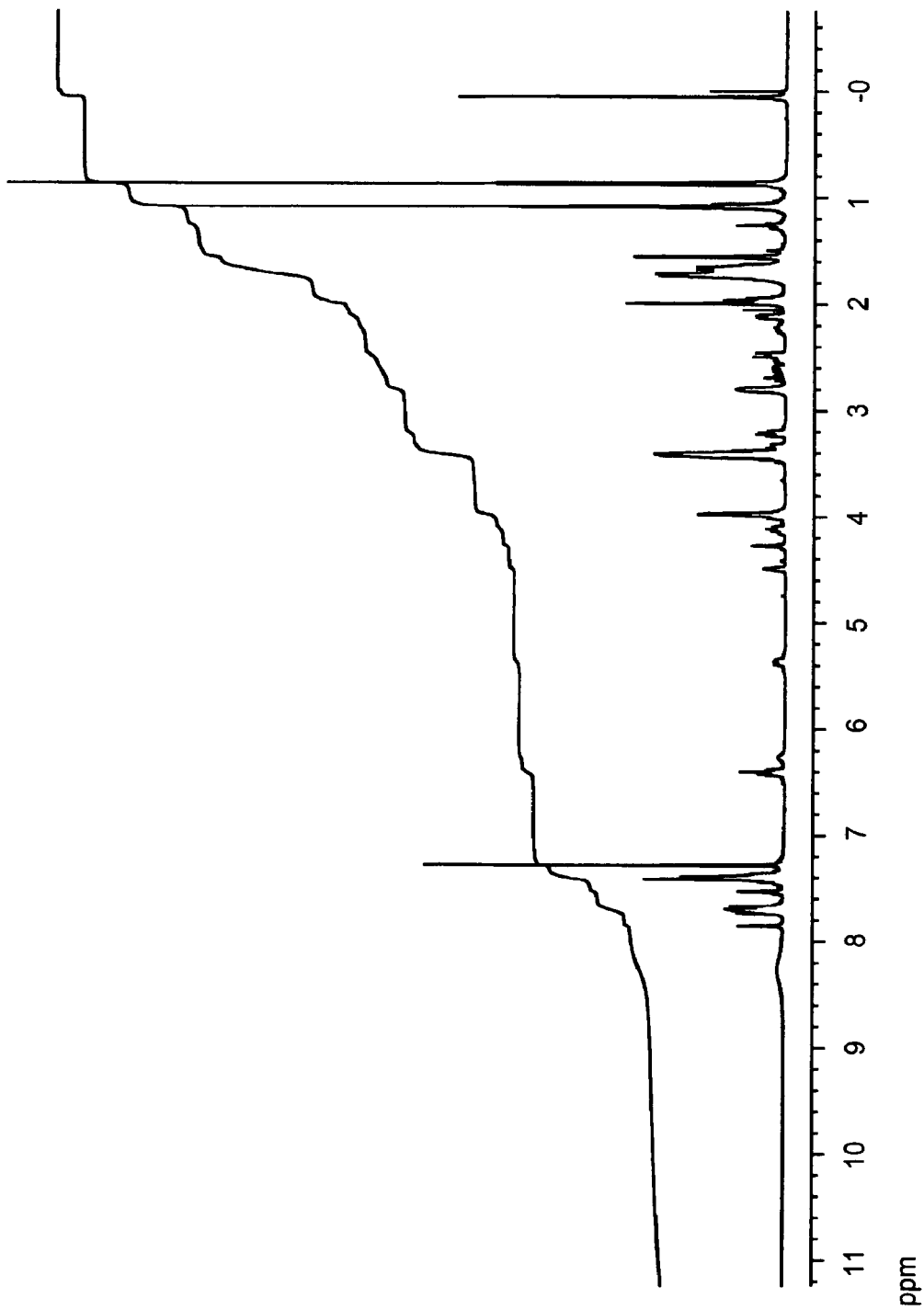
FIG. 1. $^1$H NMR spectrum of $(S_P)$-4tt (CDCl$_3$)
FIG. 2. $^{31}$P NMR spectrum of $(S_P)$-4tt (CDCl$_3$)
FIG. 3. $^1$H NMR spectrum of $(R_P)$-4tt (CDCl$_3$)
FIG. 4. $^{31}$P NMR spectrum of $(R_P)$-4tt (CDCl$_3$)
FIG. 5A. Crude UPLC® profile of $(S_P)$-5tt
FIG. 5B. Crude UPLC® profile of $(S_P)$-5tt using BTC in place of Ph3PCl2
FIG. 6A. Crude UPLC® profile of $(S_P)$-5tt
FIG. 6B. Crude UPLC® profile of $(S_P)$-5tt using BTC in place of PH3PCL2
FIG. 7A. Crude UPLC® profile of $(R_P)$-5tt
FIG. 7B. Crude UPLC® profile of $(R_P)$-5tt
FIG. 8. Crude UPLC® profile of $(R_P)$-5tt
FIG. 9A. Crude UPLC® profile of $(S_P)$-5ct
FIG. 9B. Crude UPLC® profile of $(S_P)$-5ct
FIG. 10A. Crude UPLC® profile of $(R_P)$-5ct
FIG. 10B. Crude UPLC® profile of $(R_P)$-5ct
FIG. 11. Crude UPLC® profile of $(S_P)$-5at
FIG. 12. Crude UPLC® profile of $(R_P)$-5at
FIG. 13. Crude UPLC® profile of $(S_P)$-5gt
FIG. 14. Crude UPLC® profile of $(R_P)$-5gt
FIG. 15A. Crude UPLC® profile of $(S_P)$-5tt
FIG. 15B. Crude UPLC® profile of $(S_P)$-5tt
FIG. 16A. Crude UPLC® profile of $(S_P)$-5tt
FIG. 16B. Crude UPLC® profile of $(S_P)$-5tt
FIG. 17A. Crude UPLC® profile of $(R_P)$-5tt
FIG. 17B. Crude UPLC® profile of $(R_P)$-5tt
FIG. 18. Crude UPLC® profile of $(S_P)$-5ct
FIG. 19. Crude UPLC® profile of $(R_P)$-5ct.

Unless otherwise stated, the following terms used in this application, including the specification and claims, have the definitions given below. It must be noted that, as used in the specification and the appended claims, the singular forms "a" "an" and "the" include plural referents unless the context clearly dictates otherwise. Unless otherwise indicated, conventional methods of mass spectroscopy, NMR, HPLC, protein chemistry, biochemistry, recombinant DNA techniques and pharmacology are employed. In this application, the use of "or" or "and" means "and/or" unless stated otherwise. Furthermore, use of the term "including" as well as other forms, such as "include", "includes" and "included" is not limiting.

The term "nucleic acid" encompasses poly- or oligo-ribonucleotides (RNA) and poly- or oligo-deoxyribonucleotides (DNA); RNA or DNA derived from N-glycosides or C-glycosides of nucleobases and/or modified nucleobases; nucleic acids derived from sugars and/or modified sugars; and nucleic acids derived from phosphate bridges and/or modified phosphorous-atom bridges. The term encompasses nucleic acids containing any combinations of nucleobases, modified nucleobases, sugars, modified sugars, phosphate bridges or modified phosphorous atom bridges. Examples include, and are not limited to, nucleic acids containing ribose moieties, the nucleic acids containing deoxy-ribose moieties, nucleic acids containing both ribose and deoxyribose moieties, nucleic acids containing ribose and modified ribose moieties. The prefix poly- refers to a nucleic acid containing about 1 to about 10,000 nucleotide monomer units and wherein the prefix oligo- refers to a nucleic acid containing about 1 to about 200 nucleotide monomer units.

The term "nucleobase" refers to the parts of nucleic acids that are involved in the hydrogen-bonding that binds one nucleic acid strand to another complementary strand in a sequence specific manner. The most common naturally-occurring nucleobases are adenine (A), guanine (G), uracil (U), cytosine (C), and thymine (T).

The term "modified nucleobase" refers to a moiety that can replace a nucleobase. The modified nucleobase mimics the spatial arrangement, electronic properties, or some other physicochemical property of the nucleobase and retains the property of hydrogen-bonding that binds one nucleic acid strand to another in a sequence specific manner. A modified nucleobase can pair with all of the five naturally occurring bases (uracil, thymine, adenine, cytosine, or guanine) without substantially affecting the melting behavior, recognition by intracellular enzymes or activity of the oligonucleotide duplex.

The term "nucleoside" refers to a moiety wherein a nucleobase or a modified nucleobase is covalently bound to a sugar or modified sugar.

The term "sugar" refers to a monosaccharide in closed and/or open form. Sugars include, but are not limited to, ribose, deoxyribose, pentofuranose, pentopyranose, and hexopyranose moieties.

The term "modified sugar" refers to a moiety that can replace a sugar. The modified sugar mimics the spatial arrangement, electronic properties, or some other physicochemical property of a sugar.

The term "nucleotide" refers to a moiety wherein a nucleobase or a modified nucleobase is covalently linked to a sugar or modified sugar, and the sugar or modified sugar is covalently linked to a phosphate group or a modified phosphorous-atom moiety.

The term "chiral reagent" refers to a compound that is chiral or enantiopure and can be used for asymmetric induction in nucleic acid synthesis.

The term "chiral ligand" or "chiral auxiliary" refers to a moiety that is chiral or enantiopure and controls the stereochemical outcome of a reaction.

In a condensation reaction, the term "condensing reagent" refers to a reagent that activates a less reactive site and renders it more susceptible to attack by a nucleophile.

The term "blocking moiety" refers to a group that transiently masks the reactivity of a functional group. The functional group can be subsequently unmasked by removal of the blocking moiety.

The terms "boronating agents", "sulfur electrophiles", "selenium electrophiles" refer to compounds that are useful in the modifying step used to introduce $BH_3$, S, and Se groups, respectively, for modification at the phosphorus atom.

The term "moiety" refers to a specific segment or functional group of a molecule. Chemical moieties are often recognized chemical entities embedded in or appended to a molecule.

The term "solid support" refers to any support which enables synthetic mass production of nucleic acids and can be reutilized at need. As used herein, the term refers to a polymer that is insoluble in the media employed in the reaction steps performed to synthesize nucleic acids, and is derivatized to comprise reactive groups.

The term "linking moiety" refers to any moiety optionally positioned between the terminal nucleoside and the solid support or between the terminal nucleoside and another nucleoside, nucleotide, or nucleic acid.

As used herein, "treatment" or "treating," or "palliating" or "ameliorating" are used interchangeably herein. These terms refers to an approach for obtaining beneficial or desired results including but not limited to therapeutic benefit and/or a prophylactic benefit. By therapeutic benefit is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient may still be afflicted with the underlying disorder. For prophylactic benefit, the compositions may be administered to a patient at risk of developing a particular disease, or to a patient reporting one or more of the physiological symptoms of a disease, even though a diagnosis of this disease may not have been made.

A "therapeutic effect," as that term is used herein, encompasses a therapeutic benefit and/or a prophylactic benefit as described above. A prophylactic effect includes delaying or eliminating the appearance of a disease or condition, delaying or eliminating the onset of symptoms of a disease or condition, slowing, halting, or reversing the progression of a disease or condition, or any combination thereof.

An "alkyl" group refers to an aliphatic hydrocarbon group. The alkyl moiety may be a saturated alkyl group (which means that it does not contain any units of unsaturation, e.g. carbon-carbon double bonds or carbon-carbon triple bonds) or the alkyl moiety may be an unsaturated alkyl group (which means that it contains at least one unit of unsaturation). The alkyl moiety, whether saturated or unsaturated, may be branched, straight chain, or include a cyclic portion. The point of attachment of an alkyl is at a carbon atom that is not part of a ring.

The "alkyl" moiety may have 1 to 10 carbon atoms (whenever it appears herein, a numerical range such as "1 to 10" refers to each integer in the given range; e.g., "1 to 10 carbon atoms" means that the alkyl group may consist of 1 carbon atom, 2 carbon atoms, 3 carbon atoms, etc., up to and including 10 carbon atoms, although the present definition also covers the occurrence of the term "alkyl" where no numerical range is designated). Alkyl includes both branched and straight chain alkyl groups. The alkyl group of the compounds described herein may be designated as "$C_1$-$C_6$ alkyl" or similar designations. By way of example only, "$C_1$-$C_6$ alkyl" indicates that there are one, two, three, four, five, or six carbon atoms in the alkyl chain, i.e., the alkyl chain is selected from the group consisting of methyl, ethyl, propyl, iso-propyl, n-butyl, iso-butyl, sec-butyl, and t-butyl. Typical alkyl groups include, but are in no way limited to, methyl, ethyl, propyl, isopropyl, butyl, isobutyl, tertiary butyl, pentyl, hexyl, allyl, cyclopropylmethyl, cyclobutylmethyl, cyclopentylmethyl, cyclohexylmethyl, and the like. In one aspect, an alkyl is a $C_1$-$C_6$ alkyl.

As used herein, the term "aryl" refers to an aromatic ring wherein each of the atoms forming the ring is a carbon atom. Aryl rings are formed by five, six, seven, eight, nine, or more than nine carbon atoms. Aryl groups are a substituted or unsubstituted. In one aspect, an aryl is a phenyl or a naphthalenyl. Depending on the structure, an aryl group can be a monoradical or a diradical (i.e., an arylene group). In one aspect, an aryl is a $C_6$-$C_{10}$aryl.

"Heteroaryl" or alternatively, "heteroaromatic" refers to a 5- to 18-membered aromatic radical (e.g., $C_5$-$C_{13}$ heteroaryl) that includes one or more ring heteroatoms selected from nitrogen, oxygen and sulfur, and which may be a monocyclic, bicyclic, tricyclic or tetracyclic ring system. Whenever it appears herein, a numerical range such as "5 to 18" refers to each integer in the given range; e.g., "5 to 18 ring atoms" means that the heteroaryl group may consist of 5 ring atoms, 6 ring atoms, etc., up to and including 18 ring atoms. An N-containing "heteroaromatic" or "heteroaryl" moiety refers to an aromatic group in which at least one of the skeletal atoms of the ring is a nitrogen atom. The polycyclic heteroaryl group may be fused or non-fused. The heteroatom(s) in the heteroaryl radical is optionally oxidized. One or more nitrogen atoms, if present, are optionally quaternized. The heteroaryl is attached to the rest of the molecule through any atom of the ring(s). Examples of heteroaryls include, but are not limited to, azepinyl, acridinyl, benzimidazolyl, benzindolyl, 1,3-benzodioxolyl, benzofuranyl, benzooxazolyl, benzo[d]thiazolyl, benzothiadiazolyl, benzo[b][1,4]dioxepinyl, benzo[b][1,4]oxazinyl, 1,4-benzodioxanyl, benzonaphthofuranyl, benzoxazolyl, benzodioxolyl, benzodioxinyl, benzoxazolyl, benzopyranyl, benzopyranonyl, benzofuranyl, benzofuranonyl, benzofurazanyl, benzothiazolyl, benzothienyl (benzothiophenyl), benzothieno[3,2-d]pyrimidinyl, benzotriazolyl, benzo[4,6]imidazo[1,2-a]pyridinyl, carbazolyl, cinnolinyl, cyclopenta[d]pyrimidinyl, 6,7-dihydro-5H-cyclopenta[4,5]thieno[2,3-d]pyrimidinyl, 5,6-dihydrobenzo[h]quinazolinyl, 5,6-dihydrobenzo[h]cinnolinyl, 6,7-dihydro-5H-benzo[6,7]cyclohepta[1,2-c]pyridazinyl, dibenzofuranyl, dibenzothiophenyl, furanyl, furazanyl, furanonyl, furo[3,2-c]pyridinyl, 5,6,7,8,9,10-hexahydrocycloocta[d]pyrimidinyl, 5,6,7,8,9,10-hexahydrocycloocta[d]pyridazinyl, 5,6,7,8,9,10-hexahydrocycloocta[d]pyridinyl, isothiazolyl, imidazolyl, indazolyl, indolyl, indazolyl, isoindolyl, indolinyl, isoindolinyl, isoquinolyl, indolizinyl, isoxazolyl, 5,8-methano-5,6,7,8-tetrahydroquinazolinyl, naphthyridinyl, 1,6-naphthyridinonyl, oxadiazolyl, 2-oxoazepinyl, oxazolyl, oxiranyl, 5,6,6a,7,8,9,10,10a-octahydrobenzo[h]quinazolinyl, 1-phenyl-1H-pyrrolyl, phenazinyl, phenothiazinyl, phenoxazinyl, phthalazinyl, pteridinyl, purinyl, pyranyl, pyrrolyl, pyrazolyl, pyrazolo[3,4-d]pyrimidinyl, pyridinyl, pyrido[3,2-d]pyrimidinyl, pyrido[3,4-d]pyrimidinyl, pyrazinyl, pyrimidinyl, pyridazinyl, pyrrolyl, quinazolinyl, quinoxalinyl, quinolinyl, isoquinolinyl, tetrahydroquinolinyl, 5,6,7,8-tetrahydroquinazolinyl, 5,6,7,8-tetrahydrobenzo[4,5]thieno[2,3-d]pyrimidinyl, 6,7,8,9-tetrahydro-5H-cyclohepta[4,5]thieno[2,3-d]pyrimidinyl, 5,6,7,8-tetrahydropyrido[4,5-c]pyridazinyl, thiazolyl, thiadiazolyl, thiapyranyl, triazolyl, tetrazolyl, triazinyl, thieno[2,3-d]pyrimidinyl, thieno[3,2-d]pyrimidinyl, thieno[2,3-c]pridinyl, and thiophenyl (i.e. thienyl). Unless stated otherwise specifically in the specification, a heteraryl moiety is optionally substituted by one or more substituents which are independently: alkyl, heteroalkyl, alkenyl, alkynyl, cycloalkyl, heterocycloalkyl, aryl, arylalkyl, heteroaryl, heteroarylalkyl, hydroxy, halo, cyano, nitro, oxo, thioxo, trimethylsilanyl, —$OR^a$, —$SR^a$, —$OC(O)R^a$, —$N(R^a)_2$, —$C(O)R^a$, —$C(O)OR^a$, —$C(O)N(R^a)_2$, —$N(R^a)C(O)OR^a$, —$N(R^a)C(O)R^a$, —$N(R^a)S(O)_tR^a$ (where t is 1 or 2), —$S(O)_tOR^a$ (where t is 1 or 2), or —$S(O)_tN(R^a)_2$ (where t is 1 or 2) where each $R^a$ is independently hydrogen, alkyl, fluoroalkyl, carbocyclyl, carbocyclylalkyl, aryl, aralkyl, heterocyclyl, heterocyclylalkyl, heteroaryl or heteroarylalkyl.

The term "alicyclic" refers to an all carbon moiety that is both aliphatic and cyclic. Alicyclic groups contain one or more all-carbon rings which may be either saturated or unsaturated, but do not have aromatic character. Alicyclic groups are substituted or unsubstituted and may contain from one to ten carbon atoms. In one aspect, an alicyclic is a monocyclic cycloalkane. In another aspect an alicyclic is a bicyclic cycloalkane.

The term "aralkyl" refers to an alkyl group substituted with an aryl group. Suitable aralkyl groups include benzyl, picolyl, and the like, all of which may be optionally substituted.

An "acyl moiety" refers to an alkyl(C=O), aryl(C=O), or aralkyl(C=O) group. An acyl moiety can have an intervening moiety (Y) that is oxy, amino, thio, or seleno between the carbonyl and the hydrocarbon group. For example, an acyl group can be alkyl-Y—(C=O), aryl-Y—(C=O) or aralkyl-Y—(C=O).

"Alkenyl" groups are straight chain, branch chain, and cyclic hydrocarbon groups containing at least one carbon-carbon double bond. Alkenyl groups can be substituted.

"Alkynyl" groups are straight chain, branch chain, and cyclic hydrocarbon groups containing at least one carbon-carbon triple bond. Alkynyl groups can be substituted.

An "alkoxy" group refers to an alkyl group linked to oxygen i.e. (alkyl)-O— group, where alkyl is as defined herein. Examples include methoxy (—$OCH_3$) or ethoxy (—$OCH_2CH_3$) groups.

An "alkenyloxy" group refers to an alkenyl group linked to oxygen i.e. (alkenyl)-O— group, where alkenyl is as defined herein.

An "alkynyloxy" group refers to an alkynyl group linked to oxygen i.e. (alkynyl)-O— group, where alkynyl is as defined herein.

An "aryloxy" group refers to to an aryl group linked to oxygen i.e. (aryl)-O— group, where the aryl is as defined herein. An example includes phenoxy (—$OC_6H_5$).

The term "alkylseleno" refers to an alkyl group having a substituted seleno group attached thereto i.e. (alkyl)-Se— group, wherein alkyl is defined herein.

The term "alkenylseleno" refers to an alkenyl group having a substituted seleno group attached thereto i.e. (alkenyl)-Se— group, wherein alkenyl is defined herein.

The term "alkynylseleno" refers to an alkynyl group having a substituted seleno group attached thereto i.e. (alkynyl)-Se— group, wherein alkenyl is defined herein.

The term "alkylthio" refers to an alkyl group attached to a bridging sulfur atom i.e. (alkyl)-S— group, wherein alkyl is defined herein. For example, an alkylthio is a methylthio and the like.

The term "alkenylthio" refers to an alkenyl group attached to a bridging sulfur atom i.e. (alkenyl)-S— group, wherein alkenyl is defined herein.

The term "alkynylthio" refers to an alkynyl group attached to a bridging sulfur atom i.e. (alkynyl)-S— group, wherein alkenyl is defined herein.

The term "alkylamino" refers to an amino group substituted with at least one alkyl group i.e. —NH(alkyl) or —N-(alkyl)$_2$, wherein alkyl is defined herein.

The term "alkenylamino" refers to an amino group substituted with at least one alkenyl group i.e. —NH(alkenyl) or —N-(alkenyl)$_2$, wherein alkenyl is defined herein.

The term "alkynylamino" refers to an amino group substituted with at least one alkynyl group i.e. —NH(alkynyl) or —N-(alkynyl)$_2$, wherein alkynyl is defined herein.

The term "halogen" is intended to include fluorine, chlorine, bromine and iodine.

A "fluorescent group" refers to a molecule that, when excited with light having a selected wavelength, emits light of a different wavelength. Fluorescent groups include, but are not limited to, indole groups, fluorescein, tetramethylrhodamine, Texas Red, BODIPY, 5-[(2-aminoethyl)amino] napthalene-1-sulfonic acid (EDANS), coumarin and *Lucifer* yellow.

An "ammonium ion" is a positively charged polyatomic cation of the chemical formula $NH_4^+$.

An "alkylammonium ion" is an ammonium ion that has at least one of its hydrogen atoms replaced by an alkyl group, wherein alkyl is defined herein. Examples include triethylammonium ion, N,N-diisopropylethylammonium ion.

An "iminium ion" has the general structure $R_2C=NR_2^+$. The R groups refer to alkyl, alkenyl, alkynyl, aryl groups as defined herein. A "heteroaromatic iminium ion" refers to an imminium ion where the nitrogen and its attached R groups form a heteroaromatic ring. A "heterocyclic iminium ion" refers to an imminium ion where the nitrogen and its attached R groups form a heterocyclic ring.

The terms "amino" or "amine" refers to a —$N(R^h)_2$ radical group, where each $R^h$ is independently hydrogen, alkyl, fluoroalkyl, carbocyclyl, carbocyclylalkyl, aryl, aralkyl, heterocyclyl, heterocyclylalkyl, heteroaryl or heteroarylalkyl, unless stated otherwise specifically in the specification. When a —$N(R^f)_2$ group has two $R^f$ other than hydrogen they can be combined with the nitrogen atom to form a 4-, 5-, 6-, or 7-membered ring. For example, —N(R$^f$)$_2$ is meant to include, but not be limited to, 1-pyrrolidinyl and 4-morpholinyl. Any one or more of the hydrogen, alkyl, fluoroalkyl, carbocyclyl, carbocyclylalkyl, aryl, aralkyl, heterocyclyl, heterocyclylalkyl, heteroaryl or heteroarylalkyl are optionally substituted by one or more substituents which independently are alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —OR$^i$, —SR$^i$, —OC(O)R$^i$, —N(R$_i$)$_2$, —C(O)R$^i$, —C(O)OR$^i$, —OC(O)N(R$^i$)$_2$, —C(O)N(R$^i$)$_2$, —N(R$^i$)C(O)OR$^i$, —N(R$_i$)C(O)R$^i$, —N(R$^i$)C(O)N(R$^i$)$_2$, N(R$^i$)C(NR$^i$)N(R$^i$)$_2$, —N(R$^i$)S(O)$_t$R$^1$ (where t is 1 or 2), —S(O)$_t$OR$^f$ (where t is 1 or 2), or —S(O)$_t$N(R$^f$)$_2$ (where t is 1 or 2), where each R$^1$ is independently hydrogen, alkyl, fluoroalkyl, carbocyclyl, carbocyclylalkyl, aryl, aralkyl, heterocyclyl, heterocyclylalkyl, heteroaryl or heteroarylalkyl.

"Carbamate" as used herein, refers to a moiety attached to an amino group which has the formula —C(O)OR where R is alkyl, fluoroalkyl, carbocyclyl, carbocyclylalkyl, aryl, aralkyl, heterocyclyl, heterocyclylalkyl, heteroaryl or heteroarylalkyl. Examples include but are not limited to Boc (tert-butyl-OC(O)—), CBz (benzyl-OC(O)—), Teoc (Me$_3$SiCH$_2$CH$_2$OC(O)—), alloc (allyl-OC(O)—), or Fmoc (9-fluorenylmethyl-OC(O)—).

"Substituted silyl" as used herein, refers to a moiety which has the formula R$_3$Si—. Examples include, but are not limited to, TBDMS (tert-butyldimethylsilyl), TBDPS (tert-butyldiphenylsilyl) or TMS (trimethylsilyl).

The term "thiol" refers to —SH groups, and include substituted thiol groups i.e. —SR$^j$ groups, wherein R$^j$ are each independently a substituted or unsubstituted alkyl, cycloalkyl, alkenyl, alkynyl, aryl aralkyl, heterocyclyl or heterocyclylalkyl group as defined herein.

METHODS OF SYNTHESIS

General Discussion of the Methods of Synthesis of a Nucleic Acid Comprising a Chiral X-Phosphonate Moiety.

The present method provides for an efficient synthesis of phosphorus atom-modified nucleic acids wherein the stereochemical configuration at a phosphorus atom is controlled, thus producing a stereodefined oligonucleotide. The method eliminates the need for complex separations of diastereomeric mixtures and allows for the use of readily available inexpensive achiral starting materials. The method of synthesis disclosed herein comprises an asymmetric reaction of an achiral H-phosphonate moiety (Formula 2) with a nucleoside comprising a nucleophilic moiety, such as a hydroxy group, (Formula 4-1, where Q$_1$ is any of a blocking group, a linking moiety to a support or to a nucleotide chain) to provide a phosphorous atom-modified nucleic acid comprising a chiral X-phosphonate moiety, which is a compound of Formula 1, as shown in Scheme 1. In such manner, a nucleotide polymer or oligomer having high diastereomeric purity is produced. In some embodiments, the nucleic acid contains modifications at the nucleobases, sugar moiety, and/or protective groups.

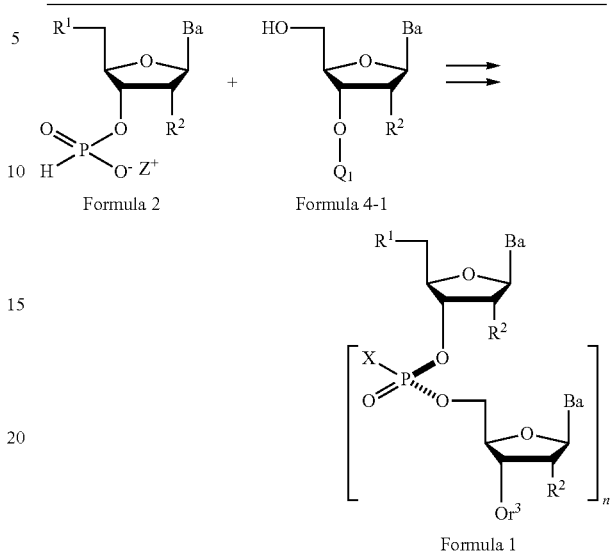

Scheme 1. Synthesis of a nucleic acid comprising a chiral X-phosphonate moiety of Formula 1.

The reaction of a molecule comprising an achiral H-phosphonate moiety of Formula 2 with a nucleoside comprising nucleophilic moiety of Formula 4-1 results in the formation of a condensed intermediate; which is converted to the nucleic acid comprising a chiral X-phosphonate moiety. The synthesis of the condensed intermediate comprises the steps of (a) activation of the compound of Formula 2 with a condensing agent, (b) reaction with a chiral reagent, followed by (c) reaction with the compound of Formula 4-1. The general scheme is shown in Scheme 2. The chiral reagent becomes attached to the condensed intermediate as a chiral auxiliary group. In the process provided herein, the steps (a)-(c) leading to the condensed intermediate may be performed without isolating any intermediates, i.e., in the same pot or in one-pot. Thus, the process obviates the need for isolation of discrete intermediates. The process disclosed herein can be performed in solution or on solid support. Depending on the reaction conditions, addition of an activating reagent may be useful for the condensation step. For example, the activating reagent can be added to the reaction after steps (a)-(c) have been completed or can be added to the reaction at the same time as steps (a)-(c).

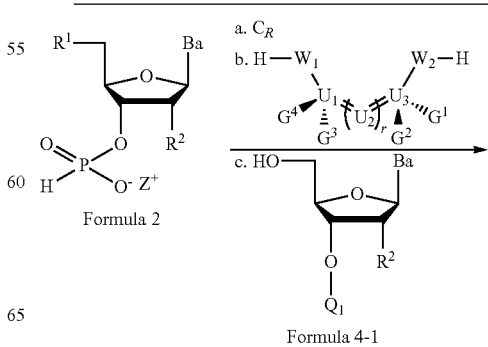

Scheme 2. Reaction steps leading to the formation of a condensed intermediate.

-continued

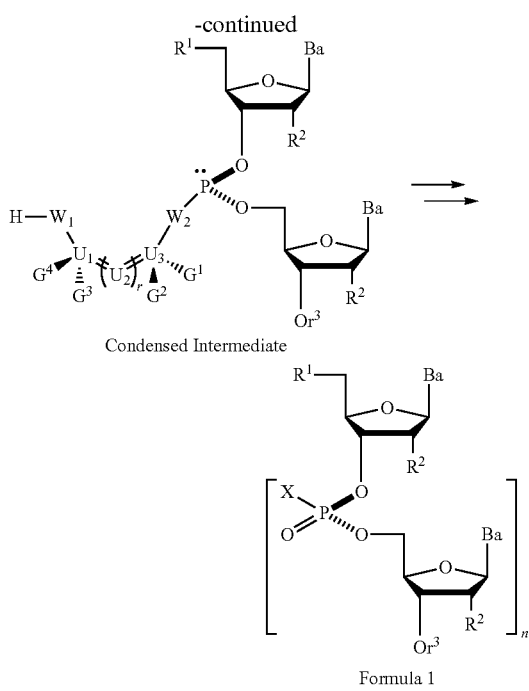

Condensed Intermediate

Formula 1

In an embodiment the condensed intermediate is converted to a nucleic acid comprising a chiral X phosphonate moiety of Formula 1 by capping the chiral auxiliary on the condensed intermediate with a moiety A, which is an acyl, aryl, alkyl, aralkyl, or silyl moiety, and modifying the phosphorus to introduce J, which is S, Se, or $BH_3$, producing a compound of Formula 5-1. In one embodiment (Option A, Scheme 3), the compound of Formula 5-1 is converted to the compound of Formula 1, where X is S, Se, or $BH_3$, and n is 1 (dimer), by cleaving the chiral auxiliary, and deblocking blocking groups and cleaving from solid support if desired. When forming the dimer, the capping step in Scheme 3 is optional. Alternatively (Option B, Scheme 3), the compound of Formula 5-1 is subjected to chain elongation by repeating the steps to produce a condensed intermediate where a further monomer of Formula 2 is added to the oligonucleotide. The steps of capping, modifying, deblocking, and chain elongation are repeated until the desired n is achieved. At that point, the chiral auxilliaries at each phosphonate are cleaved, the remaining blocking groups are cleaved, including cleaving from a solid support, if desired, to produce the compound of Formula 1, where X is S, Se, or $BH_3$, and n is greater than or equal to 2 and less than about 200.

Scheme 3. Converting the condensed intermediate to the compound of Formula 1 via Route A.

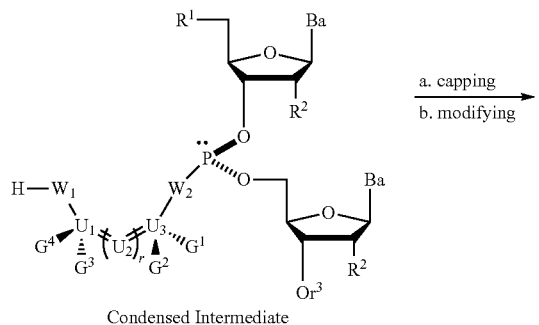

Condensed Intermediate

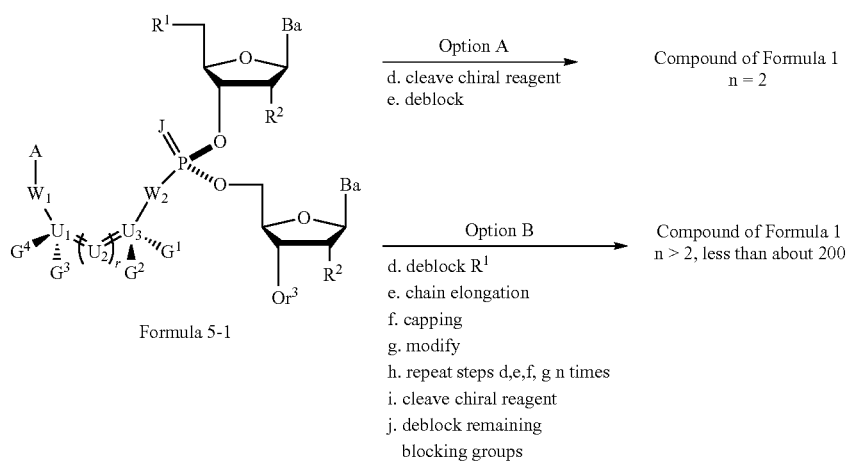

Formula 5-1

In another method provided herein, the condensed intermediate is converted to a nucleic acid comprising a chiral X phosphonate moiety of Formula 1 by acidifying the condensed intermediate to remove the blocking group at $R^1$, which also removes the chiral auxiliary. In one embodiment (Option A, Scheme 4), the compound of Formula 4 is modified to introduce an X moiety at phosphorus, to produce a compound of Formula 1, which is deblocked to remove remaining blocking groups, and remove from a synthesis support, if desired, to produce a compound of Formula 1 wherein $R^3$ is hydrogen and n is 1.

Alternatively, the compound of Formula 4 in Scheme 4 (Option B) is subjected to the step of chain elongation reaction, and then acidified to deblock the $R^1$ blocking group of the newly added nucleoside. The chain elongation step and $R^1$ deblocking step are performed for m repetitions. At that point, the compound of Formula 4, wherein m is equal to n−1, is modified to introduce an X moiety at each phosphorus, to produce a compound of Formula 1, which is deblocked to remove remaining blocking groups, and remove from a synthesis support, if desired, to produce a compound of Formula 1 wherein $R^3$ is hydrogen and n is greater than or equal to 2 and less than about 200.

In both Option A and Option B of Scheme 4, X is alkyl, alkoxy, aryl, alkylthio, acyl, —$NR^fR^f$, alkenyloxy, alkynyloxy, alkenylthio, alkynylthio, —$S^-Z^+$, —$Se^-Z^+$, or —$BH_3^-Z^+$, where each $R^f$ is independently hydrogen, alkyl, alkenyl, alkynyl, or aryl; $Z^+$ is ammonium ion, alkylammonium ion, heteroaromatic iminium ion, or heterocyclic iminium ion, any of which is primary, secondary, tertiary or quaternary, or Z is a monovalent metal ion. In other embodiments, Z is pyridinium ion, triethylammonium ion, N,N-diisopropylethylammonium ion, 1,8-diazabicyclo[5.4.0]undec-7-enium ion, sodium ion, or potassium ion.

Phosphorus Atom Modified Nucleic Acid Comprising a Chiral X-Phosphonate Moiety of Formula 1.

The process of the invention provides a nucleic acid comprising a chiral X-phosphonate moiety of the following general Formula 1-1 or Formula 1-2:

Scheme 4. Converting the Condensed Intermediate to the Compound of Formula 1 via Route B.

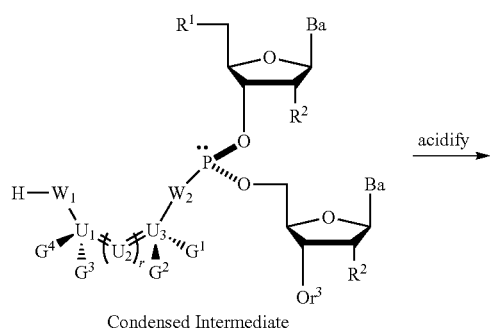

Condensed Intermediate

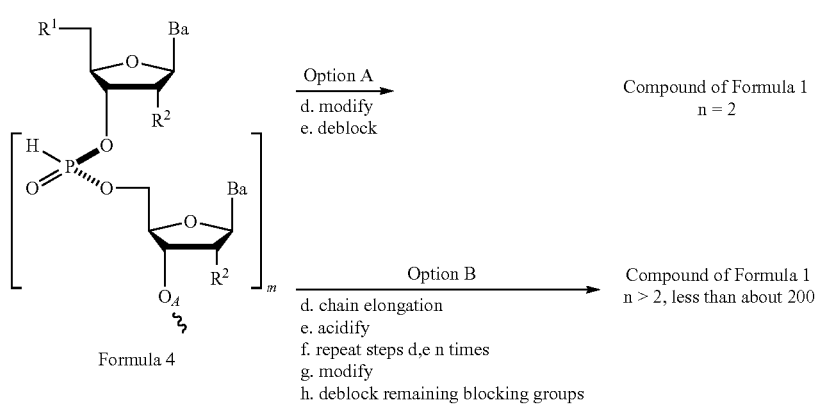

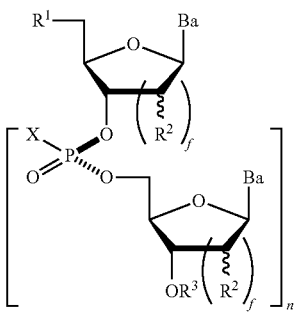

Formula 1-1

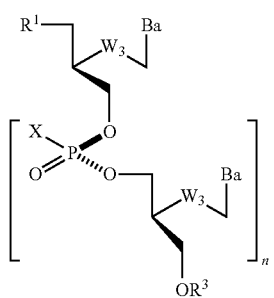

Formula 1-2

Wherein the X-phosphonate moiety connects natural nucleoside moieties or unnatural nucleoside moieties wherein the natural ribose ring is replaced by a larger or smaller oxygen containing ring or wherein the ring is replaced by a noncyclic structure wherein $W_3$ is —S—, —O—, substituted or unsubstituted amino, alkylene, alkenylene, or alkynylene. In other embodiments of the nucleic acid, the X-phosphonate moiety connects natural nucleoside moieties with unnatural nucleoside moieties. In yet other embodiments of the nucleic acid, the X-phosphonate moiety connects nucleoside moieties with different sugar moieties to one another.

In one embodiment of the invention, the nucleic acid comprising a chiral X-phosphonate moiety is a compound of Formula 1:

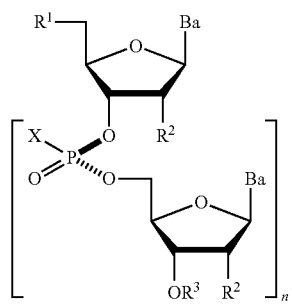

Formula 1

In Formula 1, $R^1$ is —OH, —SH, —NR$^d$R$^d$, —N$_3$, halogen, hydrogen, alkyl, alkenyl, alkynyl, alkyl-Y$^1$—, alkenyl-Y$^1$—, alkynyl-Y$^1$—, aryl-Y$^1$—, heteroaryl-Y$^1$—, —P(O)(R$^c$)$_2$, —HP(O)(R$^e$), —OR$^a$ or —SR$^c$.

$Y^1$ is O, NR$^d$, S, or Se.

$R^a$ is a blocking moiety.

$R^c$ is a blocking group.

Each instance of R$^d$ is independently hydrogen, alkyl, alkenyl, alkynyl, aryl, acyl, substituted silyl, carbamate, —P(O)(R$^e$)$_2$, or —HP(O)(R$^e$).

Each instance of R$^e$ is independently hydrogen, alkyl, aryl, alkenyl, alkynyl, alkyl-Y$^2$—, alkenyl-Y$^2$—, alkynyl-Y$^2$—, aryl-Y$^2$—, or heteroaryl-Y$^2$—, or a cation which is Na$^{+1}$, Li$^{+1}$, or K$^{+1}$.

$Y^2$ is O, NR$^d$, or S.

Each instance of R$^2$ is independently hydrogen, —OH, —SH, —NR$^d$R$^d$, —N$_3$, halogen, alkyl, alkenyl, alkynyl, alkyl-Y$^1$—, alkenyl-Y$^1$—, alkynyl-Y$^1$—, aryl-Y$^1$—, heteroaryl-Y$^1$—, —OR$^b$, or —SR$^c$, wherein R$^b$ is a blocking moiety.

Each instance of Ba is independently a blocked or unblocked adenine, cytosine, guanine, thymine, uracil or modified nucleobase.

Each instance of X is independently alkyl, alkoxy, aryl, alkylthio, acyl, —NR$^f$R$^f$, alkenyloxy, alkynyloxy, alkenylthio, alkynylthio, —S$^-$Z$^+$, —Se$^-$Z$^+$, or —BH$_3^-$Z$^+$.

Each instance of R$^f$ is independently hydrogen, alkyl, alkenyl, alkynyl, or aryl.

$Z^+$ is ammonium ion, alkylammonium ion, heteroaromatic iminium ion, or heterocyclic iminium ion, any of which is primary, secondary, tertiary or quaternary, or Z is a monovalent metal ion.

$R^3$ is hydrogen, a blocking group, a linking moiety connected to a solid support or a linking moiety connected to a nucleic acid; and n is an integer of 1 to about 200.

In an embodiment, any of the R$^2$ groups is substituted by, for example, a fluorescent moiety, a biotin moiety, or an avidin moiety.

In one embodiment, the nucleic acid described herein is prepared from all ribonucleotide monomers. In another embodiment, it is prepared from all deoxyribonucleotide monomers. In yet another embodiment, the nucleic acid is prepared from a mixture of ribonucleotide or deoxyribonucleotide monomers. In one embodiment the nucleic acid is a mixture of RNA and DNA moieties. In another embodiment, the nucleic acid comprises a substituent at R$^2$ which is not found in RNA or DNA nucleic acids.

Ba represents a nucleobase, which is a natural or modified nucleobase. Each instance of the nucleobase is independently blocked or unblocked.

Each instance of X is independently alkyl, alkoxy, aryl, alkylthio, acyl, —NR$^f$R$^f$, alkenyloxy, alkynyloxy, alkenylthio, alkynylthio, —S$^-$Z$^+$, —Se$^-$Z$^+$, or —BH$_3^-$Z$^+$, wherein each instance of R$^f$ is independently hydrogen, alkyl, alkenyl, alkynyl, or aryl; Z$^+$ is ammonium ion, alkylammonium ion, heteroaromatic iminium ion, or heterocyclic iminium ion, any of which is primary, secondary, tertiary or quaternary, or Z is a monovalent metal ion. In some embodiments, X is alkyl, alkoxy, —NR$^f$R$^f$, —S$^-$Z$^+$, or —BH$_3^-$Z$^+$. In other embodiments, Z is pyridinium ion, triethylammonium ion, N,N-diisopropylethylammonium ion, 1,8-diazabicyclo[5.4.0]undec-7-enium ion, sodium ion, or potassium ion.

$R^3$ is hydrogen, a blocking group, a linking moiety connected to a solid support or a linking moiety connected to a nucleic acid, which are prepared using methods herein or known in the art. The nucleic acid attached to R$^3$ that are prepared using any known method comprise phosphorus atoms that are modified, unmodified, or mixtures of modified and unmodified phosphorus and comprise any configuration at the phosphorus atom. In one embodiment, R$^3$ is a linking moiety attached to another nucleoside or nucleotide.

X-Phosphonate Moiety.

As used herein, X-phosphonate moiety refers to the phosphorus atom of the internucleoside backbone linkage that is modified to be covalently bonded to a moiety X, where X can be, but not limited to, sulphur, selenium, alkyl, boron, acyl, amino, thiol, or alkoxy. The X moiety modifies the phosphorus atom by replacement of one of the oxygen atoms in the internucleoside backbone. The internucleoside backbone linkages are shown below (within the dashed rectangular boxes) for two nucleic acid fragments as non-limiting examples. The left hand structure below shows the phosphate group found in natural internucleoside backbone linkages. The right hand structure below shows a X-phosphonate moiety as the internucleoside backbone linkage.

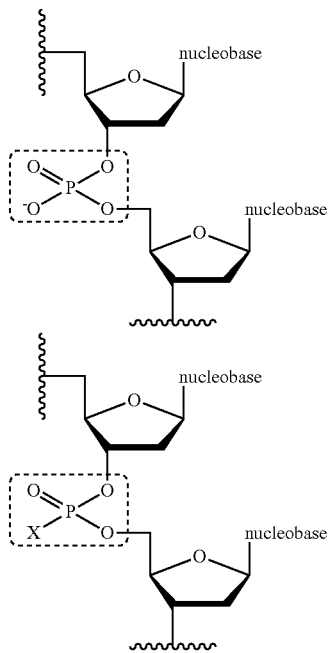

A phosphorothioate moiety comprises a sulphur moiety as the X moiety. A phosphoroselenoate moiety comprises a selenium moiety as the X moiety. An alkylphosphonate moiety (e.g. methylphosphonate) comprises an alkyl group (e.g. methyl group) as the X moiety. A boronophosphonate moiety comprises a borane group as the X moiety.

In an embodiment, the nucleic acid comprises phosphorothioate groups in the backbone linkages. In some embodiments, the nucleic acid comprises phosphoroselenoate groups in the backbone linkages. In other embodiments, the nucleic acid comprises alkylphosphonate groups (e.g. methylphosphonate) in the backbone linkages. In yet other embodiments, the nucleic acid comprise boronophosphonate groups in the backbone linkages.

Each X moiety can be independently chosen from the various X moieties described herein. This allows multiple X moieties to be present within one nucleic acid. In one embodiment, the same X moiety is used throughout the nucleic acid. In other embodiments, different X moieties are used throughout the nucleic acid. For example, within one nucleic acid, some of the X-phosphonates are phosphothioate moieties while other X-phosphonates within the same nucleic acid are alkylphosphonate moieties. It will be evident to one skilled in the art that other variations and alternations of phosphorus modifications are possible and depend on the use and applications of these nucleic acids. In some embodiments, the choice for the X moiety depends on the biochemical properties of the nucleic acid and its interactions with biological samples.

Configuration of X-Phosphonate Moiety.

The methods described herein are useful for controlling the configuration of each phosphorus atom in the internucleoside backbone linkage. The chiral reagent permits the specific control of the chirality at the X-phosphonate. Thus, either a $R_P$ or $S_P$ configuration can be selected in each synthesis cycle, permitting control of the overall three dimensional structure of the nucleic acid product. In some embodiments, the selection of $R_P$ and $S_P$ configurations is made to confer a specific three dimensional superstructure to the nucleic acid chain.

In some embodiments, each X-phosphonate moiety can have a $R_P$ configuration. In other embodiments, each X-phosphonate moiety can have a $S_P$ configuration. In another embodiment, each X-phosphonate moiety independently can have a $R_P$ configuration or a $S_P$ configuration. In specific embodiments, the X-phosphonate moieties alternate between $R_P$ and $S_P$ such as $R_P$, $S_P$, $R_P$ or $S_P$, $R_P$, $S_P$ throughout the nucleic acid. In other specific embodiments, the X-phosphonate moieties contain repeated configurations of $R_P$, $R_P$, $S_P$, $S_P$ throughout the nucleic acid. In yet other embodiments, the nucleic acid comprises all $R_P$ configurations. In further embodiments, the nucleic acid comprises all $S_P$ moieties. In some embodiments, the 5' and 3' terminal internucleoside backbone linkages are of the $S_P$ configuration and the internal internucleoside backbone linkages are all of the $R_P$ configuration. The embodiments described herein serve as examples of how the configuration can be controlled using these methods. The nucleic acid described herein is not limited to these configuration patterns. It will be evident to one skilled in the art that other variations and alternations in the $R_P$ and $S_P$ configurations are possible and depend on the use and applications of the nucleic acid.

Purity Determination of X-Phosphonate Configurations.

The purity of the configuration at each X-phosphonate moiety in the nucleic acid is determined using conventional analytical methods such as, but not limited to, $^{31}$P NMR spectroscopy or reverse-phase HPLC. Using methods described herein, in an embodiment, each X-phosphonate moiety of the compound can be more than 80% diastereomerically pure. In an embodiment, each X-phosphonate moiety of the compound can be more than 60% diastereomerically pure. In an embodiment, each X-phosphonate moiety of the compound can be more than 70% diastereomerically pure. In an embodiment, each X-phosphonate moiety of the compound can be more than 85% diastereomerically pure. In an embodiment, each X-phosphonate moiety of the compound can be more than 90% diastereomerically pure. In an embodiment, each X-phosphonate moiety of the compound can be more than 95% diastereomerically pure. In another embodiment, each X-phosphonate moiety of the compound can be more than 98% diastereomerically pure. In another embodiment, each X-phosphonate moiety of the compound can be more than 99% diastereomerically pure. In an embodiment, each X-phosphonate moiety of the compound can be more than about 60%, more than about 70%, more than about 80%, more than about 83%, more than about 84%, more than about 85%, more than about 86%, more than about 87%, more than about 88%, more than about 89%, more than about 90%, more than about 91%, more than about 92%, more than about 93%, more than about 94%, more than about 95%, more than about 96%, more than about 97%, more than about 98%, or more than about 99% diastereomerically pure. In one embodiment, each X-phosphonate moiety can be from about 60% to about 99.9% diastereomerically pure. In one embodiment, each X-phosphonate moiety can be from about 60% to about 99% diastereomerically pure. In one embodiment, each X-phosphonate moiety can be from about 60% to about 70% diastereomerically pure. In one embodiment, each X-phosphonate moiety can be from about 70% to about 80% diastereomerically pure. In one embodiment, each X-phosphonate moiety can be from about 80% to about 90% diastereomerically pure. In one embodiment, each X-phosphonate moiety can be from about 80% to about 99% diastereomerically pure. In one embodiment, each X-phosphonate moiety can be from about 85% to about 95% diastereomerically pure. In one embodiment, each X-phosphonate moiety can be from about 90% to about 95% diastereomerically pure. In one embodiment, each X-phosphonate moiety can be from about 95% to about 99% diastereomerically pure. In one embodiment, each X-phosphonate moiety can be from about 90% to about 99.9% diastereomerically pure.

The amount of a particular configuration over another configuration affects the three-dimensional structure of the nucleic acids as well as their stability. Accordingly, different configurations affect the biological, chemical, and physical properties of the nucleic acids. In one embodiment, the nucleic acid comprises a greater percentage of $S_P$ configuration than $R_P$ configuration. In another embodiment, the nucleic acid comprises a greater percentage of $R_P$ configuration than $S_P$ configuration. In another embodiment, the nucleic acid comprises the same percentage of $R_P$ configuration as $S_P$ configuration. In one embodiment, the nucleic acid can comprise 0-20% $R_P$ configuration. In one embodiment, the nucleic acid can comprise 20-40% $R_P$ configuration. In one embodiment, the nucleic acid can comprise 40-60% $R_P$ configuration. In one embodiment, the nucleic acid can comprise 60-80% $R_P$ configuration. In one embodiment, the nucleic acid can comprise 80-100% $R_P$ configuration. In one embodiment, the nucleic acid can comprise 0-20% $S_P$ configuration. In one embodiment, the nucleic acid can comprise 20-40% $S_P$ configuration. In one embodiment, the nucleic acid can comprise 40-60% $S_P$ configuration. In one embodiment, the nucleic acid can comprise 60-80% $S_P$ configuration. In one embodiment, the nucleic acid can comprise 80-100% $S_P$ configuration.

Length of the Phosphorus Atom Modified Nucleic Acid.

The nucleic acid comprising a chiral X-phosphonate moiety of Formula 1 comprises from about 1 nucleoside to about 200 nucleosides. In some embodiments, the nucleic acid comprising a chiral X-phosphonate moiety of Formula 1 are further combined into oligomers or polymers. In some embodiments, the nucleic acid of Formula 1 is a dimer. In other embodiments, the nucleic acid of Formula 1 comprises up to about 100 nucleosides. In other embodiments, the nucleic acid of Formula 1 comprises up to about 150 nucleosides. In other embodiments, the nucleic acid of Formula 1 comprises up to about 200 nucleosides. In other embodiments, the nucleic acid of Formula 1 comprises up to about 300 nucleosides. In some embodiments, the nucleic acid of Formula 1 comprises from 1 to about 200 nucleosides. In other embodiments, the nucleic acid comprises from 1 to about 150 nucleosides. In further embodiments, nucleic acid contains from 1 to about 10 nucleosides. In other embodiments, the nucleic acid contains from about 10 to about 50 nucleosides. In further embodiments, nucleic acid contains from about 10 to about 100 nucleosides. In some embodiments, the nucleic acid comprises from 1 to about 5 nucleosides, or about 5 to about 10 nucleosides, or about 5 to about 15 nucleosides, or about 10 to about 20 nucleosides, or about 15 to about 25 nucleosides, or about 20 to about 30 nucleosides, or about 25 to about 35 nucleosides, or about 30 to about 40 nucleosides. In some embodiments of Formula 1, n is an integer of 1 to about 200. In some embodiments of Formula 1, n is an integer of 1 to about 150. In some embodiments of Formula 1, n is an integer of 1 to about 10. In some embodiments of Formula 1, n is an integer of 10 to about 50. In some embodiments of Formula 1, n is an integer of 10 to about 100. In some embodiments of Formula 1, n is an integer of 1 to about 5, or about 5 to about 10, or about 5 to about 15, or about 10 to about 20, or about 15 to about 25, or about 20 to about 30, or about 25 to about 35, or about 30 to about 40.

Additional Variations of Phosphorus Atom Modified Nucleic Acid.

The nucleic acid of Formula 1 can be single-stranded. In some embodiments, the nucleic acid of Formula 1 is hybridized to a complementary strand to form a double-stranded nucleic acid.

In some embodiments, the nucleic acid of Formula 1 can comprise an open linear structure. In other embodiments, the respective ends of the nucleic acid of Formula 1 are joined to form a circular structure.

Within a nucleic acid, the sugar component of each unit comprises the same or different sugars. In some embodiments, the sugars are modified sugars or sugars that are substituted. In some embodiments, the sugars are all ribose sugar moieties. In some embodiments, the sugars are all deoxyribose sugar moieties. In other embodiments, the sugars are all pentofuranose, pentopyranose, or hexopyranose moieties. In further embodiments, the sugar component comprises closed ring structures or open structures.

Within the nucleic acid structure, the phosphorous atom bridges are commonly referred to as forming the internucleoside backbone of the nucleic acids. The internucleoside backbone linkages in nucleic acids include, and are not limited to, 2' to 5' phosphorous atom bridges, 3' to 5' phosphorous atom bridges, 5' to 3' phosphorous atom bridges, and the 3' to 2' phosphorous atom bridges and 4' to 2' bridges described in U.S. Pat. No. 6,608,186 and Joyce, G. F. *Nature*, 2002, 418, 214-220. Non-limiting examples of these variations in internucleoside backbone linkages are shown below:

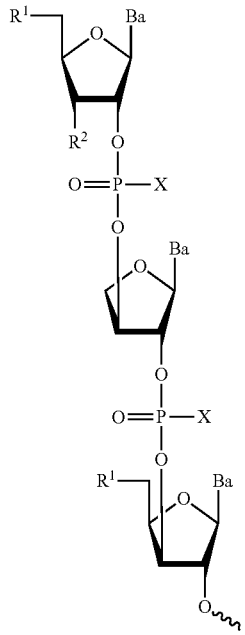

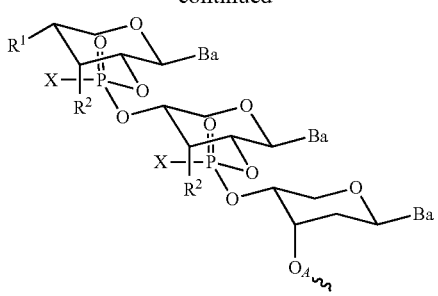

Depending on the sugar or modified sugar component, other types of phosphorous atom bridges are also contemplated including, and not limited to, methylene bisphosphonate bridges shown below and described in Xu, L. et al, *J. Med. Chem.*, 2005, 48, 4177-4181.

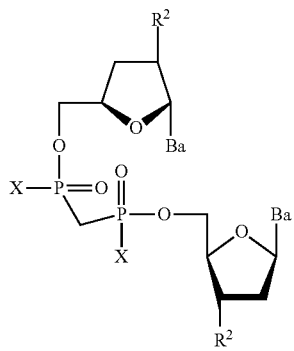

The nucleic acid of Formula 1 can comprise the same or different nucleobases. In some embodiments, the nucleic acid of Formula 1 comprises all the same nucleobases. In other embodiments, the nucleic acid of Formula 1 comprises all different nucleobases. In other embodiments, the nucleic acid of Formula 1 comprises the naturally occurring nucleobases. In some embodiments, the nucleic acid of Formula 1 comprises modified nucleobases. In yet other embodiments, the nucleic acid contain nucleobases that mimic the nucleobase sequence of a nucleic acid found in nature. In some embodiments, the nucleic acid of Formula 1 comprises a mixture of naturally occurring nucleobases and modified nucleobases.

Molecules Comprising an Achiral H-Phosphonate Moiety.

The molecule comprising an achiral H-phosphonate moiety is a compound of Formula 2:

Formula 2

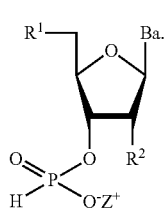

In Formula 2, $R^1$ is —$NR^dR^d$, —$N_3$, halogen, hydrogen, alkyl, alkenyl, alkynyl, alkyl-$Y^1$—, alkenyl-$Y^1$—, alkynyl-$Y^1$—, aryl-$Y^1$—, heteroaryl-$Y^1$—, —$P(O)(R^e)_2$, —$HP(O)(R^e)$, —$OR^a$, or —$SR^c$.

$Y^1$ is O, $NR^d$, S, or Se.

$R^a$ is a blocking moiety.

$R^c$ is a blocking group.

Each instance of $R^d$ is independently hydrogen, alkyl, alkenyl, alkynyl, aryl, acyl, substituted silyl, carbamate, —$P(O)(R^e)_2$, or —$HP(O)(R^e)$.

Each instance of $R^e$ is independently alkyl, aryl, alkenyl, alkynyl, alkyl-$Y^2$—, alkenyl-$Y^2$—, alkynyl-$Y^2$—, aryl-$Y^2$—, or heteroaryl-$Y^2$—.

$Y^2$ is O, $NR^d$, or S.

$R^2$ is hydrogen, —$NR^dR^d$, $N_3$, halogen, alkyl, alkenyl, alkynyl, alkyl-$Y^1$—, alkenyl-$Y^1$—, alkynyl-$Y^1$—, aryl-$Y^1$—, heteroaryl-$Y^1$—, —$OR^b$, or —$SR^c$, wherein $R^b$ is a blocking moiety.

Ba is a blocked or unblocked adenine, cytosine, guanine, thymine, uracil or modified nucleobase.

$Z^+$ is ammonium ion, alkylammonium ion, heteroaromatic iminium ion, or heterocyclic iminium ion, any of which is primary, secondary, tertiary or quaternary, or a monovalent metal ion.

In some embodiments, Z is pyridinium ion, triethylammonium ion, N,N-diisopropylethylammonium ion, 1,8-diazabicyclo[5.4.0]undec-7-enium ion, sodium ion, or potassium ion.

In some embodiments, the sugar is a ribose ring. In other embodiments, the sugar is deoxyribose, pentofuranose, pentopyranose, or hexopyranose moieties. In other embodiments, the sugar is a modified sugar. In some embodiments, the sugar is a glycerol analogue or a sugar with substitutions.

The H-phosphonate nucleoside monomers are easily prepared and stable. Methods of their preparation have been described (see e.g. Froehler, B. C. Methods in Molecular Biology. In Protocols for Oligonucleotides and Analogs; Agrawal, S., Ed.; Humana: Totowa, 1993; vol 20, p 63-80).

In some embodiments, the nucleoside monomer comprises an achiral H-phosphonate moiety attached to the nucleoside at the 3' position. In yet further embodiments, nucleoside monomer comprises an achiral H-phosphonate moiety attached to the nucleoside moiety at the 3' position through an intervening linking moiety. In specific embodiments, the intervening linking moiety is a methylene group (see. e.g. WO/2001/02415). In some embodiments the H-phosphonate moiety is attached to the 2' position of the nucleoside monomer. In other embodiments, the nucleoside monomer comprises an achiral H-phosphonate moiety attached to the nucleoside at the 5' position.

Compounds with a Free Nucleophilic Moiety.

The compound comprising a free nucleophilic moiety is a compound of Formula 4-1 and reacts at the phosphorus center of the chiral intermediate. The direction of attack at phosphorus by the nucleophilic group or moiety depends on the substituents of the chiral auxiliary on the chiral intermediate (condensed intermediate). In an embodiment, addition of an activating reagent can be useful for helping the compound comprising a free nucleophilic moiety to react at the phosphorus center of the chiral intermediate.

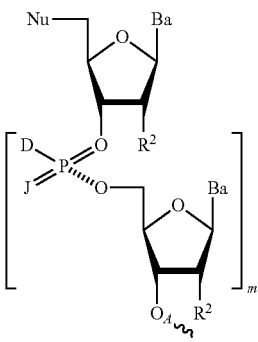

Formula 4-1

In some embodiments, the compound comprising a free nucleophilic moiety is a nucleic acid previously prepared using methods described herein or it is prepared using other known methods of nucleic acid synthesis. In one embodiment, the compound comprising a free nucleophilic moiety comprises a single nucleoside monomer. In another embodiment, the compound comprising a free nucleophilic moiety comprises more than one nucleoside unit. In some embodiments, the compound comprising a free nucleophilic moiety is a product of a chain elongation step. In yet other embodiments, the compound comprising a free nucleophilic moiety is an oligomer. In further embodiments, the compound comprising a free nucleophilic moiety is a polymer. In some embodiments the compound comprising a free nucleophilic moiety comprises a hydroxyl group as the free nucleophilic moiety. In some embodiments the compound comprising a free nucleophilic moiety comprises an amino group as the free nucleophilic moiety. In some embodiments the compound comprising a free nucleophilic moiety comprises a thiol group as the free nucleophilic moiety.

In some embodiments, the compound comprising a free nucleophilic moiety comprises a nucleophilic moiety at any position of the nucleoside sugar. In some embodiments, the nucleophilic moiety is located at the 5' position of the sugar. In some embodiments, the nucleophilic moiety is located at the 4' position of the sugar. In other embodiments, the nucleophilic moiety is located at the 3' position of the sugar. In other embodiments, the nucleophilic moiety is located at the 2' position of the sugar.

In some embodiments, the compound of Formula 4-1 is a nucleoside comprising a 5'-OH moiety and is a compound of Formula 4:

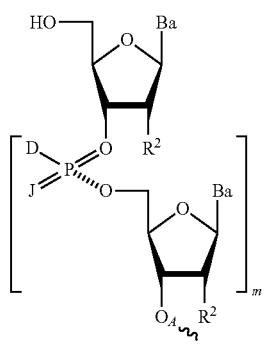

Formula 4

In Formula 4, each instance of $R^2$ is independently hydrogen, $-NR^dR^d$, $N_3$, halogen, alkyl, alkenyl, alkynyl, alkyl-$Y^1-$, alkenyl-$Y^1-$, alkynyl-$Y^1-$, aryl-$Y^1-$, heteroaryl-$Y^1-$, $-OR^b$, or $-SR^c$, wherein $R^b$ is a blocking moiety.

$Y^1$ is O, $NR^d$, S, or Se.

$R^c$ is a blocking group.

Each instance of $R^d$ is independently hydrogen, alkyl, alkenyl, alkynyl, aryl, acyl, substituted silyl, carbamate, $-P(O)(R^e)_2$, or $-HP(O)(R^e)$.

Each instance of $R^e$ is independently alkyl, aryl, alkenyl, alkynyl, alkyl-$Y^2-$, alkenyl-$Y^2-$, alkynyl-$Y^2-$, aryl-$Y^2-$, or heteroaryl-$Y^2-$.

$Y^2$ is O, $NR^d$, or S.

Each instance of Ba is independently a blocked or unblocked adenine, cytosine, guanine, thymine, uracil or modified nucleobase.

m is an integer of 0 to n–1.

n is an integer of 1 to about 200.

$O_A$ is connected to a trityl moiety, a silyl moiety, an acetyl moiety, an acyl moiety, an aryl acyl moiety, a linking moiety connected to a solid support or a linking moiety connected to a nucleic acid.

J is O and D is H, or J is S, Se, or $BH_3$ and D is a chiral ligand $C_i$ or a moiety of Formula A:

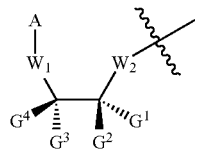

Formula A wherein $W_1$ and $W_2$ are independently $NHG^5$, OH, or SH.

A is hydrogen, acyl, aryl, alkyl, aralkyl, or silyl moiety.

$G^1$, $G^2$, $G^3$, $G^4$, and $G^5$ are independently hydrogen, alkyl, aralkyl, cycloalkyl, cycloalkylalkyl, heteroaryl, or aryl, or two of $G^1$, $G^2$, $G^3$, $G^4$, and $G^5$ are $G^6$ which taken together form a saturated, partially unsaturated or unsaturated carbocyclic or heteroatom-containing ring of up to about 20 ring atoms which is monocyclic or polycyclic, fused or unfused and wherein no more than four of $G^1$, $G^2$, $G^3$, $G^4$, and $G^5$ are $G^6$.

In other embodiments, where J is S, Se, or $BH_3$ and D is a moiety of Formula A-I:

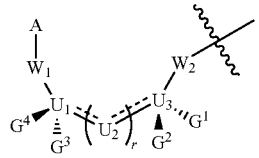

Formula A-I wherein $U^1$, $U_3$, $U_2$, r, $G^1$, $G^2$, $G^3$, $G^4$, $W_1$, $W_2$, A are as defined herein for Formula 3-I. In an embodiment of Formula A-I, A is hydrogen.

In some embodiments, the nucleoside comprising a 5'-OH moiety of Formula 4 is an intermediate from a previous chain elongation cycle as described herein. In yet other embodiments, the compound of Formula 4 is an intermediate from another known nucleic acid synthetic method. In some embodiments, the compound of Formula 4 is attached to solid support. In other embodiments, the compound of Formula 4 is not attached to solid support and is free in the solvent or solution.

In an embodiment, m is 0 and the compound of formula 4 is a single nucleoside unit and is considered the first nucleoside of the nucleic acid. In some embodiment, m is 0 and the compound of formula 4 is a nucleoside unit attached to another nucleic acid through the 3'-oxygen. In other embodiments, m is greater than 0 and the compound of formula 4 is a polymeric or oligomeric nucleic acid comprising a 5'-OH moiety. In other embodiments, m is greater than 0 and the compound of formula 4 is the end product of a previous chain elongation cycle. In some embodiments, where m is greater than 0, the compound of formula 4 is a nucleoside which is further attached to a nucleotide, through a linkage either at the 3' position or at another position on the nucleoside.

Where the compound of formula 4 is attached to another nucleotide or nucleic acid, the phosphate internucleoside backbone linkage include, and are not limited to, 2' to 5' phosphorous atom bridges, 3' to 5' phosphorous atom bridges, 5' to 3' phosphorous atom bridges, and the 3' to 2' phosphorous atom bridges and 4' to 2' bridges. The phosphate internucleoside backbone linkage includes other types of phosphorous atom bridges are also contemplated including, but not limited to, methylene bisphosphonate bridges.

The nucleic acid of Formula 1 comprises the same or different nucleobases. In some embodiments, the nucleic acid of Formula 1 comprises all the same nucleobases. In other embodiments, the nucleic acid of Formula 1 comprises different nucleobases. In other embodiments, the nucleic acid of Formula 1 comprises the naturally occurring nucleobases. In some embodiments, the nucleic acid of Formula 1 comprises modified nucleobases. In yet other embodiments, the nucleic acid contain nucleobases that mimic the nucleobase sequence of a nucleic acid found in nature. In some embodiments, the nucleic acid of Formula 1 comprises a mixture of naturally occurring nucleobases and modified nucleobases.

The compound comprising a free nucleophilic moiety is free in solution. In some embodiments, the compound comprising a free nucleophilic moiety is not attached to a solid support. This allows the nucleic acids to be synthesized in solution (liquid phase synthesis or solution phase synthesis). Alternatively, the compound comprising a free nucleophilic moiety is pre-attached to another moiety such as a solid support. In some embodiments, the compound comprising a free nucleophilic moiety is a nucleoside attached to a solid support at the 3' hydroxyl of the nucleoside. Attachment of the nucleic acid to a solid support allows synthesis using solid-phase synthesis. During nucleic acid synthesis, the compound attached to a solid support is treated with various reagents in one or repeated chain elongation cycles to achieve the stepwise elongation of a growing nucleic acid chain with individual nucleic acid units. Purification steps are typically not carried out until the fully-assembled nucleic acid sequence is synthesized. Various types of solid support materials are known and used in the synthesis of nucleic acids, proteins, and oligosaccharides. In some embodiments, the compound comprising a free nucleophilic moiety is attached to a solid support through a linking moiety. In other embodiments, the compound comprising a free nucleophilic moiety is attached to a solid support without a linking moiety.

The compound comprising a free nucleophilic moiety comprises a sugar, substitute sugar, or modified sugar. In some embodiments, the sugar is a ribose sugar. In some embodiments, the sugar is a deoxyribose sugar. In some embodiments, compound comprising a free nucleophilic moiety comprises a mixture of a ribose sugar and a deoxyribose sugar. In other embodiments, the sugar is pentofuranose, pentopyranose, hexopyranose moieties or mixtures thereof. In further embodiments, the sugar comprises a closed ring structure, an open structure, or mixtures thereof.

The nucleoside reactant comprising an unprotected-OH moiety may contain the unprotected-OH group at any position on the sugar core. In one embodiment, an achiral H-phosphonate moiety is condensed with a nucleoside comprising a 5'-OH moiety to form the condensed intermediate. In another embodiment, an achiral H-phosphonate moiety is condensed with a nucleoside comprising a 4'-OH moiety to form the condensed intermediate. In another embodiment, an achiral H-phosphonate moiety is condensed with a nucleoside comprising a 3'-OH moiety to form the condensed intermediate. In yet another embodiment, an achiral H-phosphonate moiety is condensed with a nucleoside comprising a 2'-OH moiety to form the condensed intermediate.

In some embodiments, acidifying the condensed intermediate produces a compound of Formula 4 wherein m is at least one. In other embodiments, the condensed intermediate comprises a moiety of Formula A', which is equivalent to a moiety of Formula A wherein A is hydrogen and wherein $G^1$ and $G^2$ are independently alkyl, aralkyl, cycloalkyl, cycloalkylalkyl, heteroaryl, or aryl and $G^3$, $G^4$, and $G^5$ are independently hydrogen, alkyl, aralkyl, cycloalkyl, cycloalkylalkyl, heterocyclyl, heteroaryl, or aryl, or two of $G^1$, $G^2$, $G^3$, $G^4$, and $G^5$ are $G^6$ which taken together form a saturated, partially unsaturated or unsaturated carbocyclic or heteroatom-containing ring of up to about 20 ring atoms which is monocyclic or polycyclic, fused or unfused and wherein no more than four of $G^1$, $G^2$, $G^3$, $G^4$, and $G^5$ are $G^6$.

Detailed Discussion of the Methods of Synthesis.

The extension of the nucleic acid chain can be performed in the 3' to 5' direction. In one embodiment, the nucleic acid is synthesized from the free hydroxyl at the 5'-end in repetitive cycles of chemical reactions. Alternatively, the extension of the nucleic acid chain can be performed in the 5' to 3' direction. In an embodiment, the nucleic acid is synthesized from the free hydroxyl at the 3'-end in repetitive cycles of chemical reactions.

One embodiment of the method of synthesis of the nucleic acid is shown in Scheme 5 (Route A). It is understood that the methods herein are not limited to the scheme, its sequence of events, or its intermediates as illustrated. In one embodiment, described in Scheme 5, an achiral H-phosphonate of Formula 2 is treated with a condensing reagent to form an intermediate of structure II. In one embodiment, an activating reagent is added to the reaction mixture during the condensation step. Use of an activating reagent is dependent on reaction conditions such as solvents that are used for the reaction. The intermediate of structure II is not isolated and is treated in the same pot with a chiral reagent to form a chiral intermediate of structure III. The intermediate of structure III is not isolated and undergoes a reaction in the same pot with a nucleoside or modified nucleoside of structure IV to provide a chiral phosphite compound of structure V. In some embodiments, structure V is extracted into a solvent to separate it from side products, impurities, and/or reagents. In other embodiments, when the method is performed via solid phase synthesis, the solid support comprising the compound of structure V is filtered away from side products, impurities, and/or reagents. If the final nucleic acid is larger than a dimer, the chiral auxiliary in the compound of structure V is capped with a blocking group to provide a compound of structure VI. If the final nucleic acid is a dimer, then the capping step is not necessary. The compound of structure VI is modified by reaction with an electrophile to provide a compound of structure VII. The modified and capped condensed intermediate of structure VII is deblocked to remove the blocking group at the 5'-end of the growing nucleic acid chain to provide a compound of structure IV. The compound of structure IV is optionally allowed to re-enter the chain elongation cycle to form a condensed intermediate, a capped condensed intermediate, a modified capped condensed intermediate, and a 5'-deprotected modified capped intermediate. Following at least one round of chain elongation cycle, the 5'-deprotected modified capped intermediate is further deblocked by removal of the chiral auxiliary ligand and other protecting groups, e.g., nucleobase, modified nucleobase, sugar and modified sugar protecting groups, to provide a nucleic acid of Formula 1. In other embodiments, the nucleoside comprising a 5'-OH moiety is an intermediate from a previous chain elongation cycle as described herein. In yet other embodiments, the nucleoside comprising a 5'-OH moiety is an intermediate obtained from another known nucleic acid synthetic method. After a cycle of synthesis with the first nucleoside, nucleosides, nucleotides, or nucleic acids that contain an unprotected —OH moiety can be used for subsequent elongation cycles. In embodiments where a solid support is used, the phosphorus-atom modified nucleic acid is then cleaved from the solid support. In certain embodiments, the nucleic acids is left attached on the solid support for purification purposes and then cleaved from the solid support following purification. In one embodiment, the synthesis described in Scheme 5 (Route A) is useful when the $G^1$ and $G^2$ positions of the chiral auxiliary ligand of Formula A are hydrogen. In yet other embodiments, the compounds of structure III-VII comprise a moiety of Formula A-I instead of a moiety of Formula A.

Scheme 5. Synthesis of a nucleic acid comprising a chiral X-phosphonate moiety of Formula 1 via Route A.

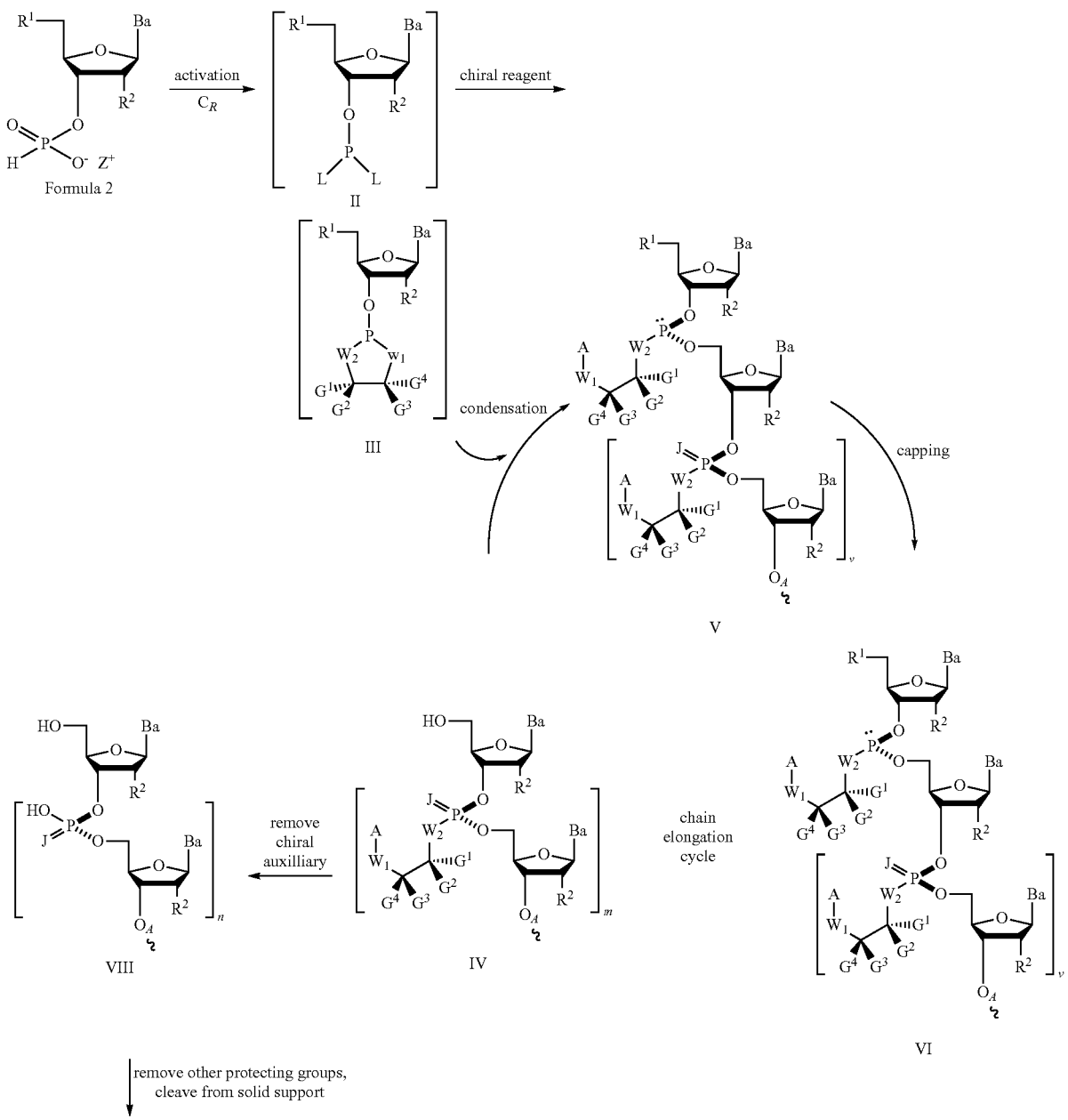

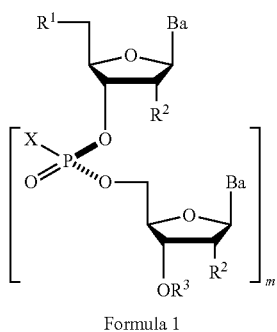

Formula 1

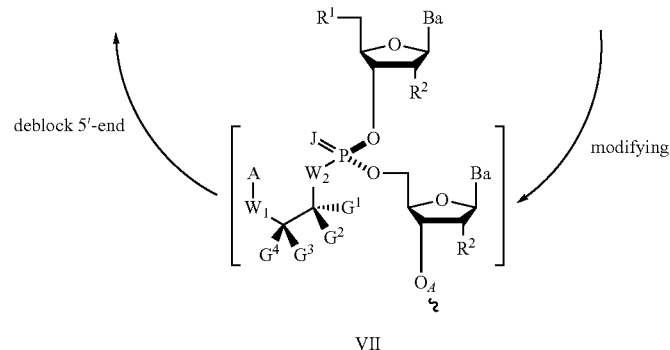

VII

In another embodiment, described in Scheme 6 (Route B), an achiral H-phosphonate of Formula 2 is treated with a condensing reagent to form an intermediate of structure II. In one embodiment, an activating reagent is added to the reaction mixture during the condensation step. Use of an activating reagent is dependent on reaction conditions such as solvents that are used for the reaction. The intermediate of structure II is not isolated and is treated in the same pot with a chiral reagent to form a chiral intermediate of structure III. The intermediate of structure III is not isolated and undergoes a reaction in the same pot with a nucleoside or modified nucleoside of structure LX to provide a chiral phosphite compound of structure X. In some embodiments, structure X is extracted into a solvent to separate it from side products, impurities, and/or reagents. In other embodiments, when the method is performed via solid phase synthesis, the solid support comprising the compound of structure X is filtered away from side products, impurities, and/or reagents. The compound of structure X is treated with an acid to remove the blocking group at the 5'-end of the growing nucleic acid chain (structure XI). The acidification step also removes the chiral auxiliary ligand to provide a compound of structure IX. The 5'-deblocked intermediate is optionally allowed to re-enter the chain elongation cycle to form a condensed intermediate containing a blocked 5'-end, which is then acidified to remove the 5'-end blocking group and chiral auxiliary ligand. Following at least one round of chain elongation cycle, the 5'-deprotected intermediate undergoes a modifying step to introduce a moiety X bonded to each of the phosphorus atoms to provide a compound of structure XII. The modified intermediate is deblocked by removal of remaining protecting groups, e.g., nucleobase, modified nucleobase, sugar or modified sugar protecting groups are removed, to provide a nucleic acid of Formula 1. In other embodiments, the nucleoside comprising a 5'-OH moiety is an intermediate from a previous chain elongation cycle as described herein. In yet other embodiments, the nucleoside comprising a 5'-OH moiety is an intermediate obtained from another known nucleic acid synthetic method. After a cycle of synthesis with the first nucleoside, the nucleoside, nucleotide, or nucleic acid that contain an unprotected —OH moiety can be used for subsequent elongation cycles. In embodiments where a solid support is used, the phosphorus-atom modified nucleic acid is then cleaved from the solid support. In certain embodiments, the nucleic acids is left attached on the solid support for purification purposes and then cleaved from the solid support following purification. In one embodiment, the synthesis described in Scheme 6 (Route B) is useful when the $G^1$ and $G^2$ positions of the chiral auxiliary ligand of Formula A are not hydrogen. In some embodiments, the compounds of structures III, X, and XI comprise a moiety of Formula A-I in place of a moiety of Formula A.

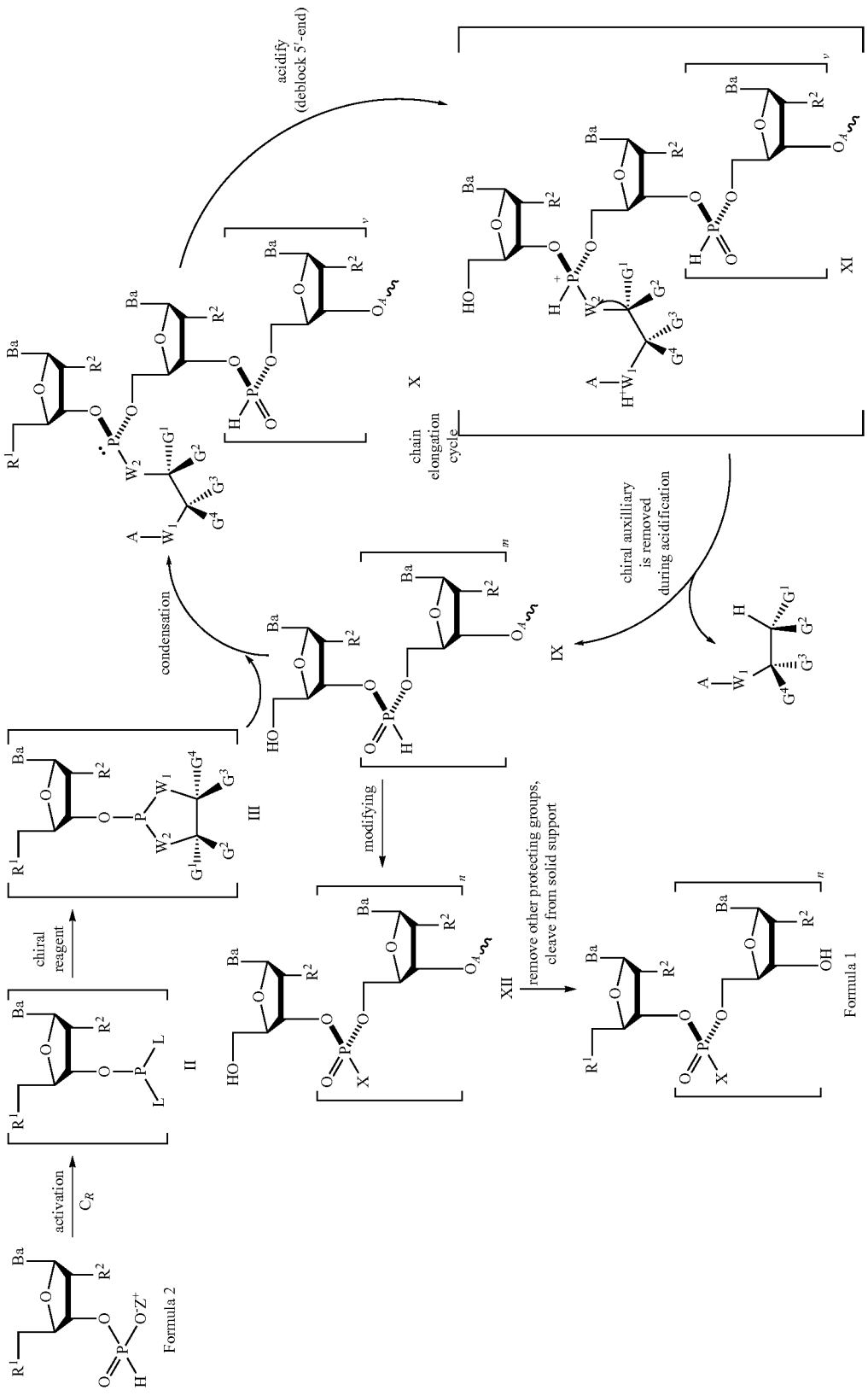

Reverse 5' to 3' Nucleic Acid Synthesis.

A nucleic acid comprising a chiral X-phosphonate moiety of Formula 1 alternatively is synthesized from the 5' to 3' direction. In embodiments where a solid support is used, the nucleic acid is attached to the solid support through its 5' end of the growing nucleic acid, thereby presenting its 3' group for reaction, including enzymatic reaction (e.g. ligation and polymerization). In some embodiments, this orientation is engineered by preparing nucleoside monomers comprising an achiral H-phosphonate moiety at the 5' position and protected hydroxyl group at the 3' position. In an embodiment, the nucleic acid is synthesized according to Scheme 7. In Scheme 7, —$R^4$ is —$OR^b$ as defined above or, in the last cycle of synthesis, is $R^4$, which is equivalent to $R^1$ as defined herein.

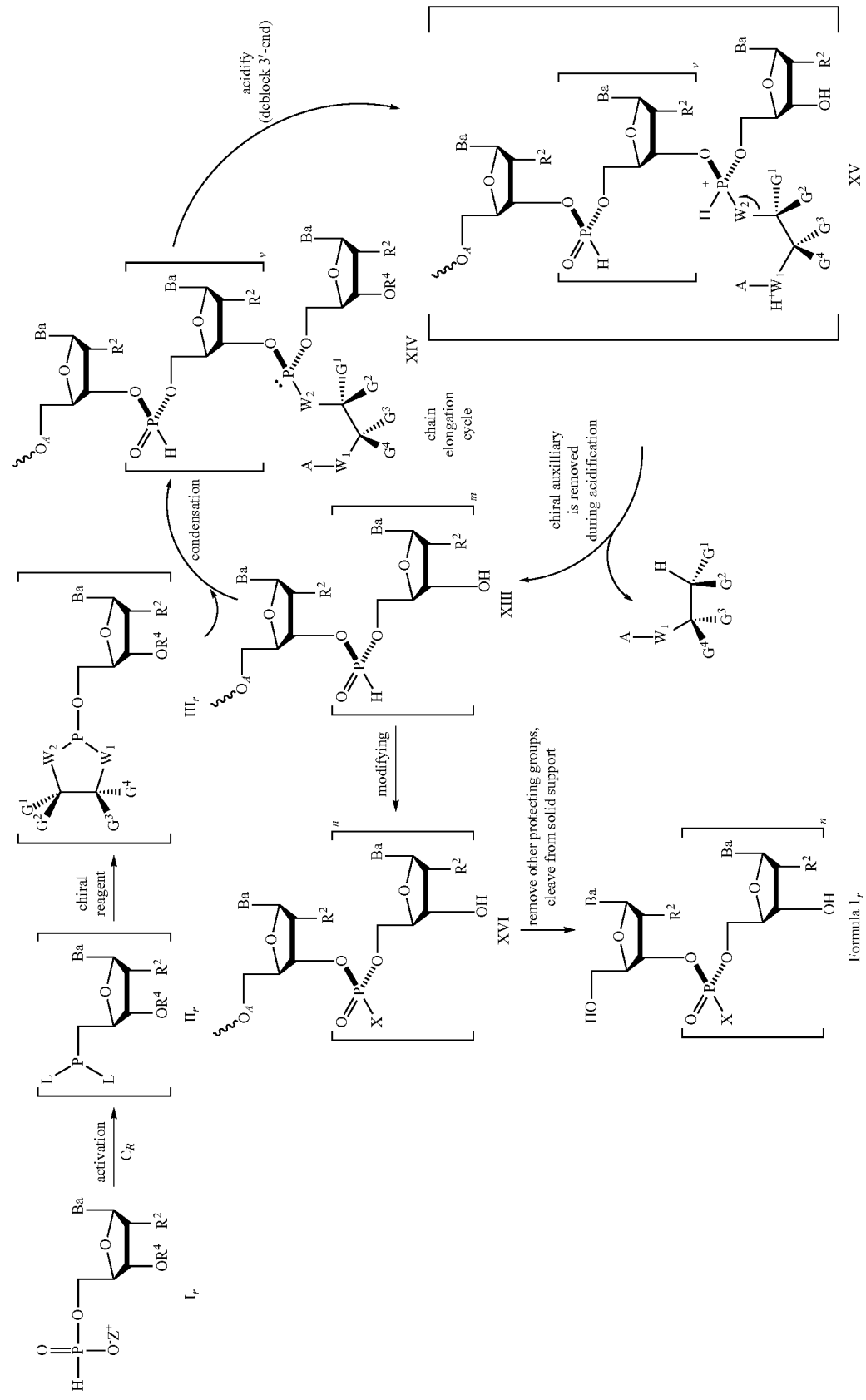

In the embodiment described in Scheme 7, an achiral H-phosphonate of structure $I_r$ is treated with a condensing reagent to form an intermediate of structure $II_r$. The intermediate of structure $II_r$ is not isolated and is treated in the same pot with a chiral reagent to form an intermediate of structure $III_r$. In one embodiment, an activating reagent is used during the condensation step. Use of an activating reagent is dependent on reaction conditions such as solvents that are used for the reaction. The intermediate of structure $III_r$ is not isolated and undergoes a reaction in the same pot with a nucleoside or modified nucleoside of structure XIII to provide a chiral phosphite compound of structure XIV. In some embodiments, structure XIV is extracted into a solvent to separate it from side products, impurities, and/or reagents. In other embodiments, when the method is performed via solid phase synthesis, the solid support comprising the compound of structure XIV is filtered away from side products, impurities, and/or reagents. The compound of structure XIV is treated with an acid to remove the blocking group at the 3'-end of the growing nucleic acid chain (structure XV). The acidification step also removes the chiral auxiliary ligand to provide a compound of structure XIII. The 3'-deblocked intermediate is optionally allowed to re-enter the chain elongation cycle to form a condensed intermediate containing a blocked 3'-end, which is then acidified to remove the 3'-end blocking group and chiral auxiliary ligand. Following at least one round of chain elongation cycle, the 3'-deprotected intermediate undergoes a modifying step to introduce a moiety X bonded to each of the phosphorus atoms to provide a compound of structure XVI. The modified intermediate is deblocked by removal of remaining protecting groups, e.g., nucleobase, modified nucleobase, sugar or modified sugar protecting groups are removed, to provide a nucleic acid of Formula 1. In other embodiments, the nucleoside comprising a 3'-OH moiety is an intermediate from a previous chain elongation cycle as described herein. In yet other embodiments, the nucleoside comprising a 3'-OH moiety is an intermediate obtained from another known nucleic acid synthetic method. After a cycle of synthesis with the first nucleoside, nucleosides, nucleotides, or nucleic acids that contain an unprotected —OH moiety can be used for subsequent elongation cycles. In embodiments where a solid support is used, the phosphorus-atom modified nucleic acid can then be cleaved from the solid support, located at the 5' end. In certain embodiments, the nucleic acids can optionally be left attached on the solid support for purification purposes and then cleaved from the solid support following purification. In one aspect, the synthesis described in Scheme 7 is useful when both of the $G^1$ and $G^2$ position of the chiral auxiliary ligand of Formula A are not hydrogen. The reverse 5' to 3' synthesis can be accomplished using the same starting materials in Scheme 7 in a mechanism analogous to steps in Route A. In some embodiments, the compounds of structures $III_r$, XIV, and XV comprise a moiety of Formula A-I in place of a moiety of Formula A.

Chain Elongation Cycle.

The stereoselective synthesis of a phosphorus atom modified nucleic acid comprises a chain elongation cycle. The chain elongation cycle begins with a condensation reaction between a compound that is the next unit (e.g. molecular comprising an achiral H-phosphonate moiety) to be added to the nucleic acid and another compound comprising a free nucleophilic moiety (e.g. hydroxyl moiety). In some embodiments, the compound comprising a free nucleophilic moiety is a monomer nucleoside. In other embodiments, compound comprising a free nucleophilic moiety is a nucleic acid oligomer or polymer from a previous chain elongation cycle as described herein. In other embodiments, compound comprising a free nucleophilic moiety is a nucleic acid oligomer or polymer from a chain elongation cycle performed using other methods known in the art.

The number of rounds of chain elongation cycles is determined by the length of the nucleic acid being synthesized. In some embodiments the chain elongation cycle occurs once. In other embodiments, the chain elongation cycle is repeated more than once to achieve the stepwise elongation of a growing oligonucleotide chain with individual nucleotide units.

In one embodiment, one round of chain elongation cycle is needed if a nucleic acid is a dimer. In another embodiment, 9 rounds of the chain elongation cycle are needed if a nucleic acid comprises ten nucleoside units. In yet another embodiment, 20 rounds of the chain elongation cycle are needed if 20 additional nucleoside units are to be added to a pre-synthesized nucleic acid chain. It will be evident to those skilled in art that the number of chain elongation cycles can be adjusted for the target length of the nucleic acid. The nucleic acids synthesized by the methods herein are not limited by the number of chain elongation cycles as described herein.

Modification of the Condensed Intermediate Obtained Via Route A to Introduce an X-Phosphonate Moiety.

Scheme 8. Modification of the condensed intermediate obtained via Route A.

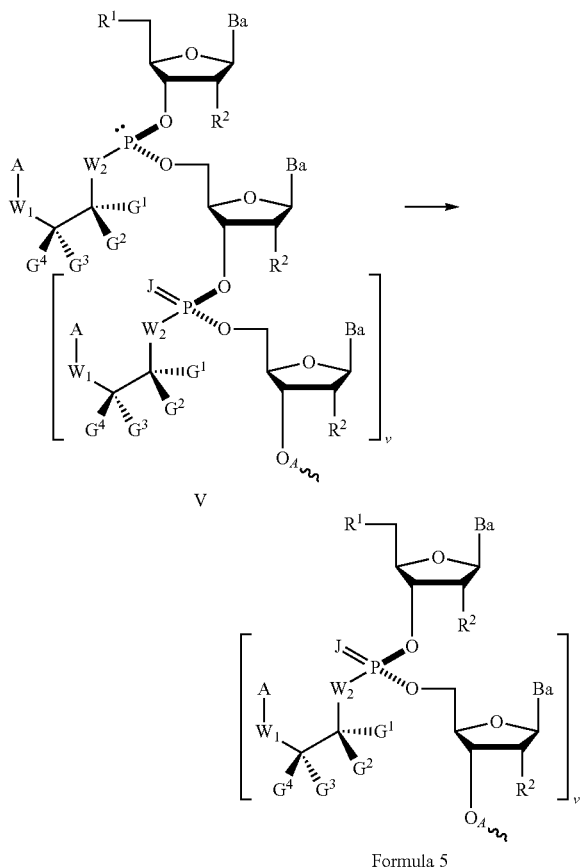

Formula 5

In the compound of Formula 5, $R^1$ is —$NR^dR^d$, —$N_3$, halogen, hydrogen, alkyl, alkenyl, alkynyl, alkyl-$Y^1$—, alkenyl-$Y^1$—, alkynyl-$Y^1$—, aryl-$Y^1$—, heteroaryl-$Y^1$—, —P(O)($R^e$)$_2$, or —HP(O)($R^e$), —$OR^a$, or —$SR^c$.

$Y^1$ is O, $NR^d$, S, or Se; $R^a$ is a blocking moiety.

$R^c$ is a blocking group.

Each instance of $R^d$ is independently hydrogen, alkyl, alkenyl, alkynyl, aryl, acyl, substituted silyl, carbamate, —P(O)($R^e$)$_2$, or —HP(O)($R^e$).

Each instance of $R^e$ is independently alkyl, aryl, alkenyl, alkynyl, alkyl-$Y^2$—, alkenyl-$Y^2$—, alkynyl-$Y^2$—, aryl-$Y^2$—, or heteroaryl-$Y^2$—.

$Y^2$ is O, $NR^d$, or S.

Each instance of $R^2$ is independently hydrogen, —$NR^dR^d$, $N_3$, halogen, alkyl, alkenyl, alkynyl, alkyl-$Y^1$—, alkenyl-$Y^1$—, alkynyl-$Y^1$—, aryl-$Y^1$—, heteroaryl-$Y^1$—, —$OR^b$, or —$SR^c$, wherein $R^b$ is a blocking moiety.

Each instance of Ba is independently a blocked or unblocked adenine, cytosine, guanine, thymine, uracil, or modified nucleobase.

Each instance of J is S, Se, or $BH_3$; v is an integer of 1 to n−1.

$O_A$ is connected to a linking moiety connected to a solid support or a linking moiety connected to a nucleic acid.

A is an acyl, aryl, alkyl, aralkyl, or silyl moiety; and $G^1$, $G^2$, $G^3$, $G^4$, and $G^5$ are independently hydrogen, alkyl, aralkyl, cycloalkyl, cycloalkylalkyl, heterocyclyl, heteroaryl, or aryl, or two of $G^1$, $G^2$, $G^3$, $G^4$, and $G^5$ are $G^6$ which taken together form a saturated, partially unsaturated or unsaturated carbocyclic or heteroatom-containing ring of up to about 20 ring atoms which is monocyclic or polycyclic, fused or unfused and wherein no more than four of $G^1$, $G^2$, $G^3$, $G^4$, and $G^5$ are $G^6$.

In some embodiments, the compound of Formula 5 comprises a moiety of Formula A-I attached at the phosphorus atom. In other embodiments, the compound of Formula 5 comprises a moiety of Formula A attached at the phosphorus atom. In the method illustrated in Route A, the condensed intermediate resulting from addition of a new nucleoside is capped to produce the compound of structure V and then is modified at the phosphorus to introduce J, which is S, Se, or $BH_3$, producing a compound of Formula 5, where v is an integer of 1 to n−1. The compound of Formula 5 is either treated to cleave the capped chiral auxiliary and deblock remaining blocking groups or it is subjected to further cycles of chain elongation and phosphorus modification. In the case that the final nucleic acid is a dimer, capping is not necessary. In one embodiment of structure V, A is hydrogen, acyl, aryl, alkyl, aralkyl, or silyl moiety. In one embodiment of Scheme 9, the condensed intermediate resulting from addition of a new nucleoside is not capped to produce a compound of structure V, where v is 0. This structure V, where v is 0, is then modified at the phosphorus to introduce J, which is S, Se, or $BH_3$, producing a compound of Formula 5, where v is an integer of 0.

In some embodiments, the modifying agent is a sulfur electrophile, selenium electrophile, or boronating agent.

In some embodiments, the sulfur electrophile is a compound having one of the following formulas:

$$S_8 \quad \text{(Formula B)},$$

$$Z^{24}\text{—S—S—}Z^{25},$$

or $$Z^{24}\text{—S—X—}Z^{25},$$

wherein $Z^{24}$ and $Z^{25}$ are independently alkyl, aminoalkyl, cycloalkyl, heterocyclic, cycloalkylalkyl, heterocycloalkyl, aryl, heteroaryl, alkyloxy, aryloxy, heteroaryloxy, acyl, amide, imide, or thiocarbonyl, or $Z^{24}$ and $Z^{25}$ are taken together to form a 3 to 8 membered alicyclic or heterocyclic ring, which may be substituted or unsubstituted; X is $SO_2$, O, or $NR^f$; and $R^f$ is hydrogen, alkyl, alkenyl, alkynyl, or aryl. In other embodiments, the sulfur electrophile is a compound of Formula B, C, D, E, or F:

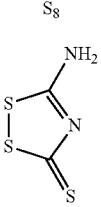

Formula B

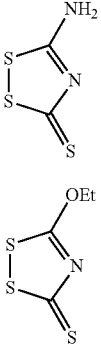

Formula C

Formula D

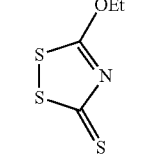

Formula E

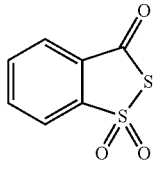

Formula F

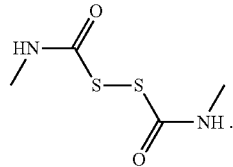

In other embodiments, the sulfur electrophile is Formula F, Formula E or Formula B.

In some embodiments, the selenium electrophile is a compound having one of the following formulas:

$$Se \quad \text{(Formula G)},$$

$$Z^{26}\text{—Se—Se—}Z^{27},$$

or $$Z^{26}\text{—Se—X—}Z^{27},$$

wherein $Z^{26}$ and $Z^{27}$ are independently alkyl, aminoalkyl, cycloalkyl, heterocyclic, cycloalkylalkyl, heterocycloalkyl, aryl, heteroaryl, alkyloxy, aryloxy, heteroaryloxy, acyl, amide, imide, or thiocarbonyl, or $Z^{26}$ and $Z^{27}$ are taken together to form a 3 to 8 membered alicyclic or heterocyclic ring, which may be substituted or unsubstituted; X is $SO_2$, S, O, or $NR^f$; and $R^f$ is hydrogen, alkyl, alkenyl, alkynyl, or aryl.

In other embodiments, the selenium electrophile is a compound of Formula G, H, I, J, K, or L.

Se    Formula G

KSeCN    Formula H

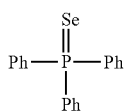    Formula I

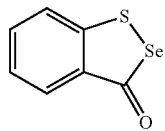    Formula J

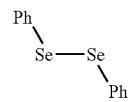    Formula K

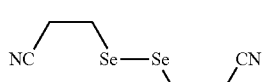    Formula L

In some embodiments, the selenium electrophile is Formula G or Formula L.

In some embodiments, the boronating agent is borane-N,N-diisopropylethylamine ($BH_3$.DIPEA), borane-pyridine ($BH_3$.Py), borane-2-chloropyridine ($BH_3$.CPy), borane-aniline ($BH_3$.An), borane-tetrahydrofuran ($BH_3$.THF), or borane-dimethylsulfide ($BH_3$.$Me_2$S), aniline-cyanoborane, triphenylphosphine-carboalkoxyboranes.

In other embodiments, the boronating agent is borane-N,N-diisopropylethylamine ($BH_3$.DIPEA), borane-2-chloropyridine ($BH_3$.CPy), borane-tetrahydrofuran ($BH_3$.THF), or borane-dimethylsulfide ($BH_3$.$Me_2$S).

In further embodiments, after modification of the condensed intermediate obtained via Route A, the compound of Formula 5 is deblocked at the $R^1$ position to produce a compound of Formula 4, wherein m is at least 1, J is S, Se, or $BH_3$ and D is a moiety of Formula A. In some embodiments, following deblocking of $R^1$, a compound of Formula 4 is produced wherein D is a moiety of Formula A-I. The compound of Formula 4 is reacted with a nucleoside of structure Ill to produce a condensed intermediate. The step of converting the condensed intermediate comprises capping the condensed intermediate and modifying the capped condensed intermediate to produce a compound of Formula 5. In some embodiments of the compound of Formula 5, v is greater than 2 and less than about 200. Deblocking at the $R^1$ position, reacting with a nucleoside of structure III, capping, and modifying is optionally repeated to form a compound of Formula 5 wherein v is increased by 1 integer. In some embodiments of the compound of Formula 5, v is greater than 3 and less than about 200.

In further embodiments, the compound of Formula 5 is converted to the compound of Formula 1 where in some embodiments, each Ba moiety is unblocked. In other embodiments, the compound of Formula 5 is converted to the compound of Formula 1 wherein not all Ba moieties are unblocked.

$R^1$ is —OH, —SH, —$NR^dR^d$, —$N_3$, halogen, hydrogen, alkyl, alkenyl, alkynyl, alkyl-$Y^1$—, alkenyl-$Y^1$—, alkynyl-$Y^1$—, aryl-$Y^1$—, heteroaryl-$Y^1$—, —P(O)$(R_e)_2$, —HP(O)($R^e$), —$OR^a$, or —$SR^c$; where $Y^1$ is O, $NR^d$, S, or Se, $R^a$ is a blocking moiety, and $R^c$ is a blocking group. In some embodiments, $R^1$ is deblocked. In yet other embodiments, $R^1$ remains blocked.

Each instance of $R^d$ is independently hydrogen, alkyl, alkenyl, alkynyl, aryl, substituted silyl, carbamate, —P(O)$(R^e)_2$, or —HP(O)($R^e$), and each instance of $R^e$ is independently hydrogen, alkyl, aryl, alkenyl, alkynyl, alkyl-$Y^2$—, alkenyl-$Y^2$—, alkynyl-$Y^2$—, aryl-$Y^2$—, or heteroaryl-$Y^2$—, or a cation which is $Na^{+1}$, $Li^{+1}$, or $K^{+1}$, where $Y^2$ is O, $NR^d$, or S.

Each instance of $R^2$ is independently hydrogen, —OH, —SH, —$NR^dR^d$, $N_3$, halogen, alkyl, alkenyl, alkynyl, alkyl-$Y^1$—, alkenyl-$Y^1$—, alkynyl-$Y^1$—, aryl-$Y^1$—, heteroaryl-$Y^1$—.

In some embodiments, $R^3$ is H. In other embodiments, $R^3$ is a blocking group or a linking moiety connected to solid support, nucleoside, nucleotide, or nucleic acid. In some embodiments, each instance of X is independently —$S^-Z^+$, —$Se^-Z^+$, or —$BH_3^-Z^+$; and $Z^+$ is ammonium ion, alkylammonium ion, heteroaromatic iminium ion, or heterocyclic iminium ion, any of which is primary, secondary, tertiary or quaternary, or $Z^+$ is a monovalent metal ion.

Modification of the Compound of Formula 4 Obtained Via Route B to Introduce an X-Phosphonate Moiety.

Methods used to modify the compound of Formula 4 obtained via Route B are illustrated in Reaction Schemes 9a and 9b. Phosphonate and phosphite are known to tautomerize and exist in equilibrium. The phosphite tautomer is less stable than the phosphonate tautomer. Equilibrium lies toward the phosphonate tautomer under neutral conditions due to the very strong P=O bond. Under acidic conditions, the phosphoryl group of the phosphonate becomes reversibly protonated. Cleavage of the P—H bond in the intermediate occurs slowly to produce the phosphite intermediate. Structure IX is then modified to form structure XII, using reagents shown in Reaction Schemes 9a and 9b.

Reaction Scheme 9a. Modification of phosphorus in intermediates synthesized via Route B, using an initial halogenation at phosphorus.

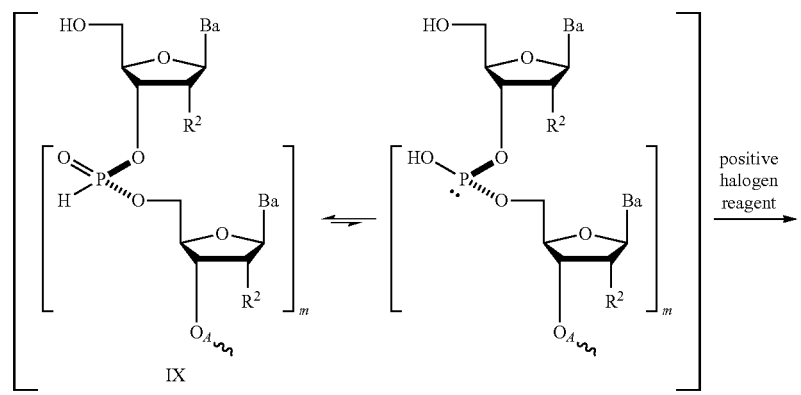

IX

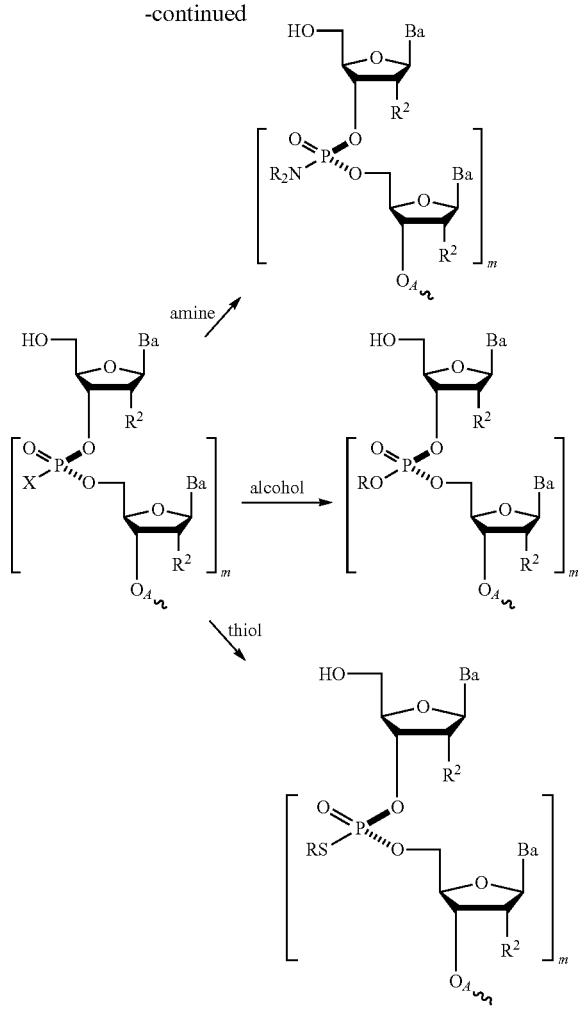

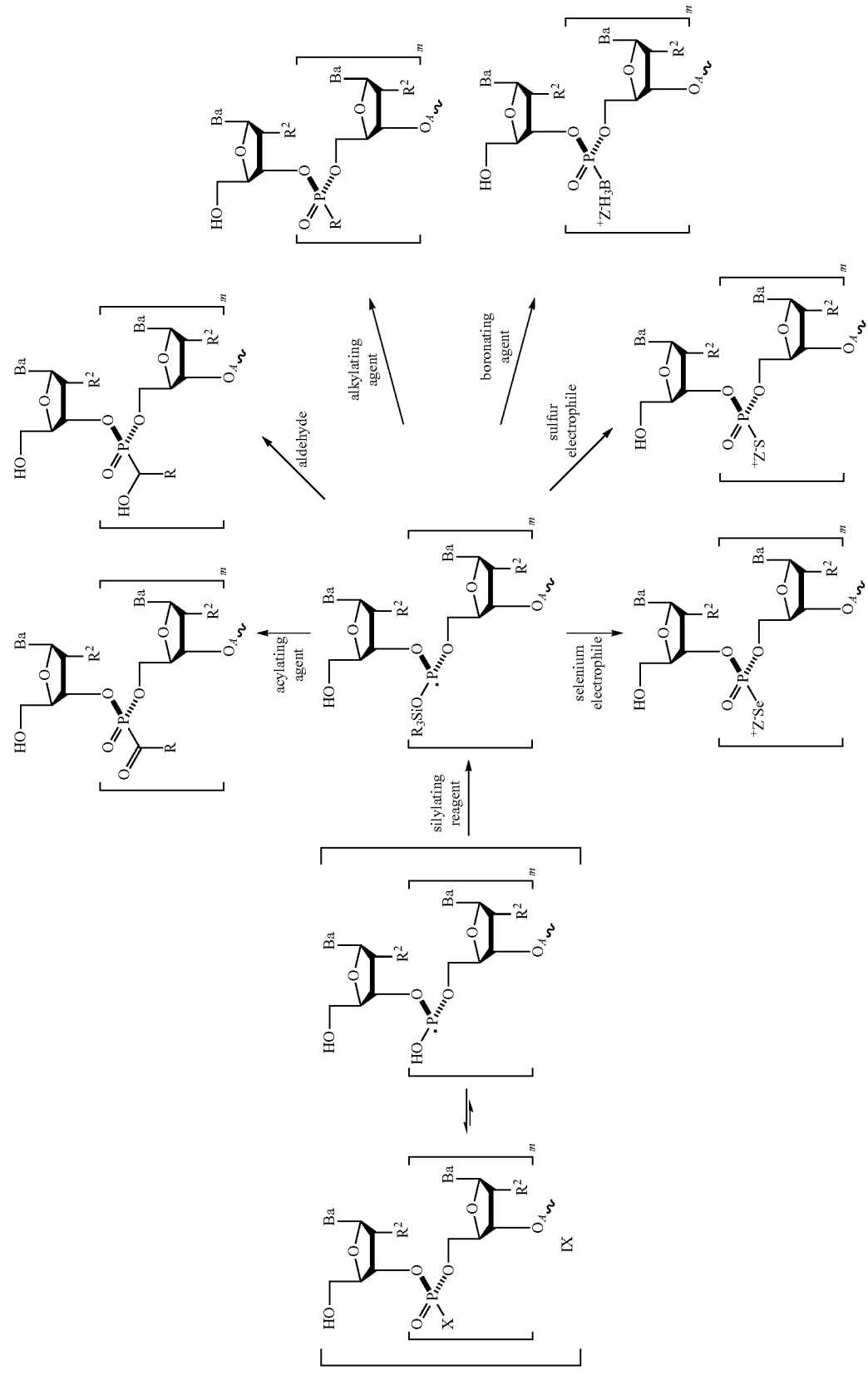
Reaction Scheme 9b. Modification of phosphorus in intermediates synthesized via Route B, using an initial silylation.

In some embodiments, the modifying step is performed by reacting structure IX with a halogenating reagent followed by reacting with a nucleophile (Scheme 9a). In specific embodiments, the halogenating reagent is $CCl_4$, $CBr_4$, $Cl_4$, $Cl_2$, $Br_2$, $I_2$, sulfuryl chloride ($SO_2Cl_2$), phosgene, bis(trichloromethyl)carbonate (BTC), sulfur monochloride, sulfur dichloride, chloramine, $CuCl_2$, N-chlorosuccinimide (NCS), N-bromosuccinimide (NBS), or N-iodosuccinimide (NIS). In other specific embodiments, the halogenating reagent is $CCl_4$, $CBr_4$, $Cl_2$, sulfuryl chloride ($SO_2Cl_2$), or N-chlorosuccinimide (NCS). In some embodiments, the nucleophile is primary or secondary amines, alcohols, or thiols. In other embodiments, the nucleophile is $NR^fR^fH$, $R^fOH$, or $R^fSH$, wherein $R^f$ is hydrogen, alkyl, alkenyl, alkynyl, or aryl, and at least one of $R^f$ of $NR^fR^fH$ is not hydrogen.

The modifying step can also be performed by reacting structure IX with a silylating reagent followed by reaction with a sulfur electrophile, a selenium electrophile, a boronating agent, an alkylating agent, an aldehyde, or an acylating agent (Scheme 9b).

In specific embodiments, the silylating reagent is chlorotrimethylsilane (TMS-Cl), triisopropylsilylchloride (TIPS-Cl), t-butyldimethylsilylchloride (TBDMS-Cl), t-butyldiphenylsilylchloride (TBDPS-Cl), 1,1,1,3,3,3-hexamethyldisilazane (HMDS), N-trimethylsilyldimethylamine (TMSDMA), N-trimethylsilyldiethylamine (TMSDEA), N-trimethylsilylacetamide (TMSA), N,O-bis(trimethylsilyl)acetamide (BSA), or N,O-bis(trimethylsilyl)trifluoroacetamide (BSTFA).

In other specific embodiments, the sulfur electrophile is a compound having one of the following formulas:

$$S_8 \quad \text{(Formula B)},$$

$$Z^{24}\text{—}S\text{—}S\text{—}Z^{25},$$

or $$Z^{24}\text{—}S\text{—}X\text{—}Z^{25},$$

wherein $Z^{24}$ and $Z^{25}$ are independently alkyl, aminoalkyl, cycloalkyl, heterocyclic, cycloalkylalkyl, heterocycloalkyl, aryl, heteroaryl, alkyloxy, aryloxy, heteroaryloxy, acyl, amide, imide, or thiocarbonyl, or $Z^{24}$ and $Z^{25}$ are taken together to form a 3 to 8 membered alicyclic or heterocyclic ring, which may be substituted or unsubstituted; X is $SO_2$, O, or $NR^f$; and $R^f$ is hydrogen, alkyl, alkenyl, alkynyl, or aryl. In other embodiments, the sulfur electrophile is a compound of Formula B, C, D, E, or F:

$$S_8 \quad \text{Formula B}$$

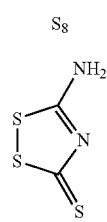

Formula C

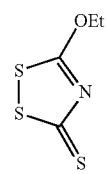

Formula D

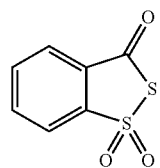

Formula E

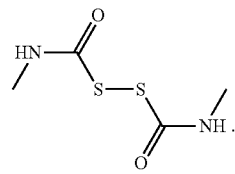

Formula F

In other embodiments, the sulfur electrophile is Formula F, Formula E or Formula B.

In some embodiments, selenium electrophile is a compound having one of the following formulas:

$$Se \quad \text{(Formula G)},$$

$$Z^{26}\text{—}Se\text{—}Se\text{—}Z^{27},$$

or $$Z^{26}\text{—}Se\text{—}X\text{—}Z^{27},$$

wherein $Z^{26}$ and $Z^{27}$ are independently alkyl, aminoalkyl, cycloalkyl, heterocyclic, cycloalkylalkyl, heterocycloalkyl, aryl, heteroaryl, alkyloxy, aryloxy, heteroaryloxy, acyl, amide, imide, or thiocarbonyl, or $Z^{26}$ and $Z^{27}$ are taken together to form a 3 to 8 membered alicyclic or heterocyclic ring, which may be substituted or unsubstituted; X is $SO_2$, S, O, or $NR^f$; and $R^f$ is hydrogen, alkyl, alkenyl, alkynyl, or aryl.

In other embodiments, the selenium electrophile is a compound of Formula G, H, I, J, K, or L.

Se     Formula G

KSeCN     Formula H

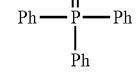

Formula I

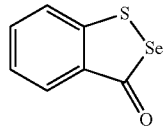

Formula J

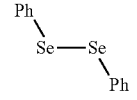

Formula K

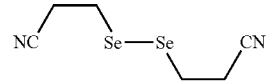

Formula L

In some embodiments, the selenium electrophile is Formula G or Formula L.

In some embodiments, the boronating agent is borane-N,N-diisopropylethylamine (BH$_3$.DIPEA), borane-pyridine (BH$_3$.Py), borane-2-chloropyridine (BH$_3$.CPy), borane-aniline (BH$_3$.An), borane-tetrahydrofuran (BH$_3$.THF), or borane-dimethylsulfide (BH$_3$.Me$_2$S), aniline-cyanoborane, triphenylphosphine-carboalkoxyboranes. In other embodiments, the boronating agent is borane-N,N-diisopropylethylamine (BH$_3$.DIPEA), borane-2-chloropyridine (BH$_3$.CPy), borane-tetrahydrofuran (BH$_3$.THF), or borane-dimethylsulfide (BH$_3$.Me$_2$S).

In other embodiments, the alkylating agent is an alkyl halide, alkenyl halide, alkynyl halide, alkyl sulfonate, alkenyl sulfonate, or alkynyl sulfonate.

In other embodiments, the aldehyde is (para)-formaldehyde, alkyl aldehyde, alkenyl aldehyde, alkynyl aldehyde, or aryl aldehyde.

In yet other embodiments, the acylating agent is a compound of Formula M or N:

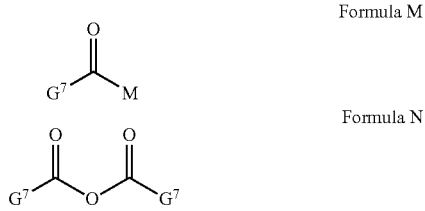

Formula M

Formula N wherein G$^7$ is alkyl, cycloalkyl, heterocyclic, cycloalkylalkyl, heterocycloalkyl, aryl, heteroaryl, alkyloxy, aryloxy, or heteroaryloxy; and M is F, Cl, Br, I, 3-nitro-1,2,4-triazole, imidazole, alkyltriazole, tetrazole, pentafluorobenzene, or 1-hydroxybenzotriazole.

In further embodiments, after acidifying, the compound of Formula 4 wherein m is at least one, J is O, and D is H, is reacted with a nucleoside of structure III to form a condensed intermediate, which is converted by acidifying to produce a compound of Formula 4 wherein m is at least 2 and less than about 200; J is O, and D is H. In other embodiments, the compound of Formula 4 is optionally further reacted with a nucleoside of structure III to form a condensed intermediate followed by acidification. Reaction with the nucleoside of structure III and acidification is repeated until a desired number of units in the growing chain is achieved. In some embodiments, a compound of Formula 4 is produced wherein m is increased by 1 integer. In some embodiments, a compound of Formula 4 wherein m is greater than 2 and less than about 200 is produced. In some embodiments, the condensed intermediate comprises a moiety of Formula A-I in place of a moiety of Formula A.

In further embodiments, the compound of Formula 4 is modified to introduce an X moiety thereby producing a compound of Formula 1. In an embodiment of the compound of Formula 1, R$^3$ is a blocking group or a linking moiety connected to a solid support. In other embodiments, R$^1$ is deblocked. In yet other embodiments, the compound of Formula 1 is treated such that R$^1$ remains blocked. In yet further embodiments, the compound of Formula 1 is treated such that R$^1$ is —OH, —SH, —NR$^d$R$^d$, —N$_3$, halogen, hydrogen, alkyl, alkenyl, alkynyl, alkyl-Y$^1$—, alkenyl-Y$^1$—, alkynyl-Y$^1$—, aryl-Y$^1$—, heteroaryl-Y$^1$—, —P(O)(R$^e$)$_2$, —HP(O)(R$^e$), —OR$^a$, or —SR$^c$; where Y$^1$ is O, NR$^d$, S, or Se, R$^a$ is a blocking moiety, and R$^c$ is a blocking group; each instance of R$^d$ is independently hydrogen, alkyl, alkenyl, alkynyl, aryl, acyl, substituted silyl, carbamate, —P(O)(R$^e$)$_2$, or —HP(O)(R$^e$), and each instance of R$^e$ is independently hydrogen, alkyl, aryl, alkenyl, alkynyl, alkyl-Y$^2$—, alkenyl-Y$^2$—, alkynyl-Y$^2$—, aryl-Y$^2$—, or heteroaryl-Y$^2$—, or a cation which is Na$^{+1}$, Li$^{+1}$, or K$^{+1}$, where Y$^2$ is O, NR$^d$, or S.

Each instance of R$^2$ is independently hydrogen, —OH, —SH, —NR$^d$R$^d$, N$_3$, halogen, alkyl, alkenyl, alkynyl, alkyl-Y$^1$—, alkenyl-Y$^1$—, alkynyl-Y$^1$—, aryl-Y$^1$—, heteroaryl-Y$^1$—. In some embodiments, R$^2$ is deblocked. In yet other embodiments, R$^2$ remains blocked.

In some embodiments, each Ba moiety is unblocked. In other embodiments, not all Ba moieties are unblocked. In other embodiments, R$^3$ is H. In some embodiments, R$^3$ is a blocking group or a linking moiety connected to solid support, nucleoside, nucleotide, or nucleic acid. In some embodiments, each instance of X is independently alkyl, alkoxy, aryl, alkylthio, acyl, —NR$^f$R$^f$, alkenyloxy, alkynyloxy, alkenylthio, alkynylthio, —S$^-$Z$^+$, —Se$^-$Z$^+$, or —BH$_3^-$Z$^+$; each instance of R$^f$ is independently hydrogen, alkyl, alkenyl, alkynyl, or aryl; Z$^+$ is ammonium ion, alkylammonium ion, heteroaromatic iminium ion, or heterocyclic iminium ion, any of which is primary, secondary, tertiary or quaternary, or Z$^+$ is a monovalent metal ion.

Reaction Conditions and Reagents Used in the Methods of the Invention
Conditions The steps of reacting a molecule comprising an achiral H-phosphonate moiety and a nucleoside comprising a 5'-OH moiety to form a condensed intermediate can occur without isolating any intermediates. In some embodiments, the steps of reacting a molecule comprising an achiral H-phosphonate moiety and a nucleoside comprising a 5'-OH moiety to form a condensed intermediate occurs is a one-pot reaction. In an embodiment, a molecule comprising an achiral H-phosphonate moiety, condensing reagent, chiral reagent, and compound comprising a free nucleophilic moiety are added to the reaction mixture at different times. In another embodiment, a molecule comprising an achiral H-phosphonate moiety, condensing reagent, and chiral reagent are present in the same reaction vessel or same pot. In another embodiment, a molecule comprising an achiral H-phosphonate moiety, condensing reagent, chiral reagent, and compound comprising a free nucleophilic moiety are present in the same reaction or same pot. This allows the reaction to be performed without isolation of intermediates and eliminates time-consuming steps, resulting in an economical and efficient synthesis. In specific embodiments, the achiral H-phosphonate, condensing reagent, chiral amino alcohol, 5'-OH nucleoside are present at the same time in a reaction. In a further embodiment, the formation of the chiral intermediate for condensation is formed in situ and is not isolated prior to the condensation reaction. In another embodiment, a molecule comprising an achiral H-phosphonate moiety has been activated by reaction with a condensing reagent, chiral reagent in a different reaction vessel from that used when reacting the chiral intermediate with the compound comprising a free 5'-OH moiety. In an embodiment, an activating reagent is added during the condensation step. In one embodiment, an activating reagent is added after achiral H-phosphonate moiety, condensing reagent, and chiral reagent have already been mixed together. In another embodiment, an activating reagent is added together with the achiral H-phosphonate moiety, condensing reagent, and chiral reagent. Depending on the reaction conditions, an activating reagent can be useful during the synthesis, for instance, in the condensation step. For example, if pyridine is used as the base in the preactivation or condensation step, an activating reagent such as CMPT need not be present since pyridine acts as a nucleophilic catalyst (i.e. activator). If another base, such as N-cyanomethyl pyrrolidine (CMP), that is not as nucleophilic as pyridine is used in the condensation step, then the use of an activating reagent, such as CMPT, can be added as an activating reagent.

Synthesis on Solid Support

In some embodiments, the synthesis of the nucleic acid is performed in solution. In other embodiments, the synthesis of the nucleic acid is performed on solid phase. The reactive groups of a solid support may be unprotected or protected. During oligonucleotide synthesis a solid support is treated with various reagents in several synthesis cycles to achieve the stepwise elongation of a growing oligonucleotide chain with individual nucleotide units. The nucleoside unit at the end of the chain which is directly linked to the solid support is termed "the first nucleoside" as used herein. The first nucleoside is bound to the solid support via a linker moiety, i.e. a diradical with covalent bonds to both the polymer of the solid support and the nucleoside. The linker stays intact during the synthesis cycles performed to assemble the oligonucleotide chain and is cleaved after the chain assembly to liberate the oligonucleotide from the support.

Solid supports for solid-phase nucleic acid synthesis include the supports described in, e.g., U.S. Pat. Nos. 4,659,774, 5,141,813, 4,458,066; Caruthers U.S. Pat. Nos. 4,415,732, 4,458,066, 4,500,707, 4,668,777, 4,973,679, and 5,132,418; Andrus et al. U.S. Pat. Nos. 5,047,524, 5,262, 530; and Koster U.S. Pat. No. 4,725,677 (reissued as Re 34,069). In some embodiments, the solid phase is an organic polymer support. In other embodiments, the solid phase is an inorganic polymer support. In some embodiments, the organic polymer support is polystyrene, aminomethyl polystyrene, a polyethylene glycol-polystyrene graft copolymer, polyacrylamide, polymethacrylate, polyvinylalcohol, highly cross-linked polymer (HCP), or other synthetic polymers, carbohydrates such as cellulose and starch or other polymeric carbohydrates, or other organic polymers and any copolymers, composite materials or combination of the above inorganic or organic materials. In other embodiments, the inorganic polymer support is silica, alumina, controlled polyglass (CPG), which is a silica-gel support, or aminopropyl CPG. Other useful solid supports include fluorous solid supports (see e.g., WO/2005/070859), long chain alkylamine (LCAA) controlled pore glass (CPG) solid supports (see e.g., S. P. Adams, K. S. Kavka, E. J. Wykes, S. B. Holder and G. R. Galluppi, *J. Am. Chem. Soc.*, 1983, 105, 661-663; G. R. Gough, M. J. Bruden and P. T. Gilham, *Tetrahedron Lett.*, 1981, 22, 4177-4180). Membrane supports and polymeric membranes (see e.g. Innovation and Perspectives in Solid Phase Synthesis, Peptides, Proteins and Nucleic Acids, ch 21 pp 157-162, 1994, Ed. Roger Epton and U.S. Pat. No. 4,923,901) are also useful for the synthesis of nucleic acids. Once formed, a membrane can be chemically functionalized for use in nucleic acid synthesis. In addition to the attachment of a functional group to the membrane, the use of a linker or spacer group attached to the membrane may be used to minimize steric hindrance between the membrane and the synthesized chain.

Other suitable solid supports include those generally known in the art to be suitable for use in solid phase methodologies, including, for example, glass sold as Primer™ 200 support, controlled pore glass (CPG), oxalyl-controlled pore glass (see, e.g., Alul, et al., *Nucleic Acids Research*, 1991, 19, 1527), TentaGel Support—an aminopolyethyleneglycol derivatized support (see, e.g., Wright, et al., *Tetrahedron Lett.*, 1993, 34, 3373), and Poros-a copolymer of polystyrene/divinylbenzene.

Surface activated polymers have been demonstrated for use in synthesis of natural and modified nucleic acids and proteins on several solid supports mediums. The solid support material can be any polymer suitably uniform in porosity, has sufficient amine content, and sufficiently flexible to undergo any attendant manipulations without losing integrity. Examples of suitable selected materials include nylon, polypropylene, polyester, polytetrafluoroethylene, polystyrene, polycarbonate, and nitrocellulose. Other materials can serve as the solid support, depending on the design of the investigator. In consideration of some designs, for example, a coated metal, in particular gold or platinum can be selected (see e.g., US publication No. 20010055761). In one embodiment of oligonucleotide synthesis, for example, a nucleoside is anchored to a solid support which is functionalized with hydroxyl or amino residues. Alternatively, the solid support is derivatized to provide an acid labile trialkoxytrityl group, such as a trimethoxytrityl group (TMT). Without being bound by theory, it is expected that the presence of the trialkoxytrityl protecting group will permit initial detritylation under conditions commonly used on DNA synthesizers. For a faster release of oligonucleotide material in solution with aqueous ammonia, a diglycoate linker is optionally introduced onto the support.

Linking Moiety

A linking moiety or linker is optionally used to connect the solid support to the compound comprising a free nucleophilic moiety. Suitable linkers are known such as short molecules which serve to connect a solid support to functional groups (e.g., hydroxyl groups) of initial nucleosides molecules in solid phase synthetic techniques. In some embodiments, the linking moiety is a succinamic acid linker, or a succinate linker (—CO—$CH_2$—$CH_2$—CO—), or an oxalyl linker (—CO—CO—). In other embodiments, the linking moiety and the nucleoside are bonded together through an ester bond. In other embodiments, the linking moiety and the nucleoside are bonded together through an amide bond. In further embodiments, the linking moiety connects the nucleoside to another nucleotide or nucleic acid. Suitable linkers are disclosed in, for example, Oligonucleotides And Analogues A Practical Approach, Ekstein, F. Ed., IRL Press, N.Y., 1991, Chapter 1.

A linker moiety is used to connect the compound comprising a free nucleophilic moiety to another nucleoside, nucleotide, or nucleic acid. In some embodiments, the linking moiety is a phosphodiester linkage. In other embodiments, the linking moiety is an H-phosphonate moiety. In yet other embodiments, the linking moiety is an X-phosphonate moiety.

Solvents for Synthesis

Synthesis of the nucleic acids is performed in an aprotic organic solvent. In some embodiments, the solvent is acetonitrile, pyridine, tetrahydrofuran, or dichloromethane. In some embodiments, when the aprotic organic solvent is not basic, a base is present in the reacting step. In some embodiments where a base is present, the base is pyridine, quinoline, or N,N-dimethylaniline or N-cyanomethylpyrrolidine. Other examples of bases include pyrrolidine, piperidine, N-methyl pyrrolidine, pyridine, quinoline, N,N-dimethylaminopyridine (DMAP), N,N-dimethylaniline or N-cyanomethylpyrrolidine. In some embodiments of the method, the base is

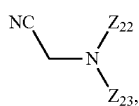

wherein $Z^{22}$ and $Z^{23}$ are independently alkyl, aminoalkyl, cycloalkyl, heterocyclic, cycloalkylalkyl, heterocycloalkyl, aryl, heteroaryl, alkyloxy, aryloxy, or heteroaryloxy, or wherein any of $Z^{22}$ and $Z^{23}$ are taken together to form a 3 to 10 membered alicyclic or heterocyclic ring. In some embodiments of the method, the base is N-cyanomethylpyrrolidine. In some embodiments, the aprotic organic solvent is anhydrous. In other embodiments, the anhydrous aprotic organic solvent is freshly distilled. In some embodiments, the freshly distilled anhydrous aprotic organic solvent is pyridine. In other embodiments, the freshly distilled anhydrous aprotic organic solvent is tetrahydrofuran. In other embodiments, the freshly distilled anhydrous aprotic organic solvent is acetonitrile. The solvent can be a combination of 2 or more solvents. Depending on which solvent is used for the synthesis, addition of an activating reagent is useful.

Acidification Conditions to Remove Blocking Groups.

Acidification to remove blocking groups is accomplished by a Brønsted acid or Lewis acid. In some embodiments, acidification is used to remove $R^1$ blocking groups. Useful Brønsted acids are carboxylic acids, alkylsulfonic acids, arylsulfonic acids, phosphoric acid and its derivatives, phosphonic acid and its derivatives, alkylphosphonic acids and their derivatives, arylphosphonic acids and their derivatives, phosphinic acid, dialkylphosphinic acids, and diarylphosphinic acids which have a pKa (25° C. in water) value of −0.6 (trifluoroacetic acid) to 4.76 (acetic acid) in an organic solvent or water (in the case of 80% acetic acid). The concentration of the acid (1 to 80%) used in the acidification step depends on the acidity of the acid. Consideration to the acid strength must be taken into account as strong acid conditions will result in depurination/depyrimidination, wherein purinyl or pyrimidinyl bases are cleaved from ribose ring.

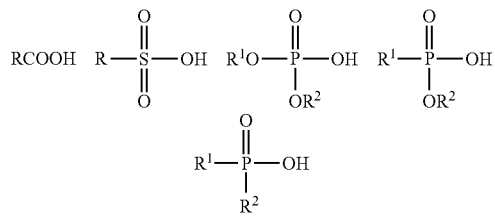

In some embodiments, acidification is accomplished by a Lewis acid in an organic solvent. Useful Lewis acids are $ZnX_2$ wherein X is Cl, Br, I, or $CF_3SO_3$.

In some embodiments, the acidifying comprises adding an amount of a Brønsted or Lewis acid effective to convert the condensed intermediate into the compound of Formula 4 without removing purine moieties from the condensed intermediate.

Acids that are useful in the acidifying step also include, but are not limited to 10% phosphoric acid in an organic solvent, 10% hydrochloric acid in an organic solvent, 1% trifluoroacetic acid in an organic solvent, 3% dichloroacetic acid in an organic solvent or 80% acetic acid in water. The concentration of any Brønsted or Lewis acid used in the process is selected such that the concentration of the acid does not exceed a concentration that causes cleavage of the nucleobase from the sugar moiety.

In some embodiments, acidification comprises adding 1% trifluoroacetic acid in an organic solvent. In some embodiments, acidification comprises adding about 0.1% to about 8% trifluoroacetic acid in an organic solvent. In other embodiments, acidification comprises adding 3% dichloroacetic acid in an organic solvent. In other embodiments, acidification comprises adding about 0.1% to about 10% dichloroacetic acid in an organic solvent. In yet other embodiments, acidification comprises adding 3% trichloroacetic acid in an organic solvent. In yet other embodiments, acidification comprises adding about 0.1% to about 10% trichloroacetic acid in an organic solvent. In some embodiments, acidification comprises adding 80% acetic acid in water. In some embodiments, acidification comprises adding about 50% to about 90%, or about 50% to about 80%, about 50% to about 70%, about 50% to about 60%, about 70% to about 90% acetic acid in water. In some embodiments, the acidification comprises the further addition of cation scavengers to the acidic solvent. In specific embodiments, the cation scavengers can be triethylsilane or triisopropylsilane. In some embodiments, $R^1$ is deblocked prior to the step of acidifying the condensed intermediate. In some embodiments, $R^1$ is deblocked by acidification, which comprises adding 1% trifluoroacetic acid in an organic solvent. In some embodiments, $R^1$ is deblocked by acidification, which comprises adding 3% dichloroacetic acid in an organic solvent. In some embodiments, $R^1$ is deblocked by acidification, which comprises adding 3% trichloroacetic acid in an organic solvent.

Removal of Blocking Moieties or Groups.

Functional groups such as hydroxyl or amino moieties which are located on nucleobases or sugar moieties are routinely blocked with blocking (protecting) groups (moieties) during synthesis and subsequently deblocked. In general, a blocking group renders a chemical functionality of a molecule inert to specific reaction conditions and can later be removed from such functionality in a molecule without substantially damaging the remainder of the molecule (see e.g., Green and Wuts, Protective Groups in Organic Synthesis, 2$^{nd}$ Ed., John Wiley & Sons, New York, 1991). For example, amino groups can be blocked with nitrogen blocking groups such as phthalimido, 9-fludrenylmethoxycarbonyl (FMOC), triphenylmethylsulfenyl, t-BOC, 4,4'-dimethoxytrityl (DMTr), 4-methoxytrityl (MMTr), 9-phenylxanthin-9-yl (Pixyl), trityl (Tr), or 9-(p-methoxyphenyl)xanthin-9-yl (MOX). Carboxyl groups can be protected as acetyl groups. Hydroxy groups can be protected such as tetrahydropyranyl (THP), t-butyldimethylsilyl (TBDMS), 1-[(2-chloro-4-methyl)phenyl]-4-methoxypiperidin-4-yl (Ctmp), 1-(2-fluorophenyl)-4-methoxypiperidin-4-yl (Fpmp), 1-(2-chloroethoxy)ethyl, 3-methoxy-1,5-dicarbomethoxypentan-3-yl (MDP), bis(2-acetoxyethoxy)methyl (ACE), triisopropylsilyloxymethyl (TOM), 1-(2-cyanoethoxy)ethyl (CEE), 2-cyanoethoxymethyl (CEM), [4-(N-dichloroacetyl-N-methylamino)benzyloxy]methyl, 2-cyanoethyl (CN), pivaloyloxymethyl (PivOM), levunyloxymethyl (ALE). Other representative hydroxyl blocking groups have been described (see e.g., Beaucage et al., Tetrahedron, 1992, 46, 2223). In some embodiments, hydroxyl blocking groups are acid-labile groups, such as the trityl, monomethoxytrityl, dimethoxytrityl, trimethoxytrityl, 9-phenylxanthin-9-yl (Pixyl) and 9-(p-methoxyphenyl)xanthin-9-yl (MOX). Chemical functional groups can also be blocked by including them in a precursor form. Thus an azido group can be considered a blocked form of an amine as the azido group is easily converted to the amine. Further representative protecting groups utilized in nucleic acid synthesis are known (see e.g. Agrawal et al., Protocols for Oligonucleotide Conjugates, Eds., Humana Press, New Jersey, 1994, Vol. 26, pp. 1-72).

Various methods are known and used for removal of blocking groups from the nucleic acids. In some embodiments, all blocking groups are removed. In other embodiments, the blocking groups are partially removed. In yet other embodiments, reaction conditions can be adjusted to remove blocking groups on certain moieties. In certain embodiments where $R^2$ is a blocking group, removal of the blocking group at $R^2$ is orthogonal to the removal of the blocking group at $R^1$. The blocking groups at $R^1$ and $R^2$ remain intact during the synthesis steps and are collectively removed after the chain assembly. In some embodiments, the $R^2$ blocking group are removed simultaneously with the cleavage of the nucleic acids from the solid support and with the removal of the nucleobase blocking groups. In specific embodiments, the blocking group at $R^1$ is removed while the blocking groups at $R^2$ and nucleobases remain intact. Blocking groups at $R^1$ are cleavable on solid supports with an organic base such as a primary amine, a secondary amine, or a mixture thereof. Deblocking of the $R^1$ position is commonly referred to as front end deprotection.

In an embodiment, the nucleobase blocking groups, if present, are cleavable after the assembly of the respective nucleic acid with an acidic reagent. In another embodiment, one or more of the nucleobase blocking groups is cleavable under neither acidic nor basic conditions, e.g. cleavable with fluoride salts or hydrofluoric acid complexes. In yet another embodiment, one or more of the nucleobase blocking groups are cleavable after the assembly of the respective nucleic acid in the presence of base or a basic solvent, and wherein the nucleobase blocking group is stable to the conditions of the front end deprotection step with amines.

In some embodiments, blocking groups for nucleobases are not required. In other embodiments, blocking groups for nucleobases are required. In yet other embodiments, certain nucleobases require blocking group while other nucleobases do not require blocking groups. In embodiments where the nucleobases are blocked, the blocking groups are either completely or partially removed under conditions appropriate to remove the blocking group at the front end. For example, $R^1$ can denote $OR^a$, wherein $R^a$ is acyl, and Ba denotes guanine blocked with an acyl group including, but not limited to isobutyryl, acetyl or 4-(tert-butylphenoxy) acetyl. The acyl groups at $R^1$ and Ba will be removed or partially removed during the same deblocking step.

Reagents

Condensing Reagent.

The condensing reagent ($C_R$) useful in the methods of the invention has one of the following general formulae: $Ar_3PL_2$, and $(ArO)_3PL_2$, $C_R1$

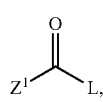

$C_R2$

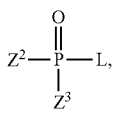

-continued $C_R3$

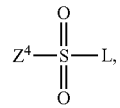

$C_R4$

$C_R5$

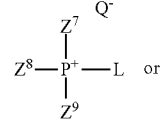

$C_R6$

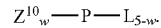

wherein $Z^1$, $Z^2$, $Z^3$, $Z^4$, $Z^5$, $Z^6$, $Z^7$, $Z^8$, $Z^9$ and $Z^{10}$ are independently selected from alkyl, aminoalkyl, cycloalkyl, heterocyclic, cycloalkylalkyl, heterocycloalkyl, aryl, heteroaryl, alkyloxy, aryloxy, or heteroaryloxy, or wherein any of $Z^2$ and $Z^3$, $Z^5$ and $Z^6$, $Z^7$ and $Z^8$, $Z^8$ and $Z^9$, $Z^9$ and $Z^7$, or $Z^7$ and $Z^8$ and $Z^9$ are taken together to form a 3 to 20 membered alicyclic or heterocyclic ring; $Q^-$ is a counter anion; w is an integer of 0 to 3; L is a leaving group; and Ar is aryl, heteroaryl, and/or one of Ar group is attached to the polymer support.

In some embodiments, the counter ion of the condensing reagent $C_R$ is $Cl^-$, $Br^-$, $BF_4^-$, $PF_6^-$, $TfO^-$, $Tf_2N^-$, $AsF_6^-$, $ClO_4^-$, or $SbF_6^-$, wherein Tf is $CF_3SO_2$. In some embodiments, the leaving group of the condensing reagent $C_R$ is F, Cl, Br, I, 3-nitro-1,2,4-triazole, imidazole, alkyltriazole, tetrazole, pentafluorobenzene, or 1-hydroxybenzotriazole.

Examples of condensing agents that can be used in the process include, and are not limited to, pentafluorobenzoyl chloride, carbonyldiimidazole (CDI), 1-mesitylenesulfonyl-3-nitrotriazole (MSNT), 1-ethyl-3-(3'-dimethylaminopropyl)carbodiimide hydrochloride (EDCI-HCl), benzotriazole-1-yloxytris(dimethylamino)phosphonium hexafluorophosphate (PyBOP), N,N'-bis(2-oxo-3-oxazolidinyl)phosphinic chloride (BopCl), 2-(1H-7-azabenzotriazol-1-yl)-1,1,3,3-tetramethyluronium hexafluorophosphate (HATU), and O-benzotriazole-N,N,N',N'-tetramethyluronium hexafluorophosphate (HBTU), DIPCDI; N,N'-bis(2-oxo-3-oxazolidinyl)phosphinic bromide (BopBr), 1,3-dimethyl-2-(3-nitro-1,2,4-triazol-1-yl)-2-pyrrolidin-1-yl-1,3,2-diazaphospholidinium hexafluorophosphate (MNTP), 3-nitro-1,2,4-triazol-1-yl-tris(pyrrolidin-1-yl)phosphonium hexafluorophosphate (PyNTP), bromotripyrrolidinophosphonium hexafluorophosphate (PyBrOP); O-(benzotriazol-1-yl)-N,N,N',N'-tetramethyluronium tetrafluoroborate (TBTU); tetramethylfluoroformamidinium hexafluorophosphate (TFFH); $(PhO)_3PCl_2$, and bis(trichloromethyl)carbonate (BTC). In certain embodiments, the counter ion of the condensing reagent $C_R$ is $Cl^-$, $Br^-$, $BF_4^-$, $PF_6^-$, $TfO^-$, $Tf_2N^-$, $AsF_6^-$, $ClO_4^-$, or $SbF_6^-$, wherein Tf is $CF_3SO_2$.

In other embodiments of the invention, the condensing reagent is 1-(2,4,6-triisopropylbenzenesulfonyl)-5-(pyridin-2-yl) tetrazolide, pivaloyl chloride, bromotrispyrrolidinophosphonium hexafluorophosphate, N,N'-bis(2-oxo-3-oxazolidinyl) phosphinic chloride (BopCl), $(PhO)_3PCl_2$, or 2-chloro-5,5-dimethyl-2-oxo-1,3,2-dioxaphosphinane, bis(trichloromethyl)carbonate (BTC), or $Ph_3PCl_2$. In one embodiment, the condensing reagent is N,N'-bis(2-oxo-3- oxazolidinyl)phosphinic chloride (BopCl). In one embodiment, the condensing reagent is bis(trichloromethyl)carbonate (BTC). In one embodiment, the condensing reagent is $Ph_3PCl_2$. Other known condensing reagents have been described (see e.g., WO/2006/066260).

In other embodiments, the condensing reagent is 1,3-dimethyl-2-(3-nitro-1,2,4-triazol-1-yl)-2-pyrrolidin-1-yl-1,3,2-diazaphospholidinium hexafluorophosphate (MNTP), 3-nitro-1,2,4-triazol-1-yl-tris(pyrrolidin-1-yl)phosphonium hexafluorophosphate (PyNTP), bis(trichloromethyl)carbonate (BTC), $(PhO)_3PCl_2$, or $Ph_3PCl_2$.

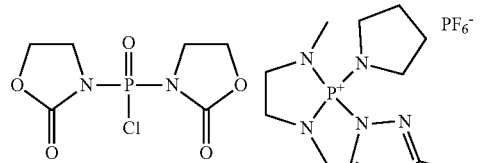

BopCl     MNTP

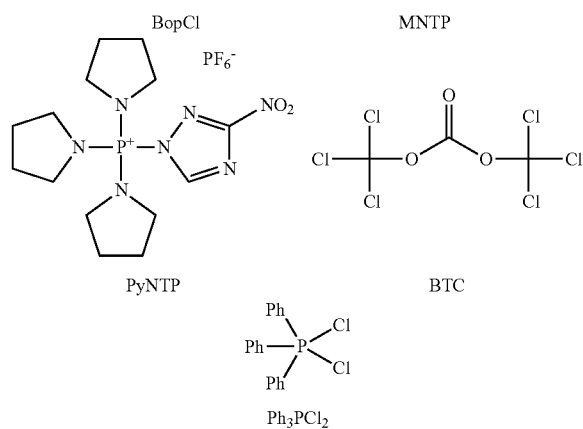

PyNTP     BTC

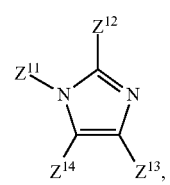

$Ph_3PCl_2$

Activating Reagent.

The activating reagent useful herein should have strong proton-donating ability to be able to activate the chiral intermediate for reaction with a compound comprising a free nucleophilic moiety. In one embodiment, the chiral intermediate is structure III shown in Scheme 5 or 6 or is structure $III_r$ shown in Scheme 7. The activating reagent acts by protonating the nitrogen atom of structure III or $III_r$ when W1 is a nitrogen. Use of an activating reagent is dependent on solvents used for the synthesis.

The activating reagent ($A_R$) useful in the method of the invention has one of the following general formulae:

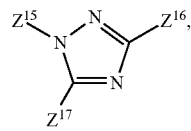

$A_R1$

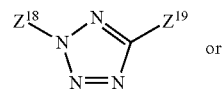

$A_R2$

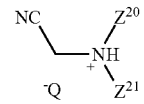

$A_R3$ $A_R4$ or $A_R5$ $Z^{11}, Z^{12}, Z^{13}, Z^{14}, Z^{15}, Z^{16}, Z^{17}, Z^{18}, Z^{19}, Z^{20}$, and $Z^{21}$ are independently hydrogen, alkyl, aminoalkyl, cycloalkyl, heterocyclic, cycloalkylalkyl, heterocycloalkyl, aryl, heteroaryl, alkyloxy, aryloxy, or heteroaryloxy, or wherein any of $Z^{11}$ and $Z^{12}$, $Z^{11}$ and $Z^{13}$, $Z^{11}$ and $Z^{14}$, $Z^{12}$ and $Z^{13}$, $Z^{12}$ and $Z^{14}$, $Z^{13}$ and $Z^{14}$, $Z^{15}$ and $Z^{16}$, $Z^{15}$ and $Z^{17}$, $Z^{16}$ and $Z^{17}$, $Z^{18}$ and $Z^{19}$, or $Z^{20}$ and $Z^{21}$ are taken together to form a 3 to 20 membered alicyclic or heterocyclic ring, or to form 5 or 20 membered aromatic irng. Q⁻ is a counter ion. In some embodiments of the method, the counter ion of the activating reagent $A_R$ is Cl⁻, Br⁻, $BF_4^-$, $PF_6^-$, TfO⁻, $Tf_2N^-$, $AsF_6^-$, $ClO_4^-$, or $SbF_6^-$, wherein Tf is $CF_3SO_2$.

In some embodiments of the method, the activating reagent is imidazole, 4,5-dicyanoimidazole (DCI), 4,5-dichloroimidazole, 1-phenylimidazolium triflate (PhIMT), benzimidazolium triflate (BIT), benztriazole, 3-nitro-1,2,4-triazole (NT), tetrazole, 5-ethylthiotetrazole, 5-(4-nitrophenyl)tetrazole, N-cyanomethylpyrrolidinium triflate (CMPT), N-cyanomethylpiperidinium triflate, N-cyanomethyldimethylammonium triflate.

In some embodiments of the method, the activating reagent is 4,5-dicyanoimidazole (DCI), 1-phenylimidazolium triflate (PhIMT), benzimidazolium triflate (BIT), 3-nitro-1,2,4-triazole (NT), tetrazole, or N-cyanomethylpyrrolidinium triflate (CMPT).

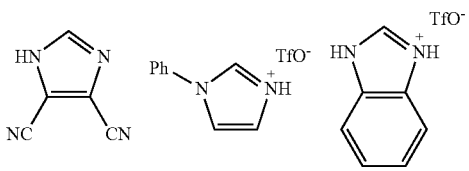

DCI     PhIMT     BIT

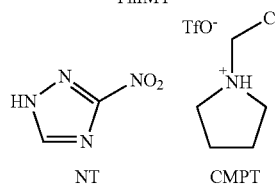

NT     CMPT

In some embodiments of the method, the activating reagent is N-cyanomethylpyrrolidinium triflate (CMPT).

Chiral Reagent.

In the methods of the present invention, chiral reagents are used to confer stereoselectivity in the production of X-phosphonate linkages. Many different chiral auxiliaries may be used in this process which are compounds of Formula 3-I where $W_1$ and $W_2$ are any of —O—, —S—, or —$NG^5$-, which are capable of reacting with the H-phosphonate starting material, a compound of Formula 2 to form the chiral intermediate, as shown in structure III of Schemes 5 and 6.

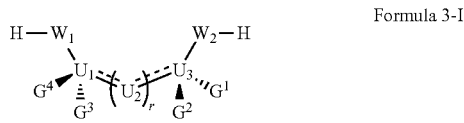

Formula 3-I $U_1$ and $U_3$ are carbon atoms which are bonded to $U_2$ if present, or to each other if r is 0, via a single, double or triple bond. $U_2$ is —C—, —$CG^8$-, —$CG^8G^8$-, —$NG^8$-, —N—, —O—, or —S— where r is an integer of 0 to 5 and no more than two heteroatoms are adjacent. When any one of $U_2$ is C, a triple bond must be formed between a second instance of $U_2$, which is C, or to one of $U_1$ or $U_3$. Similarly, when any one of $U_2$ is $CG^8$, a double bond is formed between a second instance of $U_2$ which is —$CG^8$- or —N—, or to one of $U_1$ or $U_3$.

For example, in some embodiments, —$U_1$—$(U_2)_r$—$U_3$— is —$CG^3G^4$-$CG^1G^2$-. In some embodiments, —$U_1$—$(U_2)_r$—$U_3$— is —$CG^3$=$CG^1$-. In some embodiments, —$U_1$—$(U_2)_r$—$U_3$— is —C≡C—. In some embodiments, —$U_1$—$(U_2)_r$—$U_3$— is —$CG^3$=C $G^8$-$CG^1G^2$-. In some embodiments, —$U_1$—$(U_2)_r$—$U_3$— is —$CG^3G^4$-O—$CG^1G^2$-. In some embodiments, —$U_1$—$(U_2)_r$—$U_3$— is —$CG^3G^4$-$NG^8$-$CG^1G^2$-. In some embodiments, —$U_1$—$(U_2)_r$—$U_3$— is —$CG^3G^4$-N—$CG^2$-. In some embodiments, —$U_1$—$(U_2)_r$—$U_3$— is —$CG^3G^4$-N=C $G^8$-$CG^1G^2$-.

$G^1$, $G^2$, $G^3$, $G^4$, $G^5$, and $G^8$ are independently hydrogen, alkyl, aralkyl, cycloalkyl, cycloalkylalkyl, heterocyclyl, hetaryl, or aryl, or two of $G^1$, $G^2$, $G^3$, $G^4$, and $G^5$ are $G^6$ taken together form a saturated, partially unsaturated or unsaturated carbocyclic or heteroatom-containing ring of up to about 20 ring atoms which is monocyclic or polycyclic, and is fused or unfused. In some embodiments, the ring so formed is substituted by oxo, thioxo, alkyl, alkenyl, alkynyl, heteroaryl, or aryl moieties. In some embodiments, when the ring formed by taking two $G^6$ together is substituted, it is substituted by a moiety which is bulky enough to confer stereoselectivity during the reaction.

For example, in some embodiments, the ring formed by taking two of $G^6$ together is cyclopentyl, pyrrolyl, cyclopropyl, cyclohexenyl, cyclopentenyl, tetrahydropyranyl, or piperazinyl.

In some embodiments of the invention, the chiral reagent is a compound of Formula 3.

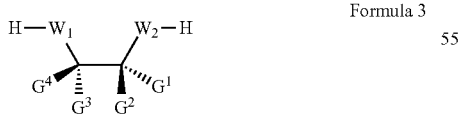

Formula 3

In some embodiments of Formula 3, $W_1$ and $W_2$ are independently —$NG^5$-, —O—, or —S—; $G^1$, $G^2$, $G^3$, $G^4$, and $G^5$ are independently hydrogen, alkyl, aralkyl, cycloalkyl, cycloalkylalkyl, heterocyclyl, hetaryl, or aryl, or two of $G^1$, $G^2$, $G^3$, $G^4$, and $G^5$ are $G^6$ taken together form a saturated, partially unsaturated or unsaturated carbocyclic or heteroatom-containing ring of up to about 20 ring atoms which is monocyclic or polycyclic, fused or unfused, and no more than four of $G^1$, $G^2$, $G^3$, $G^4$, and $G^5$ are $G^6$. Similarly to the compounds of Formula 3', any of $G^1$, $G^2$, $G^3$, $G^4$, or $G^5$ are substituted by oxo, thioxo, alkyl, alkenyl, alkynyl, heteroaryl, or aryl moieties. In some embodiments, such substitution induces stereoselectivity in X-phosphonate production.

In some embodiments of the invention, the chiral reagent has one of the following Formulae:

Formulae 3-A

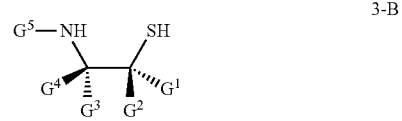

3-B

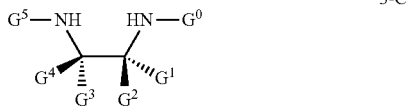

3-C

3-D

3-E

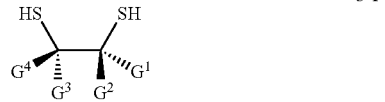

3-F

In some embodiments, the chiral reagent is an aminoalcohol. In some other embodiments, the chiral reagent is an aminothiol. In yet other embodiments, the chiral reagent is an aminophenol. In some embodiments, the chiral reagent is (S)- and (R)-2-methylamino-1-phenylethanol, (1R,2S)-ephedrine, or (1R, 2S)-2-methylamino-1,2-diphenylethanol.

In other embodiments of the invention the chiral reagent is a compound of one of the following formulae:

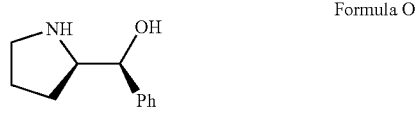

Formula O

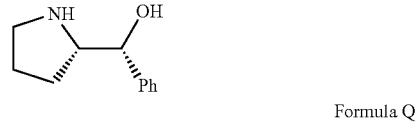

Formula P

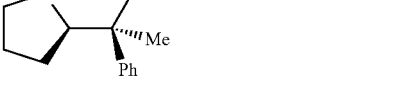

Formula Q

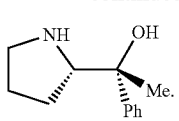

Formula R

The choice of chiral reagent, for example, the isomer represented by Formula O or its stereoisomer, Formula P, permits the specific control of the chirality at phosphorus. Thus either a $R_P$ or $S_P$ configuration can be selected in each synthesis cycle, permitting control of the overall three dimensional structure of the nucleic acid product. In some embodiments of the invention, a nucleic acid product has all $R_P$ stereocenters. In some embodiments of the invention, a nucleic acid product has all $S_P$ stereocenters. In some embodiments, the selection of $R_P$ and $S_P$ centers is made to confer a specific three dimensional superstructure to the nucleic acid chain.

Nucleobases and Modified Nucleobases

The nucleobase Ba in Formula 1 is a natural nucleobase or a modified nucleobase derived from natural nucleobases. Examples include, but are not limited to, uracil, thymine, adenine, cytosine, and guanine having their respective amino groups protected by acyl protecting groups, 2-fluorouracil, 2-fluorocytosine, 5-bromouracil, 5-iodouracil, 2,6-diaminopurine, azacytosine, pyrimidine analogs such as pseudoisocytosine and pseudouracil and other modified nucleobases such as 8-substituted purines, xanthine, or hypoxanthine (the latter two being the natural degradation products). The modified nucleobases disclosed in Chiu and Rana, *RNA*, 2003, 9, 1034-1048, Limbach et al. *Nucleic Acids Research*, 1994, 22, 2183-2196 and Revankar and Rao, *Comprehensive Natural Products Chemistry*, vol. 7, 313, are also contemplated as Ba moieties of Formula 1.

Compounds represented by the following general formulae are also contemplated as modified nucleobases:

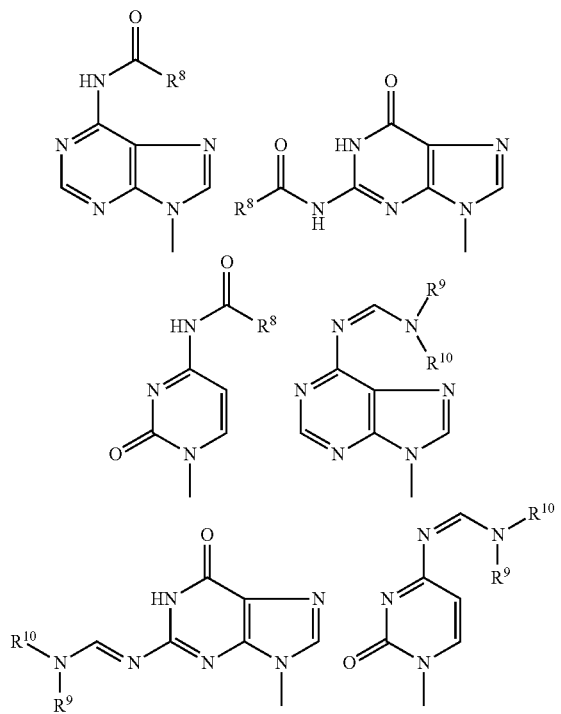

In the formulae above, $R^8$ is a linear or branched alkyl, aryl, aralkyl, or aryloxylalkyl group having 1 to 15 carbon atoms, including, by way of example only, a methyl, isopropyl, phenyl, benzyl, or phenoxymethyl group; and each of $R^9$ and $R^0$ represents a linear or branched alkyl group having 1 to 4 carbon atoms.

Modified nucleobases also include expanded-size nucleobases in which one or more benzene rings has been added. Nucleic base replacements described in the Glen Research catalog (www.glenresearch.com); Krueger A T et al, *Acc. Chem. Res.*, 2007, 40, 141-150; Kool, E T, *Acc. Chem. Res.*, 2002, 35, 936-943; Benner S. A., et al., *Nat. Rev. Genet.*, 2005, 6, 553-543; Romesberg, F. E., et al., *Curr. Opin. Chem. Biol.*, 2003, 7, 723-733; Hirao, I., *Curr. Opin. Chem. Biol.*, 2006, 10, 622-627, are contemplated as useful for the synthesis of the nucleic acids described herein. Some examples of these expanded-size nucleobases are shown below:

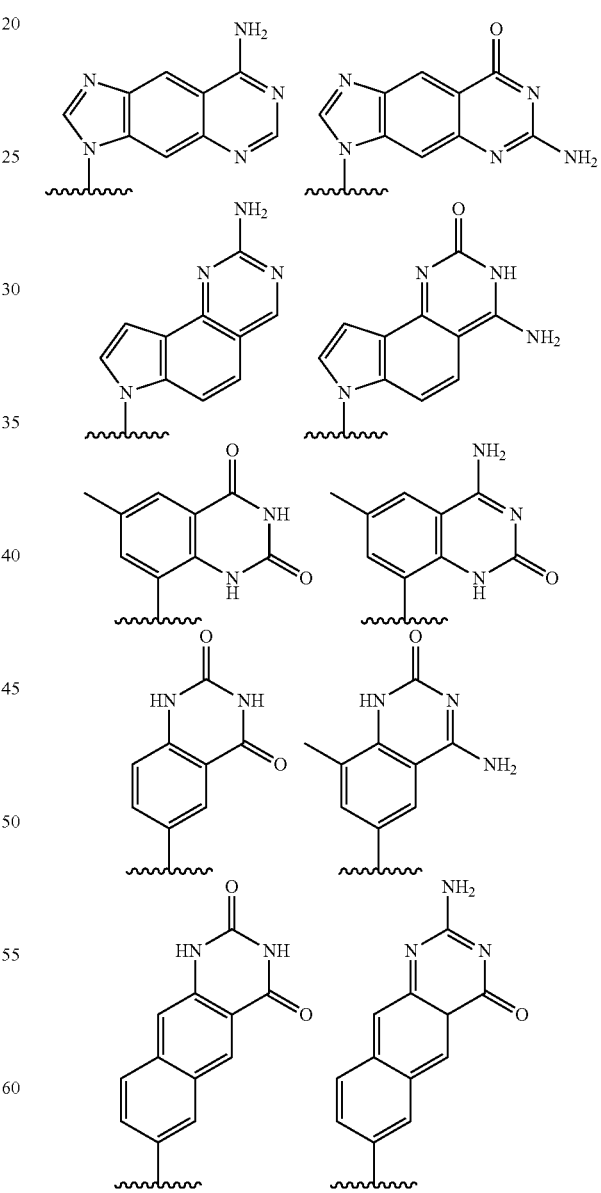

Herein, modified nucleobases also encompass structures that are not considered nucleobases but are other moieties such as, but not limited to, corrin- or porphyrin-derived rings. Porphyrin-derived base replacements have been described in Morales-Rojas, H and Kool, E T, *Org. Lett.*, 2002, 4, 4377-4380. Shown below is an example of a porphyrin-derived ring which can be used as a base replacement:

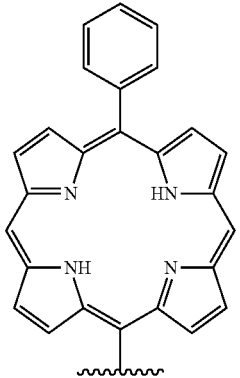 [SMILES: *c1c2nc(cc3ccc([nH]3)c(-c3ccccc3)c3nc(cc4ccc1[nH]4)C=C3)C=C2]

Other modified nucleobases also include base replacements such as those shown below:

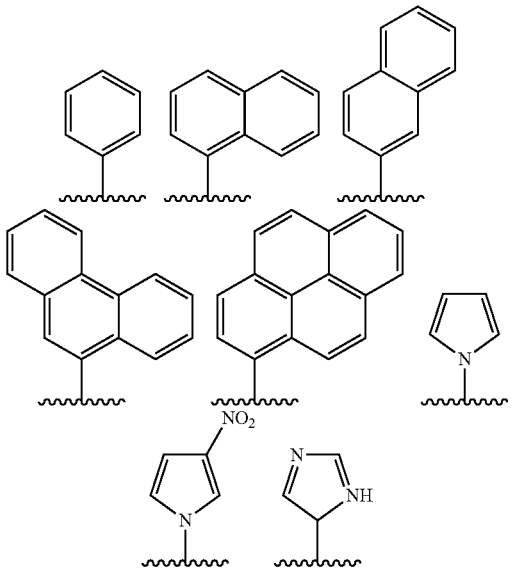

Modified nucleobases which are fluorescent are also contemplated. Non-limiting examples of these base replacements include phenanthrene, pyrene, stillbene, isoxanthine, isozanthopterin, terphenyl, terthiophene, benzoterthiophene, coumarin, lumazine, tethered stillbene, benzo-uracil, and naphtho-uracil, as shown below:

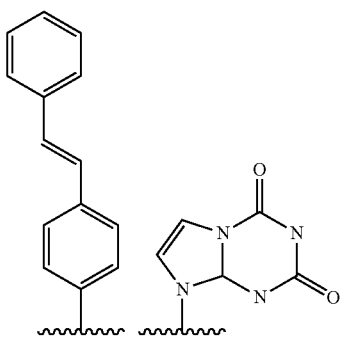

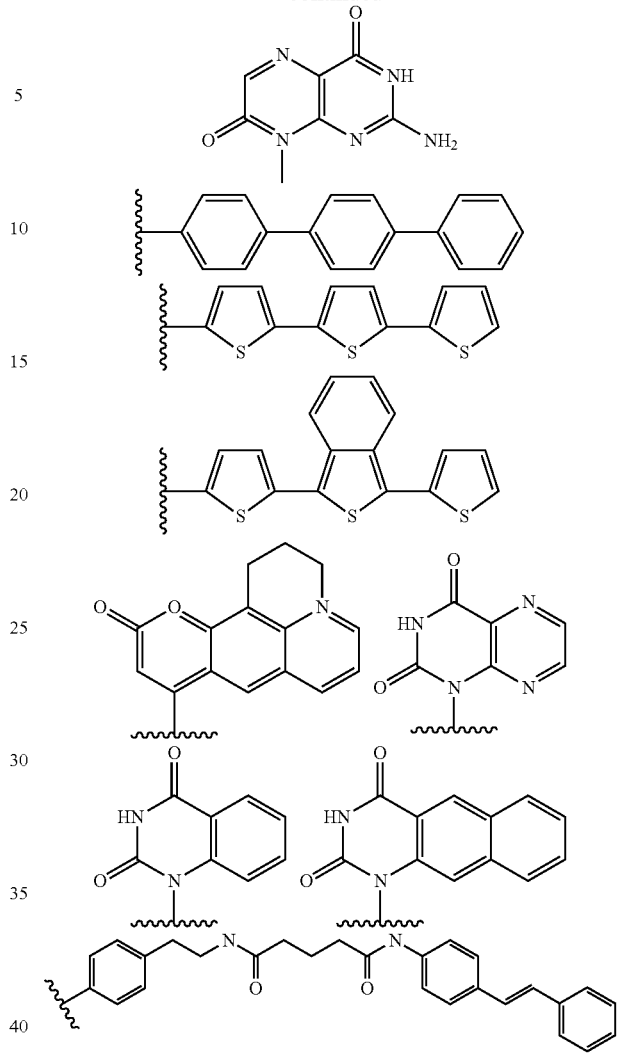

The modified nucleobases can be unsubstituted or contain further substitutions such as heteroatoms, alkyl groups, or linking moieties connected to fluorescent moieties, biotin or avidin moieties, or other protein or peptides. Modified nucleobases also include certain 'universal bases' that are not nucleobases in the most classical sense, but function similarly to nucleobases. One representative example of such a universal base is 3-nitropyrrole.

In addition to nucleosides of structure IV or IX, other nucleosides can also be used in the process disclosed herein and include nucleosides that incorporate modified nucleobases, or nucleobases covalently bound to modified sugars. Some examples of nucleosides that incorporate modified nucleobases include 4-acetylcytidine; 5-(carboxyhydroxylmethyl)uridine; 2'-O-methylcytidine; 5-carboxymethylaminomethyl-2-thiouridine; 5-carboxymethylaminomethyluridine; dihydrouridine; 2'-O-methylpseudouridine; beta,D-galactosylqueosine; 2'-O-methylguanosine; $N^6$-isopentenyladenosine; 1-methyladenosine; 1-methylpseudouridine; 1-methylguanosine; 1-methylinosine; 2,2-dimethylguanosine; 2-methyladenosine; 2-methylguanosine; $N^7$-methylguanosine; 3-methyl-cytidine; 5-methylcytidine; $N^6$-methyladenosine; 7-methylguanosine; 5-methylaminoethyluridine; 5-methoxyaminomethyl-2-thiouridine; beta,D- mannosylqueosine; 5-methoxycarbonylmethyluridine; 5-methoxyuridine; 2-methylthio-N⁶-isopentenyladenosine; N-((9-beta,D-ribofuranosyl-2-methylthiopurine-6-yl)carbamoyl)threonine; N-((9-beta,D-ribofuranosylpurine-6-yl)-N-methylcarbamoyl)threonine; uridine-5-oxyacetic acid methylester; uridine-5-oxyacetic acid (v); pseudouridine; queosine; 2-thiocytidine; 5-methyl-2-thiouridine; 2-thiouridine; 4-thiouridine; 5-methyluridine; 2'-O-methyl-5-methyluridine; and 2'-O-methyluridine.

In some embodiments, nucleosides include 6'-modified bicyclic nucleoside analogs that have either (R) or (S)-chirality at the 6'-position and include the analogs described in U.S. Pat. No. 7,399,845. In other embodiments, nucleosides include 5'-modified bicyclic nucleoside analogs that have either (R) or (S)-chirality at the 5'-position and include the analogs described in US Patent Application Publication No. 20070287831.

In some embodiments, the nucleobases or modified nucleobases comprises biomolecule binding moieties such as antibodies, antibody fragments, biotin, avidin, streptavidin, receptor ligands, or chelating moieties. In other embodiments, Ba is 5-bromouracil, 5-iodouracil, or 2,6-diaminopurine. In yet other embodiments, Ba is modified by substitution with a fluorescent or biomolecule binding moiety. In some embodiments, the substituent on Ba is a fluorescent moiety. In other embodiments, the substituent on Ba is biotin or avidin.

Modified Sugars of the Nucleotide/Nucleoside

The most common naturally occurring nucleotides are ribose sugars linked to the nucleobases adenosine (A), cytosine (C), guanine (G), and thymine (T) or uracil (U). Also contemplated are modified nucleotides wherein the phosphate group or the modified phosphorous atom moieties in the nucleotides can be linked to various positions of the sugar or modified sugar. As non-limiting examples, the phosphate group or the modified phosphorous-atom moiety can be linked to the 2', 3', 4' or 5' hydroxyl moiety of a sugar or modified sugar. Nucleotides that incorporate the modified nucleobases described above can also be used in the process disclosed herein. In some embodiments, nucleotides or modified nucleotides comprising an unprotected —OH moiety are used in the process disclosed herein.

In addition to the ribose moiety described in Schemes 1-4b, other modified sugars can also be incorporated in the nucleic acids disclosed herein. In some embodiments, the modified sugars contain one or more substituents at the 2' position including one of the following: F; CF₃, CN, N₃, NO, NO₂, O-, S-, or N-alkyl; O-, S-, or N-alkenyl; O-, S- or N-alkynyl; or O-alkyl-O-alkyl, O-alkyl-N-alkyl or N-alkyl-O-alkyl wherein the alkyl, alkenyl and alkynyl may be substituted or unsubstituted $C_1$-$C_{10}$ alkyl or $C_2$-$C_{10}$ alkenyl and alkynyl. Examples of substituents include, and are not limited to, O(CH₂)ₙOCH₃, and O(CH₂)ₙNH₂, wherein n is from 1 to about 10, MOE, DMAOE, DMAEOE. Also contemplated herein are modified sugars described in WO 2001/088198; and Martin et al., Helv. Chim. Acta, 1995, 78, 486-504. In some embodiments, modified sugars comprise substituted silyl groups, an RNA cleaving group, a reporter group, a fluorescent label, an intercalator, a group for improving the pharmacokinetic properties of a nucleic acid, or a group for improving the pharmacodynamic properties of a nucleic acid, and other substituents having similar properties. The modifications may be made at the at the 2', 3', 4', 5', or 6' positions of the sugar or modified sugar, including the 3' position of the sugar on the 3'-terminal nucleotide or in the 5' position of the 5'-terminal nucleotide.

Modified sugars also include sugar mimetics such as cyclobutyl or cyclopentyl moieties in place of the pentofuranosyl sugar. Representative United States patents that teach the preparation of such modified sugar structures include, but are not limited to, U.S. Pat. Nos. 4,981,957; 5,118,800; 5,319,080; and 5,359,044. Some modified sugars that are contemplated include

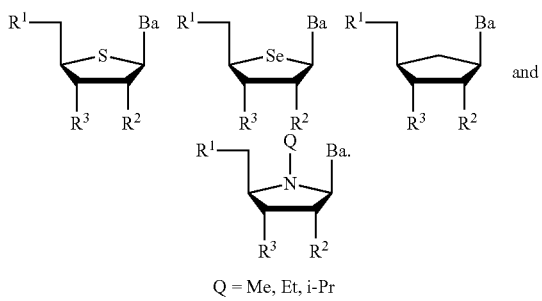

Q = Me, Et, i-Pr

Other non-limiting examples of modified sugars include glycerol, which form glycerol nucleic acid (GNA) analogues. One example of a GNA analogue is shown below and is described in Zhang, R et al., J. Am. Chem. Soc., 2008, 130, 5846-5847; Zhang L, et al., J. Am. Chem. Soc., 2005, 127, 4174-4175 and Tsai C H et al., PNAS, 2007, 14598-14603:

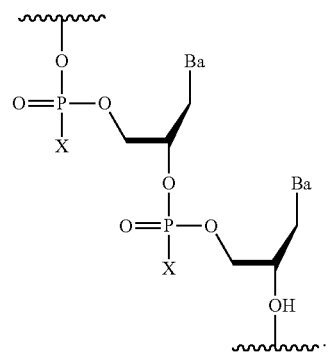

wherein X is as defined herein. Another example of a GNA derived analogue, flexible nucleic acid (FNA) based on the mixed acetal aminal of formyl glycerol, is described in Joyce G F et al., PNAS, 1987, 84, 4398-4402 and Heuberger B D and Switzer C, J. Am. Chem. Soc., 2008, 130, 412-413, and is shown below:

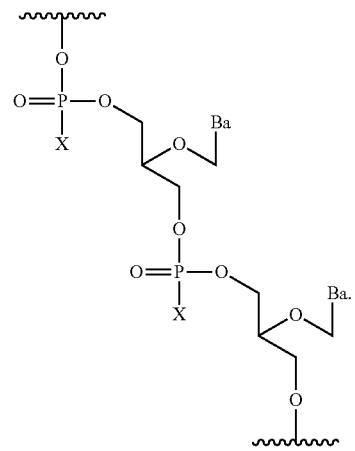

Blocking Groups

In the reactions described, it is necessary in certain embodiments to protect reactive functional groups, for example hydroxy, amino, thiol or carboxy groups, where these are desired in the final product, to avoid their unwanted participation in the reactions. Protecting groups are used to block some or all reactive moieties and prevent such groups from participating in chemical reactions until the protective group is removed. In one embodiment, each protective group is removable by a different means. Protective groups that are cleaved under totally disparate reaction conditions fulfill the requirement of differential removal. In some embodiments, protective groups are removed by acid, base, and/or hydrogenolysis. Groups such as trityl, dimethoxytrityl, acetal and t-butyldimethylsilyl are acid labile and are used in certain embodiments to protect carboxy and hydroxy reactive moieties in the presence of amino groups protected with Cbz groups, which are removable by hydrogenolysis, and/or Fmoc groups, which are base labile. In other embodiments, carboxylic acid and hydroxy reactive moieties are blocked with base labile groups such as, but not limited to, methyl, ethyl, and acetyl in the presence of amines blocked with acid labile groups such as t-butylcarbamate or with carbamates that are both acid and base stable but hydrolytically removable.

In another embodiment, hydroxy reactive moieties are blocked with hydrolytically removable protective groups such as the benzyl group, while amine groups capable of hydrogen bonding with acids are blocked with base labile groups such as Fmoc. In another embodiment, carboxylic acid reactive moieties are protected by conversion to simple ester compounds, or they are, in yet another embodiment, blocked with oxidatively-removable protective groups such as 2,4-dimethoxybenzyl, while co-existing amino groups are blocked with fluoride labile silyl or carbamate blocking groups.

Allyl blocking groups are useful in the presence of acid- and base-protecting groups since the former are stable and can be subsequently removed by metal or pi-acid catalysts. For example, an allyl-blocked hydroxy groups can be deprotected with a Pd(0)-catalyzed reaction in the presence of acid labile t-butylcarbamate or base-labile acetate amine protecting groups. Yet another form of protecting group is a resin to which a compound or intermediate is attached. As long as the residue is attached to the resin, that functional group is blocked and cannot react. Once released from the resin, the functional group is available to react.

Typically blocking/protecting groups are, by way of example only:

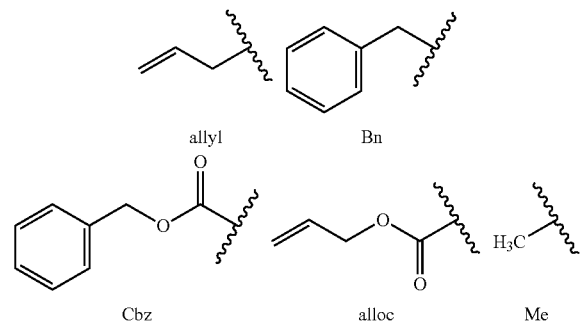

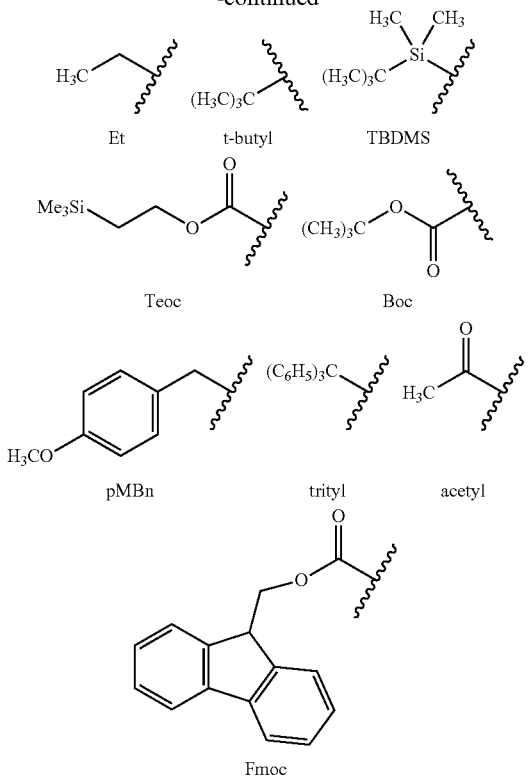

Representative protecting groups useful to protect nucleotides during synthesis include base labile protecting groups and acid labile protecting groups. Base labile protecting groups are used to protect the exocyclic amino groups of the heterocyclic nucleobases. This type of protection is generally achieved by acylation. Three commonly used acylating groups for this purpose are benzoyl chloride, phenoxyacetic anhydride, and isobutyryl chloride. These protecting groups are stable to the reaction conditions used during nucleic acid synthesis and are cleaved at approximately equal rates during the base treatment at the end of synthesis.

In some embodiments, the 5'-protecting group is trityl, monomethoxy trityl, dimethoxytrityl, trimethoxytrityl, 2-chlorotrityl, DATE, TBTr, 9-phenylxanthine-9-yl (Pixyl), or 9-(p-methoxyphenyl)xanthine-9-yl (MOX).

In some embodiments, thiol moieties are incorporated in the compounds of Formula 1, 2, 4, or 5 and are protected. In some embodiments, the protecting groups include, but are not limited to, Pixyl, trityl, benzyl, p-methoxybenzyl (PMB), or tert-butyl (t-Bu).

Other protecting groups, plus a detailed description of techniques applicable to the creation of protecting groups and their removal are described in Greene and Wuts, Protective Groups in Organic Synthesis, 3rd Ed., John Wiley & Sons, New York, N.Y., 1999, and Kocienski, Protective Groups, Thieme Verlag, New York, N.Y., 1994, which are incorporated herein by reference for such disclosure.

In some embodiments, $R^1$ is $—OR^a$, wherein $R^a$ is substituted or unsubstituted trityl or substituted silyl. In other embodiments, $R^1$ is $—N_3$, $—NR^dR^d$, alkynyloxy, or $—OH$. In some embodiments, $R^2$ is $—OR^b$, wherein $R^b$ is substituted or unsubstituted trityl, substituted silyl, acetyl, acyl, or substituted methyl ether. In other embodiments, $R^2$ is $—NR^dR^d$, alkyl, alkenyl, alkynyl, alkyl-$Y^1$—, alkenyl-$Y^1$—, alkynyl-$Y^1$—, aryl-$Y^1$—, heteroaryl-$Y^1$—, where $Y^1$ is O, NR$^d$, S, or Se, and is substituted with fluorescent or biomolecule binding moieties. In yet other embodiments, the substituent on R$^2$ is a fluorescent moiety. In some embodiments, the substituent on R$^2$ is biotin or avidin. In some embodiments, R$^2$ is —OH, —N$_3$, hydrogen, halogen, alkoxy, or alkynyloxy.

In other embodiments, R$^3$ is a blocking group which is substituted trityl, acyl, substituted silyl, or substituted benzyl. In yet other embodiments, R$^3$ is a linking moiety connected to a solid support. In further embodiments, the blocking group of the Ba moiety is a benzyl, acyl, formyl, dialkylformamidinyl, isobutyryl, phenoxyacetyl, or trityl moiety, any of which may be unsubstituted or substituted.

Methods of Use of the Nucleic Acids Comprising a Chiral X-Phosphonate Moiety

The stereodefined oligonucleotides comprising a chiral X-phosphonate moiety which are obtained by the methods of the invention are useful in a number of areas for applications due to a combination of stability, defined chirality and ease of synthesis. Broadly, the compounds synthesized by this method are useful as therapeutics, diagnostic probes and reagents, synthetic tools for producing other oligonucleotide products, and nanostructure materials suitable for a variety of new materials and computing applications.

The stereodefined oligonucleotides of the invention have improved serum stability over that of natural DNA/RNA equivalents, and in particular, stereodefined oligonucleotides of the class of phosphorothioates. Further, the S$_P$ isomer is more stable than the R$_P$ isomer. In some embodiments, the level of serum stability is modulated by the introduction of either all S$_P$ centers or S$_P$ centers at selected positions to confer resistance to degradation. In other embodiments, introduction of selectable R$_P$ and/or S$_P$ stereocenters can provide for specific base pairing association with an endogenous or exogenous target thus protecting the target from metabolism or enhancing a particular biological reaction.

RNase H activation is also modulated by the presence of the stereocontrolled phosphorothioate nucleic acid analogs, with natural DNA/RNA being more susceptible than the R$_P$ stereoisomer which in turn is more susceptible than the corresponding S$_P$ isomer.

Improved duplex stability towards RNA is seen with R$_P$ phosphorothioate oligonucleotides having greater duplex stability than corresponding S$_P$ oligonucleotides which in turn demonstrates higher stability than that of natural DNA/RNA. Improved duplex stability towards DNA is seen with S$_P$ having greater duplex stability than R$_P$ which has more stability than that of natural DNA/RNA. (P. Guga, Curr. Top Med. Chem., 2007, 7, 695-713).

These molecules may be useful as therapeutic agents, in a number of particular applications. They can be incorporated into oligonucleotides which also contain the standard DNA/RNA nucleosides, or they may be synthesized as entire sequences of the stereocontrolled oligonucleotides of the invention. Some categories of therapeutic agents include but are not limited to antisense oligonucleotides, antigene oligonucleotides which form triple helix with targeted sequences to repress transcription of undesired genes and modulate protein expression and/or activity, decoy oligonucleotides, DNA vaccines, aptamers, ribozymes, deoxyribozymes (DNAzymes or DNA enzymes), siRNAs, microRNAs, ncRNAs (non-coding RNAs), and P-modified prodrugs. Modulation encompasses indirectly or directly increasing or decreasing the activity of a protein or inhibition or promotion of the expression of a protein. These nucleic acid compounds can be used to control cell proliferation, viral replication, or any other cell signaling process.

In one example, the field of siRNA therapeutics has a need for oligonucleotide species that can afford increased stability against RNase activity, in order to improve the duration of action over that seen with siRNA composed of natural nucleosides. Additionally, A-form helix formation appears to be more indicative of success at entering RNAi than the presence of specific native elements on the oligonucleotide. Both of these requirements can be afforded by the use of the stereocontrolled oligonucleotides of the invention may provide enhanced stability (Y-L Chiu, T. M. Rana RNA, 2003, 9,1034-1048).

The nucleic acids described herein are useful as therapeutic agents against various disease states, including use as antiviral agents. The nucleic acids can be used as agents for treatment of diseases through modulation of DNA and/or RNA activity. In some embodiments, the nucleic acids can be used for inhibiting specific gene expression. For example, the nucleic acids can be complementary to a specific target messenger RNA (mRNA) sequence. They can be used to inhibit viral replication such as the orthopoxvirus, vaccinia virus, herpes, papilloma, influenza, cytomegalovirus and other viruses. Other examples include uses as antisense compounds against HIV RNA or other retroviral RNA or for hybridizing to HIV mRNA encoding the tat protein, or to the TAR region of HIV mRNA. In some embodiments, the nucleic acids mimic the secondary structure of the TAR region of HIV mRNA, and by doing so bind the tat protein. In an embodiment, the nucleic acids is used to inhibit expression of a target protein by contacting a cell with a compound of Formula 1 wherein the expression of other proteins in the cell are not inhibited or are minimally inhibited. In some embodiment, target protein inhibition occurs in vivo in a mammal. In other embodiments, a therapeutically effective amount of a compound of Formula 1 is administered for inhibiting the expression of a target protein.

Other examples of proteins where expression can be modulated include Jun N-terminal kinase (JNK) proteins, diacylglycerol acyltransferase I, apolipoprotein B, glucagon receptor, Aurora B, acyl CoA cholesterol acyltransferase-2, c-reactive protein, STAT (signal transducers and activators of transcription) family of proteins, and MDR P-glycoprotein. The nucleic acids can be used to inhibit protein phosphatase 1B (PTP1B) expression, RNA-dependent RNA viral polymerase. The nucleic acids can be used to induce events such as apoptosis in cancer cells or to make a cell more susceptible to apoptosis. The nucleic acids can be used to modulate activities of proteins. For example, it can help modulate RNase H activity on multidrug resistance (MDR) RNA molecules.

The nucleic acids described herein are useful for treating indications including, but not limited, to hypercholesterolemia, severe acute respiratory syndrome (SARS), retroviral diseases such as AIDS or HIV, other viral infections, intrauterine infections, and cancer.

When used as therapeutics, the nucleic acid described herein is administered as a pharmaceutical composition. In some embodiments, the pharmaceutical composition comprises a therapeutically effective amount of a nucleic acid comprising a chiral X-phosphonate moiety of Formula 1, or a pharmaceutically acceptable salt thereof, and at least one pharmaceutically acceptable inactive ingredient selected from pharmaceutically acceptable diluents, pharmaceutically acceptable excipients, and pharmaceutically acceptable carriers. In another embodiment, the pharmaceutical composition is formulated for intravenous injection, oral administration, buccal administration, inhalation, nasal administration, topical administration, ophthalmic administration or otic administration. In further embodiments, the pharmaceutical composition is a tablet, a pill, a capsule, a liquid, an inhalant, a nasal spray solution, a suppository, a suspension, a gel, a colloid, a dispersion, a suspension, a solution, an emulsion, an ointment, a lotion, an eye drop or an ear drop.

A second category where the compounds synthesized by the methods of the invention are useful are as primers or probes. Since the method provides for total control of sequence, natural and unnatural, and of stereochemistry at the phosphorus center, any specific molecule can be specifically produced. Additionally, the additional RNase resistance provides molecules which are robust under ex-vivo or in-vivo conditions. The stereodefined oligonucleotides of the invention can be used as probes for investigation of enzymatic reaction mechanisms involving phosphorous atoms such as digestion, ligation, and polymerization of nucleic acids. This class of molecules can be used as probes for investigation of ribozyme and deoxyribozyme reaction mechanisms. They can also function as probes for investigation of RNAi and other non-coding RNA mediated gene silencing mechanisms or as probes for analysis of protein-nucleic acid interactions. The ability to define the three dimensional structure by incorporating select $R_P$ or $S_P$ phosphorus stereocenters permits the possibility of designing novel classes of so-called molecular beacons.

As this method of synthesis is not limited to the narrow set of natural nucleobases, modified nucleobases or other modifications to the base or sugar or termini permits the use of this class of oligonucleotides as probes or sensors for nucleic acids, proteins and any biological or chemical substances in solution. They may be used similarly, without modified nucleobases, using standard detection methods in place of natural DNA/RNA as well. Any of these may be incorporated as part of a diagnostic assay.

Such diagnostic tests can be performed using biological fluids, tissues, intact cells or isolated cellular components. As with gene expression inhibition, diagnostic applications utilize the ability of the nucleic acids to hybridize with a complementary strand of nucleic acid. Hybridization is the sequence specific hydrogen bonding of oligomeric compounds via Watson-Crick and/or Hoogsteen base pairs to RNA or DNA. The bases of such base pairs are said to be complementary to one another. The nucleic acids can be used to analyze bodily states e.g. diseased states in animals. They can be used for identification of adenoviruses or influenza viruses in a sample or as intercalating agents or probes. For example, they can be used to detect DNA methylation or probe DNA interactions with other cellular components such as proteins.

In another aspect of the invention, a method is provided of identifying or detecting a target molecule in a sample, the method comprising: contacting a sample suspected of containing a target molecule with a nucleic acid sensor molecule of Formula 1, synthesized according to the methods of the invention, wherein a change in a signal generated by a signal generating unit indicates the presence of said target in said sample. The nucleic acid sensor molecule binds specifically with the target molecule. In some embodiments there is a plurality of nucleic acid sensor molecules. In some embodiments, the plurality of nucleic acid sensor molecules comprises nucleic acid sensor molecules which bind specifically to differing target molecules. In some instances, the method further comprises quantifying the change in signal generated by the signal generating unit to quantify the amount of target molecule in the sample. The signal generating unit detects any sort of signal, including but not limited to fluorescence, surface plasmon resonance, fluorescence quenching, chemiluminescence, interferometry, or refractive index detection.

The sample to be detected is an environmental sample, biohazard material, organic sample, drug, toxin, flavor, fragrance, or biological sample. The biological sample is a cell, cell extract, cell lysate, tissue, tissue extract, bodily fluid, serum, blood or blood product. In some embodiments of the method, the presence of the target molecule indicates the presence of a pathological condition. In some embodiments of the method, the presence of the target molecule indicates the presence of a desirable molecule.

In a related use, the stereodefined oligonucleotides provided by the methods of the invention are useful as primers for PCR or as templates or primers for DNA/RNA synthesis using polymerases. The melting temperatures may be optimized for a particular application depending on the select introduction of $R_P$ or $S_P$ chirality at phosphorus in the product oligonucleotide.

In another aspect of the invention, a method is provided of amplifying desired regions of nucleic acid from a nucleic acid template comprising: (a) providing a plurality of first PCR primers having a region of fixed nucleotide sequence complementary to a consensus sequence of interest; (b) providing a plurality of second PCR primers, (c) amplifying the nucleic acid template via the PCR using the plurality of first PCR primers and the plurality of second PCR primers under conditions wherein a subset of the plurality of first primers binds to the consensus sequence of interest substantially wherever it occurs in the template, and a subset of the plurality of second primers binds to the template at locations removed from the first primers such that nucleic acid regions flanked by the first primer and the second primer are specifically amplified, and wherein the plurality of first PCR primers and/or the plurality of second PCT primers are nucleic acid molecules of Formula 1 which are produced according to the methods of the invention.

In some embodiments, the template is genomic DNA. In some embodiments, the template is eukaryotic genomic DNA. In some embodiments, the template is human genomic DNA. In some embodiments, the template is prokaryotic DNA. In some embodiments, the template is DNA which is a cloned genomic DNA, a subgenomic region of DNA, a chromosome, or a subchromosomal region. In some embodiments, the template is RNA.

The stereodefined oligonucleotides are also useful, due to their increased stability and their ability to retain recognition and binding with their biological targets, as substances for DNA chips and oligonucleotide microarrays. They may also be used as stabilized oligonucleotides alternative to natural nucleic acids such as tRNA and mRNA in the cell free protein synthesis.

An additional area where the ability to control stability, molecular composition including unnatural moieties, and structure all within the same synthesis is useful is for applications within DNA nanomaterial design. The stereodefined oligonucleotides of the invention may be used as substances for construction of nucleic acid nano-structures consisting of duplex, triplex, quadruplex, and other higher-order structures. The ability to incorporate other organic moieties in the molecules produced by this methods leads to applications in nanomaterials by designing a specific, unnatural higher order structure. The stability in-vivo and flexibility of design will permit these molecules' use in DNA computers, for example. Additionally, metal chelating or conducting organic molecules can be incorporated in the stereodefined oligonucleotides of the invention and lead to their use as DNA nano-wires in electronic devices or DNA/RNA nano-machines (F. A. Aldate, A. L. Palmer, *Science*, 2008, 321, 1795-1799).

EXAMPLES

General Information:

All NMR spectra herein were recorded on a Varian Mercury 300. $^1$H NMR spectra were obtained at 300 MHz with tetramethylsilane (TMS) (δ 0.0) as an internal standard in $CDC_3$. $^{31}$P NMR spectra were obtained at 121.5 MHz with 85% $H_3PO_4$ (δ 0.0) as an external standard. MALDI TOF-MS were recorded on an Applied Biosystems Voyager System 4327. Silica gel column chromatography was carried out using Kanto silica gel 60N (spherical, neutral, 63-210 μm). Analytical TLC was performed on Merck Kieselgel 60-$F_{254}$ plates. Dry organic solvents were prepared by appropriate procedures prior to use. The other organic solvents were reagent grade and used as received. ACQUITY UPLC® was carried out using a BEH Csg (1.7 μm, 2.1×150 mm). The yield of the dTT, dCT, dAT, dGT, $rU_{OMe}U$, and $rU_FU$ phosphorothioate dimers were determined by UV absorbance measurements at 260 nm with the molar extinction coefficients of approximate values for natural dTT (16800), dCT (15200), dAT (22800), dGT (20000), rUU (19600), rUU (19600) dimers, respectively.

Figure 2:
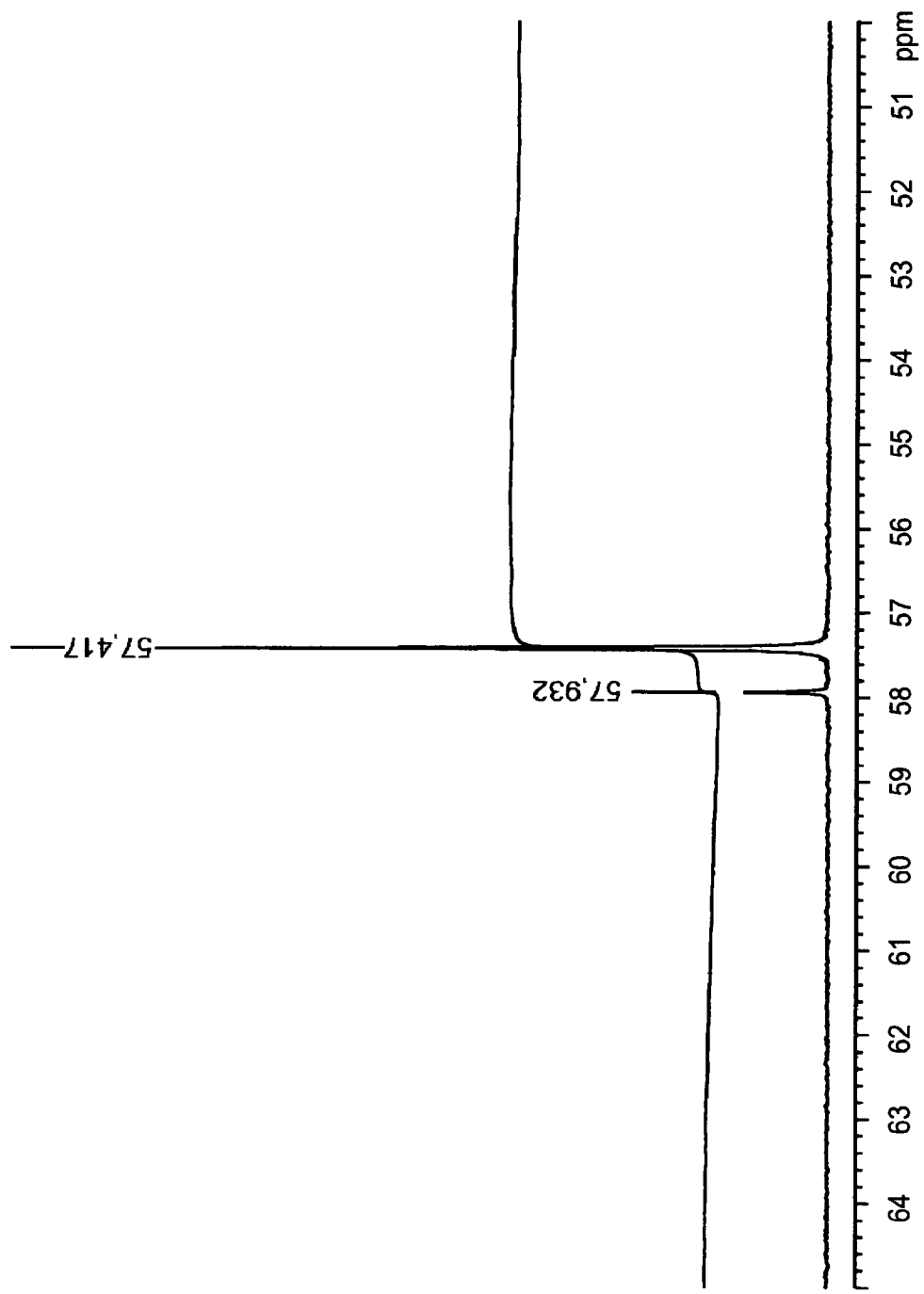

Abbreviations bz: benzoyl
Beaucage reagent: 3H-1,2-benzodithiol-3-one 1,1-dioxide
BSA: N,O-bis(trimethylsilyl)acetamide
BTC: bis(trichloromethyl)carbonate
ce: cyanoethyl
$CF_3COIm$: N-trifluoroacetylimidazole
CMP: N-cyanomethyl pyrrolidine
CMPT: N-cyanomethyl pyrrolidinium trifluoromethanesulfonate
CPG: controlled pore glass
DBU: 1,8-diazabicyclo[5.4.0]undec-7-ene
DCA: dichloroacetic acid
DCM: dichloromethane, $CH_2Cl_2$
DMAc: N,N-dimethylacetamide
DMAN: 1,8-bis(dimethylamino)naphthalene
DMTr: 4,4'-dimethoxytrityl
DTD: N,N'-dimethylthiuram disulfide
HCP: highly cross-linked polystyrene
pac: phenoxyacetyl
TBS: t-butyldimethylsilyl
TBDPS: t-butyldiphenylsilyl
TFA: trifluoroacetic acid
L-2: same as Formula P herein
D-2: same as Formula O herein
L-6: same as Formula R herein
D-6: same as Formula Q herein Example 1: Solution Synthesis of a Phosphorothioate Dimer, ($S_P$)-1,8-Diazabicyclo[5.4.0]undec-7-enium $N^3$-benzoyl-5'-O-(tert-butyldiphenylsilyl)thymidin-3'-yl $N^3$-benzoyl-3'-O-(tert-butyldimethylsilyl)thymidin-5'-yl phosphorothioate [($S_P$)-4tt] via Route A 8-Diazabicyclo[5.4.0]undec-7-enium $N^3$-benzoyl-5'-O-(tert-butyldiphenylsilyl)thymidin-3'-yl phosphonate (1t) (96.0 mg, 120 μmol) was dried by repeated coevaporations with dry pyridine and then dissolved in dry pyridine (2 mL). BTC (29.7 mg 100 μmol) was added, and the mixture was stirred for 10 min. An aminoalcohol L-2 (21.3 mg, 120 μmol) solution, which was prepared by repeatedly coevaporations with dry pyridine and dissolved in dry pyridine (1 mL), was added to the reaction mixture dropwise via syringe, and the mixture was stirred for 5 min under argon atmosphere. To the solution of $N^3$-benzoyl-3'-O-(tert-butyldimethylsilyl)thymidine (3t), which was prepared by repeated coevaporations with dry pyridine and dissolved in pyridine (500 μmol), the reaction mixture was added via syringe. After 30 min, DTD (42.5 mg, 120 μmol) was added to the reaction mixture. Following an additional 5 min, the solvent was evaporated under the reduced pressure. Concentrated $NH_3$-EtOH (40 mL; 3:1, v/v) was added to the residue, and the mixture was stirred for 12 h at room temperature. The mixture was concentrated to dryness under the reduced pressure. The crude mixture was diluted with $CHCl_3$ (15 mL), and washed with 0.2 M triethylammonium hydrogencarbonate (20 mL). The aqueous layer was back-extracted with $CHC_3$ (4×15 mL). The combined organic layers were dried over $Na_2SO_4$, filtered, and concentrated to dryness under the reduced pressure. The residue was purified by PTLC. The product was dissolved in $CHC_3$ (5 mL), washed with 0.2 M 1,8-diazabicyclo[5.4.0]undec-7-enium hydrogencarbonate buffer (10 mL) and back-extracted with $CHCl_3$ (3×5 mL). The combined organic layers was dried over $Na_2SO_4$, filtered, and concentrated to dryness to afford ($S_P$)-4tt (41.8 mg, 98% yield, $R_P$:$S_P$=9:91) as a white foam. The $^1$H and $^{31}$P NMR spectra (FIGS. 1 and 2, respectively) were identical to those of a control sample synthesized by the conventional H-phosphonate method. $^{31}$P NMR (121.5 MHz, $CDCl_3$) δ 57.4 ($R_P$ isomer: 57.9). The synthetic scheme is shown in Scheme 10.

Scheme 10. Solution Synthesis of a DNA dimer as in Scheme 5 (Route A).

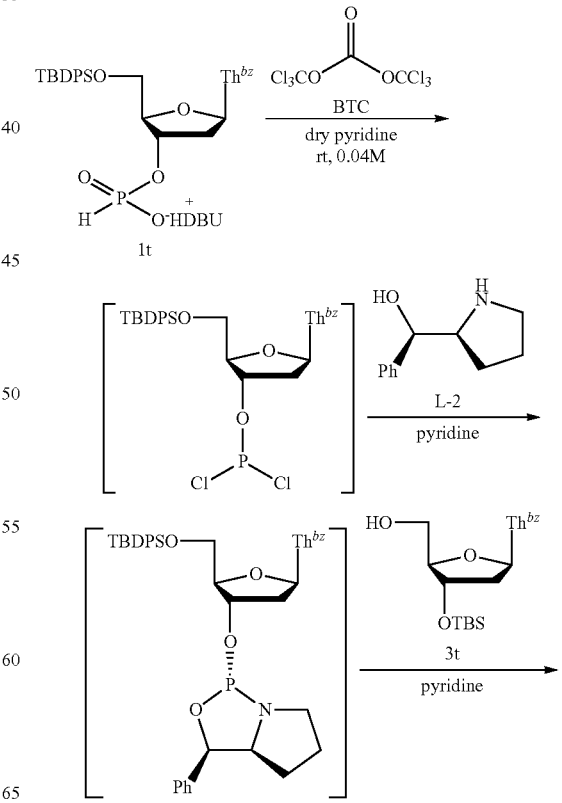

-continued

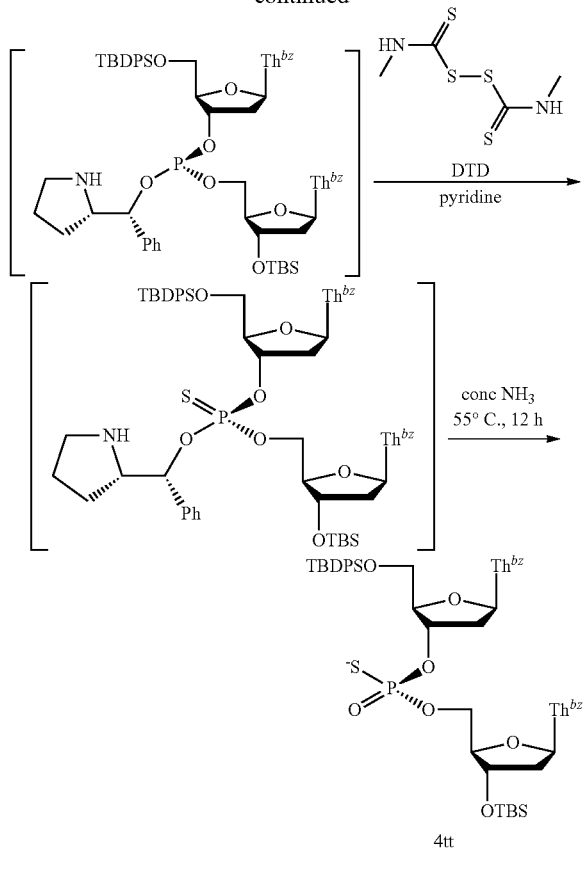

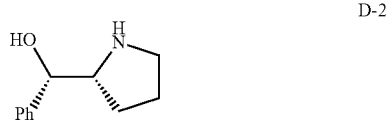 [SMILES: O[C@@H](c1ccccc1)[C@H]1CCCN1]

4tt

Example 2: Solution Synthesis of a Phosphorothioate Dimer, ($S_P$)-1,8-Diazabicyclo[5.4.0]undec-7-enium 6-N-benzoyl-5'-O-(tert-butyldiphenylsilyl)-deoxyadenosin-3'-yl 3'-O-(tert-butyldimethylsilyl) thymidin-5'-yl phosphorothioate [($S_P$)-4at] via Route A ($S_P$)-4at is obtained from 1,8-diazabicyclo[5.4.0]undec-7-enium 6-N-benzoyl-5'-O-(tert-butyldiphenylsilyl)-deoxyadenosin-3'-yl phosphonate (1a) instead of 1t, using the reaction steps described above for ($S_P$)-4tt.

Example 3: Solution Synthesis of a Phosphorothioate Dimer, ($S_P$)-1,8-Diazabicyclo[5.4.0]undec-7-enium 4-N-benzoyl-5'-O-(tert-butyldiphenylsilyl)-deoxycytidin-3'-yl 3'-O-(tert-butyldimethylsilyl) thymidin-5'-yl phosphorothioate [($S_P$)-4ct] via Route A ($S_P$)-4ct is obtained from 1,8-diazabicyclo[5.4.0]undec-7-enium 4-N-benzoyl-5'-O-(tert-butyldiphenylsilyl)-deoxycytidin-3'-yl phosphonate (1c), instead of 1t, using the reaction steps described above for ($S_P$)-4tt.

Example 4: Solution Synthesis of a Phosphorothioate Dimer, ($S_P$)-1,8-Diazabicyclo[5.4.0]undec-7-enium 2-N-phenoxyacetyl-5'-O-(tert-butyldiphenylsilyl)deoxyguanosin-3'-yl 3'-O-(tert-butyldimethylsilyl)thymidin-5'-yl phosphorothioate [($S_P$)-4gt] via Route A ($S_P$)-4gt is obtained from 1,8-diazabicyclo[5.4.0]undec-7-enium 2-N-phenoxyacetyl-5'-O-(tert-butyldiphenylsilyl) deoxyguanosin-3'-yl phosphonate (1g) instead of 1t, using the reaction steps described above for ($S_P$)-4tt.

Figure 3:
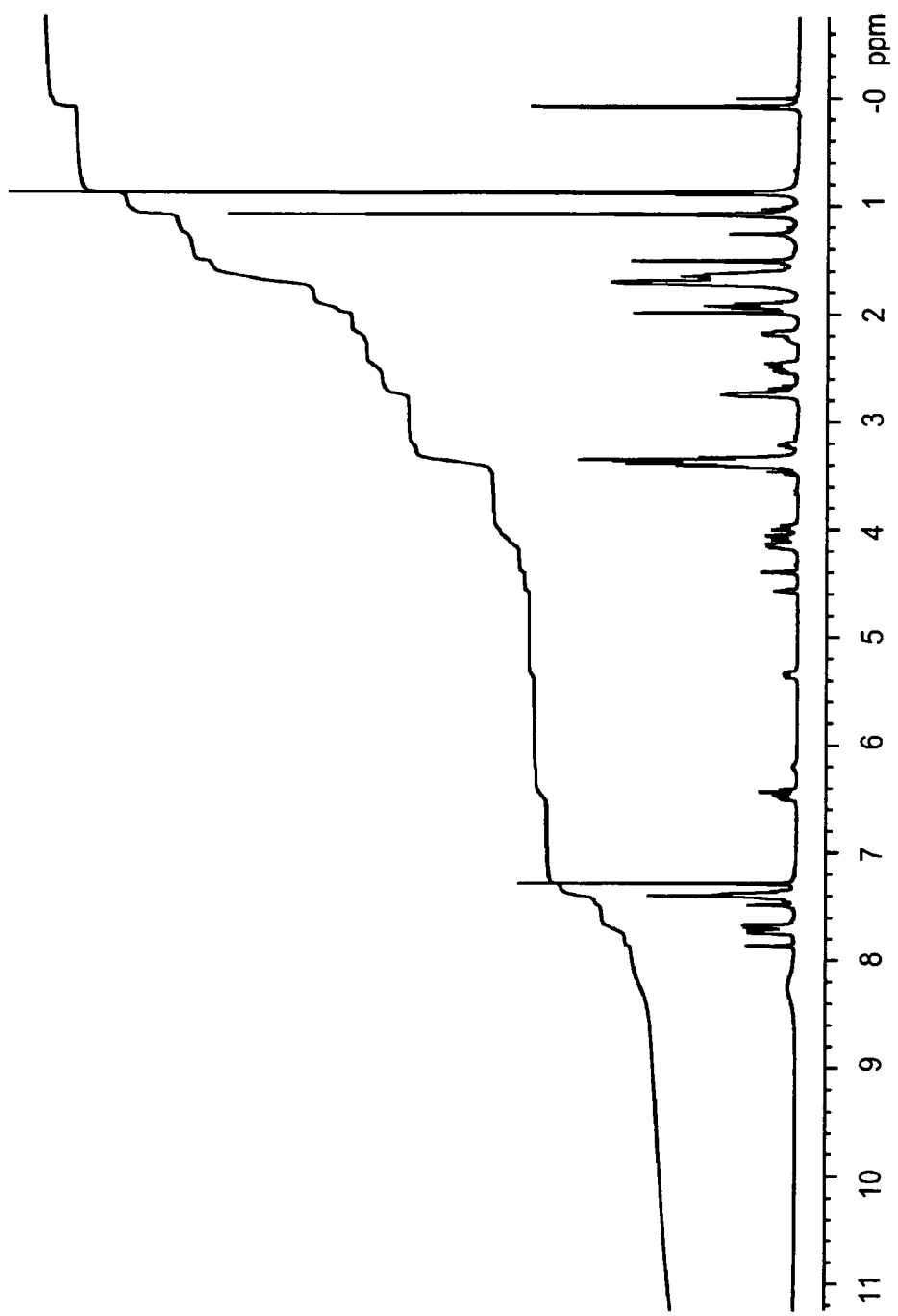
Figure 4:
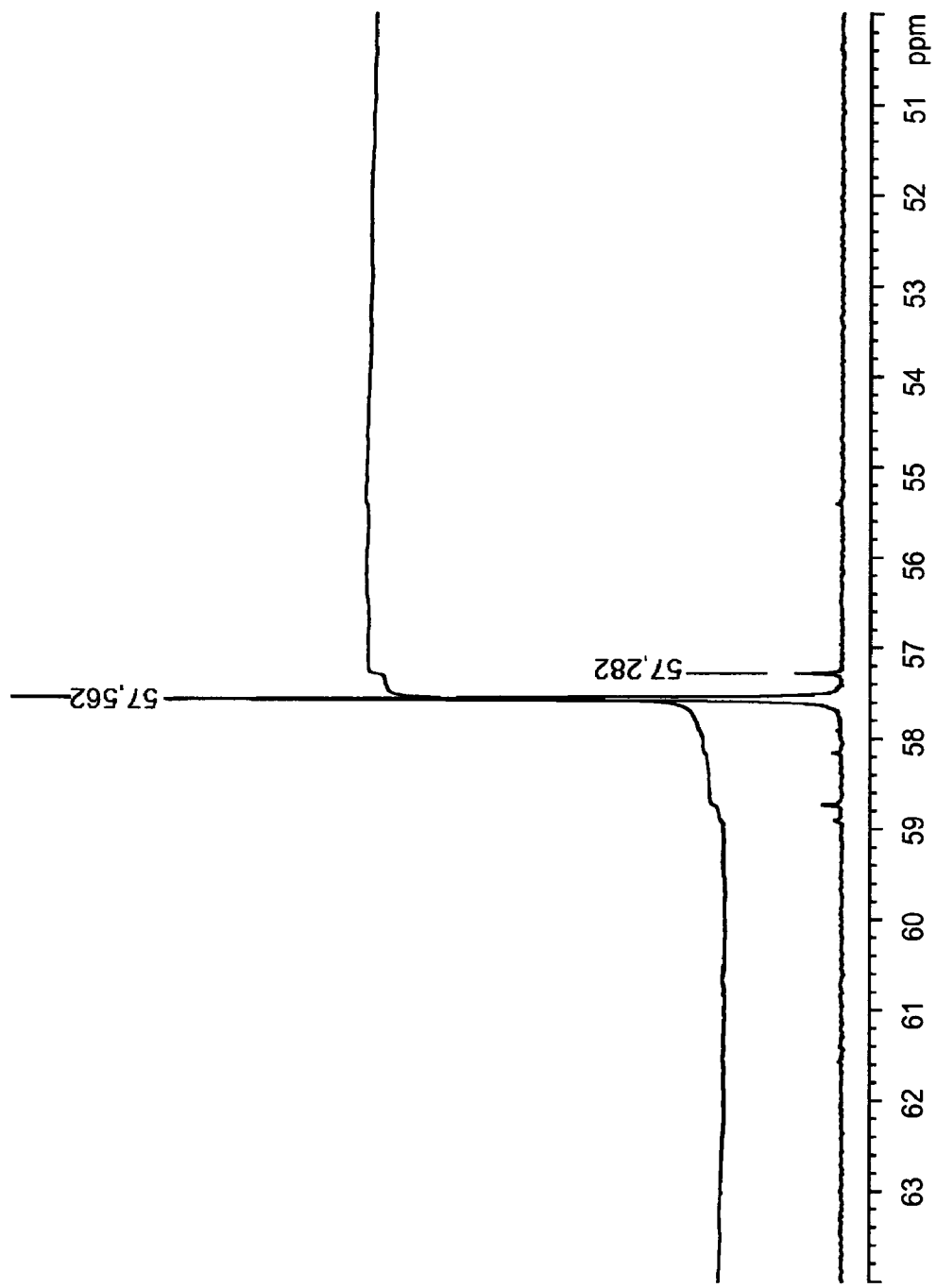

Example 5: Solution Synthesis of a Phosphorothioate Dimer, ($R_P$)-1,8-Diazabicyclo[5.4.0]undec-7-enium $N^3$-benzoyl-5'-O-(tert-butyldiphenylsilyl) thymidin-3'-yl $N^3$-benzoyl-3'-O-(tert-butyldimethylsilyl)thymidin-5'-yl phosphorothioate [($R_P$)-4tt] via Route A ($R_P$)-4tt was obtained as a white foam (93% yield, $R_P$:$S_P$=95:5) by using amino alcohol D-2 instead of L-2 in a similar manner to ($S_P$)-4tt in Example 1. The $^1$H and $^{31}$P NMR spectra are shown in FIGS. 3 and 4, respectively. $^{31}$P NMR (121.5 MHz, CDCl$_3$) δ 57.6 ($S_P$ isomer: 57.3.

Example 6: Solution Synthesis of a Phosphorothioate Dimer, ($R_P$)-1,8-Diazabicyclo[5.4.0]undec-7-enium 6-N-benzoyl-5'-O-(tert-butyldiphenylsilyl) deoxyadenosin-3'-yl 3'-O-(tert-butyldimethylsilyl) thymidin-5'-yl phosphorothioate [($R_P$)-4at] via Route A ($R_P$)-4at is produced via the transformations described above in Example 2 using compound 1a and the amino alcohol D-2 as a chiral reagent, instead of L-2.

Example 7: Solution Synthesis of a Phosphorothioate Dimer, ($R_P$)-1,8-Diazabicyclo[5.4.0]undec-7-enium 4-N-benzoyl-5'-O-(tert-butyldiphenylsilyl) deoxycytidin-3'-yl 3'-O-(tert-butyldimethylsilyl) thymidin-5'-yl phosphorothioate [($R_P$)-4ct] via Route A ($R_P$)-4ct is produced via the transformations described above in Example 3 using compound 1c and the amino alcohol D-2 as a chiral reagent, instead of L-2.

Example 8: Solution Synthesis of a Phosphorothioate Dimer, ($R_P$)-1,8-Diazabicyclo[5.4.0]undec-7-enium 2-N-phenoxyacetyl-5'-O-(tert-butyldiphenylsilyl)deoxyguanosin-3'-yl 3'-O-(tert-butyldimethylsilyl)thymidin-5'-yl phosphorothioate [($R_P$)-4gt] via Route A ($R_P$)-4gt is produced via the transformations described above in Example 4 using compound 1g and the amino alcohol D-2 as a chiral reagent, instead of L-2.

Example 9: Deprotection to Form ($S_P$)-Ammonium thymidin-3'-yl thymidin-5'-yl phosphorothioate [($S_P$)-5ttS]

($S_P$)-4tt (50 μmol) is dried by repeated coevaporations with dry pyridine and dry toluene, and then dissolved in triethylamine trihydrofluoride (500 μL). The mixture is stirred for 15 h at room temperature. A 0.1 M ammonium acetate buffer (2.5 mL) is then added to the mixture, and the mixture is washed with Et$_2$O (3×3 mL). The combined organic layers are back-extracted with 0.1 M ammonium acetate buffer (3 mL). The combined aqueous layers are then concentrated to dryness under reduced pressure, and the residue is purified by reverse-phase column chromatography [a linear gradient of acetonitrile 0-10% in 0.1 M ammonium acetate buffer (pH 7.0)] to afford ($S_P$)-5tt. The deprotection scheme is shown in Scheme 11.

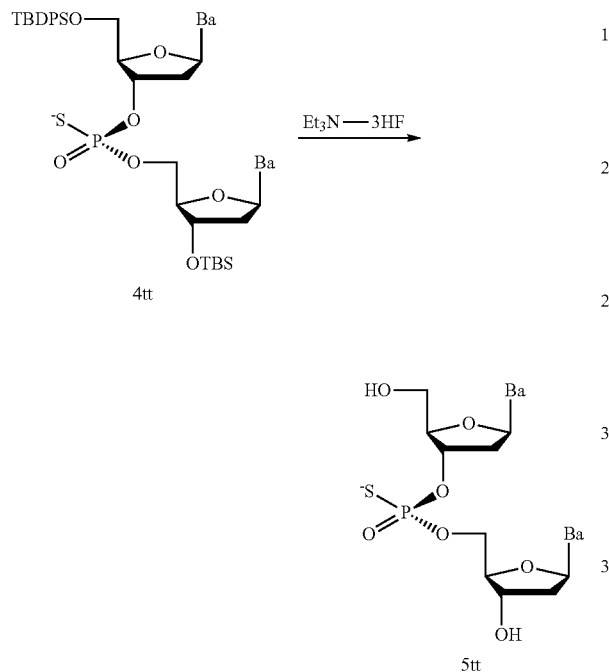

Example 10: Deprotection to Form ($S_P$)-Ammonium deoxyadenosin-3'-yl thymidin-5'-yl phosphorothioate [($S_P$)-5at]

($S_P$)-5at is produced as described above in Example 9 using ($S_P$)-4at instead of ($S_P$)-4tt.

Example 11: Deprotection to Form ($S_P$)-Ammonium deoxycytidin-3'-yl thymidin-5'-yl phosphorothioate [($S_P$)-5ct]

($S_P$)-5ct is produced as described above in Example 9 using ($S_P$)-4ct instead of ($S_P$)-4tt.

Example 12: Deprotection to Form ($S_P$)-Ammonium deoxyguanosin-3'-yl thymidin-5'-yl phosphorothioate [($S_P$)-5gt]

($S_P$)-5gt is produced as described above in Example 9 using ($S_P$)-4gt instead of ($S_P$)-4tt in.

Example 13: Deprotection to Form ($R_P$)-Ammonium thymidin-3'-yl thymidin-5'-yl phosphorothioate [($R_P$)-5tt]

($R_P$)-5tt is produced as described above in Example 9 using ($R_P$)-4tt instead of ($S_P$)-4tt in a similar manner as ($S_P$)-5tt.

Example 14: Deprotection to Form ($R_P$)-Ammonium deoxyadenosin-3'-yl thymidin-5'-yl phosphorothioate [($R_P$)-5at]

($R_P$)-5at is produced as described above in Example 9 using ($R_P$)-4at instead of ($S_P$)-4tt.

Example 15: Deprotection to Form ($R_P$)-Ammonium deoxycytidin-3'-yl thymidin-5'-yl phosphorothioate [($R_P$)-5ct]

($R_P$)-5ct is produced as described above in Example 9 using ($R_P$)-4ct instead of ($S_P$)-4tt.

Example 16: Deprotection to Form ($R_P$)-Ammonium deoxyguanosin-3'-yl thymidin-5'-yl phosphorothioate [($R_P$)-5gt]

($R_P$)-5gt is produced as described above in Example 9 using ($R_P$)-4gt instead of ($S_P$)-4tt in a similar manner as ($S_P$)-5tt.

Example 17: Synthesis of ($R_P$)-5'-O-(tert-butyldiphenylsilyl)thymidin-3'-yl 3'-O-(tert-butyldimethylsilyl)thymidin-5'-yl H-phosphonate [($R_P$)-7tt] via Route B 1t (100 μmol) is dried by repeated coevaporations with dry pyridine and then dissolved in dry pyridine (1 mL). N,N'-Bis(2-oxo-3-oxazolidinyl)phosphinic chloride (BopCl; 500 μmol) is added, and the mixture is stirred for 5 min. To the mixture, a solution of amino alcohol ((αR,2S)-6) (100 μmol), which has been dried by coevaportions with dry pyridine and dissolved in dry pyridine (1 mL), is added dropwise via syringe, and the mixture is stirred for 5 min under argon. 3'-O-(tert-butyldimethylsilyl)thymidine is dried using repeated coevaporations with dry pyridine and dissolved in 100 μmol pyridine. The above mixture is added via cannula to the solution of 3'-O-(tert-butyldimethylsilyl) thymidine 3t in dry (100 μmol) pyridine. After 15 min, the mixture is concentrated under reduced pressure. The residue is diluted with $CH_2Cl_2$ (5 mL), and washed with saturated $NaHCO_3$ (3×5 mL). The combined aqueous layers are back-extracted with with $CH_2Cl_2$ (2×5 mL). The combined organic layers are dried over $Na_2SO_4$, filtered, and concentrated to ca. 1 mL under reduced pressure. The residue is added dropwise via a syringe to a stirred 1% trifluoroacetic acid (TFA) solution in dry $CH_2Cl_2$ (20 mL) at 0° C. After an additional 5 min, the mixture is diluted with dry $CH_2Cl_2$ (100 mL), and washed with saturated $NaHCO_3$ aqueous solutions (2×100 mL). The combined aqueous layers are back-extracted with $CH_2Cl_2$ (2×100 mL). The combined organic layers are dried over $Na_2SO_4$, filtered, and concentrated to dryness under reduced pressure to afford crude ($R_P$)-7tt. The synthetic scheme is shown in Scheme 12.

93

Scheme 12. Synthesis of DNA analogs as in Scheme 6 (Route B).

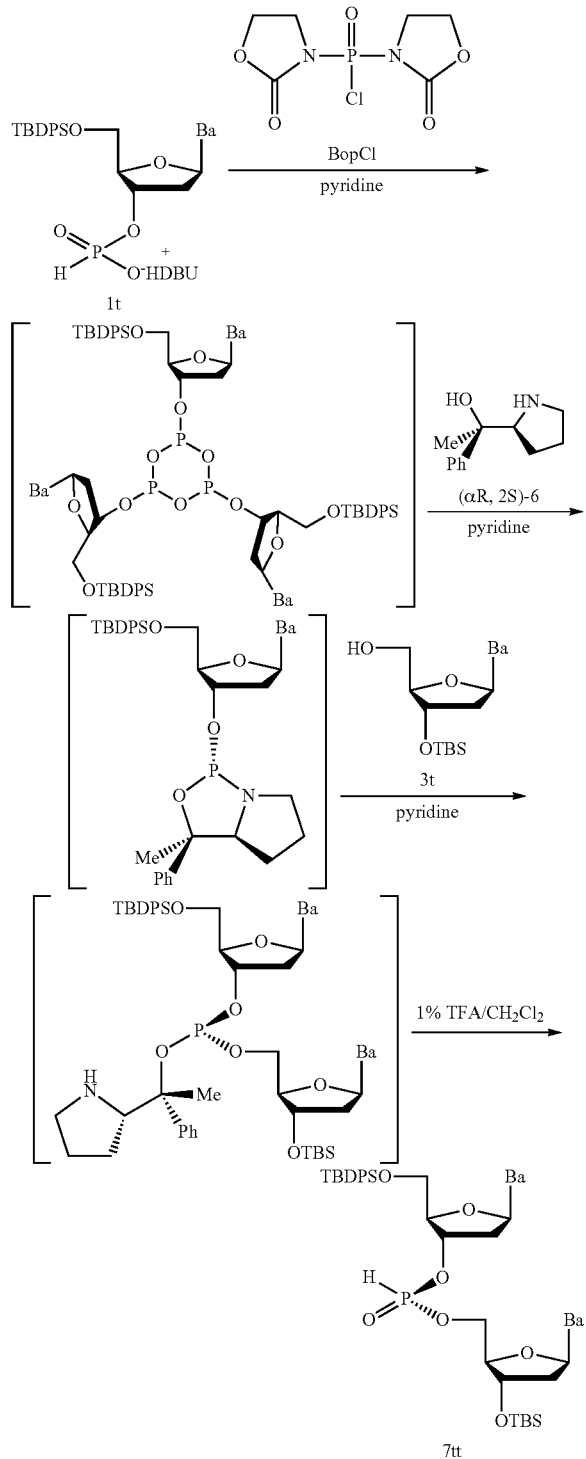

94

Example 19: Synthesis of $(R_P)$-4-N-benzoyl-5'-O-(tert-butyldiphenylsilyl)deoxycytidin-3'-yl 3'-O-(tert-butyldimethylsilyl)thymidin-5'-yl H-phosphonate [$(R_P)$-7ct] via Route B Crude $(R_P)$-7ct is produced as described in Example 17 using 1c instead of 1t.

Example 20: Synthesis of $(R_P)$-2-N-phenoxyacetyl-5'-O-(tert-butyldiphenylsilyl)deoxyguanosin-3'-yl 3'-O-(tert-butyldimethylsilyl)thymidin-5'-yl H-phosphonate [$(R_P)$-7gt] via Route B Crude $(R_P)$-7gt is produced as described in Example 17 using 1g instead of 1t.

Example 21: Synthesis of $(S_P)$-5'-O-(tert-butyldiphenylsilyl)thymidin-3'-yl 3'-O-(tert-butyldimethylsilyl)thymidin-5'-yl H-phosphonate [$(S_P)$-7tt] via Route B Crude $(S_P)$-7tt is produced as described in Example 17 using (αS, 2R)-6 instead of (αR,2S)-6 as a chiral reagent.

Example 22: Synthesis of $(S_P)$-6-N-benzoyl-5'-O-(tert-butyldiphenylsilyl)deoxyadenosin-3'-yl 3'-O-(tert-butyldimethylsilyl)thymidin-5'-yl H-phosphonate [$(S_P)$-7at] via Route B Crude $(S_P)$-7at is produced as described in Example 17 using compound 1a and (αS, 2R)-6 instead of (αR,2S)-6 as a chiral reagent.

Example 23: Synthesis of $(S_P)$-4-N-benzoyl-5'-O-(tert-butyldiphenylsilyl)deoxycytidin-3'-yl 3'-O-(tert-butyldimethylsilyl)thymidin-5'-yl H-phosphonate [$(S_P)$-7ct] via Route B Crude $(S_P)$-7ct is produced as described in Example 17 using compound 1c and (αS, 2R)-6 instead of (αR,2S)-6 as a chiral reagent.

Example 24: Synthesis of $(S_P)$-2-N-phenoxyacetyl-5'-O-(tert-butyldiphenylsilyl)deoxyguanosin-3'-yl 3'-O-(tert-butyldimethylsilyl)thymidin-5'-yl H-phosphonate [$(S_P)$-7gt] via Route B Crude $(S_P)$-7gt is produced as described in Example 17 using compound 1g instead of 1t and compound (αS, 2R)-6 instead of compound (αR,2S)-6 as a chiral reagent.

Example 25: Modification to Produce $(R_P)$-Ammonium thymidin-3'-yl thymidin-5'-yl phosphorothioate [$(R_P)$-5tt] as shown in general Scheme 13

$(S_P)$-7tt is dried by repeated coevaporations with dry pyridine and dry toluene, and then dissolved in $CH_3CN$ (1 mL). N,O-bis(trimethylsilyl)acetamide (BSA; 100 μL) is added. After 1 min, N,N'-dimethylthiuram disulfide (DTD; 120 μmol) is added. After an additional 3 min, the mixture is concentrated to dryness under reduced pressure to yield crude $(R_P)$-4tt. Then the crude $(R_P)$-4tt is dissolved in triethylamine trihydrofluoride (1 mL). The mixture is stirred for 15 h at room temperature. A 0.1 M ammonium acetate buffer (5 mL) is then added to the mixture, and the mixture is washed with $Et_2O$ (3×5 mL). The combined organic layers are back-extracted with 0.1 M ammonium acetate buffer (5

Example 18: Synthesis of $(R_P)$-6-N-benzoyl-5'-O-(tert-butyldiphenylsilyl)deoxyadenosin-3'-yl 3'-O-(tert-butyldimethylsilyl)thymidin-5'-yl H-phosphonate [$(R_P)$-7at] via Route B Crude $(R_P)$-7at is produced as described in Example 17 using 1a instead of 1t.

mL). The combined aqueous layers are then concentrated to dryness under reduced pressure, and the residue is purified by reverse-phase column chromatography [a linear gradient of acetonitrile 0-10% in 0.1 M ammonium acetate buffer (pH 7.0)] to afford $(R_P)$-5tt. The modification steps are shown in Scheme 13.

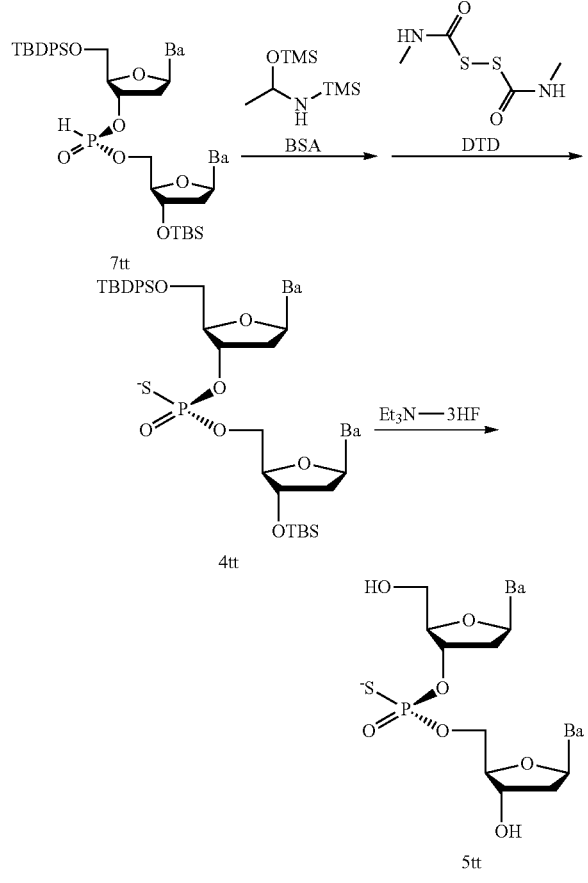

Example 26: Modification to Produce $(R_P)$-Ammonium deoxyadenosin-3'-yl thymidin-5'-yl phosphorothioate [$(R_P)$-5at]

$(R_P)$-5at is produced as described in Example 25 using $(S_P)$-7at instead of $(S_P)$-7tt.

Example 27: Modification to Produce $(R_P)$-Ammonium deoxycytidin-3'-yl thymidin-5'-yl phosphorothioate [$(R_P)$-5ct]

$(R_P)$-5ct is produced as described in Example 25 using $(S_P)$-7ct instead of $(S_P)$-7tt.

Example 28: Modification to Produce $(R_P)$-Ammonium deoxyguanosin-3'-yl thymidin-5'-yl phosphorothioate [$(R_P)$-5gt]

$(R_P)$-5gt is produced as described in Example 25 using $(S_P)$-7gt instead of $(S_P)$-7tt.

Example 29: Modification to Produce $(S_P)$-Ammonium thymidin-3'-yl thymidin-5'-yl phosphorothioate [$(S_P)$-5tt]

$(S_P)$-5tt is produced as described in Example 25 using $(R_P)$-7tt instead of $(S_P)$-7tt.

Example 30: Modification to Produce $(S_P)$-Ammonium deoxyadenosin-3'-yl thymidin-5'-yl phosphorothioate [$(S_P)$-5at]

$(S_P)$-5at is produced as described in Example 25 using $(R_P)$-7at instead of $(S_P)$-7tt.

Example 31: Modification to Produce $(S_P)$-Ammonium deoxycytidin-3'-yl thymidin-5'-yl phosphorothioate [$(S_P)$-5ct]

$(S_P)$-5ct is produced as described in Example 25 using $(R_P)$-7ct instead of $(S_P)$-7tt.

Example 32: Modification to Produce $(S_P)$-Ammonium deoxyguanosin-3'-yl thymidin-5'-yl phosphorothioate [$(S_P)$-5gt]

$(S_P)$-5gt is produced as described in Example 25 using $(R_P)$-7gt instead of $(S_P)$-7tt.

Example 33: Synthesis of an RNA Analog Dimer, $(S_P)$-1,8-Diazabicyclo[5.4.0]undec-7-enium 5'-O-(tert-butyldiphenylsilyl)-2'-O-(tert-butyldimethylsilyl)uridin-3'-yl 2',3'-O-bis(tert-butyldimethylsilyl)uridin-5'-yl phosphorothioate [$(S_P)$-10uu] via Route A 1,8-Diazabicyclo[5.4.0]undec-7-enium 5'-O-(tert-butyldiphenylsilyl)-2'-O-(tert-butyldimethylsilyl)uridin-3'-yl phosphonate (8u) (100 µmol) is dried by repeated coevaporations with dry pyridine and then dissolved in dry pyridine (1 mL). N,N'-Bis(2-oxo-3-oxazolidinyl)phosphinic chloride (BopCl; 500 µmol) is added, and the mixture is stirred for 5 min. To the mixture, a solution of amino alcohol (L-2) (100 µmol), which has been dried by repeated coevaportions with dry pyridine and dissolved in dry pyridine (1 mL), is added dropwise via syringe, and the mixture is stirred for 5 min under argon. 2',3'-O-bis(tert-butyldimethylsilyl)uridine 9u is dried by repeated coevaporations with dry pyridine and dissolved in 100 µmol pyridine. Then the above mixture is added via cannula into the solution of 2',3'-O-bis(tert-butyldimethylsilyl)uridine 9u (100 µmol). After 10 min, N-trifluoroacetyl imidazole (CF$_3$COIm; 200 µmol) is added. After an additional 30 s, N,N'-dimethylthiuram disulfide (DTD; 120 µmol) is added. After an additional 3 min, the mixture is dried in vacuum. To the residue, conc NH$_3$-EtOH (3:1, v/v, 10 mL) is added, and the mixture is stirred for 12 h, and then concentrated to dryness under reduced pressure. Then, the mixture is diluted with CHCl$_3$ (5 mL), and washed with 0.2 M phosphate buffer (pH 7.0, 5 mL). The aqueous layers are back-extracted with CHCl$_3$ (2×5 mL). The combined organic layers are dried over Na$_2$SO$_4$, filtered, and concentrated to dryness under reduced pressure. The residue is purified by PTLC. The product is dissolved in CHCl$_3$ (5 mL), washed with 0.2 M 1,8-diazabicyclo[5.4.0]undec-7-enium bicarbonate buffer (5 mL) and back-extracted with CHCl$_3$ (2×5 mL). The combined organic layers are dried over Na$_2$SO$_4$, filtered, and concentrated to dryness to afford $(S_P)$-10uu. The synthetic scheme is shown in Scheme 14.

Scheme 14. Synthesis of RNA Analogs as in Scheme 5 (Route A).

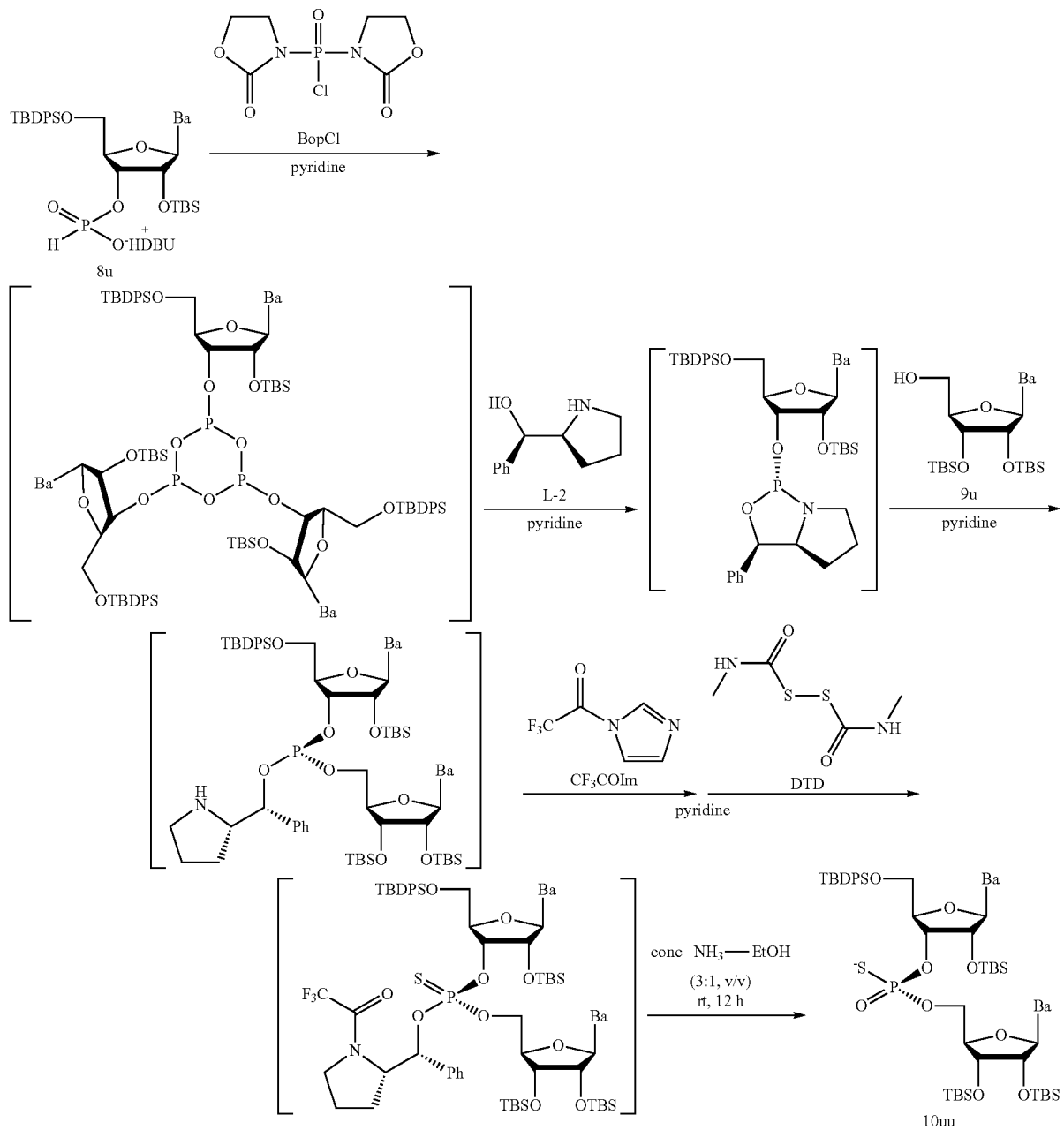

Example 34: Synthesis of an RNA Analog Dimer, ($S_P$)-1,8-Diazabicyclo[5.4.0]undec-7-enium 6-N-benzoyl-5'-O-(tert-butyldiphenylsilyl)-2'-O-(tert-butyldimethylsilyl)adenosin-3'-yl 2',3'-O-bis(tert-butyldimethylsilyl)uridin-5'-yl phosphorothioate [($S_P$)-10au] via Route A ($S_P$)-10au is produced as described in Example 33 using 1,8-diazabicyclo[5.4.0]undec-7-enium 6-N-benzoyl-5'-O-(tert-butyldiphenylsilyl)-2'-O-(tert-butyldimethylsilyl)adenosin-3'-yl phosphonate (8a) instead of 8u.

Example 35: Synthesis of an RNA Analog Dimer, ($S_P$)-1,8-Diazabicyclo[5.4.0]undec-7-enium 4-N-benzoyl-5'-O-(tert-butyldiphenylsilyl)-2'-O-(tert-butyldimethylsilyl)cytidin-3'-yl 2',3'-O-bis(tert-butyldimethylsilyl)uridin-5'-yl phosphorothioate [($S_P$)-10cu] via Route A ($S_P$)-10cu is produced as described in Example 33 using 1,8-diazabicyclo[5.4.0]undec-7-enium 4-N-benzoyl-5'-O-(tert-butyldiphenylsilyl)-2'-O-(tert-butyldimethylsilyl)cytidin-3'-yl phosphonate (8c) instead of 8u.

Example 36: Synthesis of an RNA Analog Dimer, (S$_P$)-1,8-Diazabicyclo[5.4.0]undec-7-enium 2-N-phenoxyacetyl-5'-O-(tert-butyldiphenylsilyl)-2'-O-(tert-butyldimethylsilyl)guanosin-3'-yl 2',3'-O-bis(tert-butyldimethylsilyl)uridin-5'-yl phosphorothioate [(S$_P$)-10gu] via Route A (S$_P$)-10gu is produced as described in Example 33 using 1,8-diazabicyclo[5.4.0]undec-7-enium 2-N-phenoxyacetyl-5'-O-(tert-butyldiphenylsilyl)-2'-O-(tert-butyldimethylsilyl)guanosin-3'-yl phosphonate (8g) instead of 8u.

Example 37: Synthesis of an RNA Analog Dimer, (R$_P$)-1,8-Diazabicyclo[5.4.0]undec-7-enium 5'-O-(tert-butyldiphenylsilyl)-2'-O-(tert-butyldimethylsilyl)uridin-3'-yl 2',3'-O-bis(tert-butyldimethylsilyl)uridin-5'-yl phosphorothioate [(R$_P$)-10uu] via Route A (R$_P$)-10uu is produced as described in Example 33 using chiral reagent D-2 instead of chiral reagent L-2.

Example 38: Synthesis of an RNA Analog Dimer, (R$_P$)-1,8-Diazabicyclo[5.4.0]undec-7-enium 6-N-benzoyl-5'-O-(tert-butyldiphenylsilyl)-2'-O-(tert-butyldimethylsilyl)adenosin-3'-yl 2',3'-O-bis(tert-butyldimethylsilyl)uridin-5'-yl phosphorothioate [(R$_P$)-10au] via Route A (R$_P$)-10au is produced as described in Example 33 using 8a instead of 8u and chiral reagent D-2 instead of chiral reagent L-2.

Example 39: Synthesis of an RNA Analog Dimer, (R$_P$)-1,8-Diazabicyclo[5.4.0]undec-7-enium 4-N-benzoyl-5'-O-(tert-butyldiphenylsilyl)-2'-O-(tert-butyldimethylsilyl)cytidin-3'-yl 2',3'-O-bis(tert-butyldimethylsilyl)uridin-5'-yl phosphorothioate [(R$_P$)-10cu] via Route A (R$_P$)-10cu is produced as described in Example 33 using 8c instead of 8u and chiral reagent D-2 instead of chiral reagent L-2.

Example 40: Synthesis of an RNA Analog Dimer, (R$_P$)-1,8-Diazabicyclo[5.4.0]undec-7-enium 2-N-phenoxyacetyl-5'-O-(tert-butyldiphenylsilyl)-2'-O-(tert-butyldimethylsilyl)guanosin-3'-yl 2',3'-O-bis(tert-butyldimethylsilyl)uridin-5'-yl phosphorothioate [(R$_P$)-10gu] via Route A (R$_P$)-10gu is produced as described in Example 33 using 8g instead of 8u and chiral reagent D-2 instead of chiral reagent L-2.

Example 41: Deprotection to Form (S$_P$)-Triethylammonium uridin-3'-yl uridin-5'-yl phosphorothioate [(S$_P$)-11uu]

(S$_P$)-10uu (50 µmol) is dried by repeated coevaporations with dry pyridine and dry toluene, and then dissolved in 1M tetrabutylammonium fluoride (TBAF) solution in dry THF (500 µL). The mixture is stirred for 12 h at room temperature. A 0.05M triethylammonium acetate buffer solution (pH 6.9, 2.5 mL) is added to the mixture, and the mixture is washed with Et$_2$O (3×3 mL). The combined organic layers are back-extracted with 0.05M triethylammonium acetate buffer (3 mL). The combined aqueous layers are then concentrated to dryness under reduced pressure, and the residue is purified by reverse-phase column chromatography [a linear gradient of acetonitrile 0-10% in 0.1M triethylammonium acetate buffer (pH 6.9)] to afford (S$_P$)-11uu. The deprotection scheme is shown in Scheme 15.

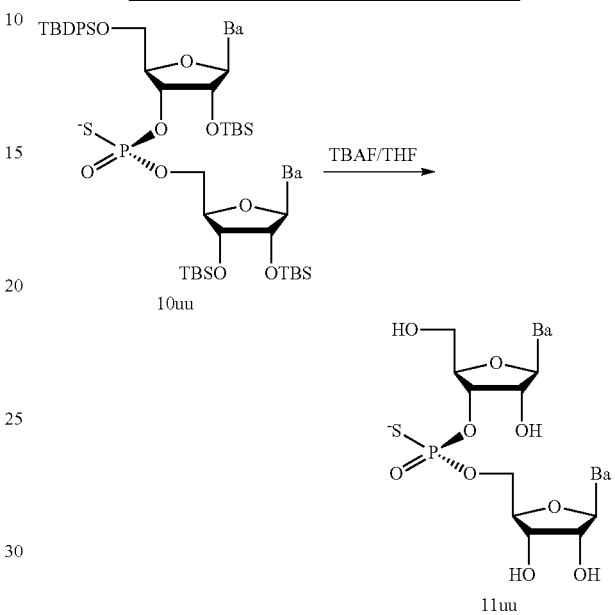

Scheme 15. Deprotection as in Scheme 5 (Route A).

Example 42: Deprotection to Form (S$_P$)-Triethylammonium adenosin-3'-yl uridin-5'-yl phosphorothioate [(S$_P$)-11au]

(S$_P$)-11au is produced as described in Example 41 using (S$_P$)-10au instead of (S$_P$)-10uu.

Example 43: Deprotection to Form (S$_P$)-Triethylammonium cytidin-3'-yl uridin-5'-yl phosphorothioate [(S$_P$)-11cu]

(S$_P$)-11cu is produced as described in Example 41 using (S$_P$)-10cu instead of (S$_P$)-10uu.

Example 44: Deprotection to Form (S$_P$)-Triethylammonium guanosin-3'-yl uridin-5'-yl phosphorothioate [(S$_P$)-11gu]

(S$_P$)-11gu is produced as described in Example 41 using (S$_P$)-10gu instead of (S$_P$)-10uu.

Example 45: Deprotection to Form (R$_P$)-Triethylammonium uridin-3'-yl uridin-5'-yl phosphorothioate [(R$_P$)-11uu]

(R$_P$)-11uu is produced as described in Example 41 using (R$_P$)-10uu instead of (S$_P$)-10uu.

Example 46: Deprotection to Form (R$_P$)-Triethylammonium adenosin-3'-yl uridin-5'-yl phosphorothioate [(R$_P$)-11au]

(R$_P$)-11au is produced as described in Example 41 using (R$_P$)-10au instead of (S$_P$)-10uu.

Example 47: Deprotection to Form ($R_P$)-Triethylammonium cytidin-3'-yl uridin-5'-yl phosphorothioate [($R_P$)-11cu]

($R_P$)-11cu is produced as described in Example 41 using ($R_P$)-10cu instead of ($S_P$)-10uu.

Example 48: Deprotection to Form ($R_P$)-Triethylammonium guanosin-3'-yl uridin-5'-yl phosphorothioate [($R_P$)-11gu]

($R_P$)-11gu is produced as described in Example 41 using ($R_P$)-10gu instead of ($S_P$)-10uu.

Example 49: Synthesis of an RNA Analog Dimer, ($R_P$)-5'-O-(tert-butyldiphenylsilyl)-2'-O-(tert-butyldimethylsilyl)uridin-3'-yl 2',3'-O-bis(tert-butyldimethylsilyl)uridin-5'-yl H-phosphonate [($R_P$)-12uu] via Route B 8u (100 μmol) is dried by repeated coevaporations with dry pyridine and then dissolved in dry pyridine (1 mL). N,N'-Bis(2-oxo-3-oxazolidinyl)phosphinic chloride (BopCl; 500 μmol) is added, and the mixture is stirred for 5 min. To the mixture, a solution of amino alcohol ((αR,2S)-6) (100 μmol), which is dried by coevaportions with dry pyridine and dissolved in dry pyridine (1 mL), is added dropwise via syringe, and the mixture is stirred for 5 min under argon. Then the mixture is added via cannula into a solution of 9u (100 μmol), which is prepared by repeated coevaporations with dry pyridine and dissolution in pyridine. After 15 min, the mixture is concentrated under reduced pressure. The residue is diluted with $CH_2Cl_2$ (5 mL), and washed with saturated $NaHCO_3$ (3×5 mL). The combined aqueous layers are back-extracted with with $CH_2Cl_2$ (2×5 mL). The combined organic layers are dried over $Na_2SO_4$, filtered, and concentrated to ca. 1 mL under reduced pressure. The residue is added dropwise via a syringe to a stirred 1% trifluoroacetic acid (TFA) solution in dry $CH_2Cl_2$ (20 mL) at 0° C. After an additional 5 min, the mixture is diluted with dry $CH_2Cl_2$ (100 mL), and washed with saturated $NaHCO_3$ aqueous solutions (2×100 mL). The combined aqueous layers are back-extracted with $CH_2Cl_2$ (2×100 mL). The combined organic layers are dried over $Na_2SO_4$, filtered, and concentrated to dryness under reduced pressure to afford crude (Rp)-12uu, which is analyzed by $^{31}P$ NMR. The synthetic scheme is shown in Scheme 16.

Scheme 16. Synthesis of RNA analogs via Scheme 6 (Route B).

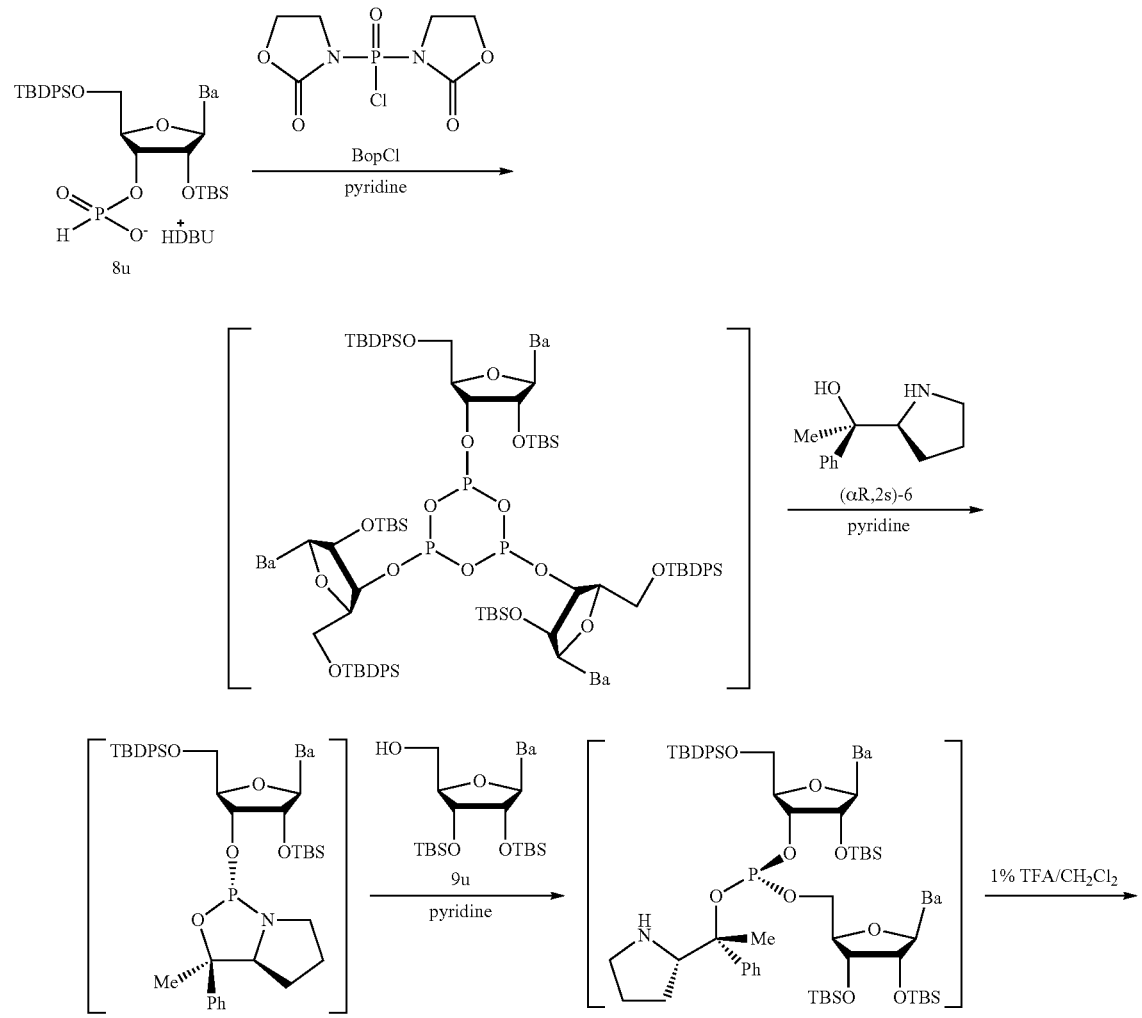

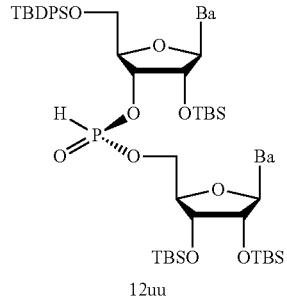

12uu

Example 50: Synthesis of an RNA Analog Dimer, ($R_P$)-6-N-Benzoyl-5'-O-(tert-butyldiphenylsilyl)-2'-O-(tert-butyldimethylsilyl)adenosin-3'-yl 2',3'-O-bis(tert-butyldimethylsilyl)uridin-5'-yl H-phosphonate [($R_P$)-12au] via Route B Crude ($R_P$)-12au is produced as described in Example 49 using 8a instead of 8u.

Example 51: Synthesis of an RNA Analog Dimer, ($R_P$)-4-N-Benzoyl-5'-O-(tert-butyldiphenylsilyl)-2'-O-(tert-butyldimethylsilyl)cytidin-3'-yl 2',3'-O-bis(tert-butyldimethylsilyl)uridin-5'-yl H-phosphonate [($R_P$)-12cu] via Route B Crude ($R_P$)-12cu is produced as described in Example 49 using 8c instead of 8u.

Example 52: Synthesis of an RNA Analog Dimer, ($R_P$)-2-N-Phenoxyacetyl-5'-O-(tert-butyldiphenylsilyl)-2'-O-(tert-butyldimethylsilyl)guanosin-3'-yl 2',3'-O-bis(tert-butyldimethylsilyl)uridin-5'-yl H-phosphonate [($R_P$)-12gu] via Route B Crude ($R_P$)-12gu is produced as described in Example 49 using 8g instead of 8u.

Example 53: Synthesis of an RNA Analog Dimer, ($S_P$)-5'-O-(tert-butyldiphenylsilyl)-2'-O-(tert-butyldimethylsilyl)uridin-3'-yl 2',3'-O-bis(tert-butyldimethylsilyl)uridin-5'-yl H-phosphonate [($S_P$)-12uu] via Route B Crude ($S_P$)-12uu is produced as described in Example 49 using chiral reagent (αS, 2R)-6 instead of chiral reagent (αR,2S)-6.

Example 54: Synthesis of an RNA Analog Dimer, ($S_P$)-6-N-Benzoyl-5'-O-(tert-butyldiphenylsilyl)-2'-O-(tert-butyldimethylsilyl)adenosin-3'-yl 2',3'-O-bis(tert-butyldimethylsilyl)uridin-5'-yl H-phosphonate [($S_P$)-12au] via Route B Crude ($S_P$)-12au is produced as described in Example 49 using 8a instead of 8u and chiral reagent (αS, 2R)-6 instead of chiral reagent (αR,2S)-6.

Example 55: Synthesis of an RNA Analog Dimer, ($S_P$)-4-N-Benzoyl-5'-O-(tert-butyldiphenylsilyl)-2'-O-(tert-butyldimethylsilyl)cytidin-3'-yl 2',3'-O-bis(tert-butyldimethylsilyl)uridin-5'-yl H-phosphonate [($S_P$)-12cu] via Route B Crude ($S_P$)-12cu is produced as described in Example 49 using 8c instead of 8u and chiral reagent (αS, 2R)-6 instead of chiral reagent (αR,2S)-6.

Example 56: Synthesis of an RNA Analog Dimer, ($S_P$)-2-N-Phenoxyacetyl-5'-O-(tert-butyldiphenylsilyl)-2'-O-(tert-butyldimethylsilyl)guanosin-3'-yl 2',3'-O-bis(tert-butyldimethylsilyl)uridin-5'-yl H-phosphonate [($S_P$)-12gu] via Route B Crude ($S_P$)-12gu is produced as described in Example 49 using 8g instead of 8u and chiral reagent (αS, 2R)-6 instead of chiral reagent (αR,2S)-6.

Example 57: Modification to Form ($R_P$)-Triethylammonium uridin-3'-yl uridin-5'-yl phosphorothioate [($R_P$)-11uu]

($S_P$)-12uu is dried by repeated coevaporation with dry pyridine and dry toluene, and then dissolved in $CH_3CN$ (1 mL). N,O-bis(trimethylsilyl)acetamide (BSA; 100 μL) is added. After 1 min, N,N'-dimethylthiuram disulfide (DTD; 120 μmol) is added. After an additional 3 min, the mixture is concentrated to dryness under reduced pressure to yield crude ($R_P$)-10uu. Then the crude ($R_P$)-10uu is dissolved in 1M tetrabutylammonium fluoride (TBAF) solution in dry THF (1 mL). The mixture is stirred for 12 h at room temperature. A 0.05M triethylammonium acetate buffer solution (pH 6.9, 5 mL) is added to the mixture, and the mixture is washed with $Et_2O$ (3×5 mL). The combined organic layers are back-extracted with 0.05M triethylammonium acetate buffer (5 mL). The combined aqueous layers are then concentrated to dryness under reduced pressure, and the residue is purified by reverse-phase column chromatography [a linear gradient of acetonitrile 0-10% in 0.1M triethylammonium acetate buffer (pH 6.9)] to afford ($R_P$)-11uu. The modification scheme is shown in Scheme 17.

Scheme 17. Synthesis of chiral phosphorothioate.

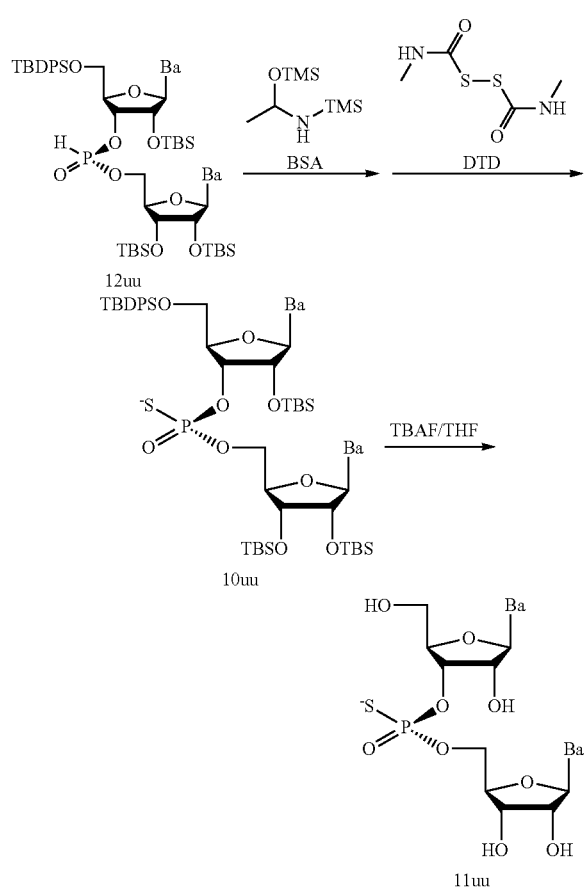

Example 58: Modification to Form ($R_P$)-Triethylammonium adenosin-3'-yl uridin-5'-yl phosphorothioate [($R_P$)-11 au]

($R_P$)-11au is produced as described in Example 57 using ($S_P$)-12au instead of ($S_P$)-12uu.

Example 59: Modification to Form ($R_P$)-Triethylammonium cytidin-3'-yl uridin-5'-yl phosphorothioate [($R_P$)-11cu]

($R_P$)-11cu is produced as described in Example 57 using ($R_P$)-12cu instead of ($R_P$)-12uu.

Example 60: Modification to Form ($R_P$)-Triethylammonium guanosin-3'-yl uridin-5'-yl phosphorothioate [($R_P$)-11gu]

($R_P$)-11gu is produced as described in Example 57 using ($S_P$)-12gu instead of ($S_P$)-12uu.

Example 61: Modification to Form ($S_P$)-Triethylammonium uridin-3'-yl uridin-5'-yl phosphorothioate [($S_P$)-11uu]

($S_P$)-11uu is produced as described in Example 57 using ($R_P$)-12uu instead of ($S_P$)-12uu.

Example 62: Modification to Form ($S_P$)-Triethylammonium adenosin-3'-yl uridin-5'-yl phosphorothioate [($S_P$)-11au]

($S_P$)-11au is produced as described in Example 57 using ($R_P$)-12au instead of ($S_P$)-12uu.

Example 63: Modification to Form ($S_P$)-Triethylammonium cytidin-3'-yl uridin-5'-yl phosphorothioate [($S_P$)-11cu]

($S_P$)-11cu is produced as described in Example 57 using ($R_P$)-12cu instead of ($S_P$)-12uu.

Example 64: Modification to Form ($S_P$)-Triethylammonium guanosin-3'-yl uridin-5'-yl phosphorothioate [($S_P$)-11gu]

($S_P$)-11gu is produced as described in Example 57 using ($R_P$)-12gu instead of ($S_P$)-12uu in a similar manner as ($R_P$)-11uu.

Example 65: Solid Phase Synthesis of DNA Analogs Having X-Phosphonate Moieties Via Scheme 5 (Route A)

5'-O-(DMTr)thymidine-loaded HCP or CPG resin (0.5 µmol) via a succinyl linker is used for the synthesis. Chain elongation is performed by repeating the steps in Table 1. After the chain elongation, the 5'-O-DMTr group is removed by treatment with 3% DCA in $CH_2C_2$ (3×5 s), and washed with $CH_2Cl_2$. The oligomer on the HCP or CPG resin is then treated with 25% $NH_3$-pyridine (9:1, v/v) for 15 h at 55° C. to remove the chiral auxiliaries and the protecting groups of the nucleobases and also to release the oligomer from the HCP or CPG resin. The HCP or CPG resin is removed by filtration and washed with $H_2O$. The filtrate is concentrated to dryness. The residue is dissolved in $H_2O$, washed with $Et_2O$, and the combined washings are back-extracted with $H_2O$. The combined aqueous layers are concentrated to dryness. The resulting crude product is analyzed and/or purified by reversed-phase HPLC with a linear gradient of 0-20% acetonitrile in 0.1M ammonium acetate buffer (pH 7.0) for 60 min at 50° C. at a rate of 0.5 ml/min to afford stereoregular X-phosphonate DNAs.

TABLE 1

| step | Operation | reagents and solvent | time |
|---|---|---|---|
| 1 | detritylation | 3% DCA in $CH_2Cl_2$ | 3 × 30 s |
| 2 | washing | (i) $CH_2Cl_2$ (ii) dry pyridine (iii) drying in vacuo. | — |
| 3 | coupling | pre-activated monomer (0.2M)* in dry pyridine | 15 min |
| 4 | washing | (i) dry pyridine (ii) dry $CH_3CN$ (iii) drying in vacuo. | — |
| 5 | transformation | sulfur electrophile, selenium electrophile, or borane agent | 5 min |
| 6 | washing | (i) dry THF (ii) drying in vacuo. | — |

TABLE 1-continued

| step | Operation | reagents and solvent | time |
|---|---|---|---|
| 7 | capping | $CF_3COIm$-2,6-lutidine - dry THF (1:1:8, v/v/v) under argon | 30 s |
| 8 | washing | (i) dry THF (ii) $CH_2Cl_2$ | — |

*preparation of pre-activated monomer in Step 3 of Table 1: 1,8-Diazabicyclo[5.4.0]undec-7-enium 5'-O-(DMTr)-2'-deoxyribonucleoside-3'-yl phosphonate is dried by repeated coevaporations with dry pyridine and then dissolved in dry pyridine. BopCl is added to the solution, and the mixture is stirred for 5 min. To the mixture, a solution of amino alcohol (L-2 or D-2), which is dried by repeated coevaportions with dry pyridine and dissolved in dry pyridine, is added dropwise via syringe, and the mixture is stirred for 5 min under argon.

All-($R_P$)-[$T_{PS}$]$_9$T (Phosphorothioate)

According to the typical procedure described above, 5'-O-(DMTr)thymidine 3'-O-succinate bound to HCP (0.5 μmol) give all-(Rp)-[$T_{PS}$]$_9$T [1.52 $A_{260}$ units, 17.7 nmol (35%) based on the assumption of 7% hypochoromicity: UV ($H_2O$) $α_{max}$ 267 nm, $α_{min}$ 236 nm] after purification of one-tenth of the crude product by RP-HPLC. <4% of the purified oligomer is digested by incubation with nuclease P1 for 1 h at 37° C.

Example 66: Solid Phase Synthesis of DNA Analogs Having X-Phosphonate Moieties Via Scheme 6 (Route B)

5'-O-(DMTr)thymidine-loaded CPG resin via a succinyl or oxalyl linker is treated 1% TFA in $CH_2Cl_2$ (3×5 s) for the removal of the 5'-O-DMTr group, washed with $CH_2Cl_2$ and dry pyridine and dried in vacuo. Chain elongation is performed by repeating the following steps (a) and (b). (a) Coupling reaction using a solution containing the corresponding pre-activated monomer* (0.2M) in dry pyridine (10 min) under argon. After the condensation, the solid-support is washed with dry pyridine and $CH_2Cl_2$. (b) Removal of the 5'-O-DMTr group and the chiral auxiliary simultaneously by treatment with 1% TFA in $CH_2Cl_2$-$Et_3SiH$ (1:1, v/v) (3×5 s), and following washings with $CH_2Cl_2$ and dry pyridine. The resultant oligonucleoside H-phosphonates on the resin are converted to X-phosphonate DNAs as described below.

*Preparation of Pre-Activated Monomer:

1,8-Diazabicyclo[5.4.0]undec-7-enium 5'-O-(DMTr)-2'-deoxyribonucleoside-3'-yl phosphonate is dried by repeated coevaporations with dry pyridine and then dissolved in dry pyridine. BopCl is added to the solution, and the mixture is stirred for 5 min. To the mixture, a solution of amino alcohol (L-6 or D-6), which is dried by repeated coevaportion with dry pyridine and dissolved in dry pyridine, is added dropwise via syringe, and the mixture is stirred for 5 min under argon.

Phosphorothioate (X=$S^-$)

Oligonucleoside H-phosphonate loaded to a CPG resin via a succinyl linker obtained as above is treated with 10 wt % $S_8$ in $CS_2$-pyridine-triethylamine (35:35:1, v/v/v) at RT for 3 h, and successively washed with $CS_2$, pyridine, and $CH_3CN$. The resin is treated with a 25% $NH_3$ aqueous solution at RT over 12 h, and washed with $H_2O$. The aqueous solutions are combined and concentrated to dryness under reduced pressure, and the residue is purified by RP-HPLC to afford stereoregulated phosphorothioate DNAs.

Boranophosphate (X=$BH_3^-$)

Dry DMF, N,O-bis(trimethylsilyl)acetamide (BSA), and $BH_3$·$SMe_2$ are added to the oligonucleoside H-phosphonate loaded to a CPG resin via a oxalyl linker obtained as above at RT. After 15 min, the resin is successively washed with DMF, $CH_3CN$, and $CH_3OH$. The resin is then treated with a saturated $NH_3$ solution in $CH_3OH$ at RT for 12 h, and washed with $CH_3OH$. The $CH_3OH$ solutions are combined and concentrated to dryness under reduced pressure, and the residue is purified by RP-HPLC to afford stereoregulated boranophosphate DNAs.

Hydroxymethylphosphonate (X=$CH_2OH$)

Oligonucleoside H-phosphonate loaded to a CPG resin via a oxalyl linker obtained as above is treated with 0.1 M trimethylsilylchloride (TMSCl) in pyridine-1-methyl-2-pyrrolidone (NMP) (1:9, v/v) at RT for 10 min, and with gaseous formaldehyde at RT for 30 min, and then washed with NMP, and $CH_3CN$. The resin is then treated with a 25% $NH_3$ aqueous solution at RT for 12 h, and washed with $H_2O$. The combined aqueous solutions are concentrated to dryness under reduced pressure, and the residue is purified by RP-HPLC to afford stereoregulated hydroxymethylphosphonate DNAs.

Phosphoramidate (X=$NH_2$)

Oligonucleoside H-phosphonate loaded to a CPG resin via an oxalyl linker obtained as above is treated with a saturated $NH_3$ solution in $CCl_4$-1,4-dioxane (4:1, v/v) at 0° C. for 30 min, and washed with 1,4-dioxane. The combined organic solutions are concentrated to dryness under reduced pressure, treated with a 25% $NH_3$ aqueous solution at RT for 12 h, and washed with $H_2O$. The combined aqueous solutions are concentrated to dryness under reduced pressure, and the residue is purified by RP-HPLC to afford stereoregulated phosphoramidate DNAs.

N-propylphosphoramidate (X=NHPr)

Oligonucleoside H-phosphonate loaded to a CPG resin via a oxalyl linker obtained as above is treated with $CCl_4$-propylamine (9:1, v/v) at RT for 1 h, and washed with $CH_3OH$. The combined organic solutions are concentrated to dryness under reduced pressure, treated with a 25% $NH_3$ aqueous solution at RT for 12 h, and washed with $H_2O$. The combined aqueous solutions are concentrated to dryness under reduced pressure, and the residue is purified by RP-HPLC to afford stereoregulated N-propylphophoramidate DNAs.

N-[(2-dimethylamino)ethyl]phosphoramidate [X=$NH(CH)_2NMe_2$]

Oligonucleoside H-phosphonate loaded to a CPG resin via a oxalyl linker obtained as above is treated with $CCl_4$-2-dimethylaminoethylamine (9:1, v/v) at RT for 1 h, and washed with $CH_3CN$. The combined organic solutions are concentrated to dryness under reduced pressure, treated with a 25% NH₃ aqueous solution at RT for 12 h, and washed with H₂O. The combined aqueous solutions are concentrated to dryness under reduced pressure, and the residue is purified by RP-HPLC to afford stereoregulated N-[(2-dimethylamino)ethyl]phosphoramidate DNAs.

Example 67: Synthesis of all-$(S_P)$-d[$C_S A_S G_S$T] (phosphorothioate)

The corresponding oligonucleoside H-phosphonate is synthesized on a CPG resin via a succinyl linker as described above, and treated with a 0.2M solution of Beaucage reagent in BSA-CH₃CN (1:8, v/v) at RT for 30 min, and the resin is washed with CH₃CN. The resin is then treated with a 25% NH₃ aqueous solution at RT for 12 h, and washed with H₂O. The combined aqueous solutions are concentrated to dryness under reduced pressure, and the residue is analyzed and characterized by RP-HPLC and MALDI-TOF-MS. The RP-HPLC is performed with a linear gradient of 0-20% acetonitrile in 0.1M ammonium acetate buffer (pH 7.0) for 60 min at 50° C. at a flow rate of 0.5 mL/min using a μBondasphere 5 μm C18 column (100 Å, 3.9 mm×150 mm) (Waters).

Example 68: Synthesis of all-$(R_P)$-d[$C_S A_S G_S$T] (phosphorothioate)

The corresponding oligonucleoside H-phosphonate is synthesized on a CPG resin via a succinyl linker as described above, and treated with a 0.2M solution of Beaucage reagent in BSA-CH₃CN (1:8, v/v) (0.2 mL) at RT for 30 min, and the resin is washed with CH₃CN. The resin is treated with a 25% NH₃ aqueous solution (5 mL) at RT for 12 h, and washed with H₂O. The combined aqueous solutions are concentrated to dryness under reduced pressure, and the residue is analyzed and characterized by RP-HPLC and MALDI-TOF-MS. The RP-HPLC is performed with a linear gradient of 0-20% acetonitrile in 0.1 M ammonium acetate buffer (pH 7.0) for 60 min at 50° C. at a flow rate of 0.5 ml/min using a ρBondasphere 5 μm C18 column (100 Å, 3.9 mm×150 mm) (Waters).

Example 69: Synthesis of all-$(S_P)$-[$T_S$]₉T (phosphorothioate)

The corresponding oligonucleoside H-phosphonate is synthesized on a CPG resin via a succinyl linker as described above, and treated with a 0.2M solution of Beaucage reagent in BSA-CH₃CN (1:8, v/v) (0.2 mL) at RT for 30 min, and the resin is washed with CH₃CN. The CPG resin is treated with a 25% NH₃ aqueous solution (5 mL) at RT for 24 h, and washed with H₂O. The combined aqueous solutions are concentrated to dryness under reduced pressure, and the residue is analyzed and characterized by RP-HPLC and MALDI-TOF-MS. The RP-HPLC is performed with a linear gradient of 0-20% acetonitrile in 0.1M ammonium acetate buffer (pH 7.0) for 80 min at 30° C. at a flow rate of 0.5 mL/min using a ρBondasphere 5 μm C18 column (100 Å, 3.9 mm×150 mm) (Waters).

Example 70: Synthesis of all $(R_P)$-[$T_S$]₉T (phosphorothioate)

The corresponding oligonucleoside H-phosphonate is synthesized on a CPG resin via a succinyl linker as described above, and treated with a 0.2M solution of Beaucage reagent in BSA-CH₃CN (1:8, v/v) (0.2 mL) at RT for 30 min, and the resin is washed with CH₃CN. The resin is treated with a 25% NH₃ aqueous solution (5 mL) at RT for 24 h, and washed with H₂O. The combined aqueous solutions are concentrated to dryness under reduced pressure, and the residue is analyzed and characterized by RP-HPLC and MALDI-TOF-MS. The RP-HPLC is performed with a linear gradient of 0-20% acetonitrile in 0.1M ammonium acetate buffer (pH 7.0) for 80 min at 30° C. at a flow rate of 0.5 mL/min using a μBondasphere 5 μm C18 column (100 Å, 3.9 mm×150 mm) (Waters).

Example 71: Synthesis of al $(R_P)$-[$T_B$]₃T (boranophosphate)

The corresponding oligonucleoside H-phosphonate is synthesized on a CPG resin via a succinyl linker as described above, and treated with a mixture of dry DMF (0.8 mL), BSA (0.1 mL) and BH₃.S(CH₃)₂ (0.1 mL) at RT for 15 min, and the resin is successively washed with DMF, CH₃CN, and CH₃OH. The resin is then treated with a saturated solution of NH₃ in CH₃OH (5 mL) at RT for 2 h, and washed with CH₃OH. The combined organic solutions are concentrated to dryness under reduced pressure, and the residue is analyzed and characterized by RP-HPLC and MALDI-TOF-MS. The RP-HPLC is performed with a linear gradient of 0-20% acetonitrile in 0.1M ammonium acetate buffer (pH 7.0) for 60 min at 30° C. at a flow rate of 0.5 mL/min using a PEGASIL ODS 5 μm (120 Å, 4.0 mm×150 mm) (Senshu Pak).

Example 72: Synthesis of all-$(S_P)$-[$T_B$]₃T (boranophosphate)

The corresponding oligonucleoside H-phosphonate is synthesized on a CPG resin via a succinyl linker as described above, and treated with a mixture of dry DMF (0.8 mL), BSA (0.1 mL) and BH₃.S(CH₃)₂ (0.1 mL) at RT for 15 min, and the resin is successively washed with DMF, CH₃CN, and CH₃OH. The resin is then treated with a saturated solution of NH₃ in CH₃OH (5 mL) at RT for 2 h, and washed with CH₃OH. The combined organic solutions are concentrated to dryness under reduced pressure, and the residue is analyzed and characterized by RP-HPLC and MALDI-TOF-MS. The RP-HPLC is performed with a linear gradient of 0-20% acetonitrile in 0.1M ammonium acetate buffer (pH 7.0) for 60 min at 30° C. at a flow rate of 0.5 mL/min using a PEGASIL ODS 5 μm (120 Å, 4.0 mm×150 mm) (Senshu Pak).

Example 73: Synthesis of all-$(S_P)$-[$T_N$]₃T (N-[(2-dimethylamino)ethyl]phosphoramidate)

The corresponding oligonucleoside H-phosphonate is synthesized on a CPG resin via an oxalyl linker as described above, and treated with CCl₄-2-dimethylaminoethylamine (9:1, v/v) at RT for 1 h, and washed with CH₃CN. The combined organic solutions are concentrated to dryness under reduced pressure, and the residue is analyzed and characterized by RP-HPLC and MALDI-TOF-MS. The RP-HPLC is performed with a linear gradient of 0-20% acetonitrile in 0.1M triethylammonium acetate buffer (pH 7.0) for 60 min at 30° C. at a flow rate of 0.5 mL/min using a PEGASIL ODS 5 μm (120 Å, 4.0 mm×150 mm) (Senshu Pak).

Example 74: Synthesis of all-$(R_P)$-[$T_N$]₃T (N-[(2-dimethylamino)ethyl]phosphoramidate)

The corresponding oligonucleoside H-phosphonate is synthesized on a CPG resin via an oxalyl linker as described above, and treated with CCl$_4$-2-dimethylaminoethylamine (9:1, v/v) at RT for 1 h, and washed with CH$_3$CN. The combined organic solutions are concentrated to dryness under reduced pressure, and the residue is analyzed and characterized by RP-HPLC and MALDI-TOF-MS. The RP-HPLC is performed with a linear gradient of 0-20% acetonitrile in 0.1M triethylammonium acetate buffer (pH 7.0) for 60 min at 30° C. at a flow rate of 0.5 ml/min using a PEGASIL ODS 5 μm (120 Å, 4.0 mm×150 mm) (Senshu Pak).

Example 75: A General Procedure for Solid-Phase Synthesis of X-Phosphonate RNA Via Scheme 5 (Route A)

5'-O-(DMTr)uridine-loaded HCP or CPG resin via a succinyl linker is used for the synthesis. Chain elongation is performed by repeating the steps in Table 2. After the chain elongation, the 5'-O-DMTr group is removed by treatment with 3% DCA in CH$_2$Cl$_2$ and the resin is successively washed with CH$_2$Cl$_2$ and EtOH. The resin is then treated with a 25% NH$_3$ aqueous solution-EtOH (3:1, v/v) for 2 h at room temperature and removed by filtration. The filtrate is diluted with a 25% NH$_3$ aqueous solution-EtOH (3:1, v/v) and placed in a tightly-sealed flask for 48 h at room temperature. The solution is concentrated under reduced pressure, and the residue is purified by RP-HPLC. Fractions containing the desired 2'-O-TBS-protected X-phosphonate RNAs are collected and lyophilized. The residue is treated with a 1M TBAF solution in dry THF for 24 h at room temperature. A 0.05M TEAA buffer solution (pH 6.9) is added, and THF is removed by evaporation. The residue is desalted with a Sep-pak C$_{18}$ cartridge, and purified by RP-HPLC to afford stereoregular X-phosphonate RNAs.

resultant oligonucleoside H-phosphonates on the resin are converted to backbone-modified RNA analogues as described below.

*Preparation of Pre-Activated Monomer 1,8-Diazabicyclo[5.4.0]undec-7-enium 5'-O-(DMTr)-2'-O-(TBS)-ribonucleoside-3'-yl phosphonate is dried by repeated coevaporations with dry pyridine and then dissolved in dry pyridine. BopCl is added to the solution, and the mixture is stirred for 5 min. To the mixture, a solution of amino alcohol (L-6 or D-6), which is dried by repeated coevaportions with dry pyridine and dissolved in dry pyridine, is added dropwise via syringe, and the mixture is stirred for 5 min under argon.

Phosphorothioate (X=S$^-$)

Oligonucleoside H-phosphonate loaded to a CPG resin via a succinyl linker obtained as above is treated with 10 wt % S$_8$ in CS$_2$-pyridine-triethylamine (35:35:1, v/v/v) at RT for 3 h, and successively washed with CS$_2$, pyridine, and EtOH. The resin is then treated with a 25% NH$_3$ aqueous solution-EtOH (3:1, v/v) for 2 h at room temperature and removed by filtration. The filtrate is diluted with a 25% NH$_3$ aqueous solution-EtOH (3:1, v/v) and placed in a tightly-sealed flask for 12 h at room temperature. The solution is concentrated under reduced pressure, and the residue is purified by RP-HPLC. Fractions containing the desired 2'-O-TBS-protected phosphorothioate RNAs are collected and lyophilized. The residue is treated with a 1M TBAF solution in dry THF for 24 h at room temperature. A 0.05M TEAA buffer solution (pH 6.9) is added, and THF is removed by evaporation. The residue is desalted with a Sep-pak C$_{18}$ cartridge, and purified by RP-HPLC to afford stereoregular phosphorothioate RNAs.

TABLE 2

| step | Operation | reagents and solvent | time |
| --- | --- | --- | --- |
| 1 | detritylation | 3% DCA in CH$_2$Cl$_2$ | 4 × 30 s |
| 2 | washing | (i) CH$_2$Cl$_2$ (ii) dry pyridine (iii) drying in vacuo. | — |
| 3 | coupling | pre-activated monomer (0.2M)* in dry pyridine | 15 min |
| 4 | washing | (i) dry pyridine (ii) dry CH$_3$CN (iii) drying in vacuo. | — |
| 5 | transformation | sulfur electrophile, selenium electrophile, or borane agent | 5 min |
| 6 | washing | (i) dry THF (ii) drying in vacuo. | — |
| 7 | capping | CF$_3$COIm-2,6-lutidine - dry THF (1:1:8, v/v/v) under argon | 30 s |
| 8 | washing | (i) dry THF (ii) CH$_2$Cl$_2$ | — |

*preparation of pre-activated monomer in Step 3 of Table 2: 1,8-Diazabicyclo[5.4.0]undec-7-enium 5'-O-(DMTr)-2'-O-(TBS)-ribonucleoside-3'-yl phosphonate is dried by repeated coevaporations with dry pyridine and then dissolved in dry pyridine. BopCl is added to the solution, and the mixture is stirred for 5 min. To the mixture, a solution of amino alcohol (L-2 or D-2), which is repeated coevaportions with dry pyridine and dissolved in dry pyridine, is added dropwise via syringe, and the mixture is stirred for 5 min under argon.

Example 76: A General Procedure for Solid-Phase Synthesis of X-Phosphonate RNA Via Scheme 6 (Route B)

Procedure to synthesis H-phosphonate RNA. 5'-O-(DMTr)uridine-loaded CPG resin via a succinyl or oxalyl linker is treated 1% TFA in CH$_2$Cl$_2$ (3×5 s) for the removal of the 5'-O-DMTr group, washed with CH$_2$Cl$_2$ and dry pyridine and dried in vacuo. Chain elongation is performed by repeating the following steps (a) and (b). (a) Coupling reaction using a solution containing the corresponding pre-activated monomer* (0.2M) in dry pyridine (10 min) under argon. After the condensation, the solid-support is washed with dry pyridine and CH$_2$Cl$_2$. (b) Removal of the 5'-O-DMTr group and the chiral auxiliary simultaneously by treatment with 1% TFA in CH$_2$Cl$_2$-Et$_3$SiH (1:1, v/v) (3×5 s), and following washings with CH$_2$Cl$_2$ and dry pyridine. The Boranophosphate (X=BH$_3^-$)

Dry DMF, N,O-bis(trimethylsilyl)acetamide (BSA), and BH$_3$.SMe$_2$ are added to the oligonucleside H-phosphonate loaded to a CPG resin via a oxalyl linker obtained as above at RT. After 15 min, the resin is successively washed with DMF, CH$_3$CN, and EtOH. The resin is then treated with a 25% NH$_3$ aqueous solution-EtOH (3:1, v/v) for 2 h at room temperature and removed by filtration. The filtrate is diluted with a 25% NH$_3$ aqueous solution-EtOH (3:1, v/v) and placed in a tightly-sealed flask for 12 h at room temperature. The solution is concentrated under reduced pressure, and the residue is purified by RP-HPLC. Fractions containing the desired 2'-O-TBS-protected boranophosphate RNAs are collected and lyophilized. The residue is treated with a 1M TBAF solution in dry THF for 24 h at room temperature. A 0.05M TEAA buffer solution (pH 6.9) is added, and THF is removed by evaporation. The residue is desalted with a Sep-pak $C_{18}$ cartridge, and purified by RP-HPLC to afford stereoregular boranophosphate RNAs.

Hydroxymethylphosphonate (X=$CH_2OH$)

Oligonucleoside H-phosphonate loaded to a CPG resin via a oxalyl linker obtained as above is treated with 0.1M trimethylsilylchloride (TMSCl) in pyridine-1-methyl-2-pyrolidone (NMP) (1:9, v/v) at RT for 10 min, and with gaseous formaldehyde at RT for 30 min, and then washed with NMP, and EtOH. The resin is then treated with a 25% $NH_3$ aqueous solution-EtOH (3:1, v/v) for 2 h at room temperature and removed by filtration. The filtrate is diluted with a 25% $NH_3$ aqueous solution-EtOH (3:1, v/v) and placed in a tightly-sealed flask for 12 h at room temperature. The solution is concentrated under reduced pressure, and the residue is purified by RP-HPLC. Fractions containing the desired 2'-O-TBS-protected hydroxymethylphosphonate RNAs are collected and lyophilized. The residue is treated with a 1M TBAF solution in dry THF for 24 h at room temperature. A 0.05M TEAA buffer solution (pH 6.9) is added, and THF is removed by evaporation. The residue is desalted with a Sep-pak $C_{18}$ cartridge, and purified by RP-HPLC to afford stereoregular hydroxymethylphosphonate RNAs.

Phosphoramidate (X=$NH_2$)

Oligonucleoside H-phosphonate loaded to a CPG resin via an oxalyl linker obtained as above is treated with a saturated $NH_3$ solution in $CCl_4$-1,4-dioxane (4:1, v/v) at 0° C. for 30 min, and washed with 1,4-dioxane. The combined organic solutions are concentrated to dryness under reduced pressure. The filtrate is diluted with a 25% $NH_3$ aqueous solution-EtOH (3:1, v/v) and placed in a tightly-sealed flask for 12 h at room temperature. The solution is concentrated under reduced pressure, and the residue is purified by RP-HPLC. Fractions containing the desired 2'-O-TBS-protected phosphoramidate RNAs are collected and lyophilized. The residue is treated with a 1M TBAF solution in dry THF for 24 h at room temperature. A 0.05M TEAA buffer solution (pH 6.9) is added, and THF is removed by evaporation. The residue is desalted with a Sep-pak $C_{18}$ cartridge, and purified by RP-HPLC to afford stereoregular phosphoramidate RNAs.

N-propylphosphoramidate (X=NHPr)

Oligonucleoside H-phosphonate loaded to a CPG resin via an oxalyl linker obtained as above is treated with $CCl_4$-propylamine (9:1, v/v) at RT for 1 h, and washed with $CH_3OH$. The combined organic solutions are concentrated to dryness under reduced pressure. The filtrate is diluted with a 25% $NH_3$ aqueous solution-EtOH (3:1, v/v) and placed in a tightly-sealed flask for 12 h at room temperature. The solution is concentrated under reduced pressure, and the residue is purified by RP-HPLC. Fractions containing the desired 2'-O-TBS-protected N-propylphophoramidate RNAs are collected and lyophilized. The residue is treated with a 1M TBAF solution in dry THF for 24 h at room temperature. A 0.05M TEAA buffer solution (pH 6.9) is added, and THF is removed by evaporation. The residue is desalted with a Sep-pak $C_{18}$ cartridge, and purified by RP-HPLC to afford stereoregular N-propylphophoramidate RNAs.

N-[(2-dimethylamino)ethyl]phosphoramidate [X=$NH(CH_2)_2NMe_2$]

Oligonucleoside H-phosphonate loaded to a CPG resin via an oxalyl linker obtained as above is treated with $CCl_4$-2-dimethylaminoethylamine (9:1, v/v) at RT for 1 h, and washed with $CH_3CN$. The combined organic solutions are concentrated to dryness under reduced pressure. The filtrate is diluted with a 25% $NH_3$ aqueous solution-EtOH (3:1, v/v) and placed in a tightly-sealed flask for 12 h at room temperature. The solution is concentrated under reduced pressure, and the residue is purified by RP-HPLC. Fractions containing the desired 2'-O-TBS-protected N-[(2-dimethylamino)ethyl]phosphoramidate RNAs are collected and lyophilized. The residue is treated with a 1M TBAF solution in dry THF for 24 h at room temperature. A 0.05M TEAA buffer solution (pH 6.9) is added, and THF is removed by evaporation. The residue is desalted with a Sep-pak $C_{18}$ cartridge, and purified by RP-HPLC to afford stereoregular N-[(2-dimethylamino)ethyl]phosphoramidate RNAs.

Example 77: Solid-Phase Synthesis; General Procedure for the Preparation of Pre-Activated Monomer Solution Appropriate H-phosphonate monoester was dried by repeated coevaporations with dry pyridine and dry toluene, then dissolved in dry solvent. To the solution, condensing reagent was added dropwise, and stirred for 10 min. Amino-alcohol was then added and stirred for additional 10 min to give pre-activated monomer solution.

Example 78: Solid-Phase Synthesis of a Phosphorothioate Dimer, ($S_P$)-Ammonium thymidin-3'-yl thymidin-5'-yl phosphorothioate [($S_P$)-5tt] via Route A

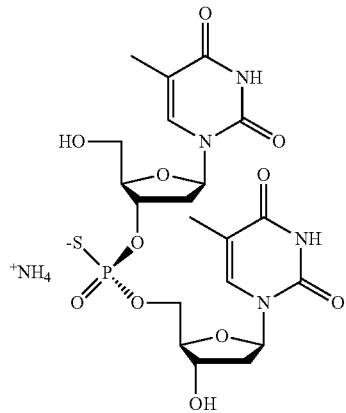

Figure 5A:
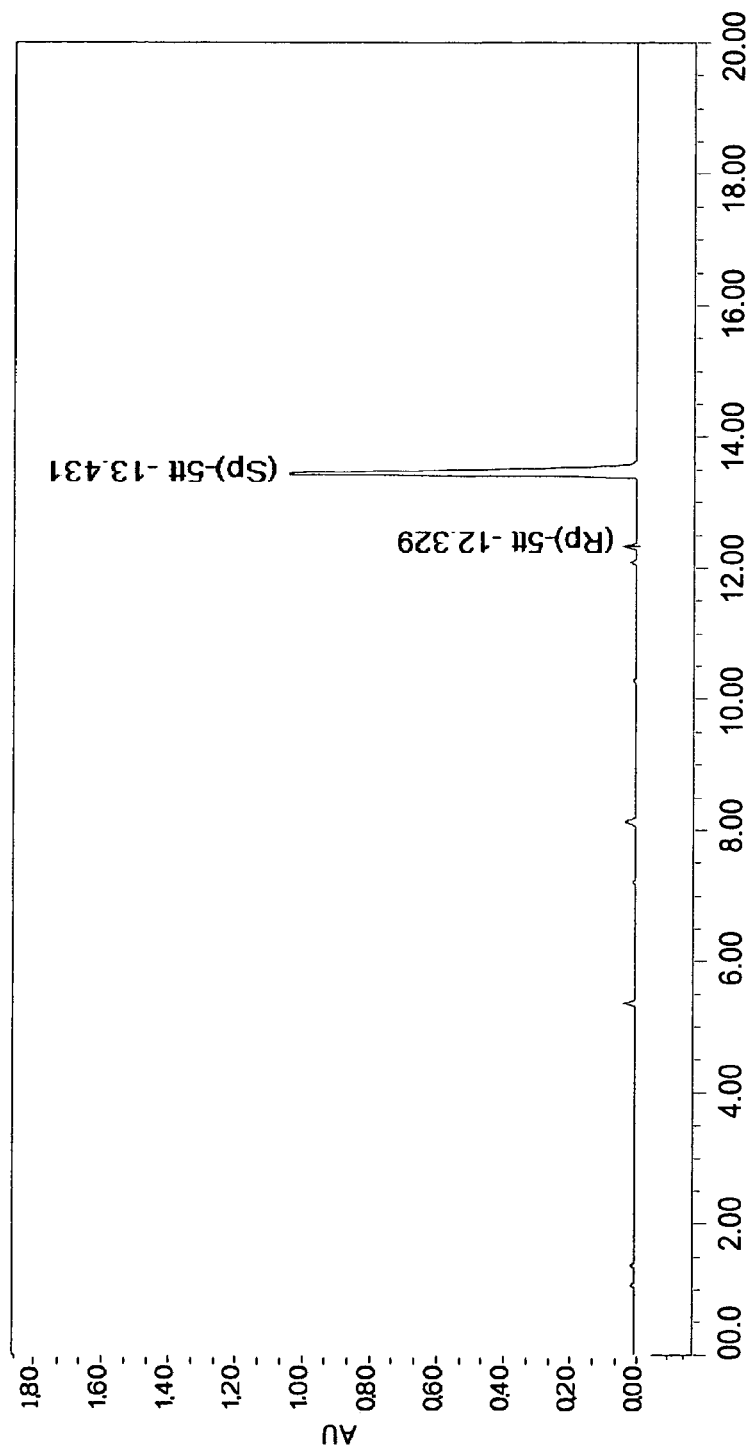
Figure 5B:
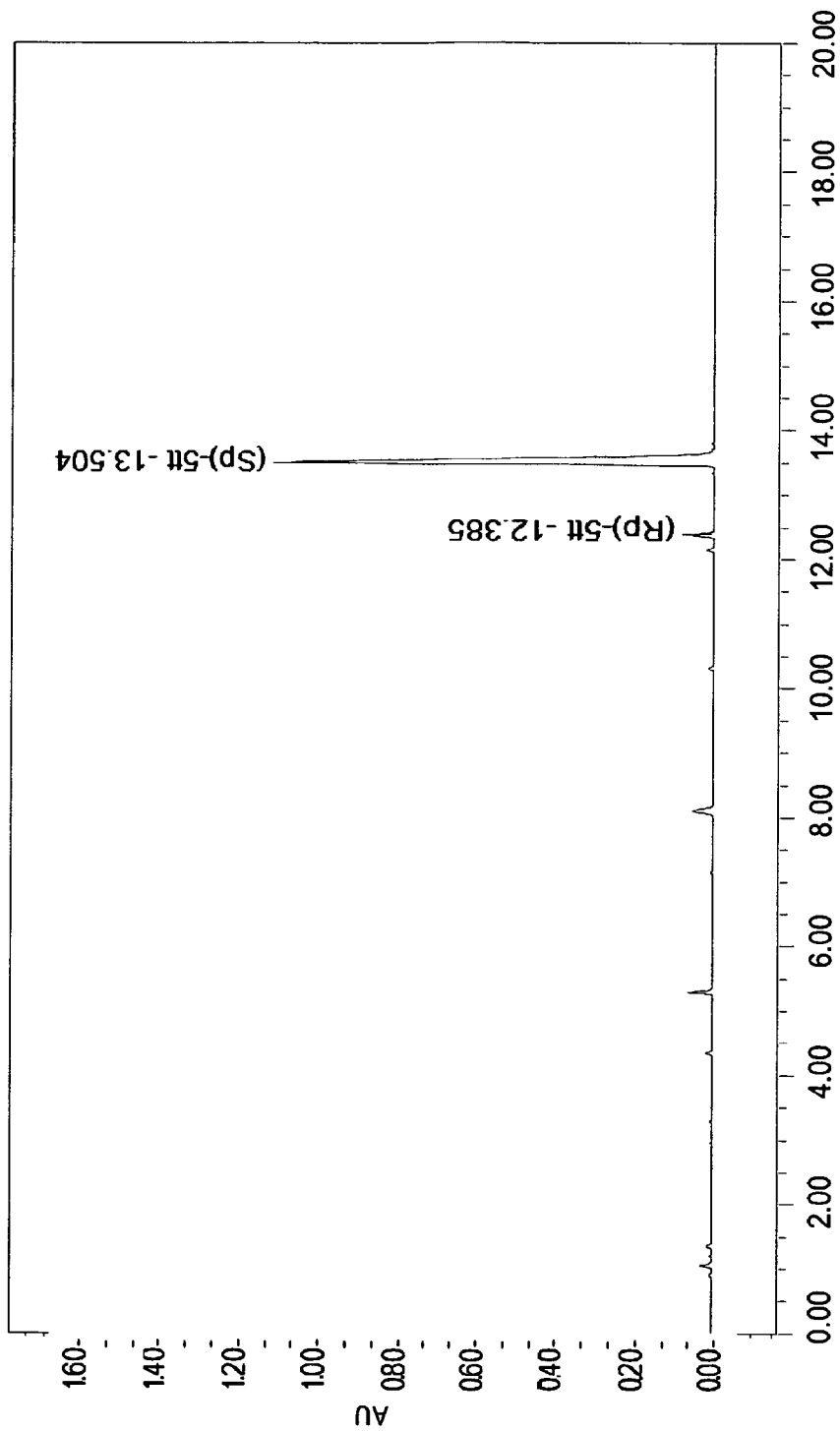

5tt $N^3$-Benzoyl-5'-O-(4,4'-dimethoxytrityl)thymidine-loaded HCP resin (16.4 mg; 30.5 µmol/g, 0.5 µmol) via a succinyl linker was treated with 3% DCA/DCM (3×1 mL), then washed with DCM (3×1 mL) and dry MeCN (3×1 mL). After the resin was dried under the reduced pressure (>5 min), pre-activated monomer solution (250 µL, 25 µmol; which consists of 8-diazabicyclo[5.4.0]undec-7-enium $N^3$-benzoyl-5'-O-(4,4'-dimethoxytrityl)thymidin-3'-yl phosphonate (25 µmol, for H-phosphonate monoester), MeCN-pyridine (9:1, v/v, for solvent), $Ph_3PCl_2$ (62.5 µmol, for condensing reagent), and L-2 (30 µmol, for aminoalcohol)) was added. Being stirred for 2 min, the reaction solution was removed, and the resin was washed with MeCN (3×1 mL), and dried under the reduced pressure (>5 min). For the modification step, the resulting intermediate on the resin was sulfurized by treatment with 0.3 M DTD/MeCN (500 µL, 150 µmol) for 5 min, the resin was then washed with MeCN (3×1 mL) and DCM (3×1 mL). The 5'-O-DMTr group was removed by treatment with 3% DCA/DCM (3×1 mL), and the resin was washed with DCM (3×1 mL). The phosphorothioate dimer on the resin was then treated with 25% $NH_3$ (1 mL) for 12 h at 55° C. to remove the chiral auxiliary and the protecting groups of the nucleobases and also to release the dimer from the resin. The resin was removed by filtration and washed with $H_2O$. The filtrate was concentrated to dryness. The residue was dissolved in $H_2O$ (2 mL), washed with $Et_2O$ (3×2 mL), and the combined washings were back-extracted with $H_2O$ (2 mL). The combined aqueous layers were concentrated to dryness. The resulting crude product was analyzed by reversed-phase UPLC® with a linear gradient of 0-20% MeOH in 0.1 M ammonium acetate buffer (pH 7.0) for 15 min at 55° C. at a rate of 0.4 ml/min. The product was identical to that of a control sample synthesized by the conventional H-phosphonate method. The yield of $(S_P)$-5tt was 97% ($R_P:S_P=2:98$). Retention time: 13.4 min (($R_P$)-5tt: 12.3 min). The general scheme is shown in Scheme 18. The UPLC profile is shown in FIG. 5A. In another synthesis of $(S_P)$-5tt, BTC (20 μmol) was used in placed of $Ph_3PCl_2$ (62.5 μmol). The product was identical to that of a control sample synthesized by the conventional H-phosphonate method. The yield of $(S_P)$-5tt was 95% yield ($R_P:S_P=3:97$). Retention time: 13.5 min (($R_P$)-5tt: 12.4 min). the UPLC profile is shown in FIG. 5B.

washed with DCM (3×1 mL) and dry MeCN (3×1 mL). After the resin was dried under the reduced pressure (>5 min), pre-activated monomer solution (200 μL, 25 μmol; which consists of 8-diazabicyclo[5.4.0]undec-7-enium $N^3$-benzoyl-5'-O-(4,4'-dimethoxytrityl)thymidin-3'-yl phosphonate (25 μmol, for H-phosphonate monoester), MeCN-CMP (9:1, v/v, for solvent), $Ph_3PCl_2$ (62.5 μmol, for condensing reagent), and L-2 (30 μmol, for aminoalcohol)) was added followed by the addition of 5 M CMPT/MeCN (50 μL, 250 μmol, for activating reagent). Being stirred for 10 min, the reaction solution was removed, and the resin was washed with MeCN (3×1 mL), dried under the reduced pressure (>5 min). The resulting intermediate on the resin was sulfurized by treatment with 0.3 M DTD/MeCN (500 μL, 150 μmol) for 5 min, then the resin was washed with MeCN (3×1 mL) and DCM (3×1 mL). The 5'-O-DMTr group was removed by treatment with 3% DCA/DCM (3×1 mL), and washed with DCM (3×1 mL). The phosphorothioate dimer on the resin was then treated with 25% $NH_3$ (1 mL) for 12 h at 55° C. to remove the chiral auxiliary and the protecting groups of the nucleobases and also to release the dimer from the resin. The resin was removed by filtration and washed with $H_2O$. The filtrate was concentrated to Scheme 18: General solid-phase synthesis of Phosphorothioate Dimers via Route A

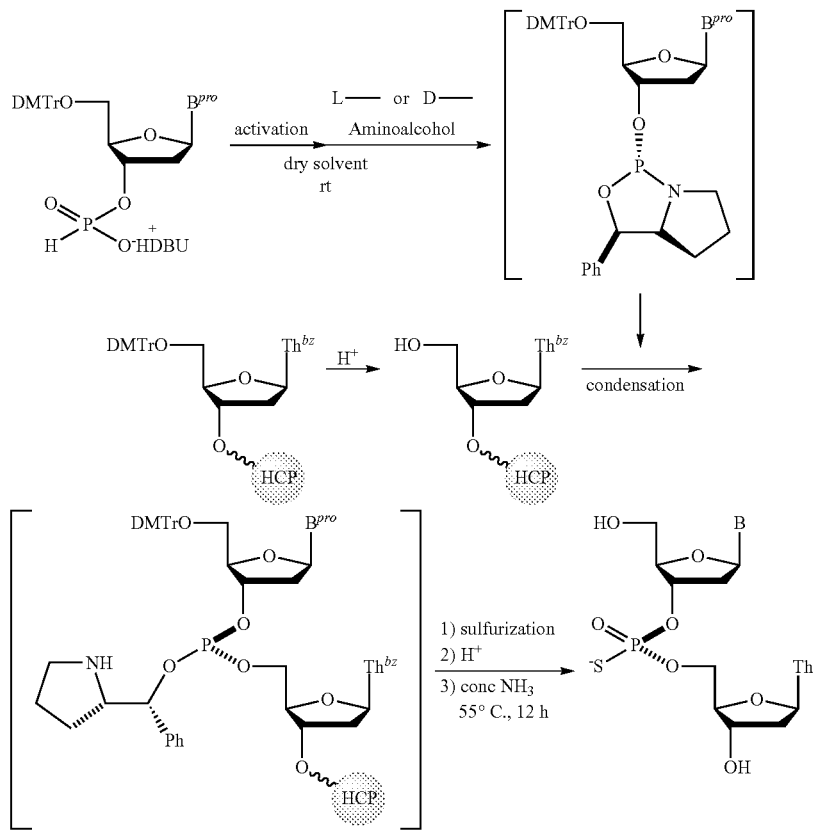

Example 79: Solid-Phase Synthesis of a Phosphorothioate Dimer, $(S_P)$-Ammonium thymidin-3'-yl thymidin-5'-yl phosphorothioate [$(S_P)$-5tt]

$N^3$-Benzoyl-5'-O-(4,4'-dimethoxytrityl)thymidine-loaded HCP resin (16.4 mg; 30.5 μmol/g, 0.5 μmol) via a succinyl linker was treated with 3% DCA/DCM (3×1 mL), then dryness. The residue was dissolved in $H_2O$ (2 mL), washed with $Et_2O$ (3×2 mL), and the combined washings were back-extracted with $H_2O$ (2 mL). The combined aqueous layers were concentrated to dryness. The resulting crude product was analyzed by reversed-phase UPLC® with a linear gradient of 0-20% MeOH in 0.1 M ammonium acetate buffer (pH 7.0) for 15 min at 55° C. at a rate of 0.4 ml/min.

Figure 6A:
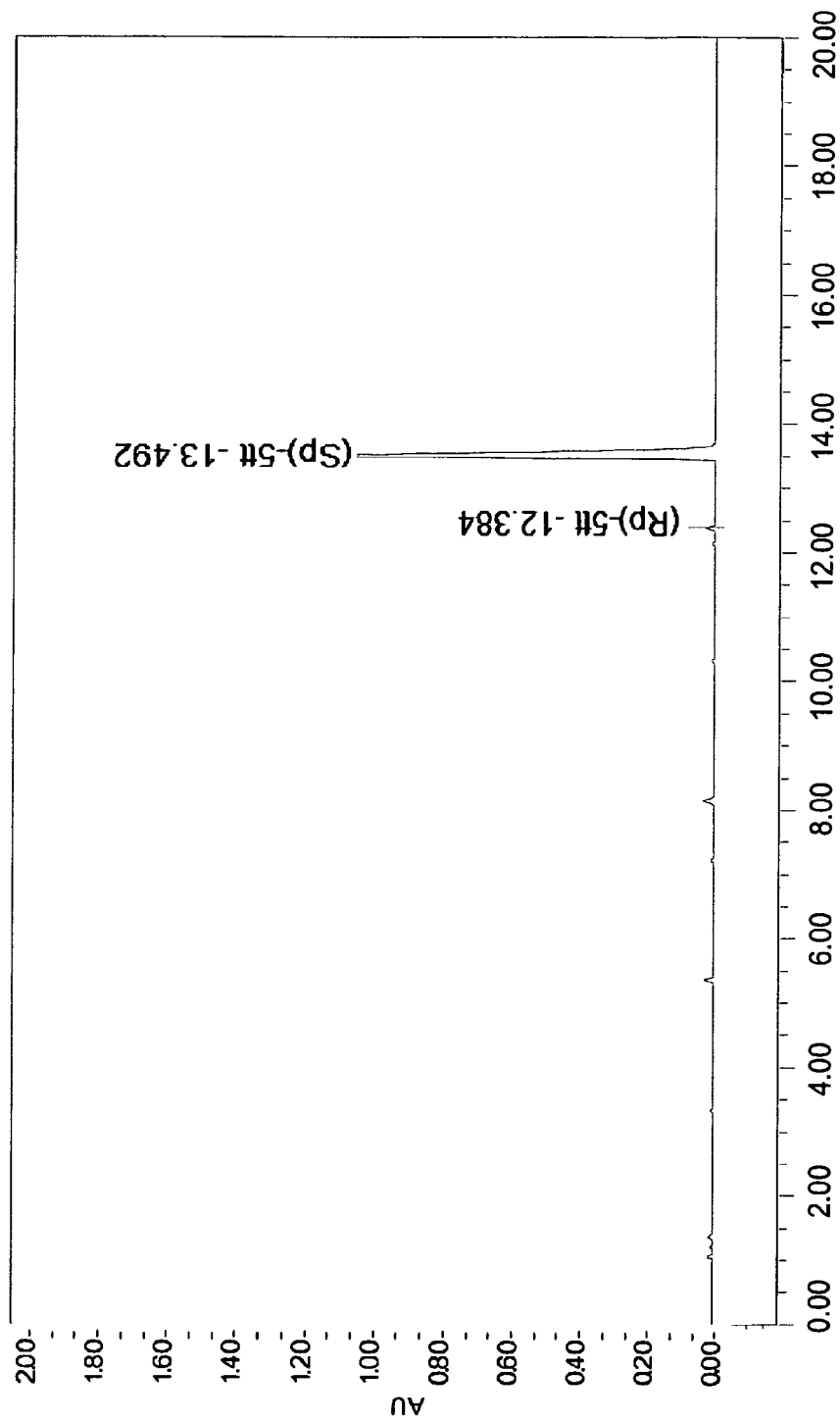
Figure 6B:
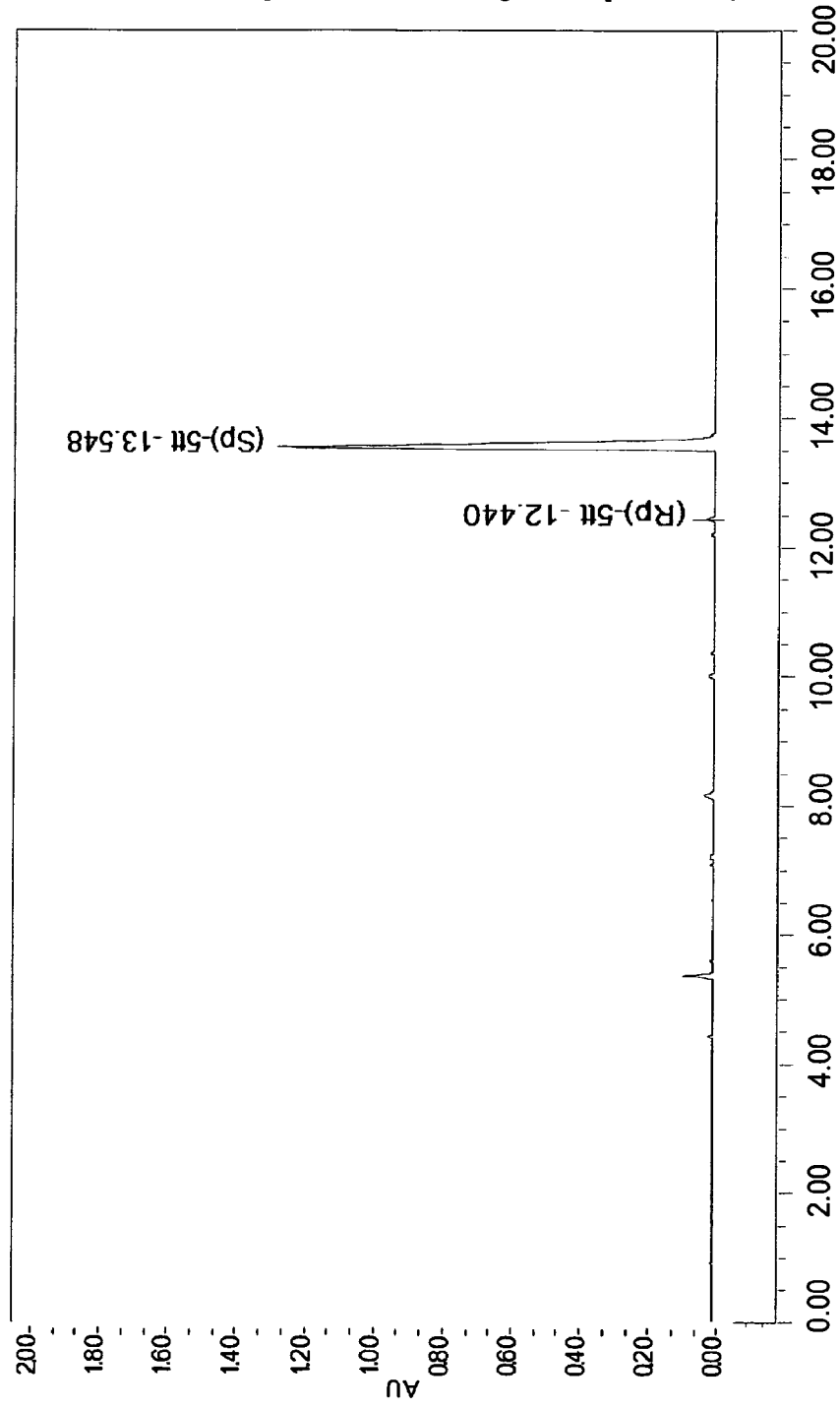

The product was identical to that of a control sample synthesized by the conventional H-phosphonate method. The yield of ($S_P$)-5tt was 98% yield ($R_P$:$S_P$=1:99). Retention time: 13.5 min (($R_P$)-5tt: 12.4 min). The UPLC profile is shown in FIG. 6A. This compound was also obtained by using "BTC (16 μmol) and L-2 (26 μmol)" instead of "Ph$_3$PCl$_2$ (62.5 μmol) and L-2 (30 μmol)" in a similar manner described. The product was identical to that of a control sample synthesized by the conventional H-phosphonate method. The yield of ($S_P$)-5tt was 95% yield ($R_P$:$S_P$=1:99). Retention time: 13.5 min (($R_P$)-5tt: 12.4 min). The UPLC profile is shown in FIG. 6B.

Figure 7B:
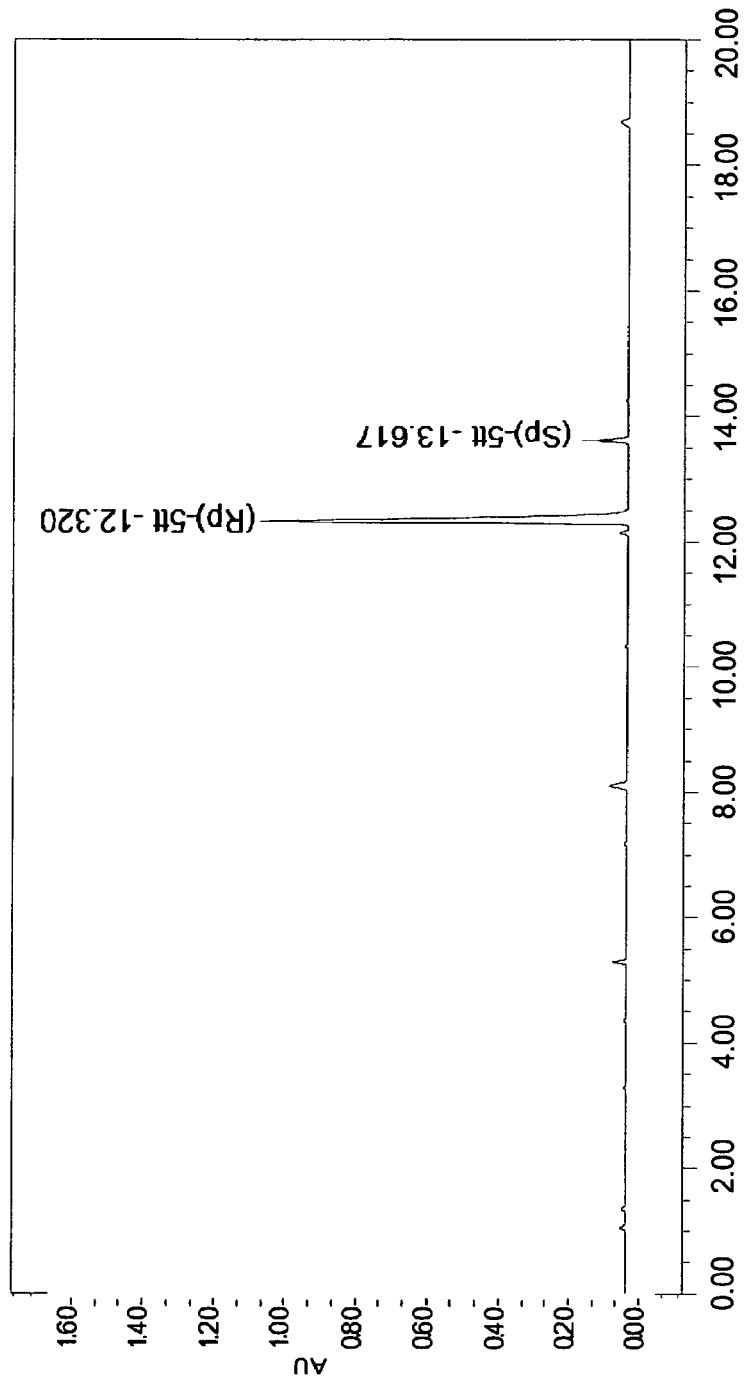

Example 80: Solid-Phase Synthesis of a Phosphorothioate Dimer, ($R_P$)-Ammonium thymidin-3'-yl thymidin-5'-yl phosphorothioate [($R_P$)-5tt] via Route A This compound was obtained by using "D-2 (30 μmol)" instead of "L-2 (30 μmol)" in a similar manner to "Example 78". The product was identical to that of a control sample synthesized by the conventional H-phosphonate method. The yield of ($R_P$)-5tt was 98% ($R_P$:$S_P$=97:3). Retention time: 12.2 min (($S_P$)-5tt: 13.5 min). The UPLC profile is shown in FIG. 7A. In another synthesis of ($R_P$)-5tt, BTC (20 μmol) was used in placed of Ph$_3$PCl$_2$ (62.5 μmol). The product was identical to that of a control sample synthesized by the conventional H-phosphonate method. The yield of ($R_P$)-5tt was 97% ($R_P$:$S_P$=95:5). Retention time: 12.3 min (($S_P$)-5tt: 13.6 min). The UPLC profile is shown in FIG. 7B.

Figure 8:
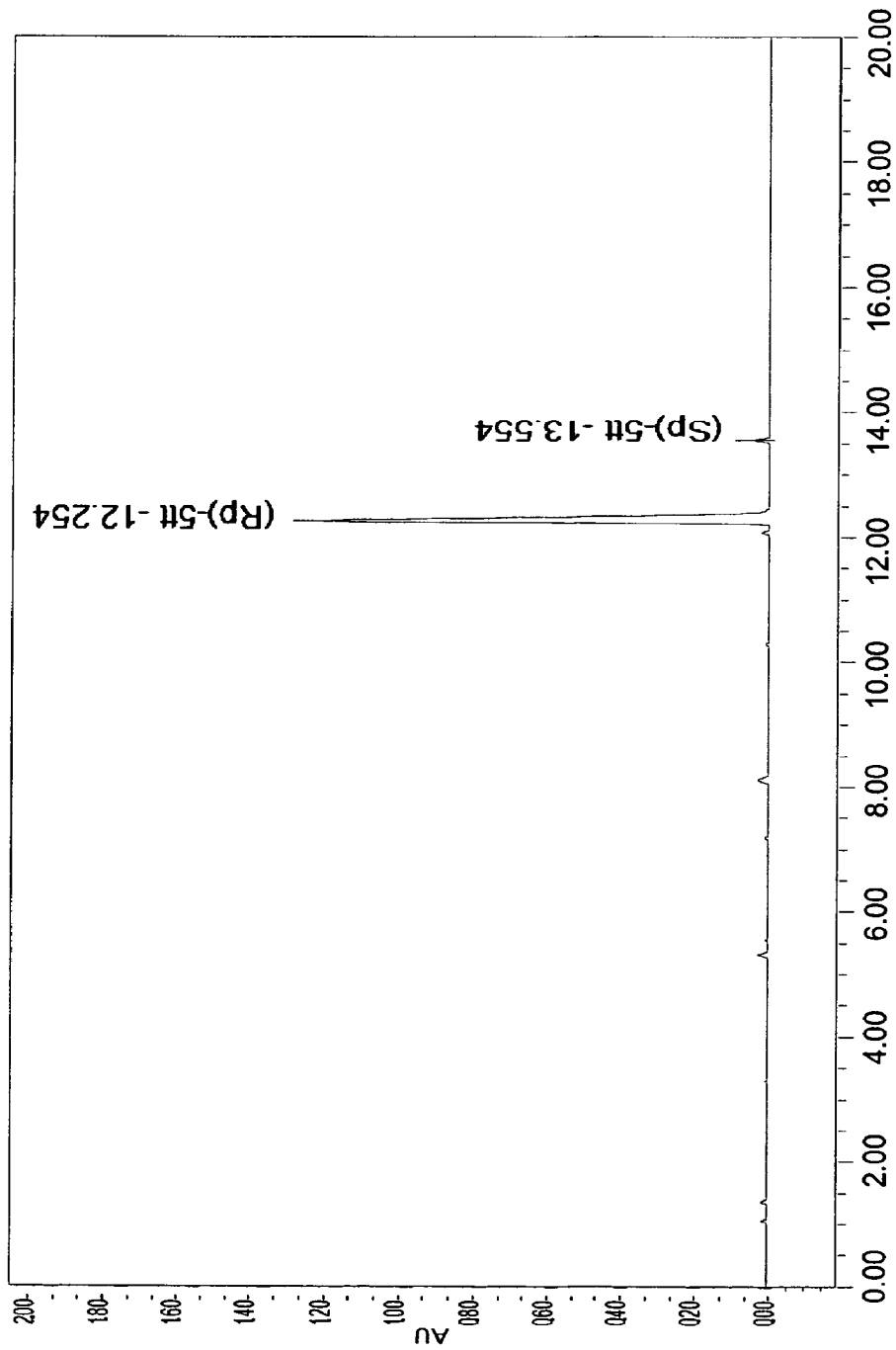

Example 81: Solid-Phase Synthesis of a Phosphorothioate Dimer, ($R_P$)-Ammonium thymidin-3'-yl thymidin-5'-yl phosphorothioate [($R_P$)-5tt] via Route A This compound was obtained by using "D-2 (30 μmol)" instead of "L-2 (30 μmol)" in a similar manner to "Example 79". The product was identical to that of a control sample synthesized by the conventional H-phosphonate method. The yield of ($R_P$)-5tt was 98% ($R_P$:$S_P$=98:2). Retention time: 12.3 min (($S_P$)-5tt: 13.6 min). The UPLC profile is shown in FIG. 8.

Figure 9A:
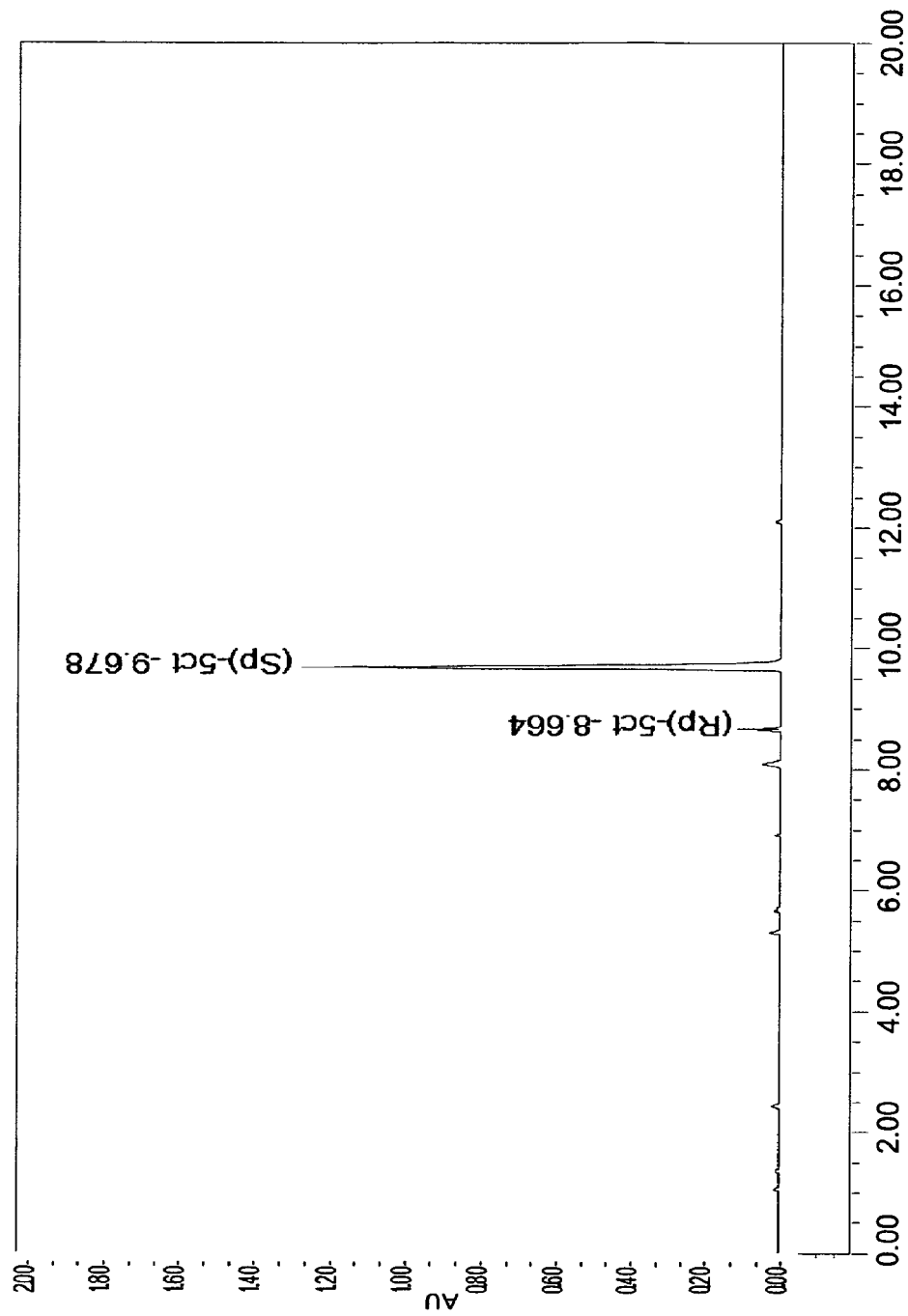
Figure 9B:
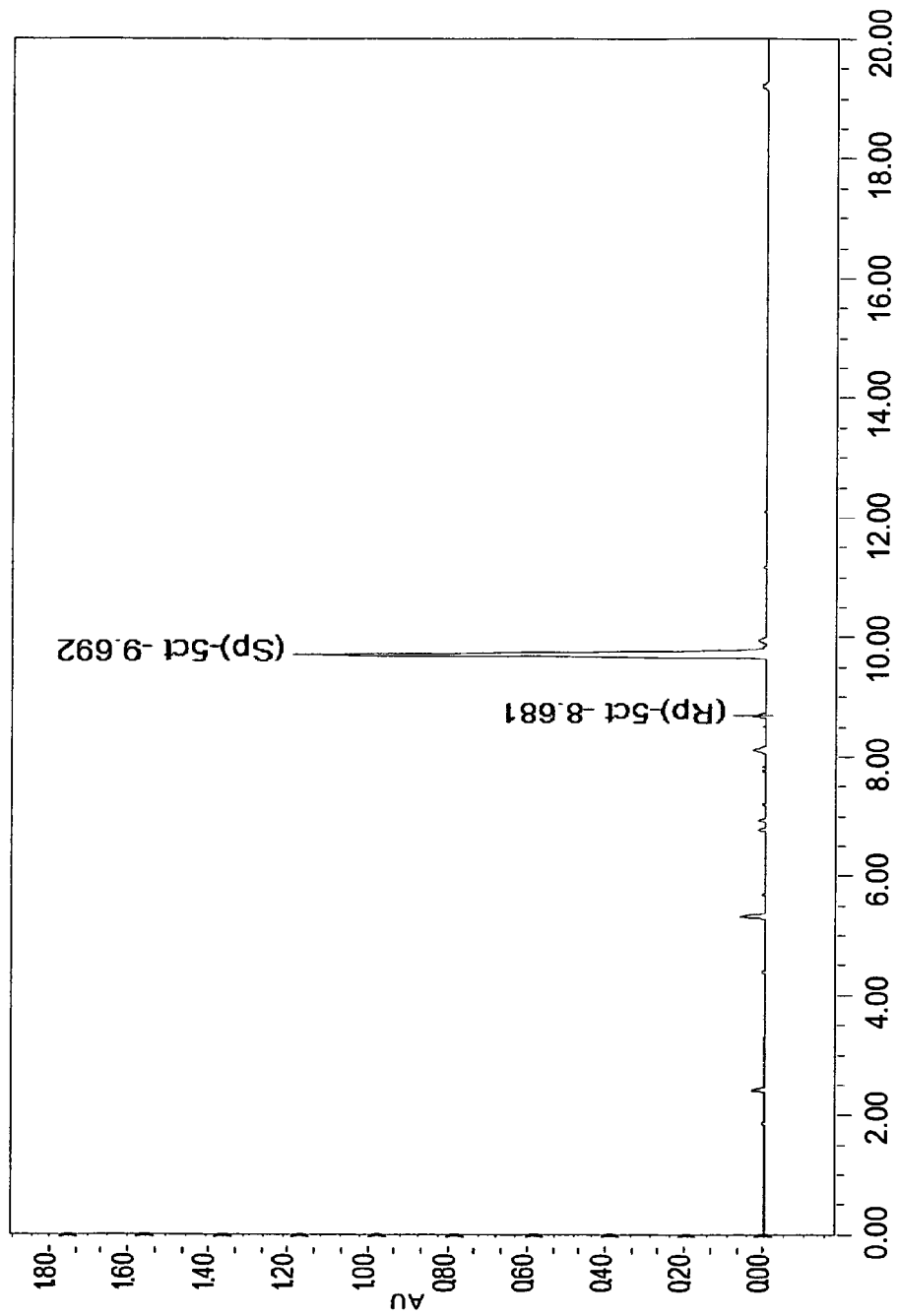

Example 82: Solid-Phase Synthesis of a Phosphorothioate Dimer, ($S_P$)-Ammonium 2'-deoxycytidin-3'-yl thymidin-5'-yl phosphorothioate [($S_P$)-5ct] via Route A This compound was obtained by using "8-diazabicyclo[5.4.0]undec-7-enium 4-N-benzoyl-5'-O-(4,4'-dimethoxytrityl)-2'-deoxycytidin-3'-yl phosphonate (25 μmol)" instead of "8-diazabicyclo[5.4.0]undec-7-enium N$^3$-benzoyl-5'-O-(4,4'-dimethoxytrityl)thymidin-3'-yl phosphonate (25 μmol)" in a similar manner to Example 78. The product was identical to that of a control sample synthesized by the conventional H-phosphonate method. The yield of ($S_P$)-5ct was 98% ($R_P$:$S_P$=3:97). Retention time: 9.7 min (($R_P$)-5ct: 8.7 min). The UPLC profile is shown in FIG. 9A. This compound was also obtained by using "BTC (16 μmol) and L-2 (26 μmol)" instead of "Ph$_3$PCl$_2$ (62.5 μmol) and L-2 (30 μmol)" as described. The product was identical to that of a control sample synthesized by the conventional H-phosphonate method. The yield of ($S_P$)-5ct was 94% ($R_P$:$S_P$=3:97). Retention time: 9.7 min (($R_P$)-5ct: 8.7 min). The UPLC profile is shown in FIG. 9B.

Figure 10A:
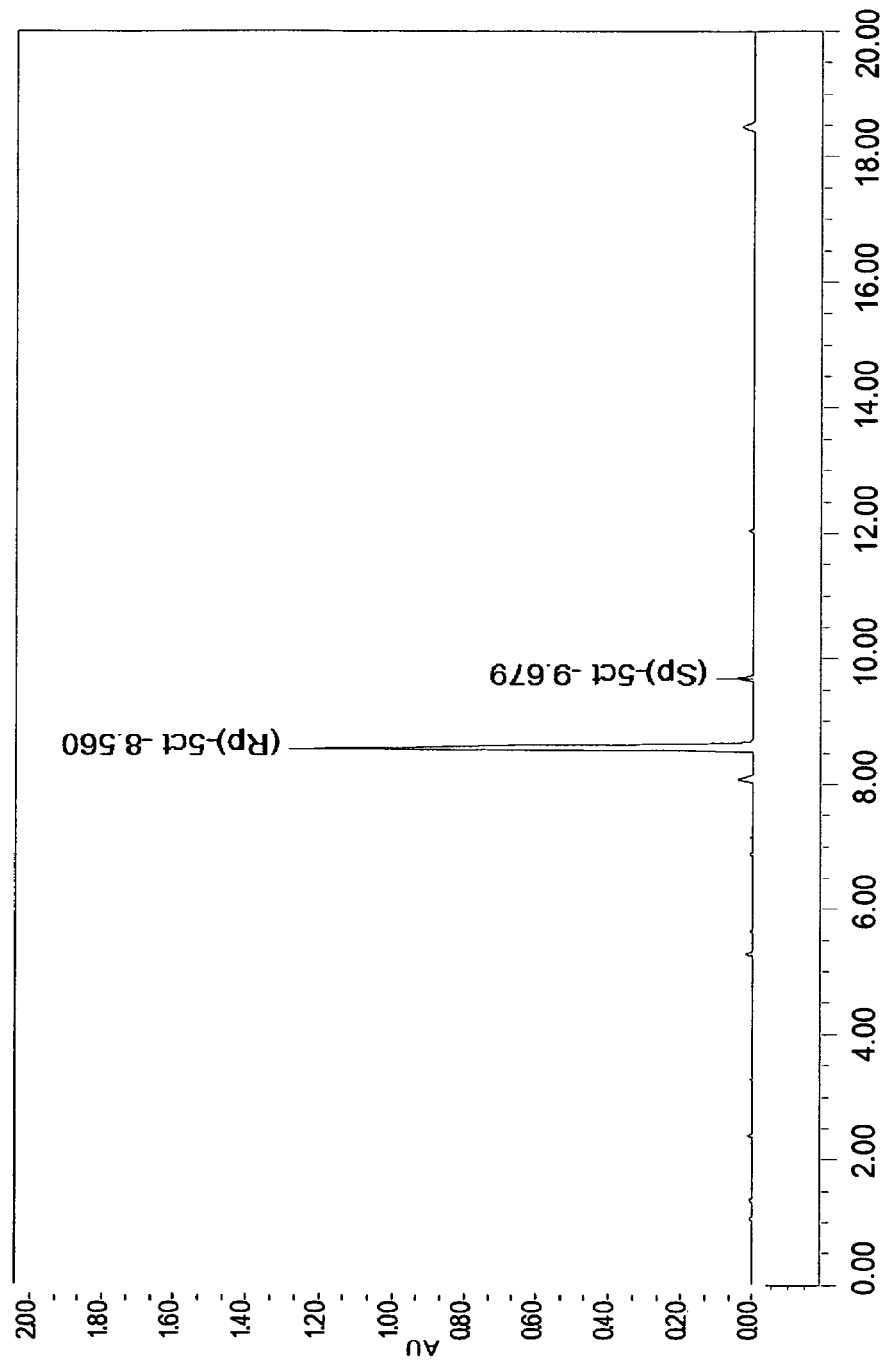
Figure 10B:
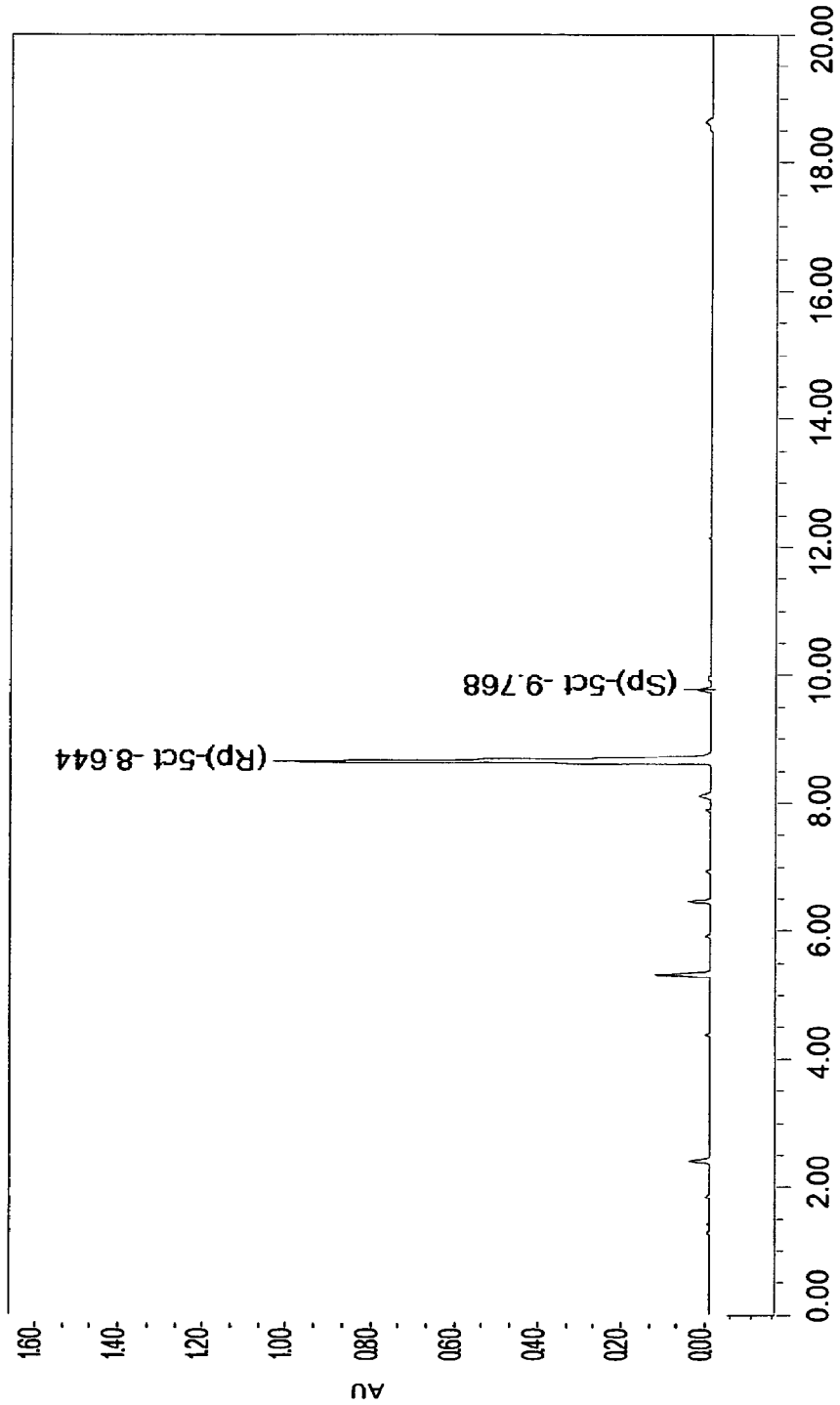

Example 83: Solid-Phase Synthesis of a Phosphorothioate Dimer, ($R_P$)-Ammonium 2'-deoxycytidin-3'-yl thymidin-5'-yl phosphorothioate [($R_P$)-5ct] via Route A This compound was obtained by using "D-2 (30 μmol)" instead of "L-2 (30 μmol)" in a similar manner to the experiment for Example 82, FIG. 9A. The product was identical to that of a control sample synthesized by the conventional H-phosphonate method. The yield of ($R_P$)-5ct was 98% ($R_P$:$S_P$=97:3). Retention time: 8.6 min (($S_P$)-5ct: 9.7 min). The UPLC profile is shown in FIG. 10A. This compound was also obtained by using "D-2 (30 μmol)" instead of "L-2 (30 μmol)" in a similar manner to Example 82, FIG. 9B. The yield of ($R_P$)-5ct was 87% ($R_P$:$S_P$=98:2). Retention time: 8.6 min (($S_P$)-5ct: 9.8 min). The UPLC profile is shown in FIG. 10B.

Example 84: Solid-Phase Synthesis of a Phosphorothioate Dimer, ($S_P$)-Ammonium 2'-deoxyadenin-3'-yl thymidin-5'-yl phosphorothioate [($S_P$)-5at] via Route A

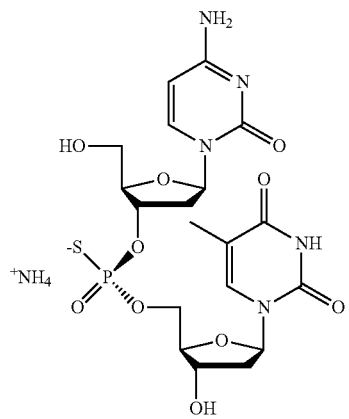

5ct

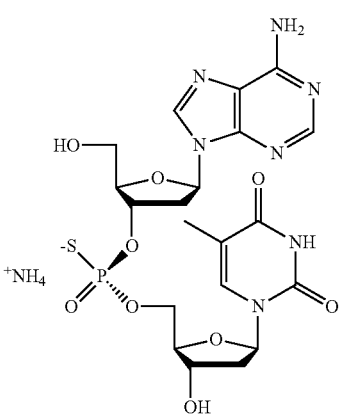

5at

Figure 11:
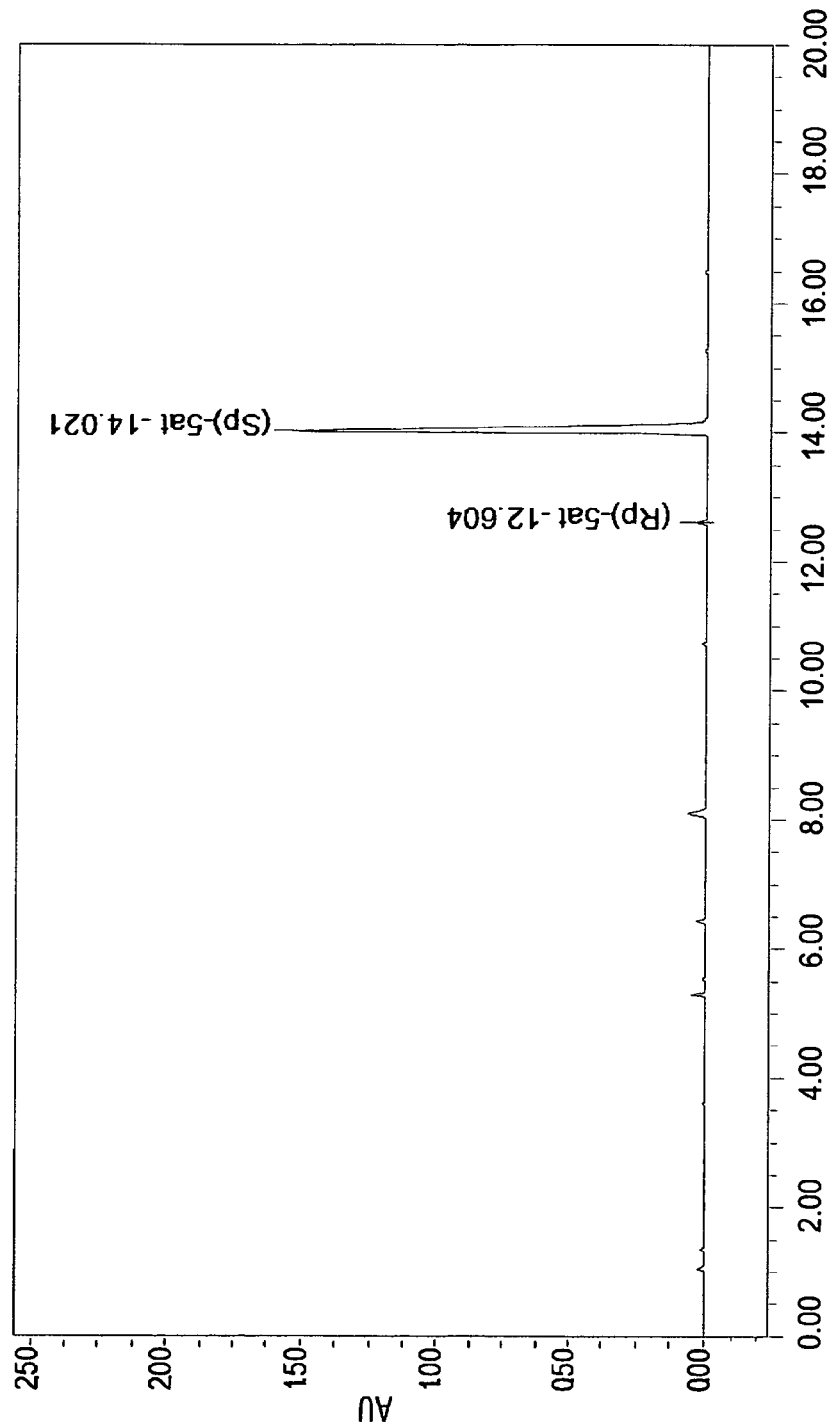

This compound was obtained by using "8-diazabicyclo[5.4.0]undec-7-enium 6-N,N-dibenzoyl-5'-O-(4,4'-dimethoxytrityl)-2'-deoxyadenin-3'-yl phosphonate (25 μmol)" instead of "8-diazabicyclo[5.4.0]undec-7-enium N$^3$-benzoyl-5'-O-(4,4'-dimethoxytrityl)thymidin-3'-yl phosphonate (25 μmol)" in a similar manner to Example 78. The product was identical to that of a control sample synthesized by the conventional H-phosphonate method. The yield of $(S_P)$-5at was 96% yield $(R_P:S_P=1:99)$. Retention time: 14.0 min $((R_P)$-5at: 12.6 min). The UPLC profile is shown in FIG. 11.

Figure 12:
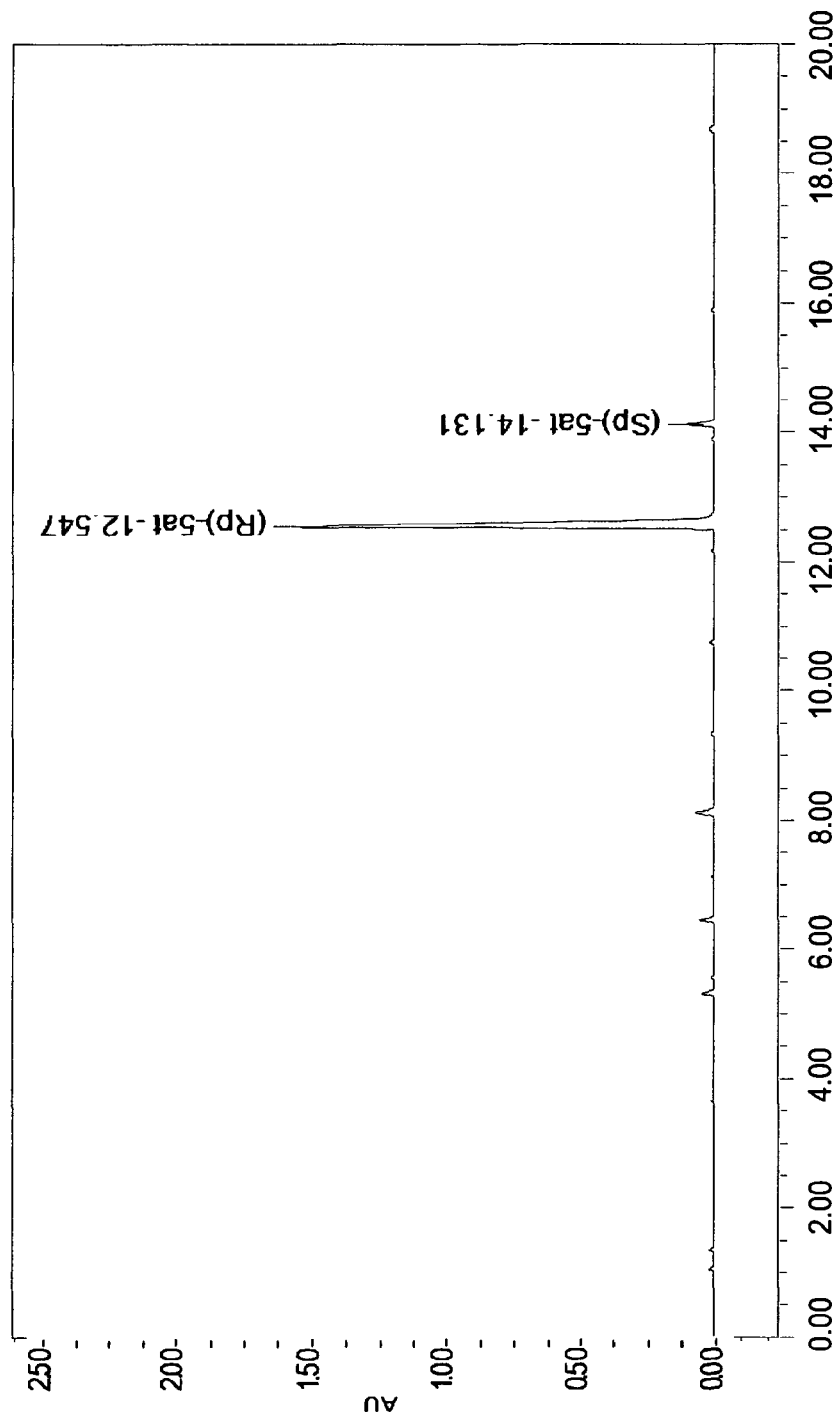

Example 85: Solid-Phase Synthesis of a Phosphorothioate Dimer, $(R_P)$-Ammonium 2'-deoxyadenin-3'-yl thymidin-5'-yl phosphorothioate [$(R_P)$-5at] via Route A This compound was obtained by using "D-2 (30 μmol)" instead of "L-2 (30 μmol)" in a similar manner to Example 83. The product was identical to that of a control sample synthesized by the conventional H-phosphonate method. The yield of $(R_P)$-5at was 96% $(R_P:S_P=96:4)$. Retention time: 12.5 min $((S_P)$-5at: 14.1 min). The UPLC profile is shown in FIG. 12.

Example 86: Solid-Phase Synthesis of a Phosphorothioate Dimer, $(S_P)$-Ammonium 2'-deoxyguanin-3'-yl thymidin-5'-yl phosphorothioate [$(S_P)$-5gt] via Route A

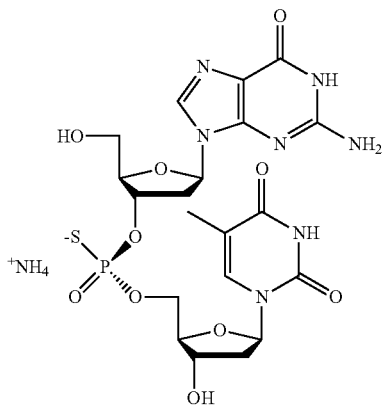

5gt

Figure 13:
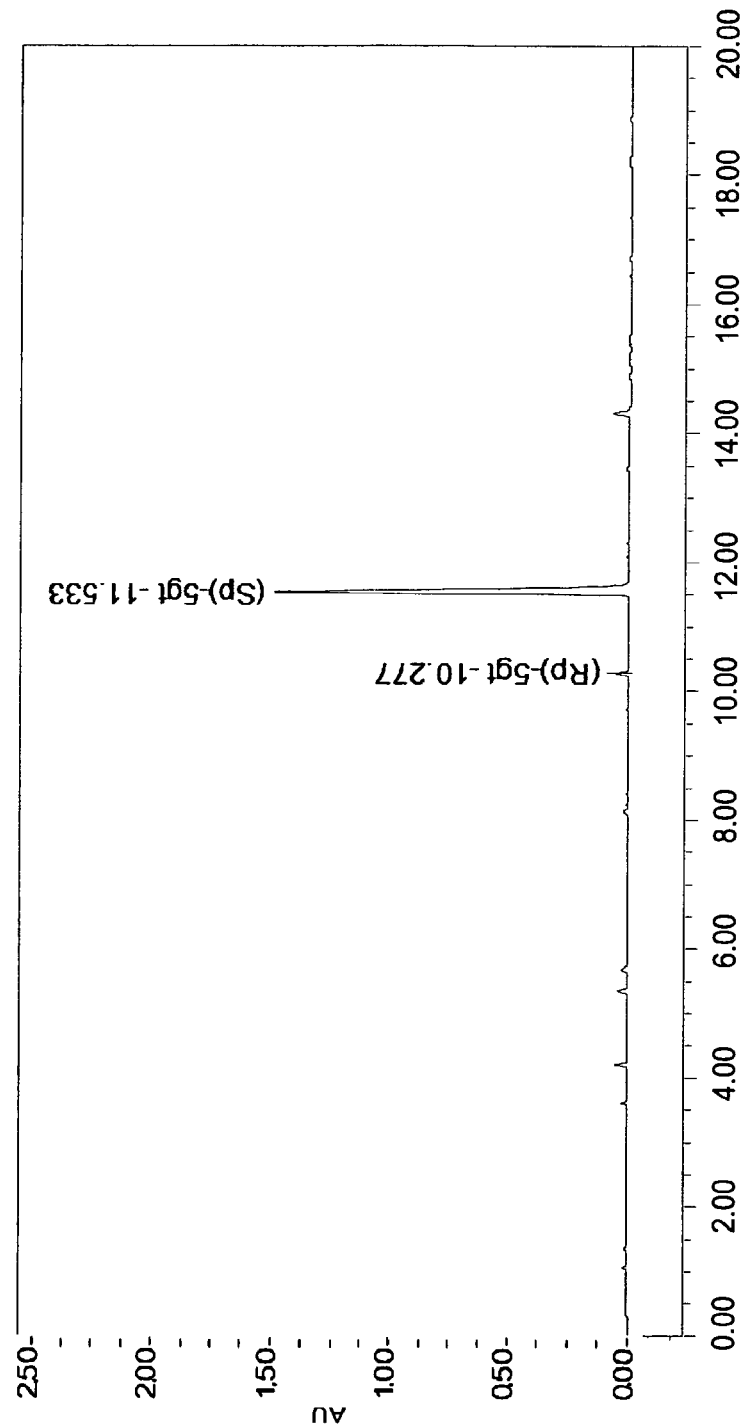

This compound was obtained by using "8-diazabicyclo[5.4.0]undec-7-enium $O^6$-cyanoethyl-2-N-phenoxyacetyl-5'-O-(4,4'-dimethoxytrityl)-2'-deoxyguanin-3'-yl phosphonate (25 μmol)" instead of "8-diazabicyclo[5.4.0]undec-7-enium $N^3$-benzoyl-5'-O-(4,4'-dimethoxytrityl)thymidin-3'-yl phosphonate (25 μmol)" in a similar manner to Example 78. The product was identical to that of a control sample sample synthesized by the conventional H-phosphonate method. The yield of $(S_P)$-5gt was 96% $(R_P:S_P=2:98)$. Retention time: 11.5 min $((R_P)$-5gt: 10.3 min). The UPLC profile is shown in FIG. 13.

Figure 14:
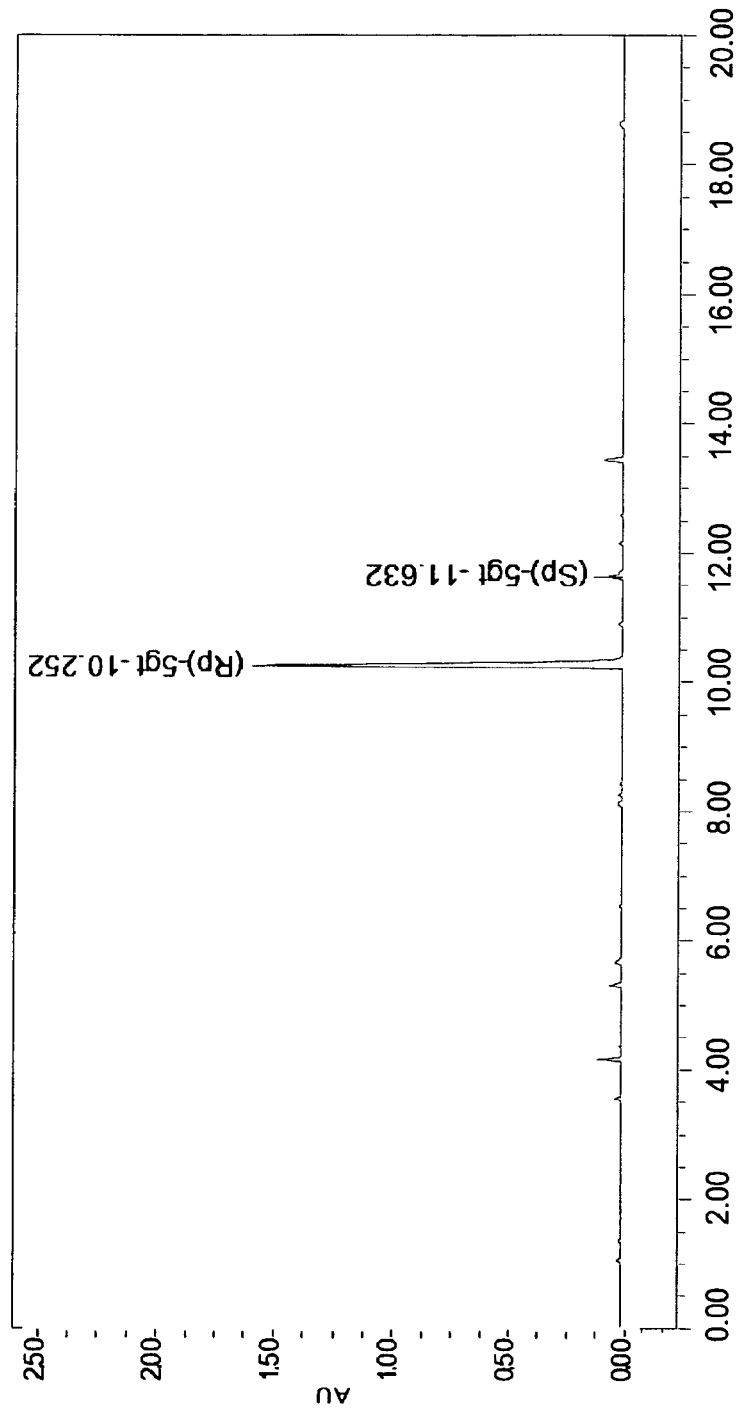

Example 87: Solid-Phase Synthesis of a Phosphorothioate Dimer, $(R_P)$-Ammonium 2'-deoxyguanin-3'-yl thymidin-5'-yl phosphorothioate [$(R_P)$-5gt] via Route A This compound was obtained by using "D-2 (30 μmol)" instead of "L-2 (30 μmol)" in a similar manner to Example 86. The product was identical to that of a control sample sample synthesized by the conventional H-phosphonate method. The yield of $(R_P)$-5gt was 96% $(R_P:S_P=97:3)$. Retention time: 10.3 min $((S_P)$-5gt: 11.6 min). The UPLC profile is shown in FIG. 14.

Example 88: Solid-Phase Synthesis of a Phosphorothioate Dimer, $(S_P)$-Ammonium thymidin-3'-yl thymidin-5'-yl phosphorothioate [$(S_P)$-5tt] via Route B

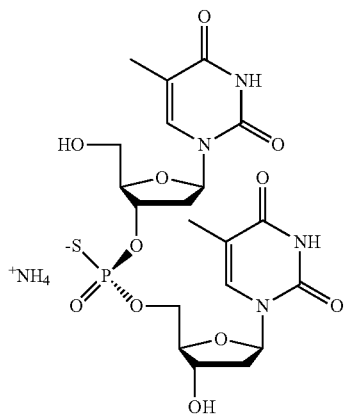

Figure 15A:
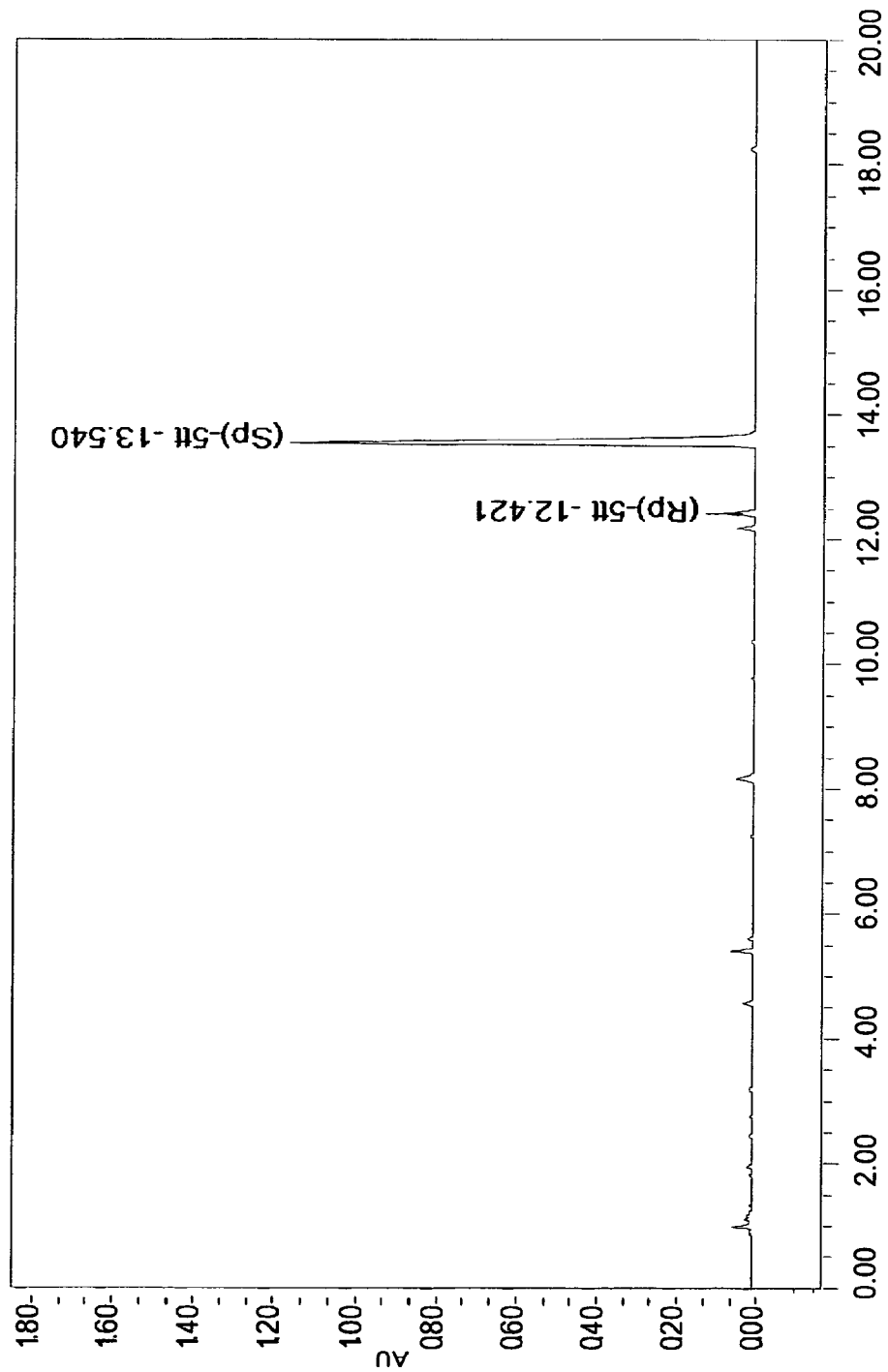

5tt $N^3$-Benzoyl-5'-O-(4,4'-dimethoxytrityl)thymidine-loaded HCP resin (16.4 mg; 30.5 μmol/g, 0.5 μmol) via a succinyl linker was treated with 1% TFA/DCM (3×1 mL) for the removal of the 5'-O-DMTr group, washed with DCM (3×1 mL) and dry MeCN (3×1 mL), and dried in vacuo. Preactivated monomer solution (200 μL, 50 μmol; which consists of 8-diazabicyclo[5.4.0]undec-7-enium $N^3$-benzoyl-5'-O-(4,4'-dimethoxytrityl)thymidin-3'-yl phosphonate (50 μmol, for H-phosphonate monoester), MeCN-CMP (9:1, v/v, for solvent), $Ph_3PCl_2$ (125 μmol, for condensing reagent), and L-6 (52 μmol, for aminoalcohol)) was added followed by the addition of 5 M CMPT/MeCN (50 μL, 250 μmol). Being stirred for 2 min, the reaction solution was removed, and the resin was washed with MeCN (3×1 mL), DCM (3×1 mL), and dried under the reduced pressure (>5 min). The 5'-O-DMTr group and the chiral auxiliary was simultaneously removed by treatment with 1% TFA in DCM (3×1 mL), washed with DCM (3×1 mL) and dry MeCN (3×1 mL), and dried in vacuo. The resulting intermediate on the resin was sulfurized by treatment with the solution mixture of 0.2 M Beaucage reagent/MeCN (200 μL, 40 μmol) and BSA (25 μl, 100 μmol) for 20 min, the resin was then washed with MeCN (3×1 mL). The phosphorothioate dimer on the resin was then treated with 25% $NH_3$-EtOH (2 mL, 4:1, v/v) for 12 h at room temperature to remove the protecting groups of the nucleobases and also to release the dimer from the resin. The resin was removed by filtration and washed with $H_2O$. The filtrate was concentrated to dryness. The residue was dissolved in $H_2O$ (2 mL), washed with $Et_2O$ (3×2 mL), and the combined washings were back-extracted with $H_2O$ (2 mL). The combined aqueous layers were concentrated to dryness. The resulting crude product was analyzed by reversed-phase UPLC® with a linear gradient of 0-20% MeOH in 0.1 M ammonium acetate buffer (pH 7.0) for 15 min at 55° C. at a rate of 0.4 ml/min. The product was identical to that of a control sample synthesized by the conventional H-phosphonate method. The yield of $(S_P)$-5tt was 96% $(R_P:S_P=4:96)$. Retention time: 13.5 min $((R_P)$-5tt: 12.4 min). The UPLC profile is shown in FIG. 15A.

Figure 15B:
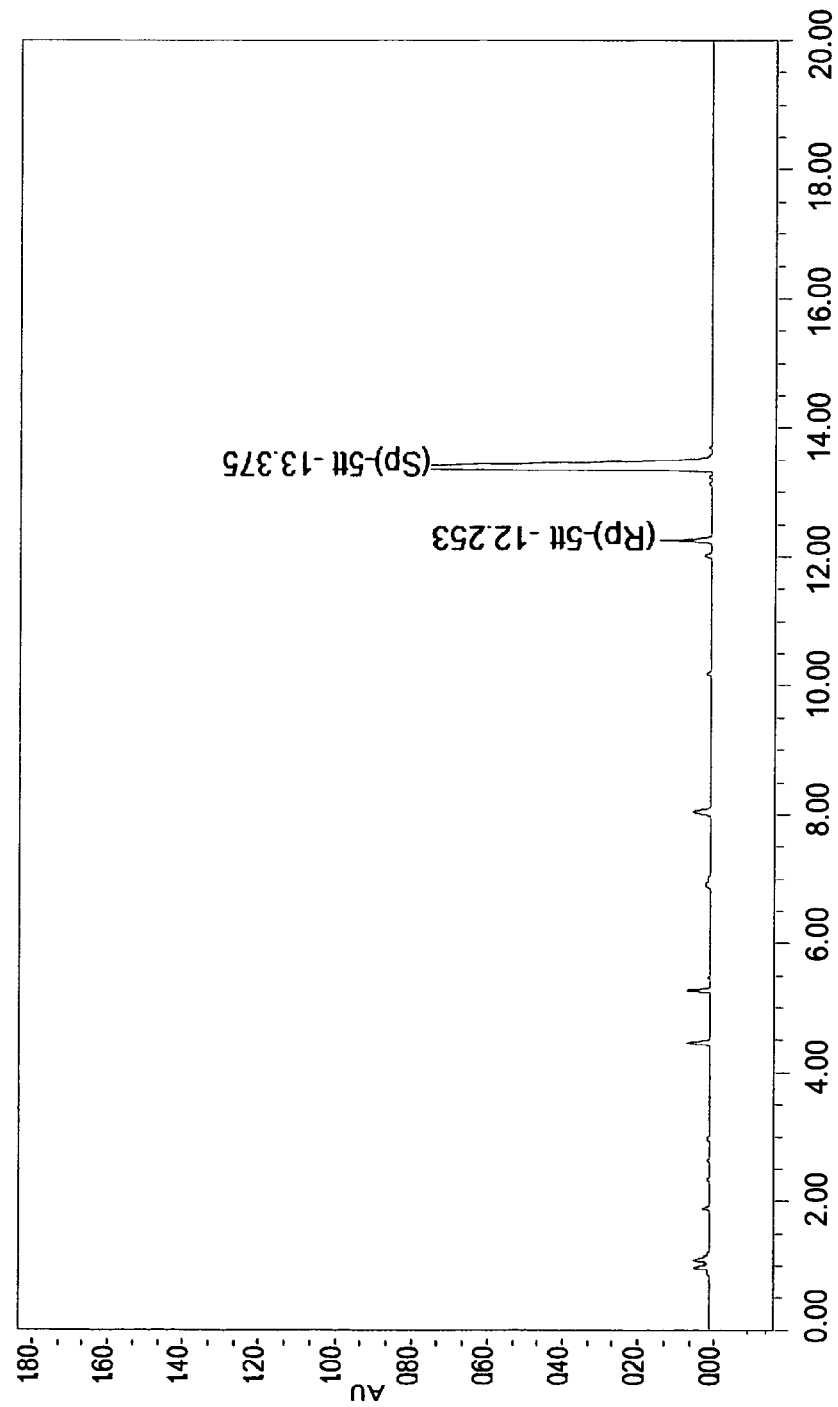

In an alternative synthesis, this compound was also obtained by using "BTC (32 µmol)" instead of "Ph$_3$PCl$_2$ (125 µmol)" in a similar manner as described. The product was identical to that of a control sample synthesized by the conventional H-phosphonate method. The yield of (S$_P$)-5tt was 96% (R$_P$:S$_P$=5:95). Retention time: 13.4 min ((R$_P$)-5tt: 12.3 min). The UPLC profile is shown in FIG. 15B.

Figure 16A:
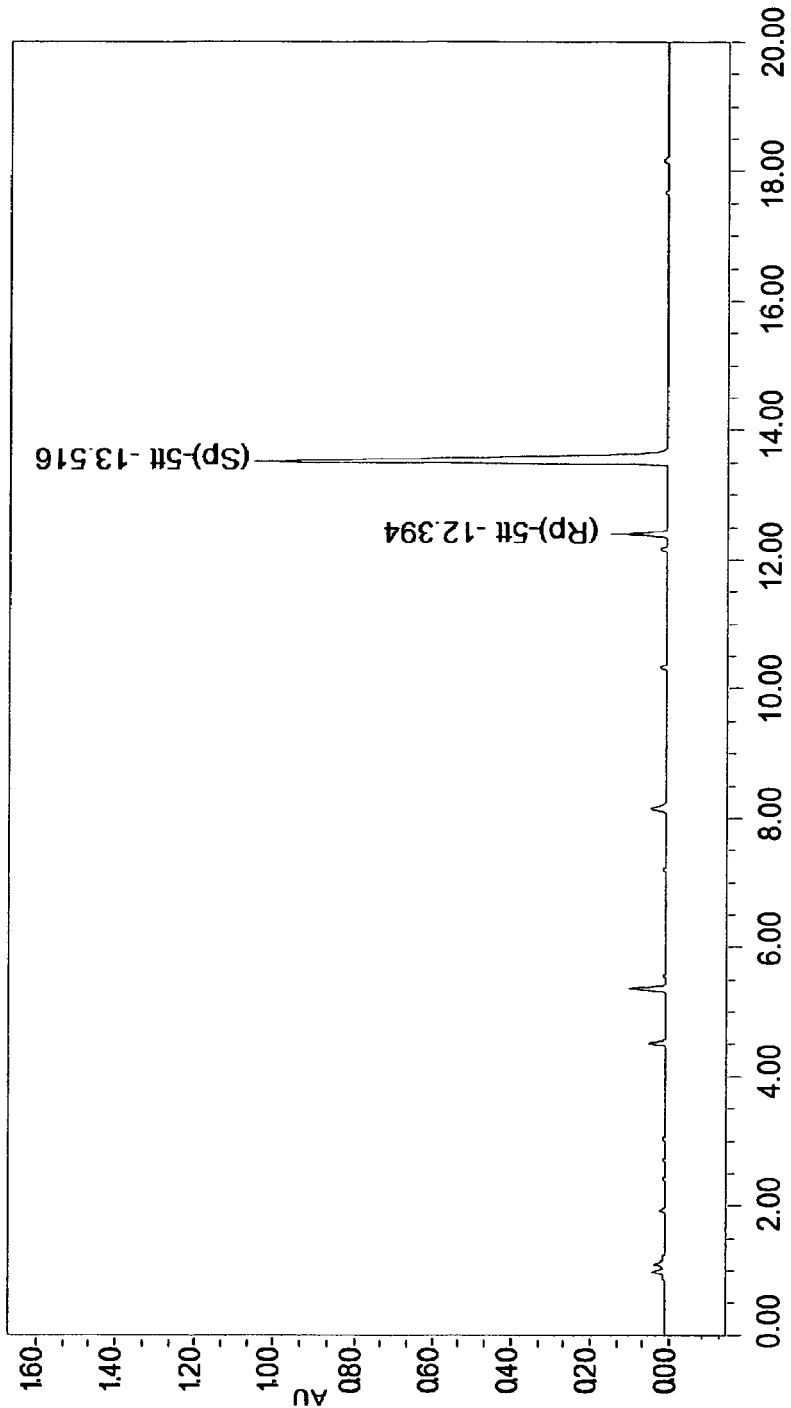
Figure 16B:
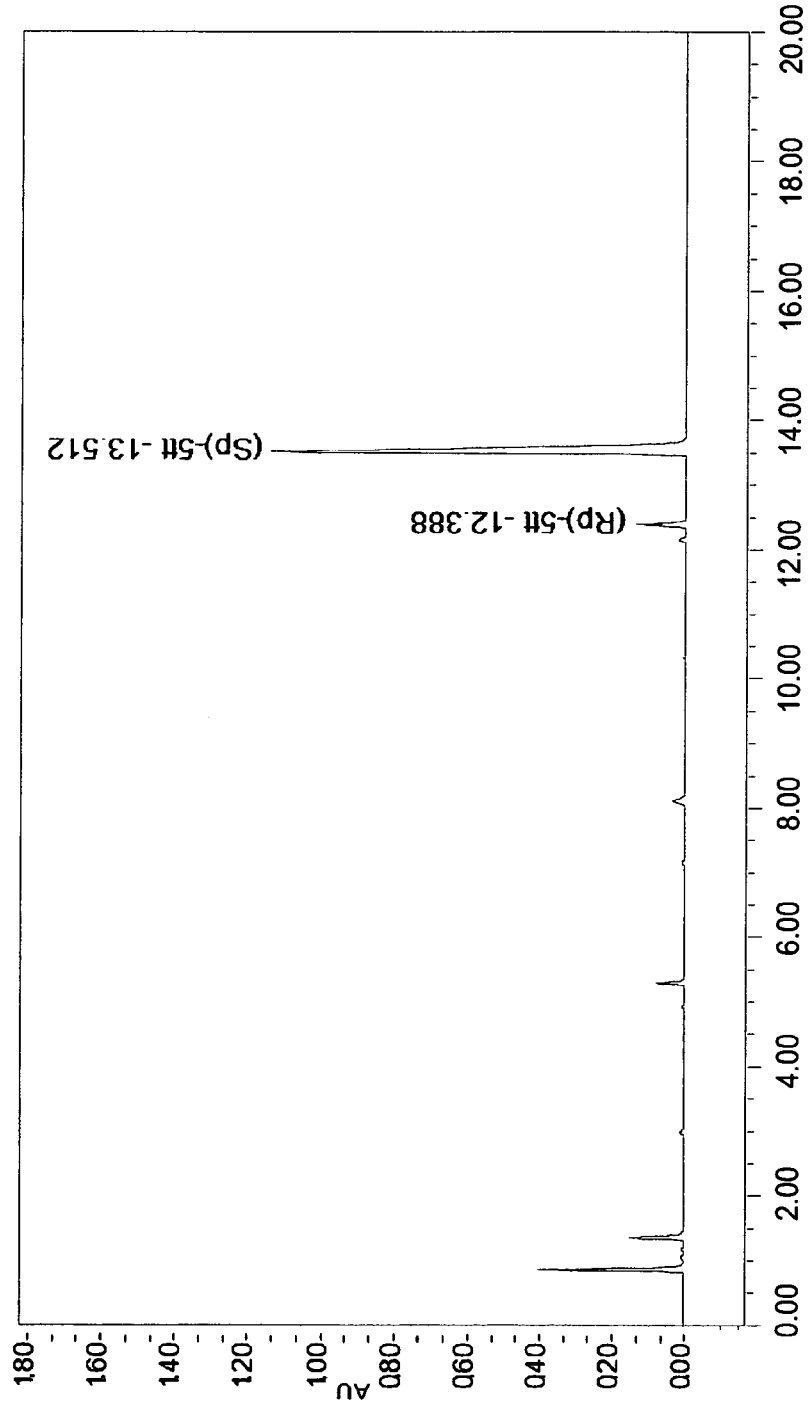

Example 89: Solid-Phase Synthesis of a Phosphorothioate Dimer, (S$_P$)-Ammonium thymidin-3'-yl thymidin-5'-yl phosphorothioate [(S$_P$)-5tt] via Route B In another alternative synthesis, [(S$_P$)-5tt] was obtained by using "8-diazabicyclo[5.4.0]undec-7-enium N$^3$-benzoyl-5'-O-(4,4'-dimethoxytrityl)thymidin-3'-yl phosphonate (25 µmol), BTC (16 µmol), and L-6 (26 µmol))" instead of "8-diazabicyclo[5.4.0]undec-7-enium N$^3$-benzoyl-5'-O-(4,4'-dimethoxytrityl)thymidin-3'-yl phosphonate (50 µmol), Ph$_3$PCl$_2$ (125 µmol), and L-6 (52 µmol)" in a similar manner to FIG. 15A Example 88. The general scheme is shown in Scheme 19. The product was identical to that of a control sample synthesized by the conventional H-phosphonate method. The yield of (S$_P$)-5tt was 93% (R$_P$:S$_P$=6:94). Retention time: 13.5 min ((R$_P$)-5tt: 12.4 min). The UPLC profile is shown in FIG. 16A. This compound was obtained by using "0.2 M DTD/MeCN (200 µl, 80 µmol)" instead of "0.2 M Beaucage reagent/MeCN (200 µL, 40 µmol)" in a similar manner as described. The product was identical to that of a control sample synthesized by the conventional H-phosphonate method. The yield of (S$_P$)-5tt was 95% (R$_P$:S$_P$=6:94). Retention time: 13.5 min ((R$_P$)-5tt: 12.4 min). The UPLC profile is shown in FIG. 16B.

Scheme 19

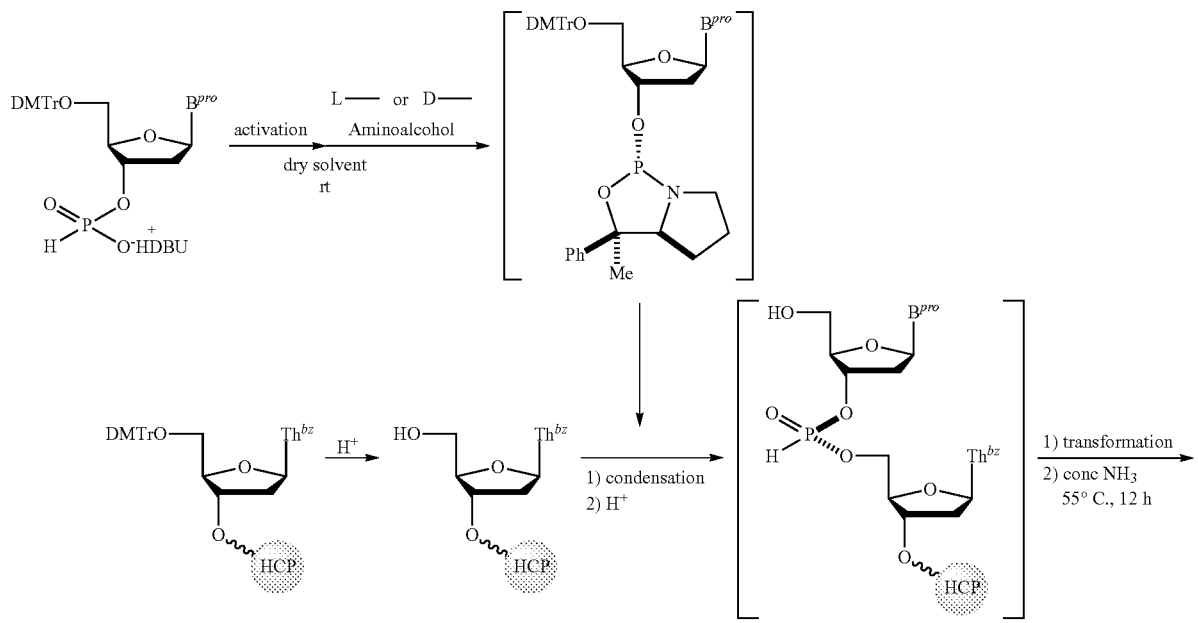

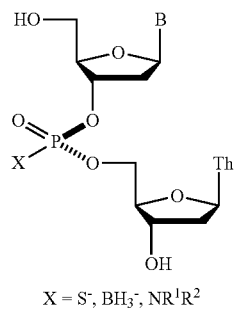

X = S$^-$, BH$_3^-$, NR$^1$R$^2$

Figure 17A:
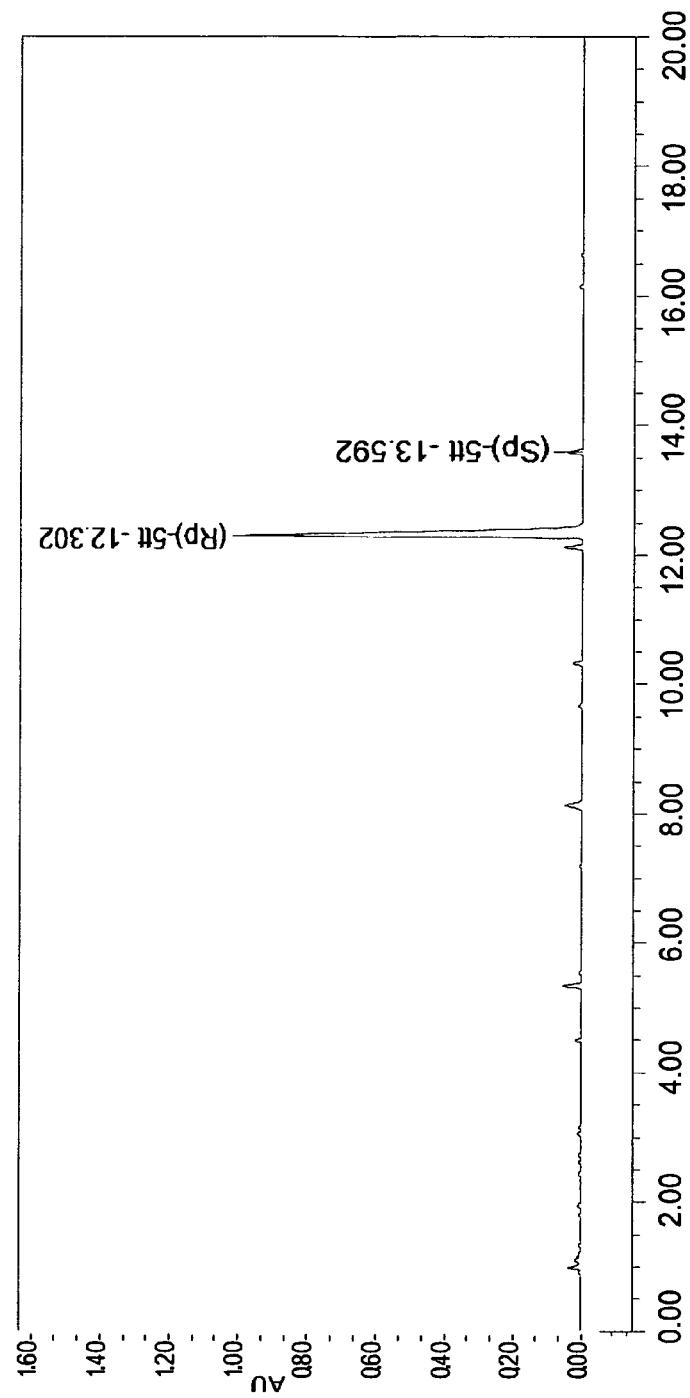

Example 90: Solid-Phase Synthesis of a Phosphorothioate Dimer, ($R_P$)-Ammonium thymidin-3'-yl thymidin-5'-yl phosphorothioate [($R_P$)-5tt] via Route B This compound was obtained by using "D-6 (52 µmol)" instead of "L-6 (52 µmol)" in a similar manner to the methods in Example 88, FIG. 15A. The product was identical to that of a control sample synthesized by the conventional H-phosphonate method. The yield of ($R_P$)-5tt was 95% ($R_P$:$S_P$=97:3). Retention time: 12.3 min (($S_P$)-5tt: 13.6 min). The UPLC profile is shown in FIG. 17A.

Figure 17B:
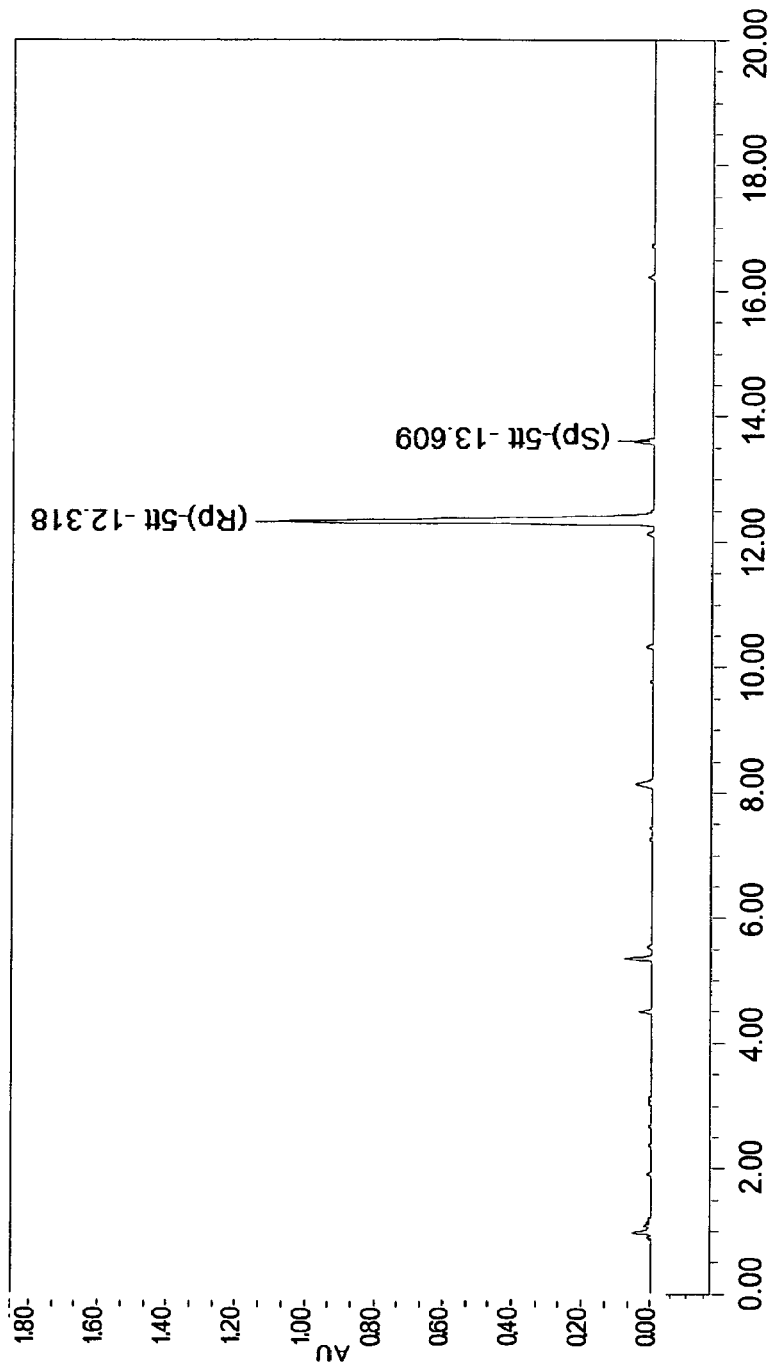

This compound was obtained by using "D-6 (52 µmol)" instead of "L-6 (52 µmol)" in a similar manner to the methods in Example 88, FIG. 15B. The product was identical to that of a control sample synthesized by the conventional H-phosphonate method. The yield of ($R_P$)-5tt was 94% ($R_P$:$S_P$=97:3). Retention time: 12.3 min (($S_P$)-5tt: 13.6 min). The UPLC profile is shown in FIG. 17B.

Example 91: Solid-Phase Synthesis of a Phosphorothioate Dimer, ($S_P$)-Ammonium 2'-deoxycytidin-3'-yl thymidin-5'-yl phosphorothioate [($S_P$)-5ct] via Route B

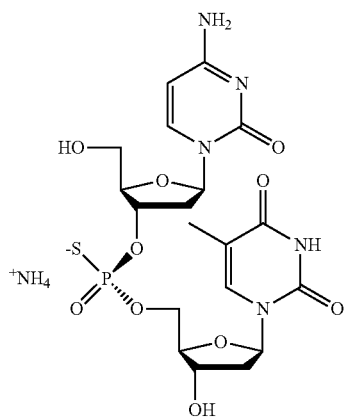

5ct

Figure 18:
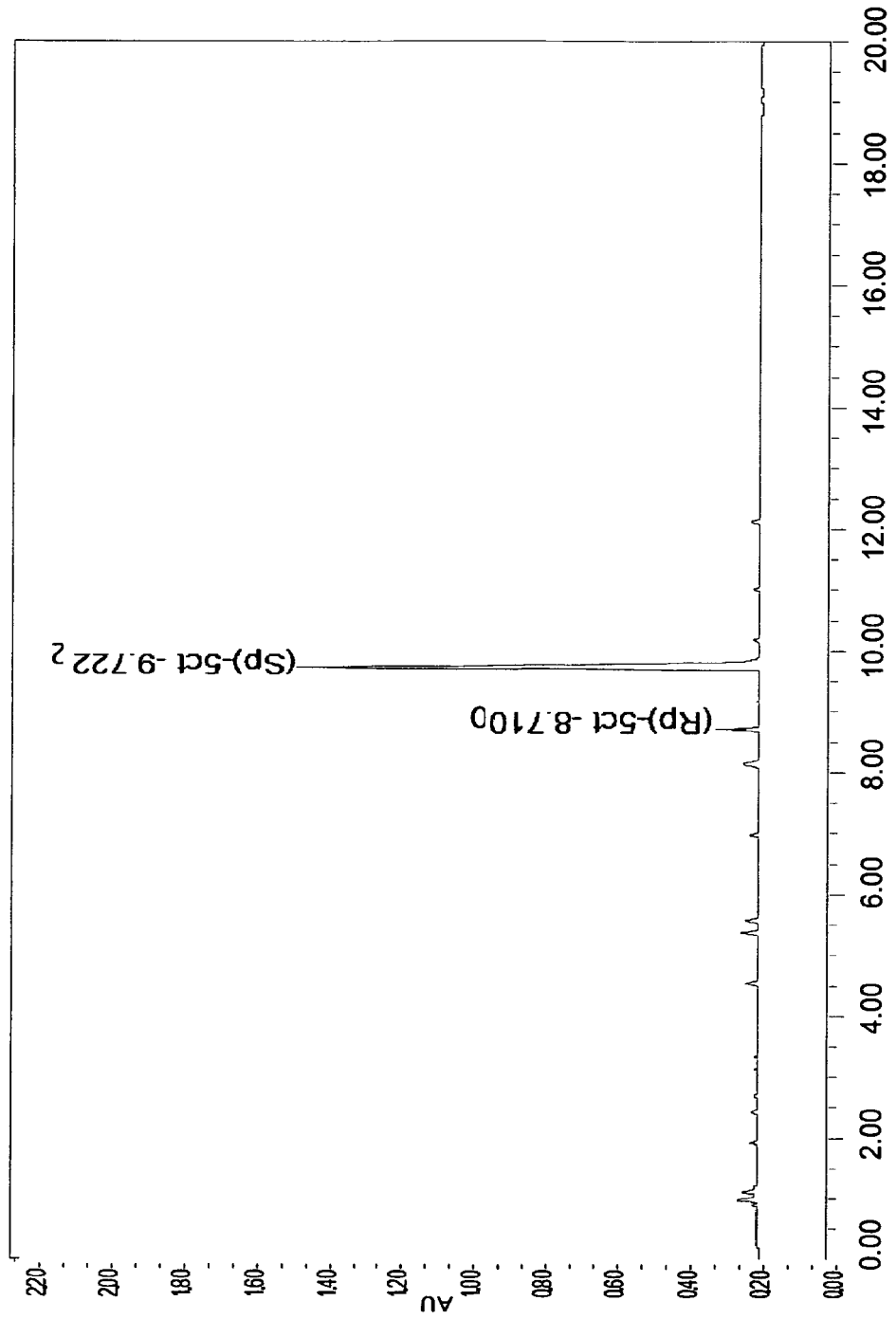

This compound was obtained by using "8-diazabicyclo[5.4.0]undec-7-enium 4-N-benzoyl-5'-O-(4,4'-dimethoxytrityl)-2'-deoxycytidin-3'-yl phosphonate (50 µmol)" instead of "8-diazabicyclo[5.4.0]undec-7-enium N³-benzoyl-5'-O-(4,4'-dimethoxytrityl)thymidin-3'-yl phosphonate (50 µmol)" in a similar manner to Example 88. The product was identical to that of a control sample synthesized by the conventional H-phosphonate method. The yield of ($S_P$)-5ct was 95% ($R_P$:$S_P$=4:96). Retention time: 9.7 min (($R_P$)-5ct: 8.7 min). The UPLC profile is shown in FIG. 18.

Figure 19:
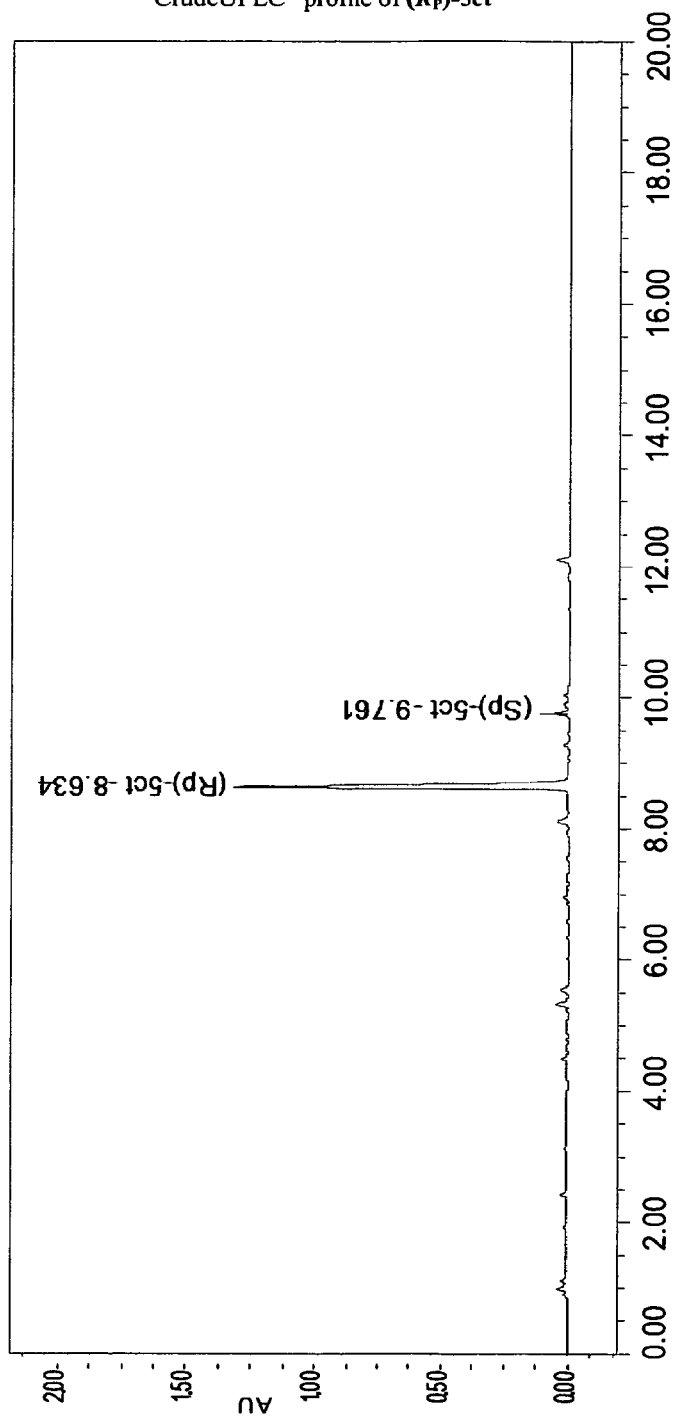

Example 92: Solid-Phase Synthesis of a Phosphorothioate Dimer, ($R_P$)-Ammonium 2'-deoxycytidin-3'-yl thymidin-5'-yl phosphorothioate [($R_P$)-5ct] via Route B This compound was obtained by using "D-6 (52 µmol)" instead of "L-6 (52 µmol)" in a similar manner to Example 91. The product was identical to that of a control sample synthesized by the conventional H-phosphonate method. The yield of ($R_P$)-5et was 96% ($R_P$:$S_P$=97:3). Retention time: 8.6 min (($S_P$)-5ct: 9.8 min). The UPLC profile is shown in FIG. 19.

Example 93: Solid-Phase Synthesis of a Phosphorothioate Dimer, ($S_P$)-Ammonium 2'-deoxyadenin-3'-yl thymidin-5'-yl phosphorothioate [($S_P$)-5at] via Route B

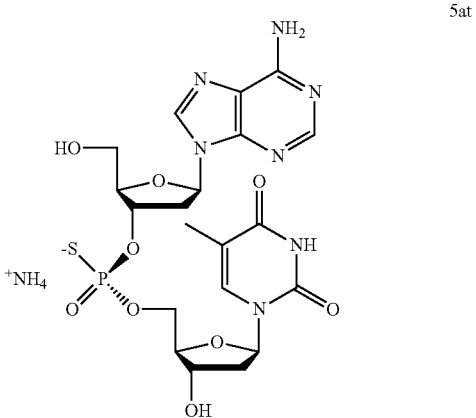

5at

This compound was obtained by using "8-diazabicyclo[5.4.0]undec-7-enium 6-N,N-dibenzoyl-5'-O-(4,4'-dimethoxytrityl)-2'-deoxyadenin-3'-yl phosphonate (50 µmol)" instead of "8-diazabicyclo[5.4.0]undec-7-enium N³-benzoyl-5'-O-(4,4'-dimethoxytrityl)thymidin-3'-yl phosphonate (50 µmol)" in a similar manner to Example 88. The product was identical to that of a control sample synthesized by the conventional H-phosphonate method. The yield of ($S_P$)-5at was 95% yield, $R_P$:$S_P$=5:95. Retention time: 14.0 min (($R_P$)-5at: 12.5 min). The UPLC profile is shown in FIG. 20A.

Figure 20A:
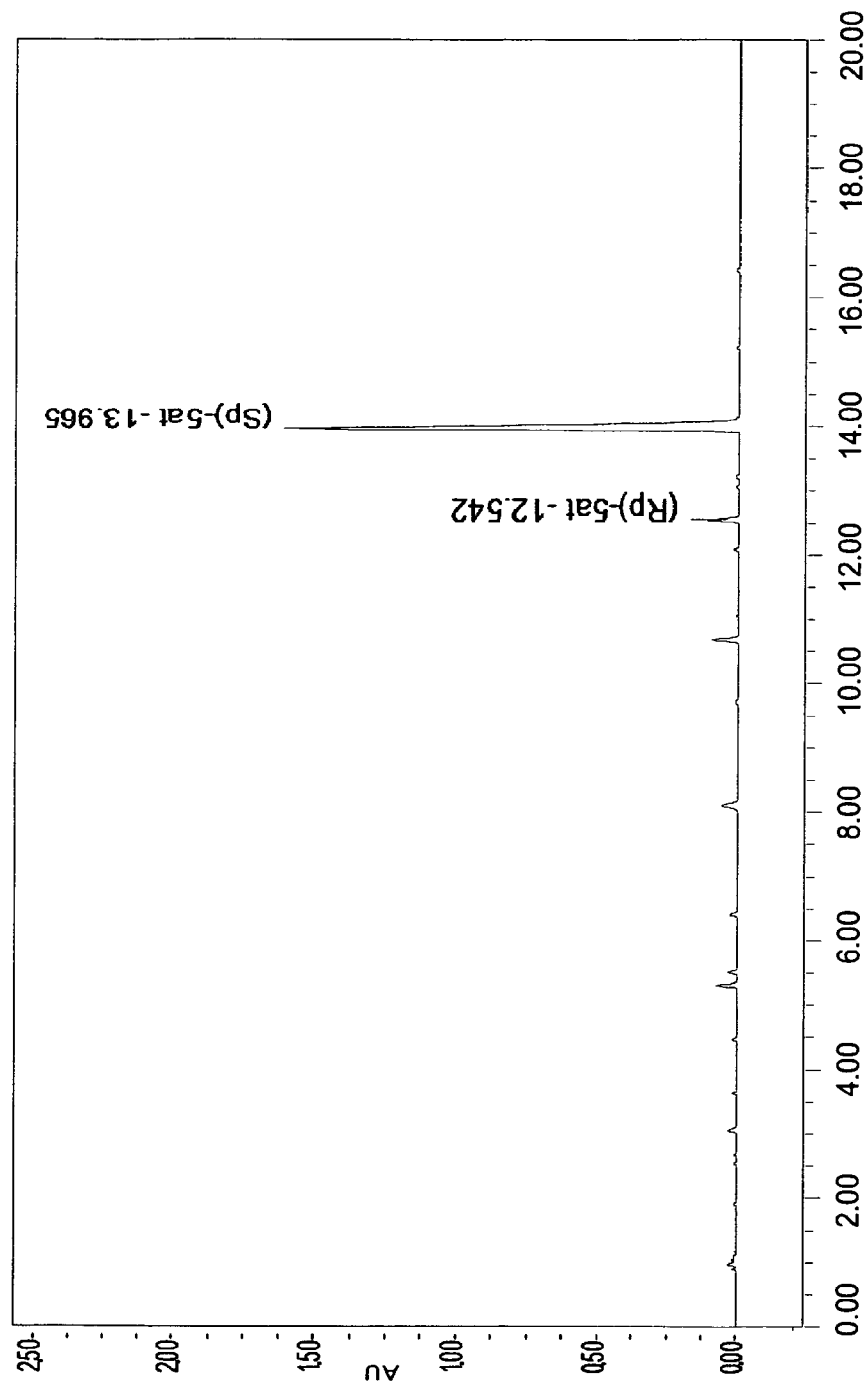
FIG. 20A. Crude UPLC® profile of $(S_P)$-5at
FIG. 20B. Crude UPLC® profile of $(S_P)$-5at
FIG. 21. Crude UPLC® profile of $(S_P)$-5at
FIG. 22A. Crude UPLC® profile of $(R_P)$-5at
FIG. 22B. Crude UPLC® profile of $(R_P)$-5at
FIG. 23. Crude UPLC® profile of $(S_P)$-5gt
FIG. 24. Crude UPLC® profile of $(R_P)$-5gt
FIG. 25. Crude UPLC® profile of $(S_P)$-7tt
FIG. 26. Crude UPLC® profile of $(R_P)$-7tt
FIG. 27. Crude UPLC® profile of $(S_P)$-8tt
FIG. 28. Crude UPLC® profile of $(R_P)$-8tt
FIG. 29A. Crude UPLC® profile of All-$(S_P)$-$[T_{PS}]_3$T
FIG. 29B. MALDI TOF-MS spectrum of All-$(S_P)$-$[T_{PS}]_3$T
FIG. 30A. Crude UPLC® profile of $(S_P, R_P, S_P)$-$[T_{PS}]_3$T
FIG. 30B. MALDI TOF-MS spectrum of $(S_P, R_P, S_P)$-$[T_{PS}]_3$T
FIG. 31A. Crude UPLC® profile of $(R_P, S_P, R_P)$-$[T_{PS}]_3$T
FIG. 31B. MALDI TOF-MS spectrum of $(R_P, S_P, R_P)$-$[T_{PS}]_3$T
FIG. 32A. Crude UPLC® profile of All-$(R_P)$-$[T_{PS}]_3$T
FIG. 32B. MALDI TOF-MS spectrum of All-$(R_P)$-$[T_{PS}]_3$T
FIG. 33A. Crude UPLC® profile of $(S_P)$-9u$_M$u
FIG. 33B. MALDI TOF-MS spectrum of $(S_P)$-9u$_M$u
FIG. 34A. Crude UPLC® profile of $(R_P)$-9uMu
FIG. 34B. MALDI TOF-MS spectrum of $(R_P)$-9u$_M$u
FIG. 35A. Crude UPLC® profile of $(S_P)$-10uFu
FIG. 35B. MALDI TOF-MS spectrum of $(S_P)$-10u$_F$u
FIG. 36A. Crude UPLC® profile of $(R_P)$-10uFu
FIG. 36B. MALDI TOF-MS spectrum of $(R_P)$-10u$_F$u
FIG. 37A. Crude UPLC® profile of $(S_P)$-11nt
FIG. 37B. MALDI TOF-MS spectrum of $(S_P)$-11nt
FIG. 38A. Crude UPLC® profile of $(R_P)$-11nt
FIG. 38B. MALDI TOF-MS spectrum of $(R_P)$-11nt

This compound was also obtained by using "BTC (32 µmol)" instead of "Ph₃PCl₂ (125 µmol)" in a similar manner to the method described in this example for FIG. 20A. The product was identical to that of a control sample synthesized by the conventional H-phosphonate method. The yield of ($S_P$)-5at was 94% ($R_P$:$S_P$=5:95). Retention time: 13.9 min (($R_P$)-5at: 12.5 min). The UPLC profile is shown in FIG. 20B.

Figure 21:
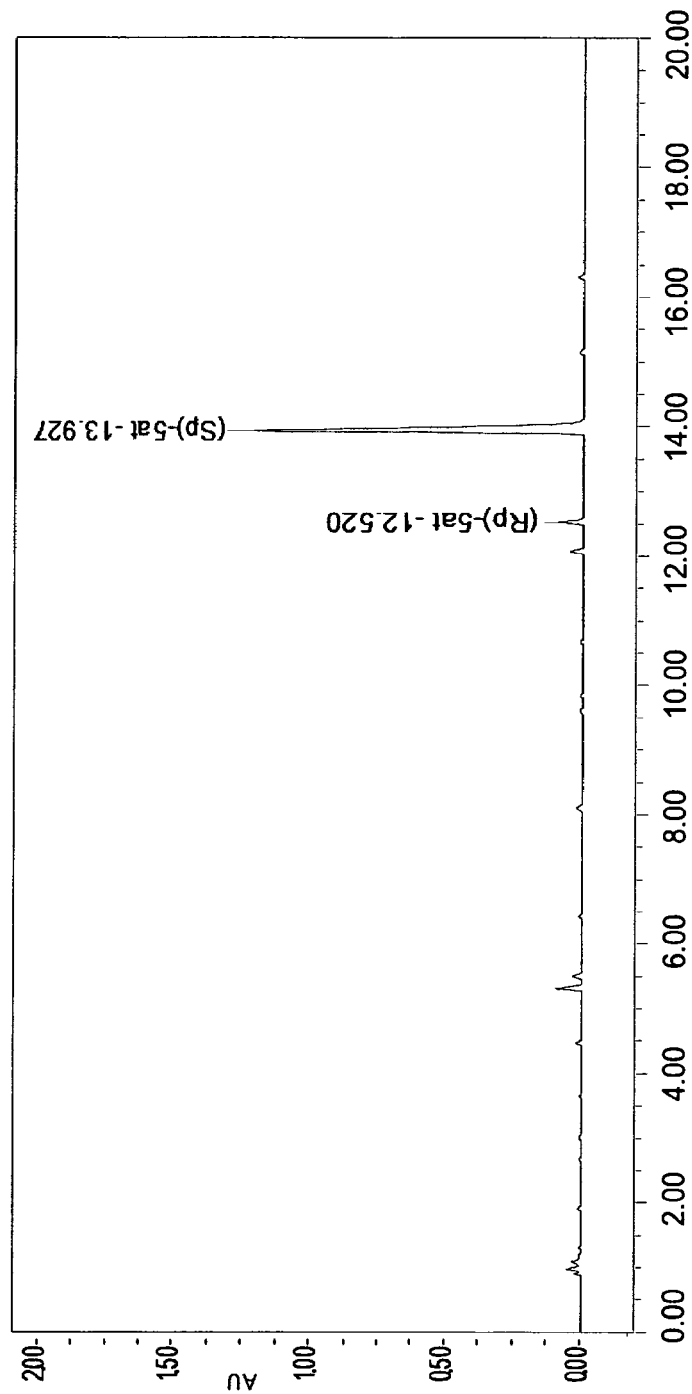

Example 94: Solid-Phase Synthesis of a Phosphorothioate Dimer, ($S_P$)-Ammonium 2'-deoxyadenin-3'-yl thymidin-5'-yl phosphorothioate [($S_P$)-5at] via Route B This compound was obtained by using "8-diazabicyclo[5.4.0]undec-7-enium 6-N-((dimethylamino)methylene)-5'-O-(4,4'-dimethoxytrityl)-2'-deoxyadenin-3'-yl phosphonate (50 µmol)" instead of "8-diazabicyclo[5.4.0]undec-7-enium N³-benzoyl-5'-O-(4,4'-dimethoxytrityl)thymidin-3'-yl phosphonate (50 µmol)" in a similar manner to Example 88. The product was identical to that of a control sample synthesized by the conventional H-phosphonate method. The yield of ($S_P$)-5at was 91% yield, $R_P$:$S_P$=5:95. Retention time: 13.9 min (($R_P$)-5at: 12.5 min). The UPLC profile is shown in FIG. 21.

Figure 22A:
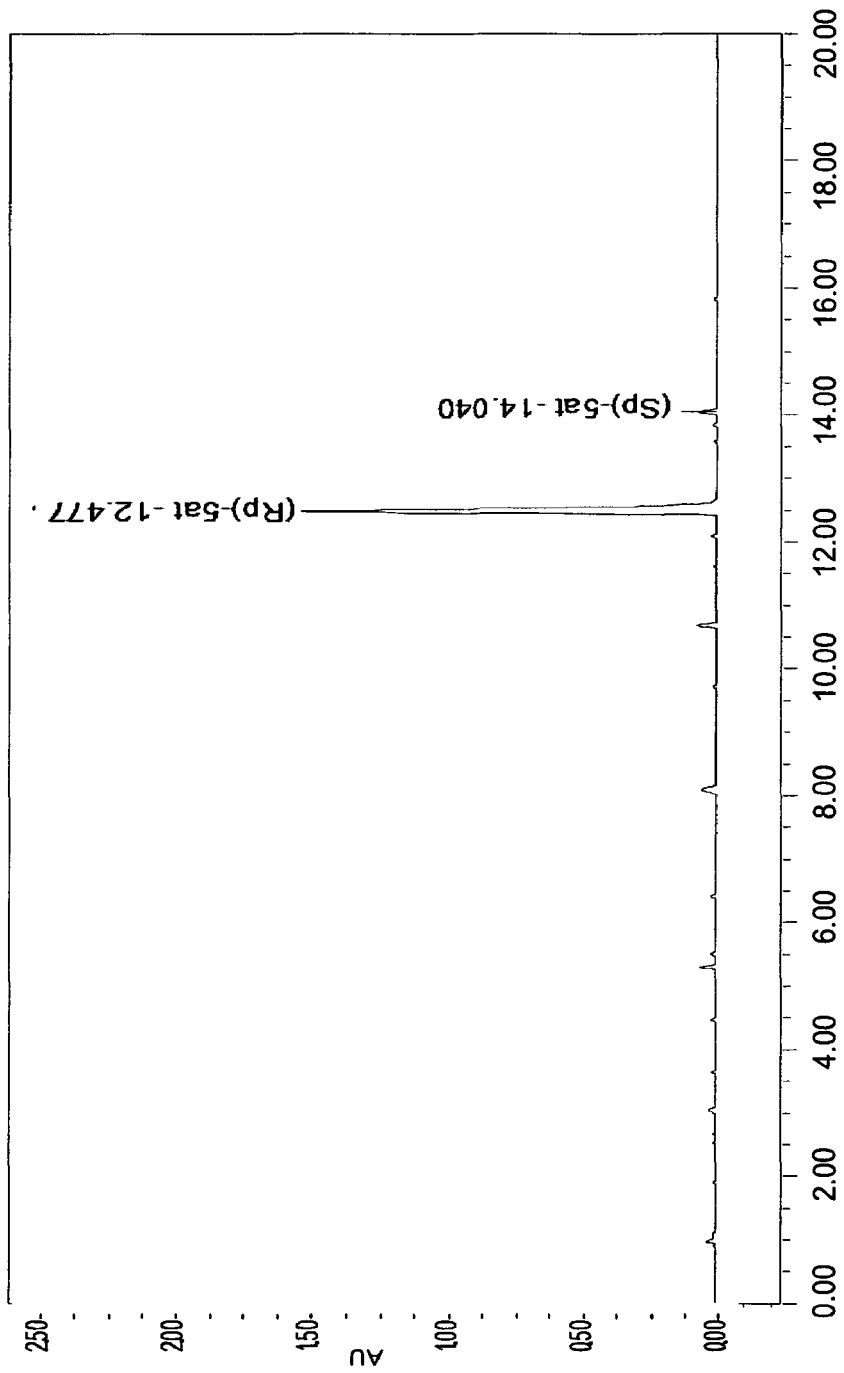

Example 95: Solid-Phase Synthesis of a Phosphorothioate Dimer, ($R_P$)-Ammonium 2'-deoxyadenin-3'-yl thymidin-5'-yl phosphorothioate [($R_P$)-5at] via Route B This compound was obtained by using "D-6 (52 µmol)" instead of "L-6 (52 µmol)" in a similar manner to the method for Example 93, FIG. 20A. The product was identical to that of a control sample synthesized by the conventional H-phosphonate method. The yield of $(R_P)$-5at was 96% yield, $R_P:S_P$=97:3. Retention time: 12.5 min (($S_P$)-5at: 14.0 min). The UPLC profile is shown in FIG. 22A.

Figure 20B:
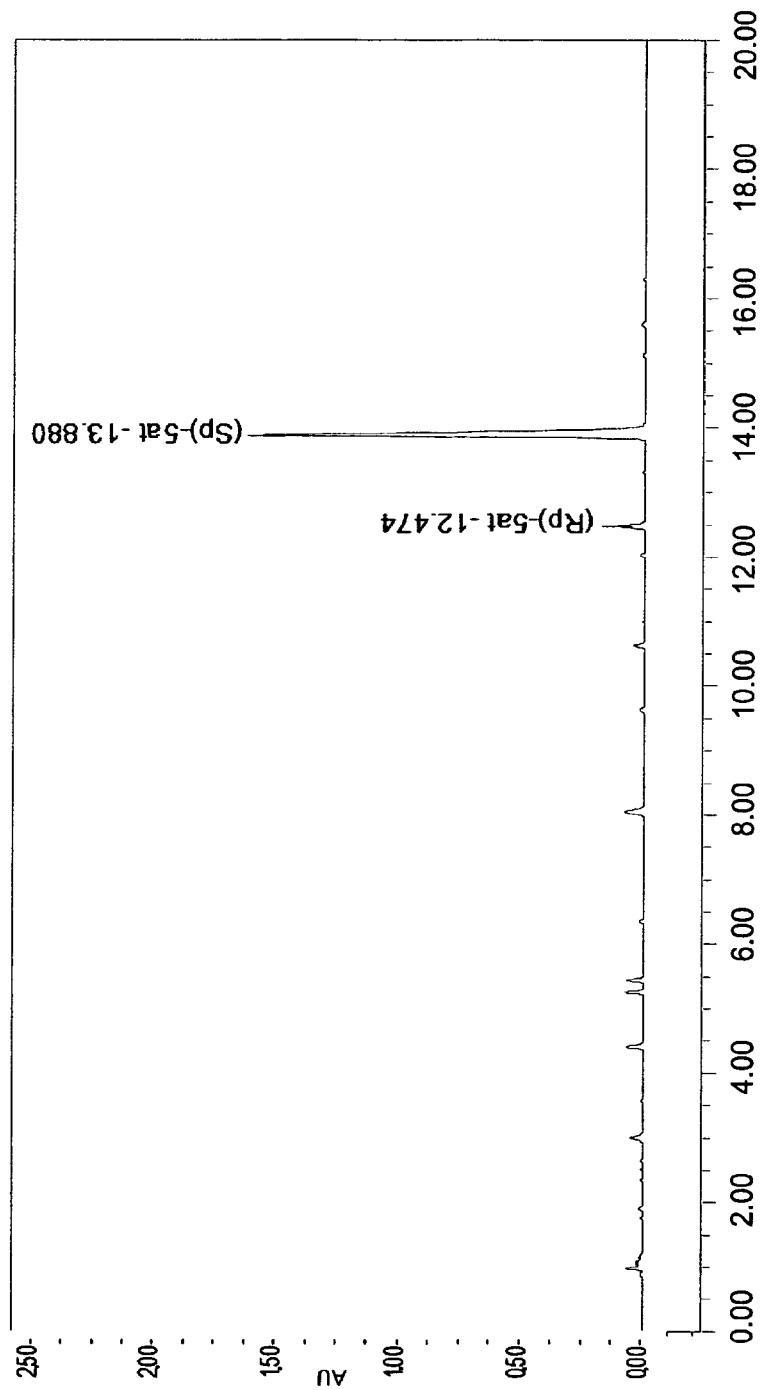
Figure 22B:
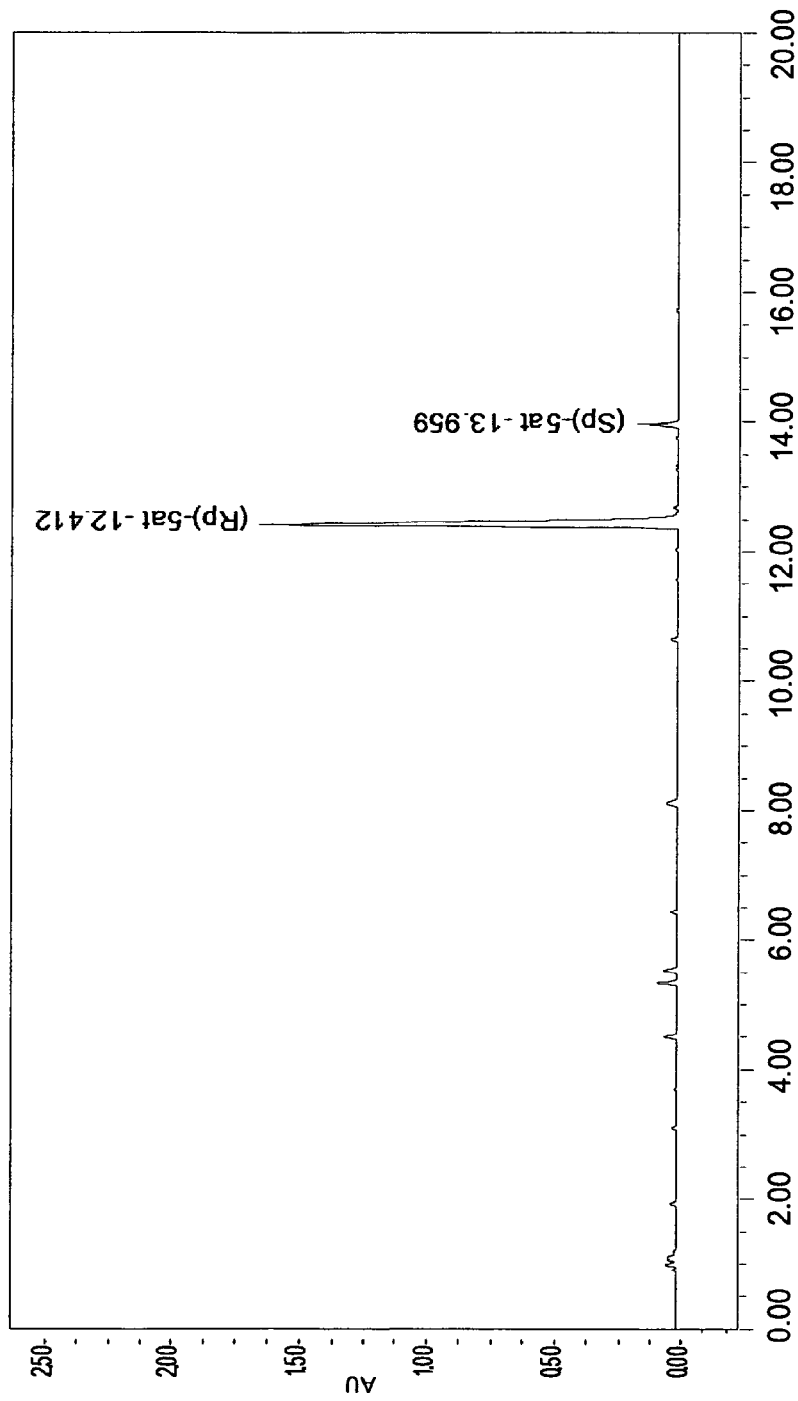

This compound was obtained by using "D-6 (52 μmol)" instead of "L-6 (52 μmol)" in a similar manner to the method for Example 93, FIG. 20B. The product was identical to that of a control sample synthesized by the conventional H-phosphonate method. The yield of $(R_P)$-5at was 94% ($R_P:S_P$=95:5). Retention time: 12.4 min (($R_P$)-5at: 14.0 min). The UPLC profile is shown in FIG. 22B.

Figure 23:
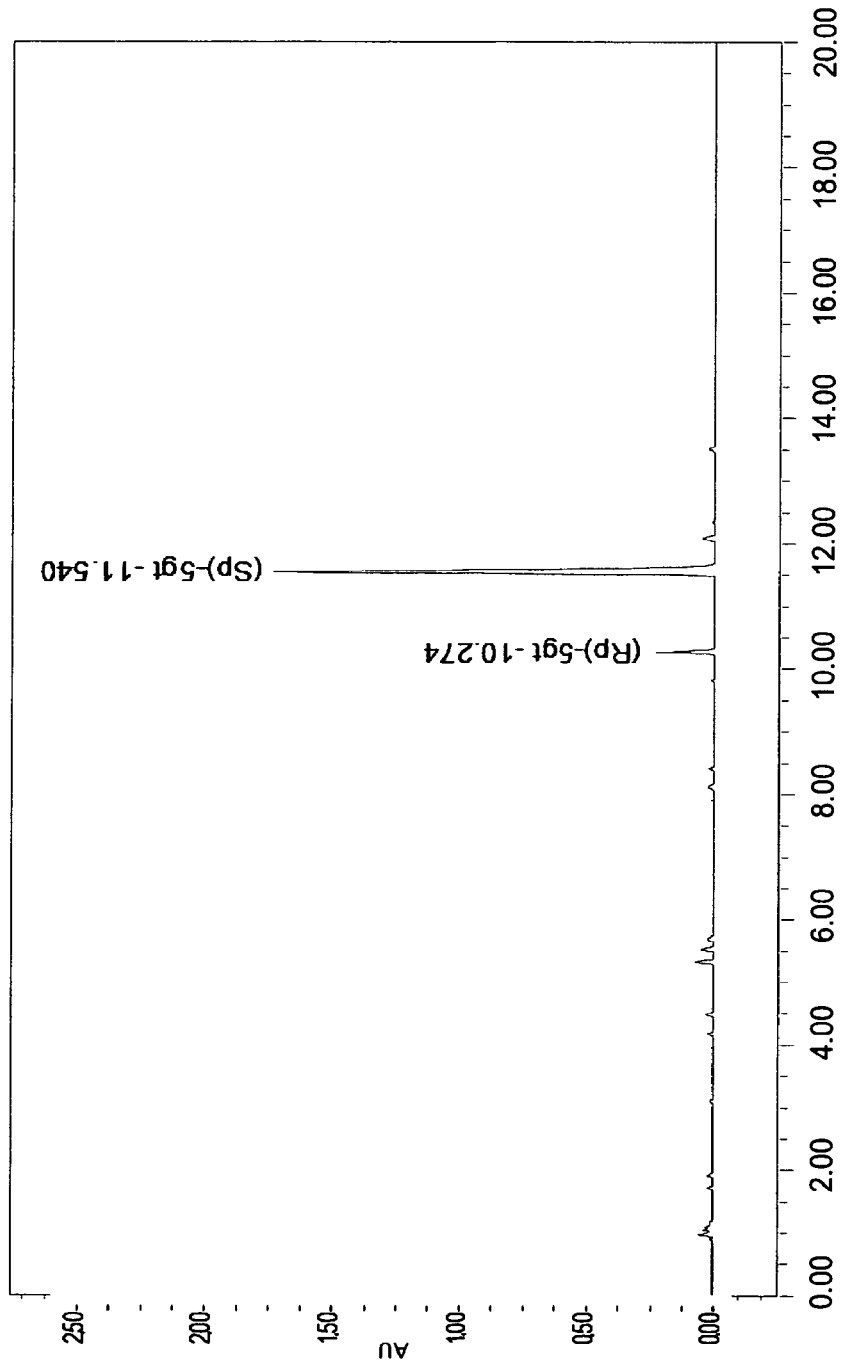

Example 96: Solid-Phase Synthesis of a Phosphorothioate Dimer, $(S_P)$-Ammonium 2'-deoxyguanin-3'-yl thymidin-5'-yl phosphorothioate [$(S_P)$-5gt] via Route B This compound was obtained by using "8-diazabicyclo[5.4.0]undec-7-enium $O^6$-cyanoethyl-2-N-phenoxyacetyl-5'-O-(4,4'-dimethoxytrityl)-2'-deoxyguanin-3'-yl phosphonate (50 μmol)" instead of "8-diazabicyclo[5.4.0]undec-7-enium $N^3$-benzoyl-5'-O-(4,4'-dimethoxytrityl)thymidin-3'-yl phosphonate (50 μmol)" in a similar manner to Example 88. The product was identical to that of a control sample synthesized by the conventional H-phosphonate method. The yield of $(S_P)$-5gt was 95% ($R_P:S_P$=6:94). Retention time: 11.5 min (($R_P$)-5gt: 10.3 min). The UPLC profile is shown in FIG. 23.

Figure 24:
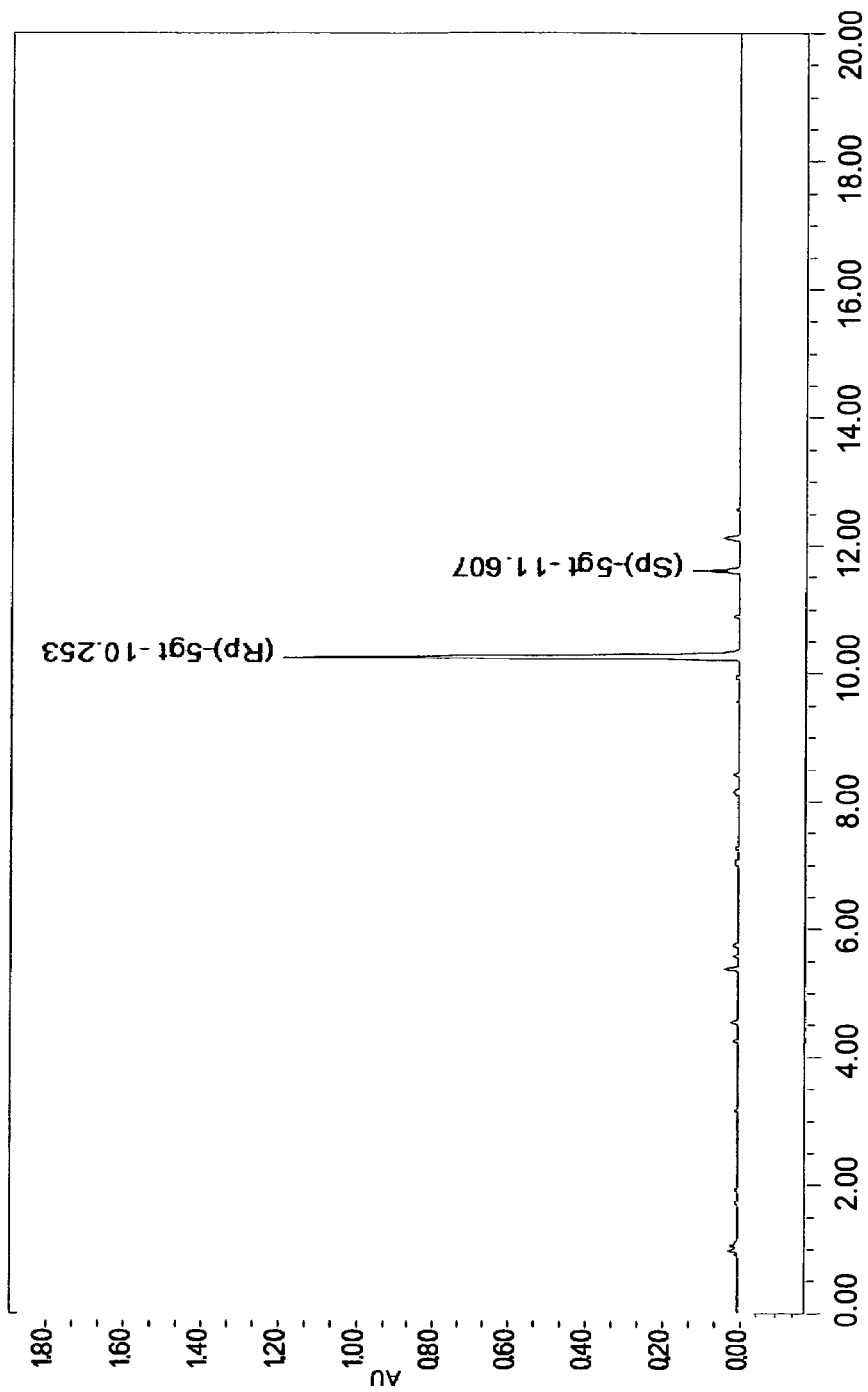

Example 97: Solid-Phase Synthesis of a Phosphorothioate Dimer, $(R_P)$-Ammonium 2'-deoxyguanin-3'-yl thymidin-5'-yl phosphorothioate [$(R_P)$-5gt] via Route B This compound was obtained by using "D-2 (52 μmol)" instead of "L-2 (52 μmol)" in a similar manner to Example 96. The product was identical to that of a control sample synthesized by the conventional H-phosphonate method. The yield of $(R_P)$-5gt was 95% ($R_P:S_P$=94:6). Retention time: 10.3 min (($S_P$)-5gt: 11.6 min). The UPLC profile is shown in FIG. 24.

Example 98: Solid-Phase Synthesis of a Boranophoshate Dimer, $(S_P)$-Ammonium thymidin-3'-yl thymidin-5'-yl boranophosphate [$(S_P)$-7tt] via Route B

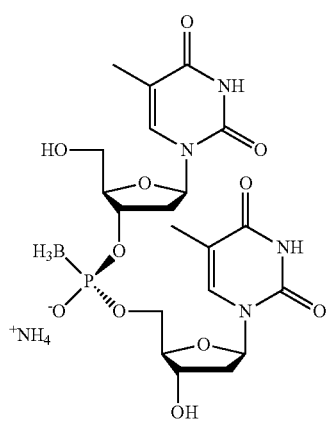

Figure 25:
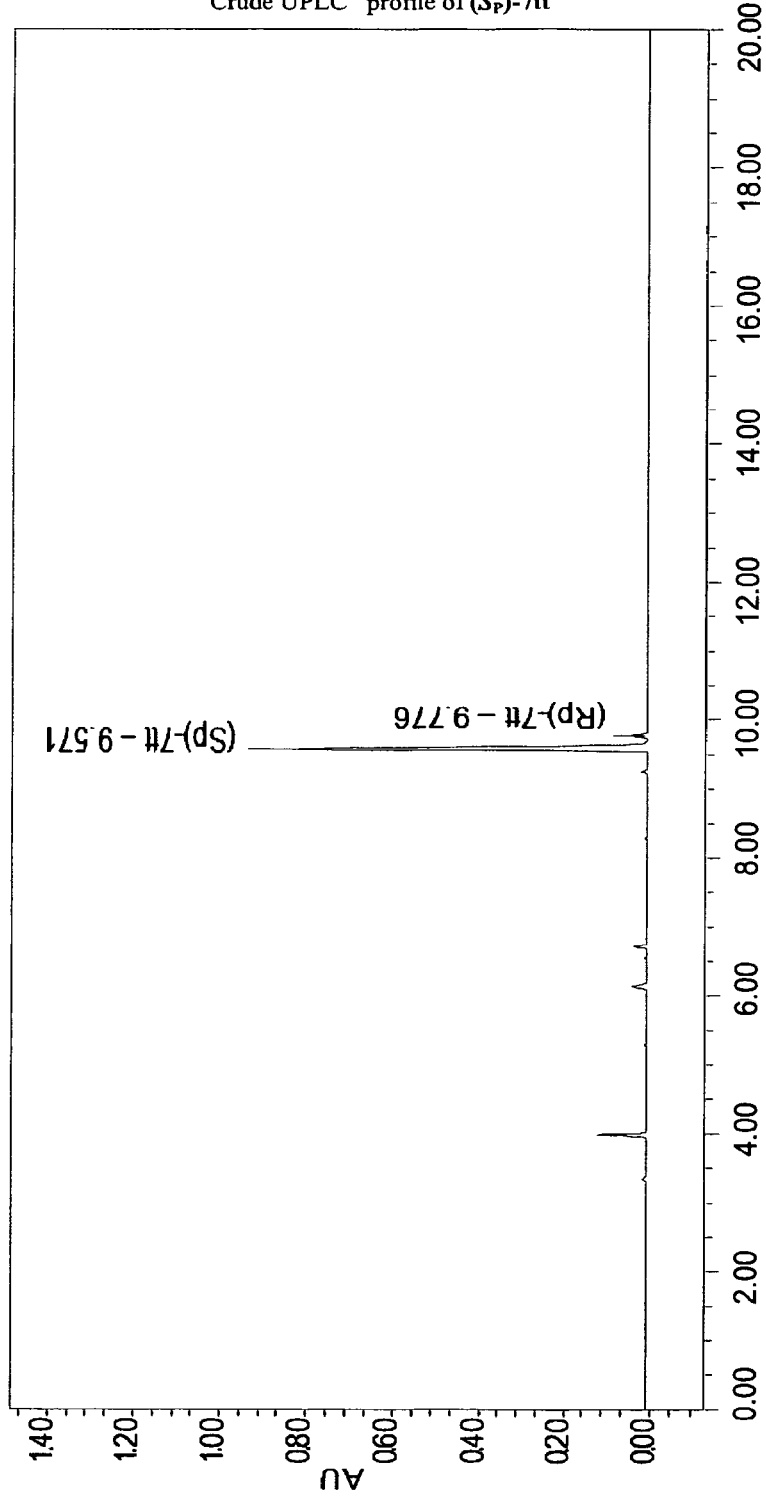

7tt $N^3$-Benzoyl-5'-O-(4,4'-dimethoxytrityl)thymidine-loaded HCP resin (16.4 mg; 30.5 μmol/g, 0.5 μmol) via a succinyl linker was treated with 1% TFA/DCM (3×1 mL) for the removal of the 5'-O-DMTr group, washed with DCM (3×1 mL) and dry MeCN (3×1 mL), and dried in vacuo. Preactivated monomer solution (200 μL, 50 μmol; which consists of 8-diazabicyclo[5.4.0]undec-7-enium $N^3$-benzoyl-5'-O-(4,4'-dimethoxytrityl)thymidin-3'-yl phosphonate (50 μmol, for H-phosphonate monoester), MeCN-CMP (9:1, v/v, for solvent), BTC (32 μmol, for condensing reagent), and D-6 (52 μmol, for aminoalcohol)) was added followed by the addition of 5 M CMPT/MeCN (50 μL, 250 μmol). Being stirred for 2 min, the reaction solution was removed, and the resin was washed with MeCN (3×1 mL), DCM (3×1 mL), and dried under the reduced pressure (>5 min). The 5'-O-DMTr group and the chiral auxiliary was simultaneously removed by treatment with 1% TFA in DCM (3×1 mL), and the resin was washed with DCM (3×1 mL) and dry MeCN (3×1 mL), and dried in vacuo. The resulting intermediate on the resin was boronated by treatment with a mixture of $BH_3$—$SMe_2$-BSA-DMAc (1 mL, 1:1:8, v/v/v) for 15 min, the resin was then washed with DMAc (3×1 mL), MeCN (3×1 mL), and MeOH (3×1 mL). The boranophosphate dimer on the resin was then treated with 2 M $NH_3$/EtOH (2 mL) for 12 h at room temperature to remove the protecting groups of the nucleobases and also to release the dimer from the resin. The resin was removed by filtration and washed with MeOH. The filtrate was concentrated to dryness. The residue was dissolved in $H_2O$ (2 mL), washed with $Et_2O$ (3×2 mL), and the combined washings were back-extracted with $H_2O$ (2 mL). The combined aqueous layers were concentrated to dryness. The resulting crude product was analyzed by reversed-phase UPLC® with a linear gradient of 0-15% MeCN in 0.1 M ammonium acetate buffer (pH 7.0) for 15 min at 60° C. at a rate of 0.5 ml/min. The product was identical to that of a control sample synthesized by the conventional H-phosphonate method. The yield of $(S_P)$-7tt was determined by a UV absorbance measurement at 260 nm with the molar extinction coefficient of an approximate value for natural TT dimer (16800). The yield of $(S_P)$-7tt was 89% ($R_P:S_P$=4:96). Retention time: 9.6 min (($R_P$)-7tt: 9.8 min). The UPLC profile is shown in FIG. 25.

Figure 26:
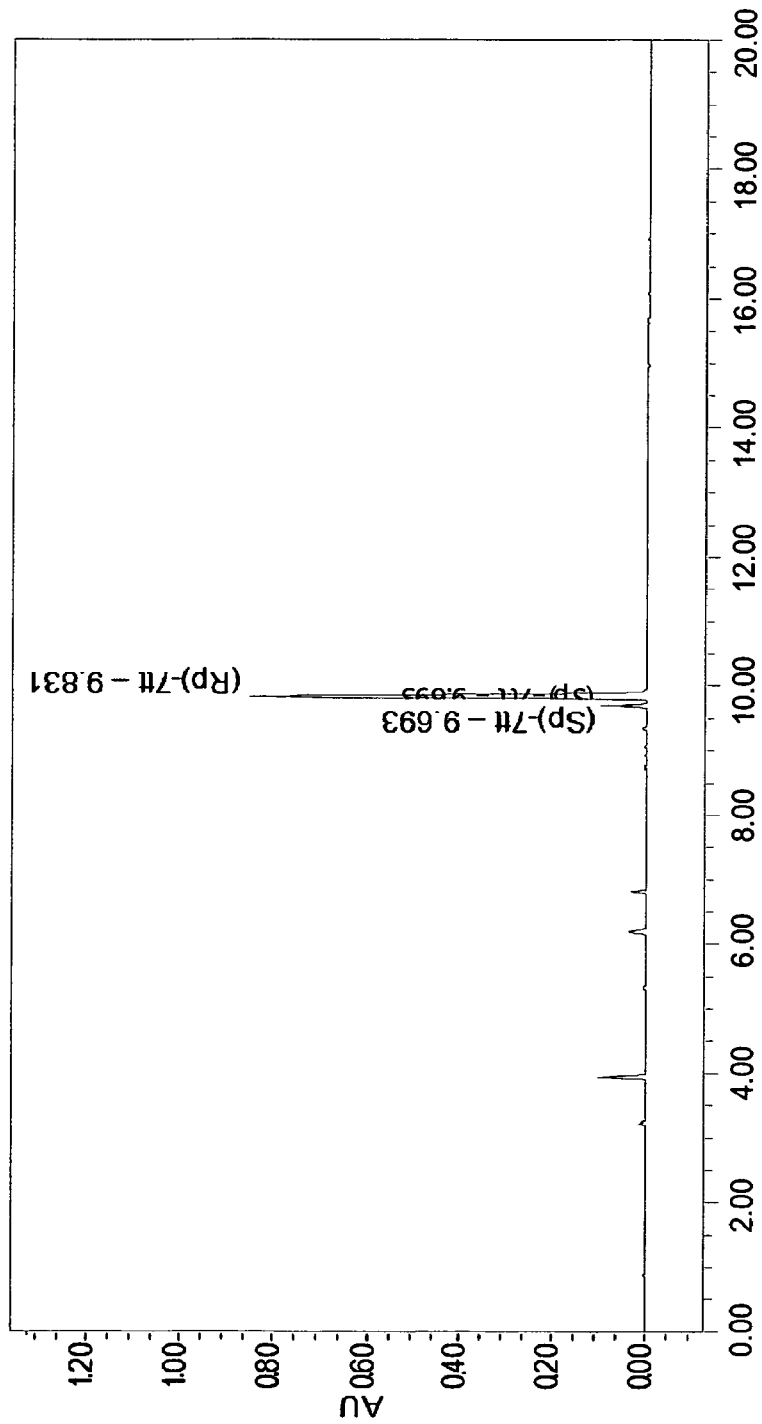

Example 99: Solid-Phase Synthesis of a Boranophoshate Dimer, $(R_P)$-Ammonium thymidin-3'-yl thymidin-5'-yl boranophosphate [$(R_P)$-7tt] via Route B This compound was obtained by using "L-2 (52 μmol)" instead of "D-2 (52 μmol)" in a similar manner to Example 98. The product was identical to that of a control sample synthesized by the conventional H-phosphonate method. The yield of $(R_P)$-7tt was determined by a UV absorbance measurement at 260 nm with the molar extinction coefficient of an approximate value for natural TT dimer (16800). The yield of $(R_P)$-7tt was 90% yield, $R_P:S_P$=95:5. Retention time: 9.8 min (($S_P$)-7tt: 9.7 min). The UPLC profile is shown in FIG. 26.

Example 100: Solid-Phase Synthesis of a N-[(2-dimethylamino)ethyl]phosphoramidate Dimer, ($S_P$)-Thymidin-3'-yl thymidin-5'-yl N-[(2-dimethylamino)ethyl]phosphoramidate [($S_P$)-8tt] via Route B

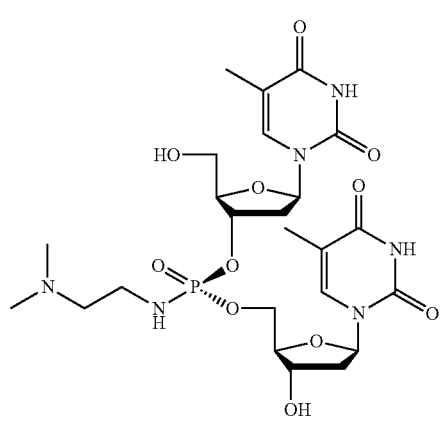

8tt

Figure 27:
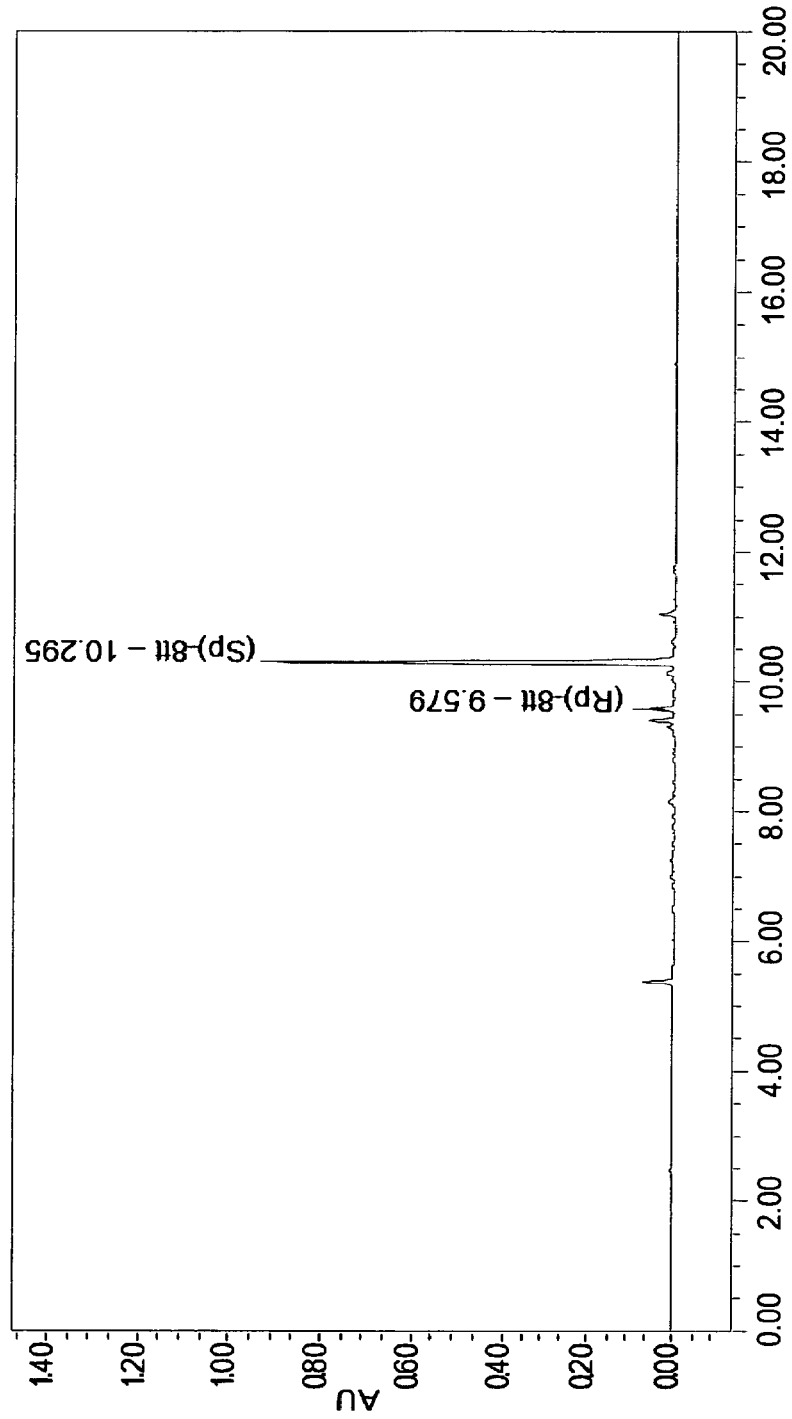

N³-Benzoyl-5'-O-(4,4'-dimethoxytrityl)thymidine-loaded HCP resin (16.4 mg; 30.5 μmol/g, 0.5 μmol) via a succinyl linker was treated with 1% TFA/DCM (3×1 mL) for the removal of the 5'-O-DMTr group, washed with DCM (3×1 mL) and dry MeCN (3×1 mL), and dried in vacuo. Pre-activated monomer solution (200 μL, 50 μmol; which consists of 8-diazabicyclo[5.4.0]undec-7-enium N³-benzoyl-5'-O-(4,4'-dimethoxytrityl)thymidin-3'-yl phosphonate (50 μmol, for H-phosphonate monoester), MeCN-CMP (9:1, v/v, for solvent), BTC (32 μmol, for condensing reagent), and L-6 (52 μmol, for aminoalcohol)) was added followed by the addition of 5 M CMPT/MeCN (50 μL, 250 μmol). Being stirred for 2 min, the reaction solution was removed, and the resin was washed with MeCN (3×1 mL), DCM (3×1 mL), and dried under the reduced pressure (>5 min). The 5'-O-DMTr group and the chiral auxiliary was simultaneously removed by treatment with 1% TFA in DCM (3×1 mL), and the resin was washed with DCM (3×1 mL) and dry MeCN (3×1 mL), and dried in vacuo. The resulting intermediate on the resing was amidated by treatment with a mixture of $CCl_4$-$Me_2N(CH_2)_2NH_2$ (1 mL, 1:9, v/v) for 30 min, the resin was then washed with DCM (3×1 mL). The phosphoramidate dimer on the resin was then treated with 2 M $NH_3$/EtOH (2 mL) for 12 h at room temperature to remove the protecting groups of the nucleobases and also to release the dimer from the resin. The resin was removed by filtration and washed with MeOH. The filtrate was concentrated to dryness. The residue was dissolved in $H_2O$ (2 mL), washed with $Et_2O$ (3×2 mL), and the combined washings were back-extracted with $H_2O$ (2 mL). The combined aqueous layers were concentrated to dryness. The resulting crude product was analyzed by reversed-phase UPLC® with a linear gradient of 0-20% MeOH in 0.1 M ammonium acetate buffer (pH 7.0) for 15 min at 55° C. at a rate of 0.4 ml/min. The product was identical to that of a control sample synthesized by the conventional H-phosphonate method. The yield of ($S_P$)-8tt was determined by a UV absorbance measurement at 260 nm with the molar extinction coefficient of an approximate value for natural TT dimer (16800). The yield of ($S_P$)-8tt was 90% ($R_P$:$S_P$=6:94). Retention time: 10.3 min (($R_P$)-8tt: 9.6 min). The UPLC profile is shown in FIG. 27.

Figure 28:
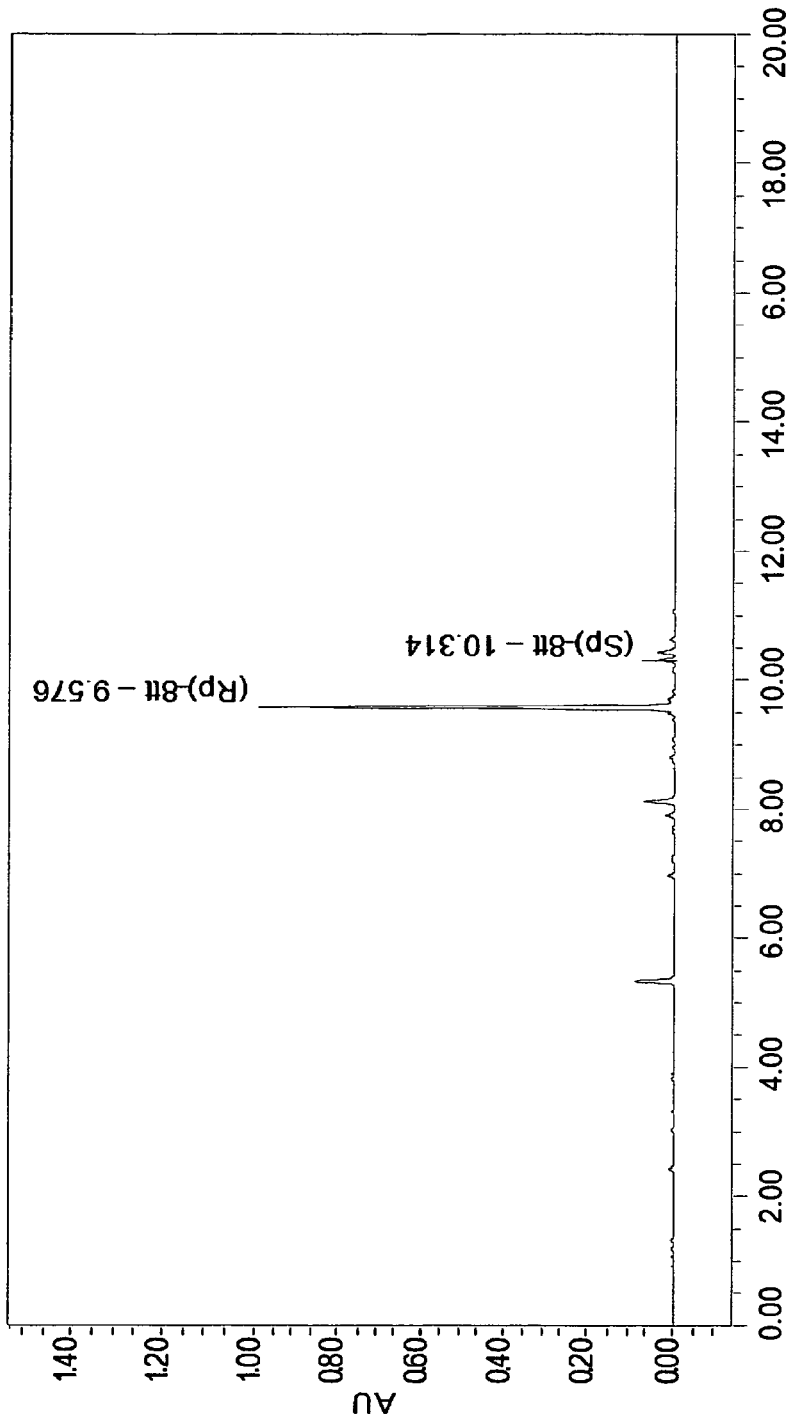

Example 101: Solid-Phase Synthesis of a N-[(2-dimethylamino)ethyl]phosphoramidate Dimer, ($R_P$)-Thymidin-3'-yl thymidin-5'-yl N-[(2-dimethylamino)ethyl]phosphoramidate [($R_P$)-8tt] via Route B This compound was obtained by using "D-2 (52 μmol)" instead of "L-2 (52 μmol)" in a similar manner to Example 100. The product was identical to that of a control sample synthesized by the conventional H-phosphonate method. The yield of ($R_P$)-8tt was determined by a UV absorbance measurement at 260 nm with the molar extinction coefficient of an approximate value for natural TT dimer (16800). The yield of ($R_P$)-8tt was 86% yield, $R_P$:$S_P$=96:4. Retention time: 9.6 min (($S_P$)-8tt: 10.3 min). The UPLC profile is shown in FIG. 28.

Figure 29A:
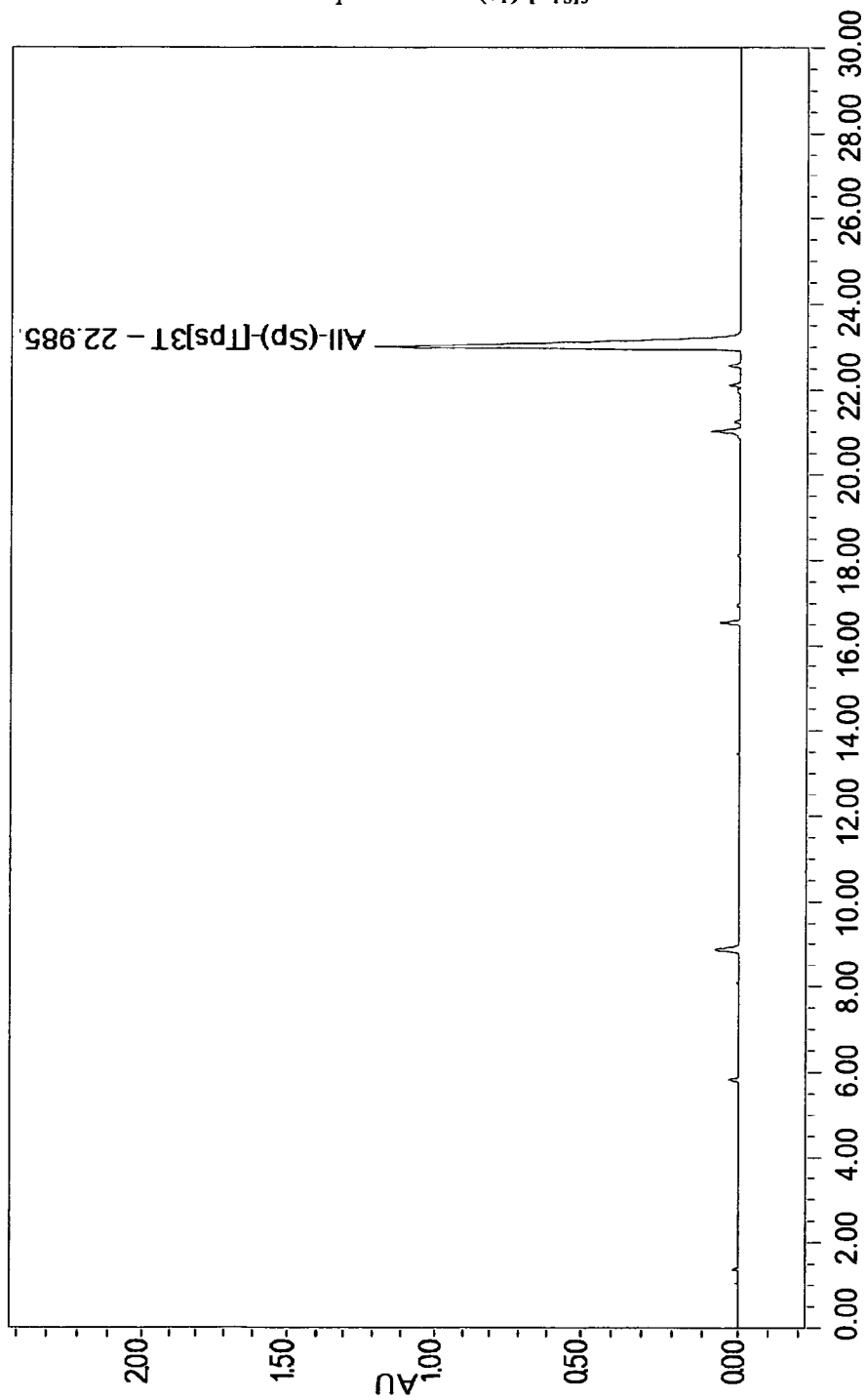
Figure 29B:
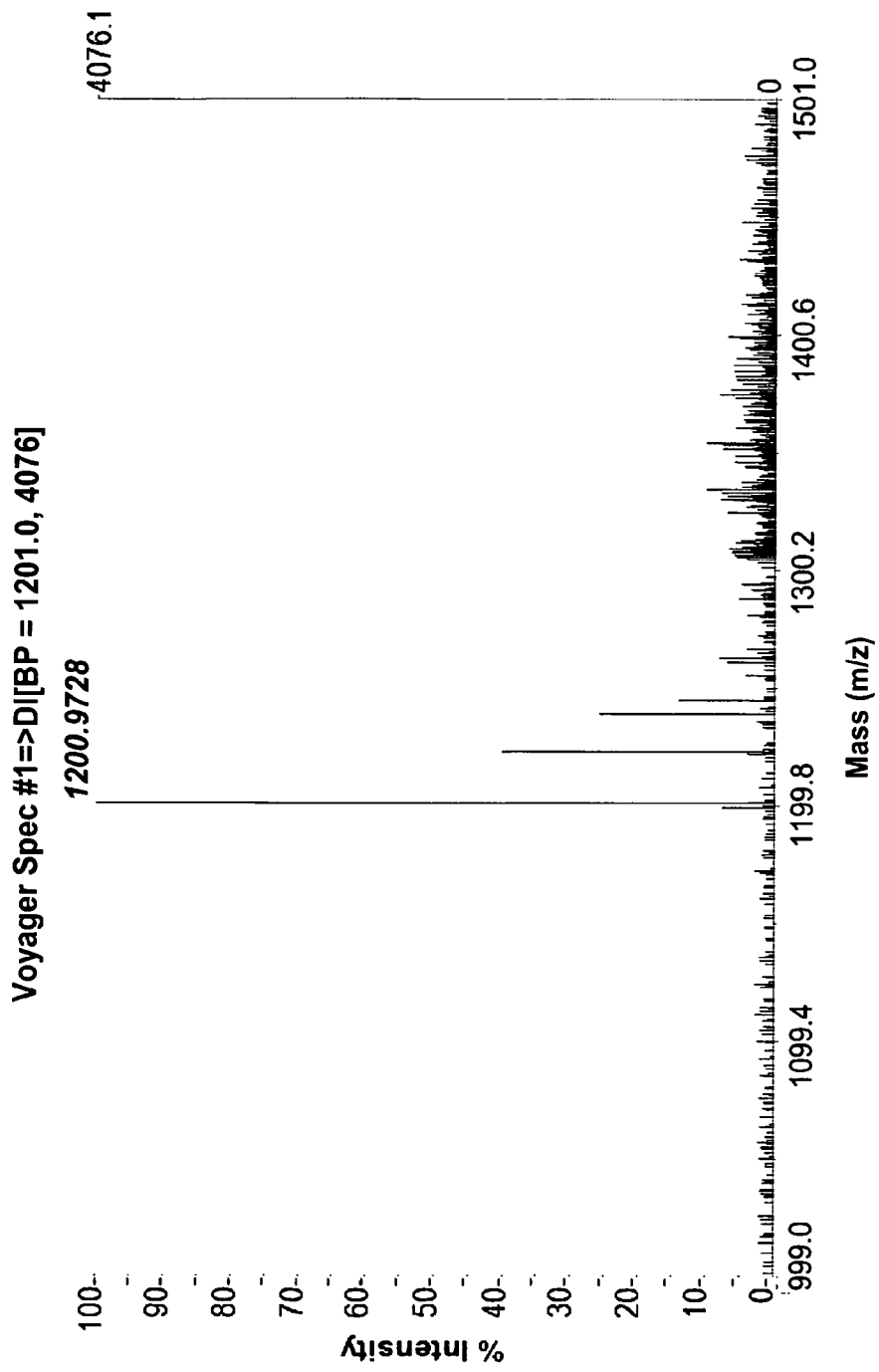

Example 102: Solid-Phase Synthesis of a Phosphorothioate Tetramer, All-($S_P$)-[$T_{PS}$]$_3$T (Phosphorothioate) Via Route A 5'-O-(4,4'-dimethoxytrityl)thymidine-loaded HCP resin (0.5 μmol) via a succinyl linker was used for the synthesis. Repeating the steps in Table 3 performs chain elongation. After the chain elongation, the 5'-O-DMTr group was removed by treatment with 3% DCA/DCM (3×1 mL), and washed with DCM (3×1 mL). The phosphorothioate tetramer on the resin was then treated with 25% $NH_3$ for 12 h at 55° C. to remove the chiral auxiliaries and the protecting groups of the nucleobases and also to release the tetramer from the resin. The resin was removed by filtration and washed with $H_2O$. The filtrate was concentrated to dryness. The residue was dissolved in $H_2O$ (2 mL), washed with $Et_2O$ (3×2 mL), and the combined washings were back-extracted with $H_2O$ (2 mL). The combined aqueous layers were concentrated to dryness. The resulting crude product was analyzed by reversed-phase UPLC® with a linear gradient of 0-30% MeOH in 0.1 M ammonium acetate buffer (pH 7.0) for 30 min at 55° C. at a rate of 0.4 ml/min. The product was identical to that of a control sample synthesized by the conventional phosphoramidite method. The yield of the product was determined by a UV absorbance measurement at 260 nm with the molar extinction coefficient of an approximate value for natural $T_4$ tetramer (33000). Average coupling yield was 96%, optical purity was 96% (average: 99%). Retention time: 23.0 min; MS (MALDI TOF-MS) m/z Calcd for $C_{40}H_{52}N_8O_{23}P_3S_3$ [M-H]⁻ 1201.15, found 1200.97. The UPLC profile is shown in FIG. 29.

TABLE 3

| step | operation | reagents and solvents | time |
|---|---|---|---|
| 1 | detritylation | 3% DCA/DCM | 3 × 30 s |
| 2 | washing | (i) DCM (ii) dry MeCN (iii) drying in vacuo. | — |

TABLE 3-continued

| step | operation | reagents and solvents | time |
|---|---|---|---|
| 3 | coupling | 5M CMPT/MeCN (50 µL, 250 µmol) pre-activated ($R_P$)- or ($S_P$)-monomer solution (200 µL, 25 µmol)* | 5 min |
| 4 | washing | (i) MeCN (ii) drying in vacuo. | — |
| 5 | capping | (i) 0.5M CF$_3$COIm/dry THF (ii) 1M DMAN/dry THF | 30 s |
| 6 | washing | (i) dry MeCN (ii) drying in vacuo. | — |
| 7 | sulfuryzation | 0.3M DTD/MeCN | 5 min |
| 8 | washing | (i) MeCN (ii) DCM | — |

*Preparation of "pre-activated ($R_P$)- or ($S_P$)-monomer solution"

8-Diazabicyclo[5.4.0]undec-7-enium $N^3$-benzoyl-5'-O-(4,4'-dimethoxytrityl)thymidin-3'-yl phosphonate (25 µmol) was dried by repeated coevaporations with dry pyridine and dry toluene, then dissolved in dry MeCN-CMP (9:1, v/v). To the solution, Ph$_3$PCl$_2$ (62.5 µmol) was added, and stirred for 10 min. L-2 (30 µmol; D-2 for "$S_P$" solution) was then added and stirred for additional 10 min to give pre-activated monomer solution.

Figure 30A:
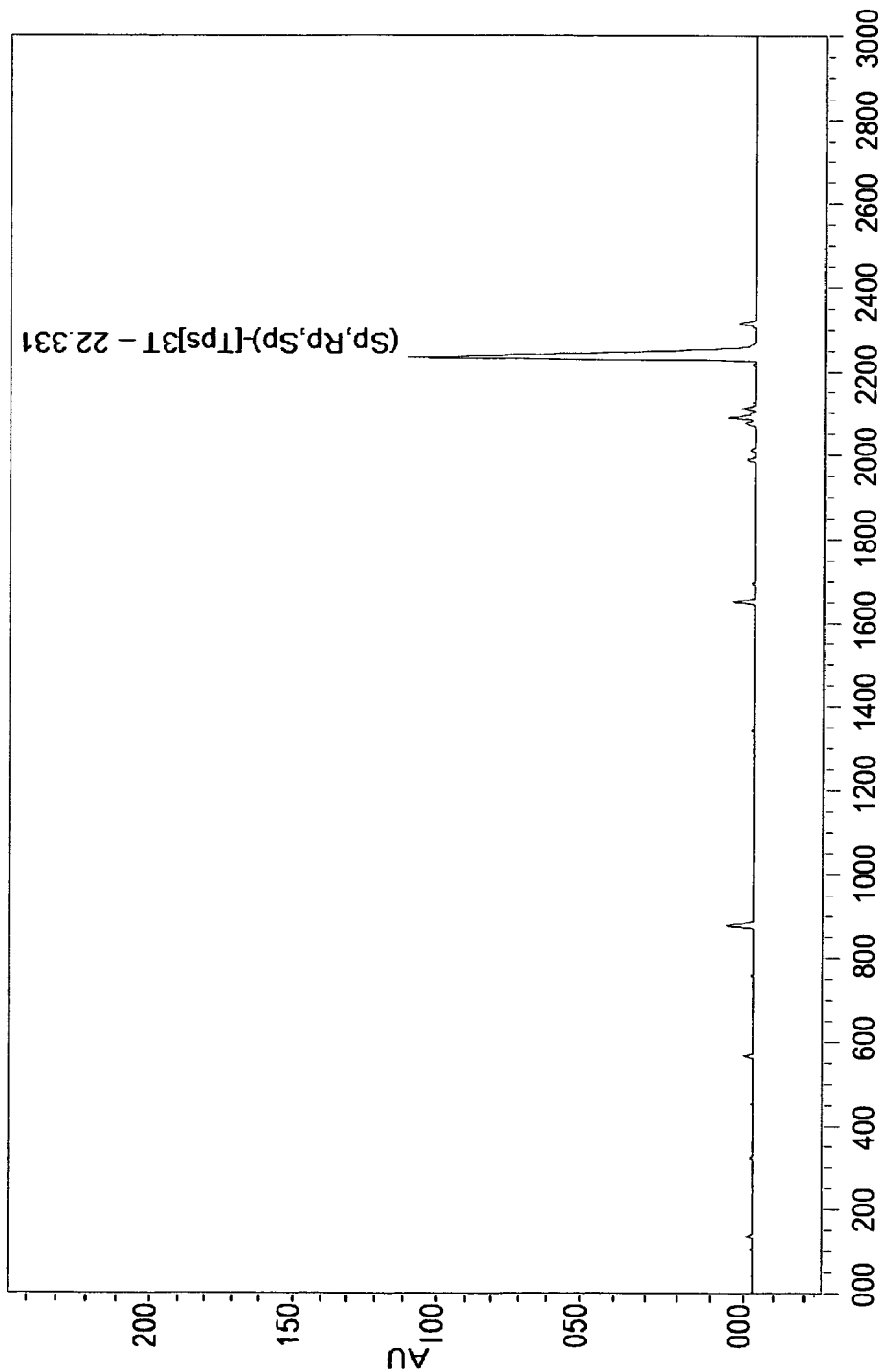
Figure 30B:
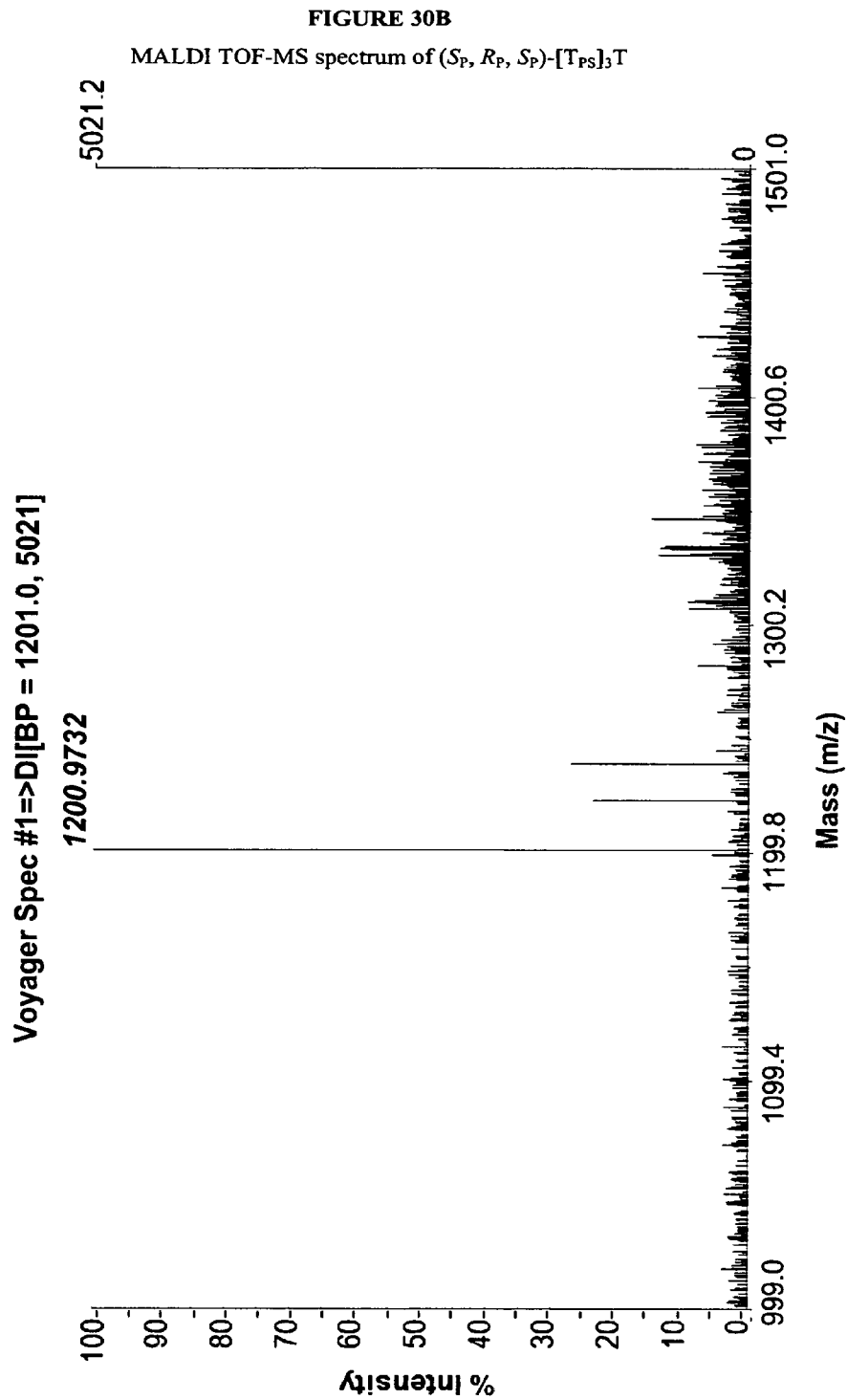

Example 103: Solid-Phase Synthesis of a Phosphorothioate Tetramer, ($S_P$, $R_P$, $S_P$)-[$T_{PS}$]$_3$T (Phosphorothioate) Via Route A This compound was obtained in a similar manner to All-($S_P$)-[$T_{PS}$]$_3$T in Example 102. The yield of the product was determined by a UV absorbance measurement at 260 nm with the molar extinction coefficient of an approximate value for natural $T_4$ tetramer (33000). The product was identical to that of a control sample synthesized by the conventional phosphoramidite method. Average coupling yield is 96%, optical purity is 94% (average: 98%). Retention time: 22.3 min; MS (MALDI TOF-MS) m/z Calcd for $C_{40}H_{52}N_8O_{23}P_3S_3$ [M-H]$^-$ 1201.15, found 1200.97. The UPLC profile is shown in FIG. 30.

Figure 31A:
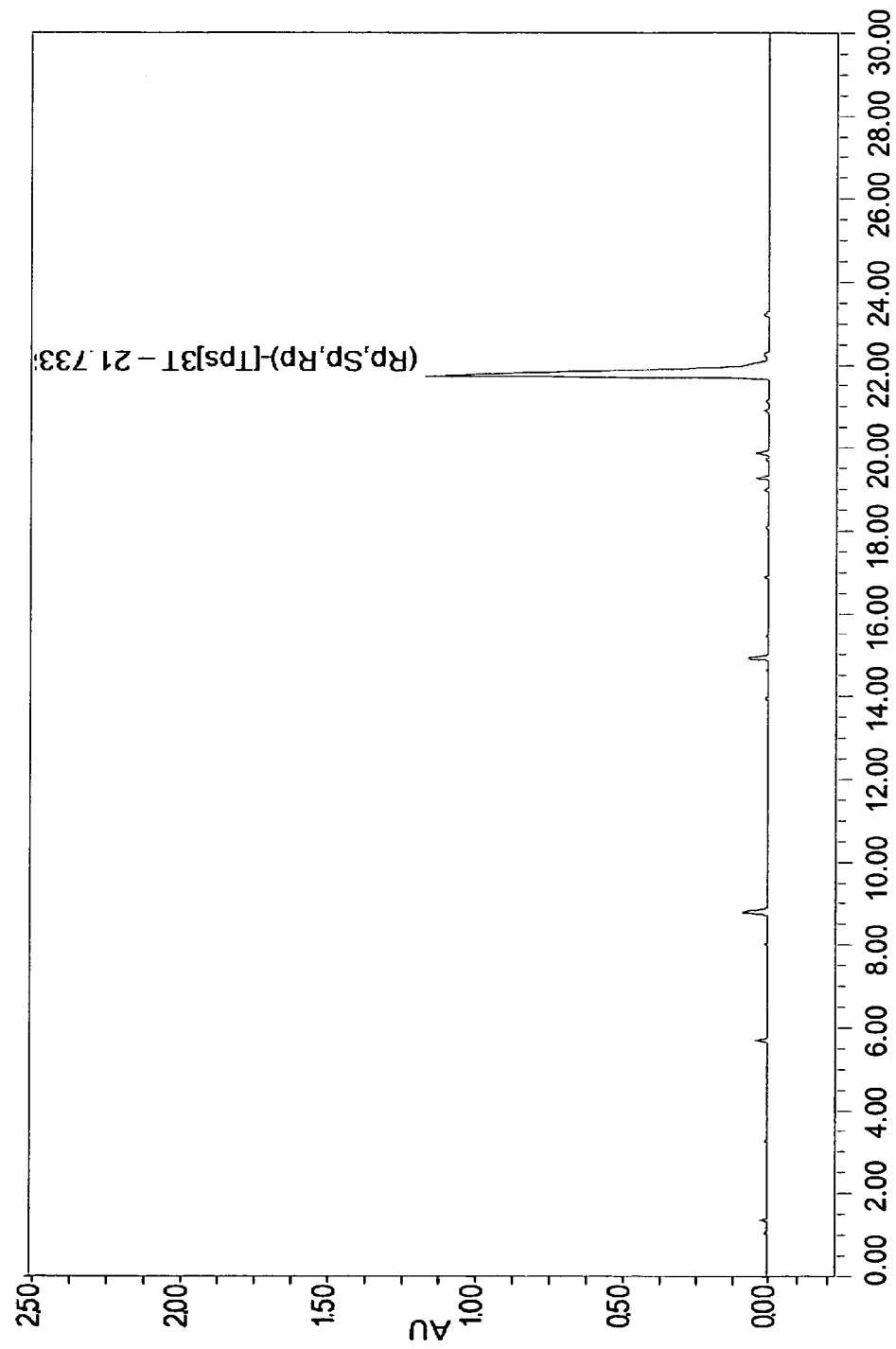
Figure 31B:
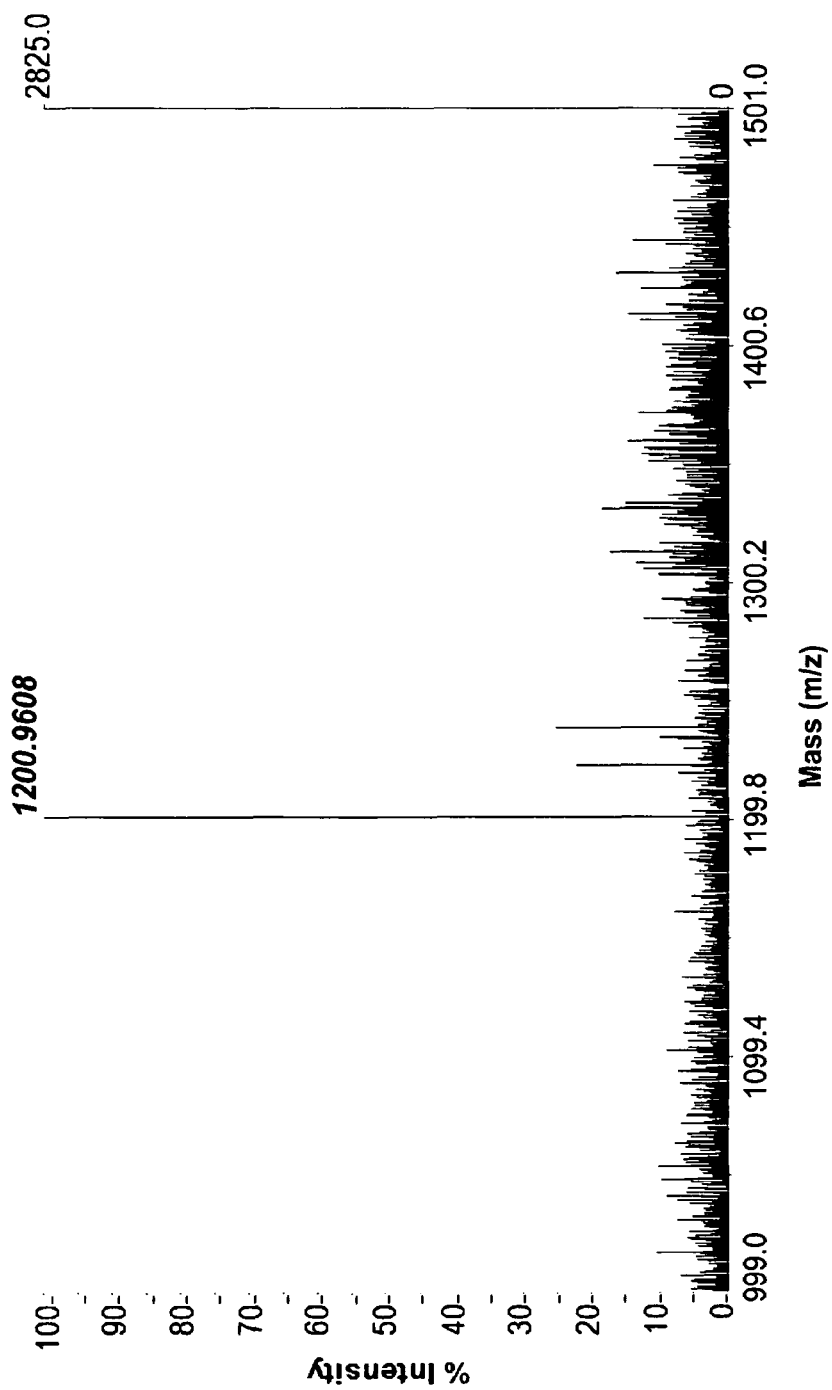

Example 104: Solid-Phase Synthesis of a Phosphorothioate Tetramer, ($R_P$, $S_P$, $R_P$)-[$T_{PS}$]$_3$T (Phosphorothioate) Via Route A This compound was obtained in a similar manner to All-($S_P$)-[$T_{PS}$]$_3$T in Example 102. The yield of the product was determined by a UV absorbance measurement at 260 nm with the molar extinction coefficient of an approximate value for natural $T_4$ tetramer (33000). The product was identical to that of a control sample synthesized by the conventional phosphoramidite method. Average coupling yield is 97%, optical purity is 96% (average: 99%). Retention time: 21.7 min; MS (MALDI TOF-MS) m/z Calcd for $C_{40}H_{52}N_8O_{23}P_3S_3$ [M-H]$^-$ 1201.15, found 1200.96. The UPLC profile is shown in FIG. 31.

Figure 32A:
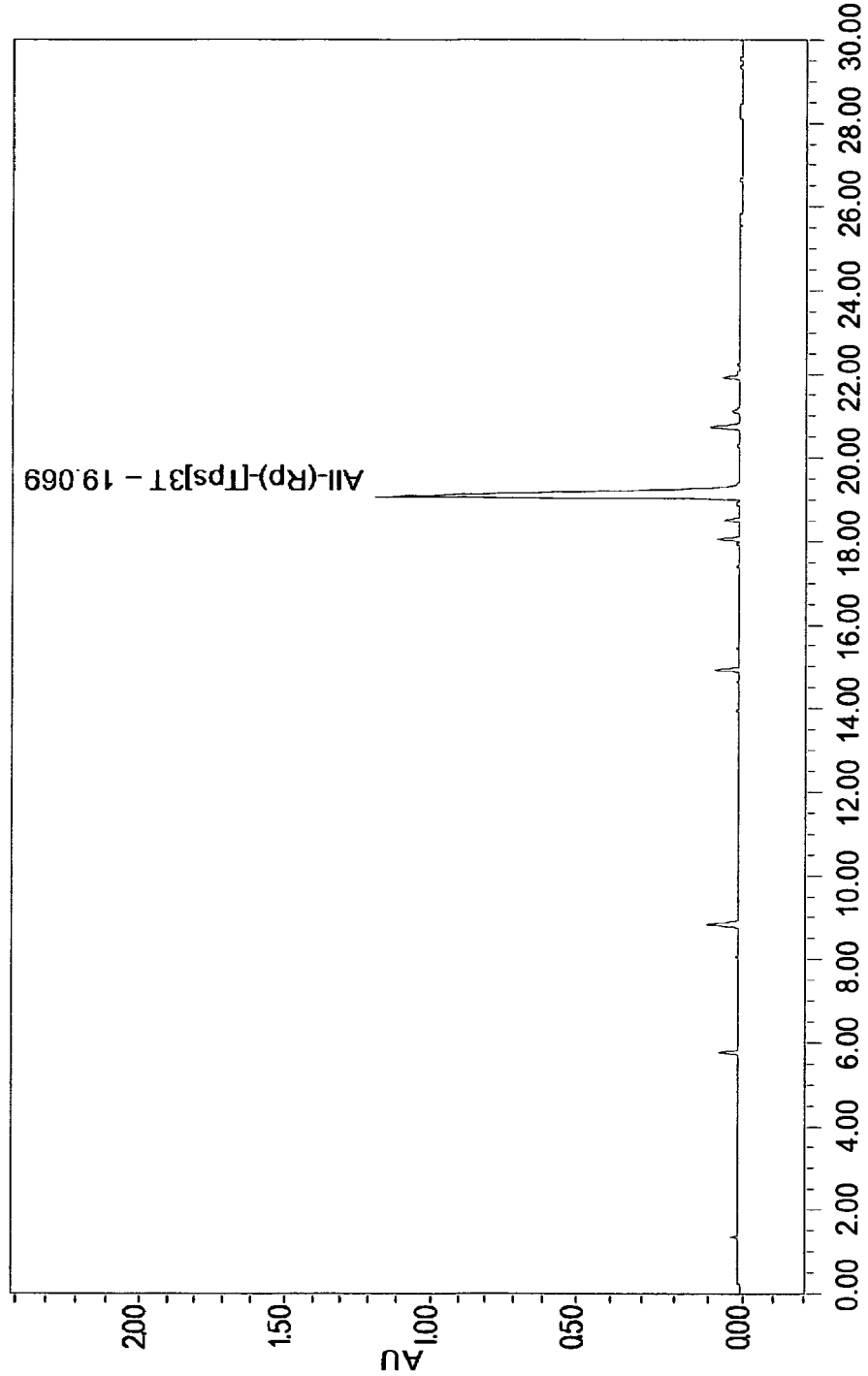
Figure 32B:
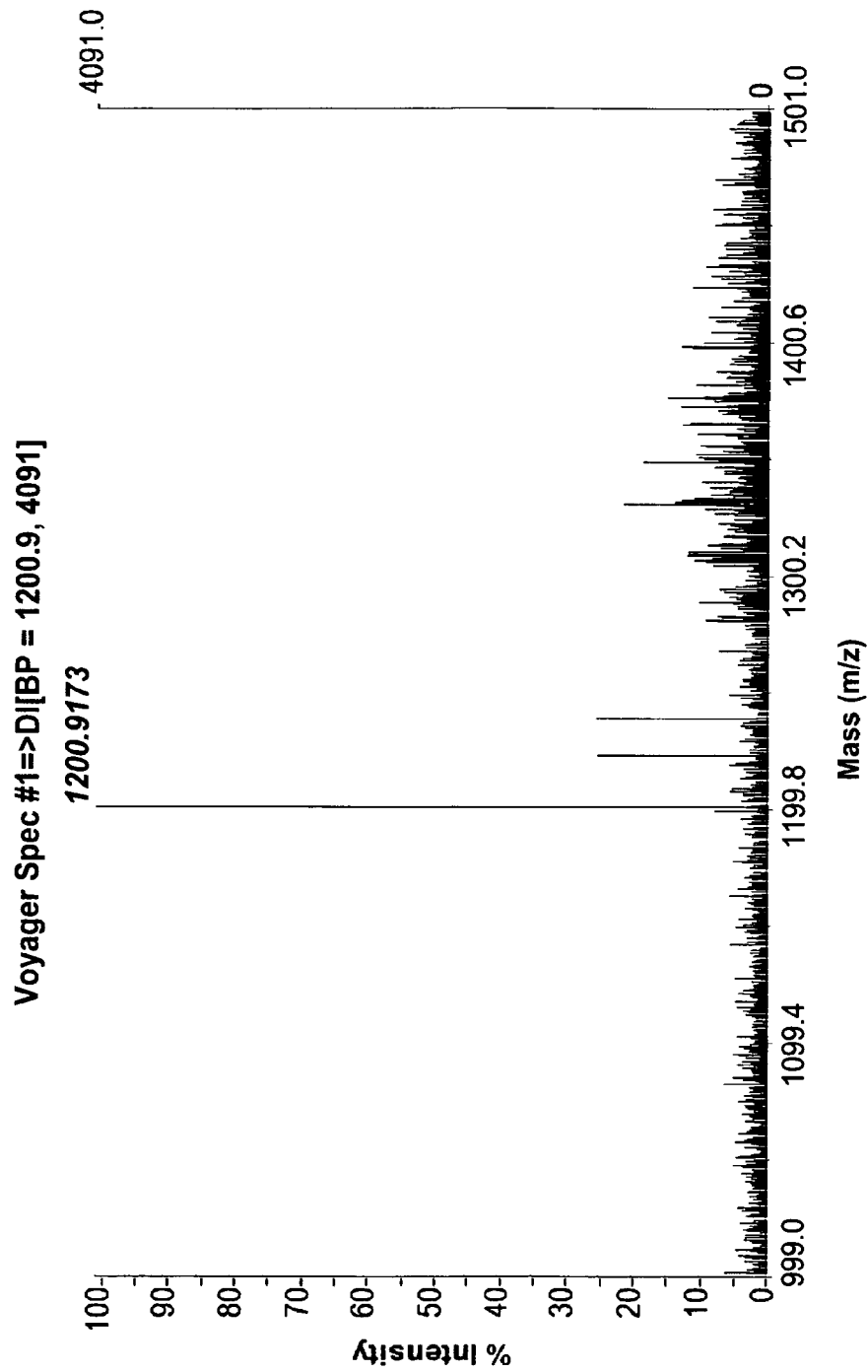

Example 105: Solid-Phase Synthesis of a Phosphorothioate Tetramer, All-($R_P$)-[$T_{PS}$]$_3$T (Phosphorothioate) Via Route A This compound was obtained in a similar manner to All-($S_P$)-[$T_{PS}$]$_3$T. The yield of the product was determined by a UV absorbance measurement at 260 nm with the molar extinction coefficient of an approximate value for natural $T_4$ tetramer (33000). The product was identical to that of a control sample synthesized by the conventional phosphoramidite method. Average coupling yield is 95%, optical purity is 92% (average: 97%). Retention time: 19.1 min; MS (MALDI TOF-MS) m/z Calcd for $C_{40}H_{52}N_8O_{23}P_3S_3$ [M-H]$^-$ 1201.15, found 1200.92. The UPLC profile is shown in FIG. 32.

Example 106: Solid-Phase Synthesis of a RNA Phosphorothioate Tetramer, ($S_P$)-Ammonium 2'-O-methyluridin-3'-yl uridin-5'-yl phosphorothioate [($S_P$)-9U$_M$U] via Route A

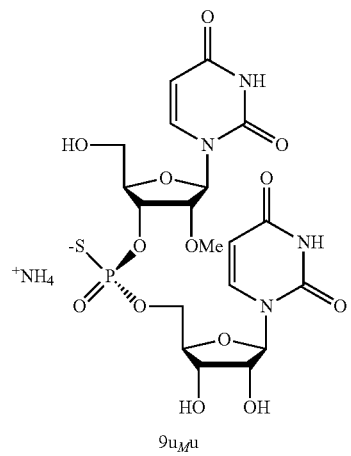

9u$_M$u

Figure 33A:
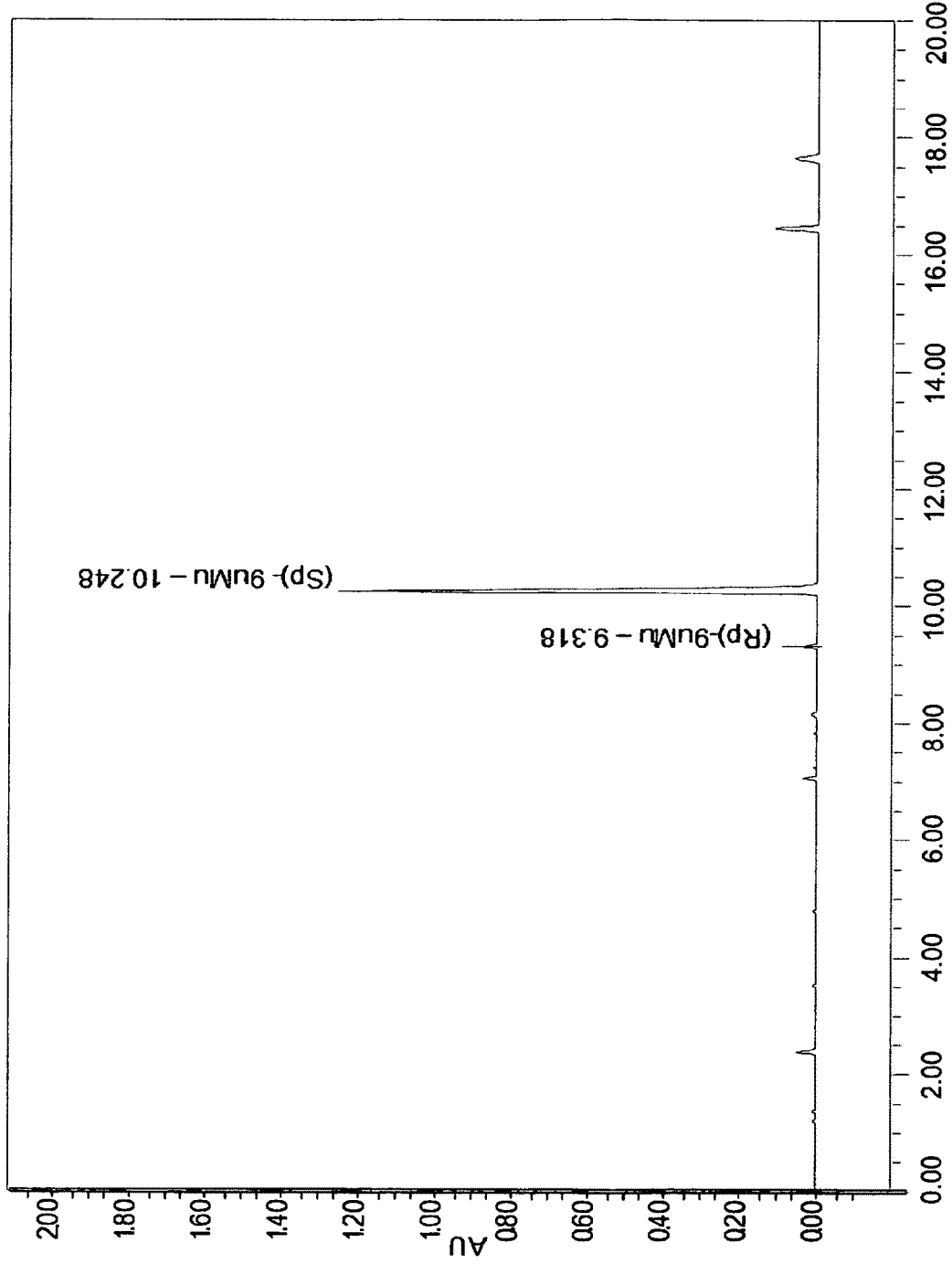
Figure 33B:
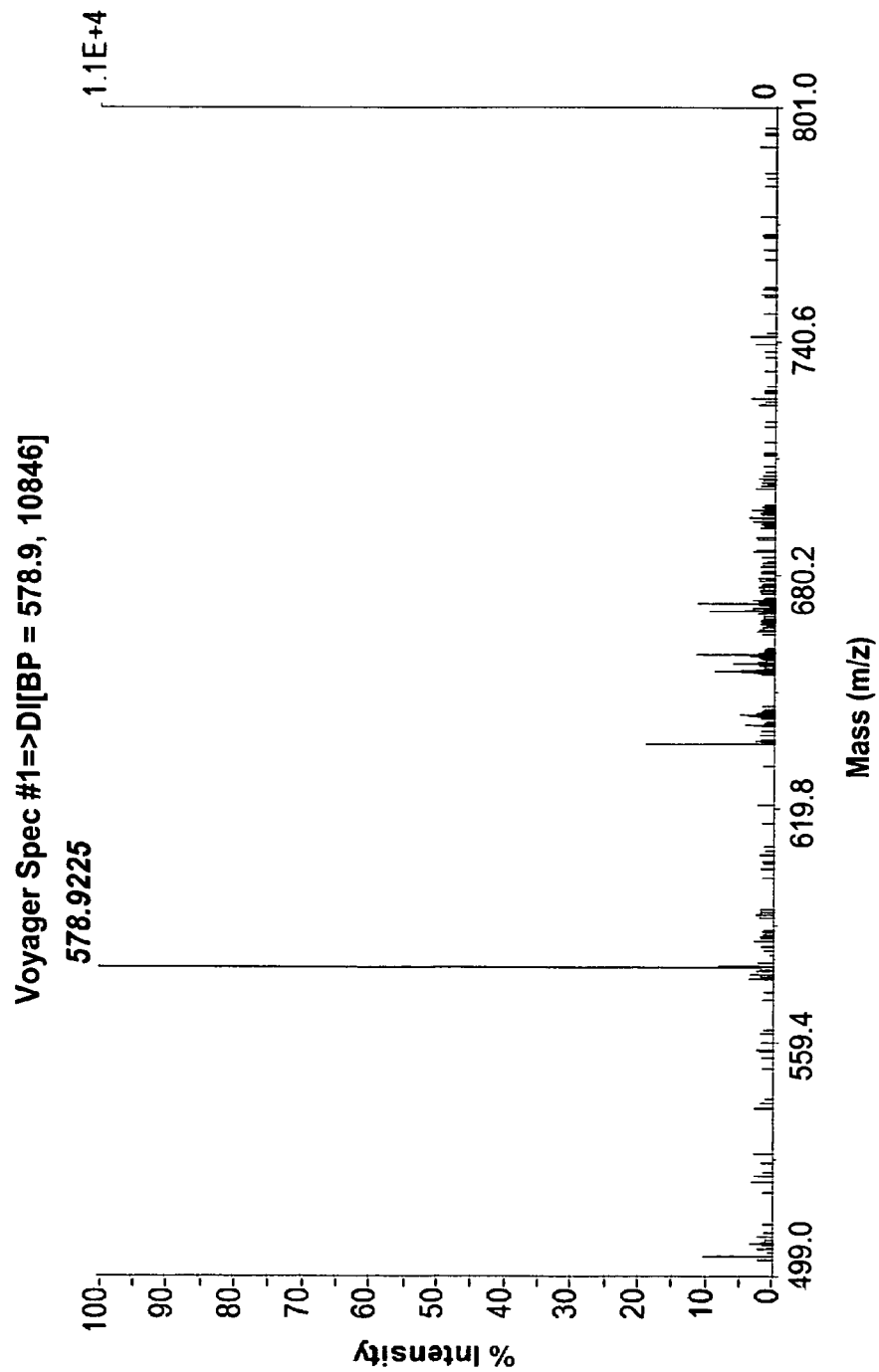

2'-O-Acetyl-$N^3$-benzoyl-5'-O-(4,4'-dimethoxytrityl)uridine-loaded CPG resin (21.4 mg; 23.4 mol/g, 0.5 µmol) via a succinyl linker was treated with 3% DCA/DCM (3×1 mL), then washed with DCM (3×1 mL) and dry MeCN (3×1 mL). After the resin was dried under the reduced pressure (>5 min), pre-activated monomer solution (250 µL, 25 µmol; which consists of 8-diazabicyclo[5.4.0]undec-7-enium $N^3$-benzoyl-5'-O-(4,4'-dimethoxytrityl)-2'-O-methyluridin-3'-yl phosphonate (25 µmol, for H-phosphonate monoester), MeCN-pyridine (9:1, v/v, for solvent), Ph$_3$PCl$_2$ (62.5 µmol, for condensing reagent), and L-2 (30 µmol, for aminoalcohol)) was added. Being stirred for 5 min, the reaction solution was removed, and the resin was washed with MeCN (3×1 mL), dried under the reduced pressure (>5 min). The resulting intermediate was sulfurized by treatment with 0.3 M DTD/MeCN (500 µL, 150 µmol) for 5 min, then washed with MeCN (3×1 mL) and DCM (3×1 mL). The 5'-O-DMTr group was removed by treatment with 3% DCA/DCM (3×1 mL), and washed with DCM (3×1 mL). The phosphorothioate dimer on the resin was then treated with 25% NH$_3$ (1 mL) for 12 h at 55° C. to remove the chiral auxiliary and the protecting groups of the nucleobases and also to release the dimer from the resin. The resin was removed by filtration and washed with H$_2$O. The filtrate was concentrated to dryness. The residue was dissolved in H$_2$O (2 mL), washed with Et$_2$O (3×2 mL), and the combined washings were back-extracted with H$_2$O (2 mL). The combined aqueous layers were concentrated to dryness. The resulting crude product was analyzed by reversed-phase UPLC® with a linear gradient of 0-20% MeOH in 0.1 M ammonium acetate buffer (pH 7.0) for 15 min at 55° C. at a rate of 0.4 ml/min. The yield of (S$_P$)-9u$_M$u was 95% (R$_P$:S$_P$=2:98). Retention time: 10.2 min ((R$_P$)-9u$_M$u: 9.3 min); MS (MALDI TOF-MS) m/z Calcd for C$_{19}$H$_{24}$N$_4$O$_{13}$PS [M-H]$^-$ 579.08, found 578.92. The UPLC profile is shown in FIG. 33.

Figure 34A:
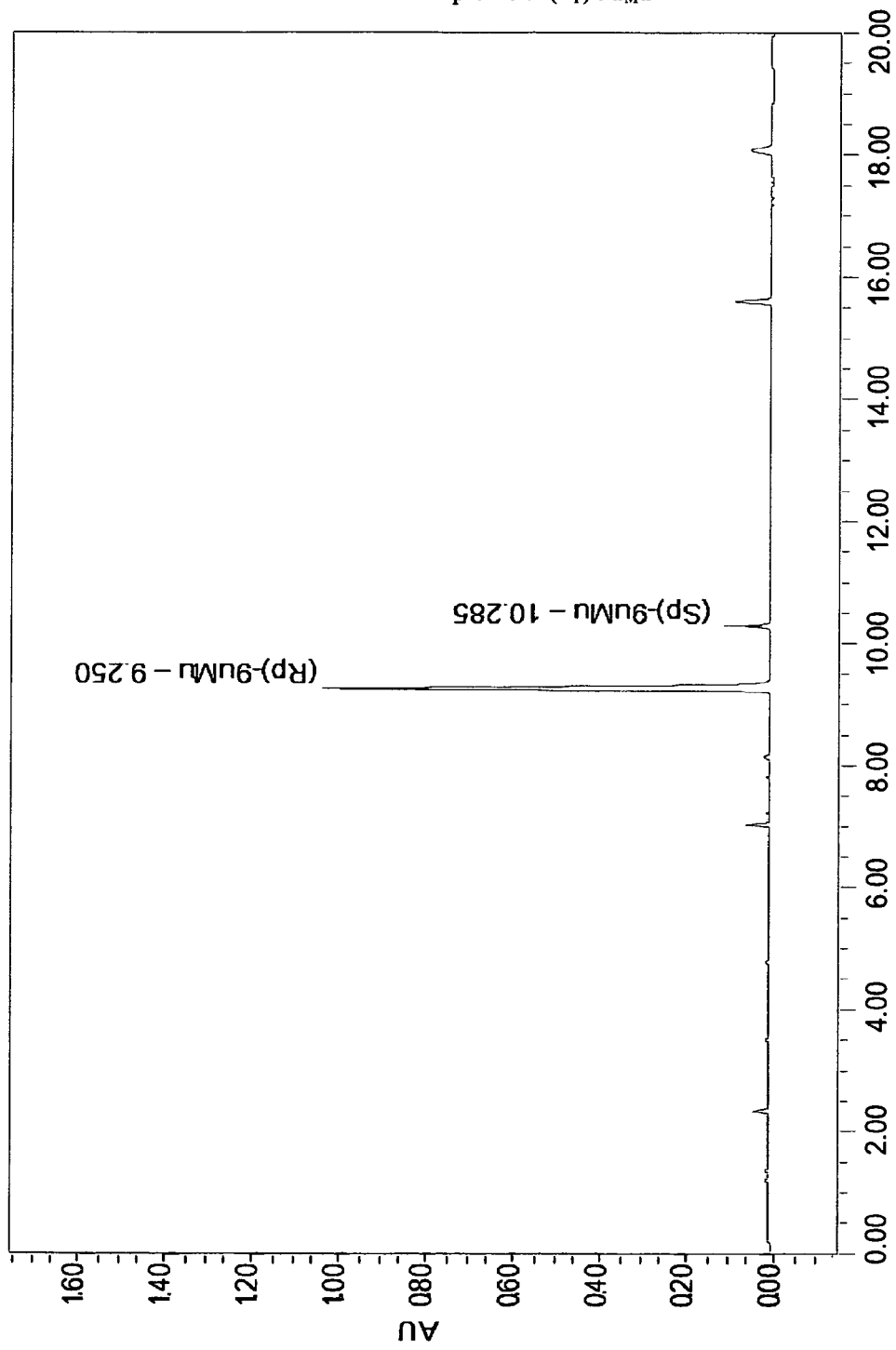
Figure 34B:
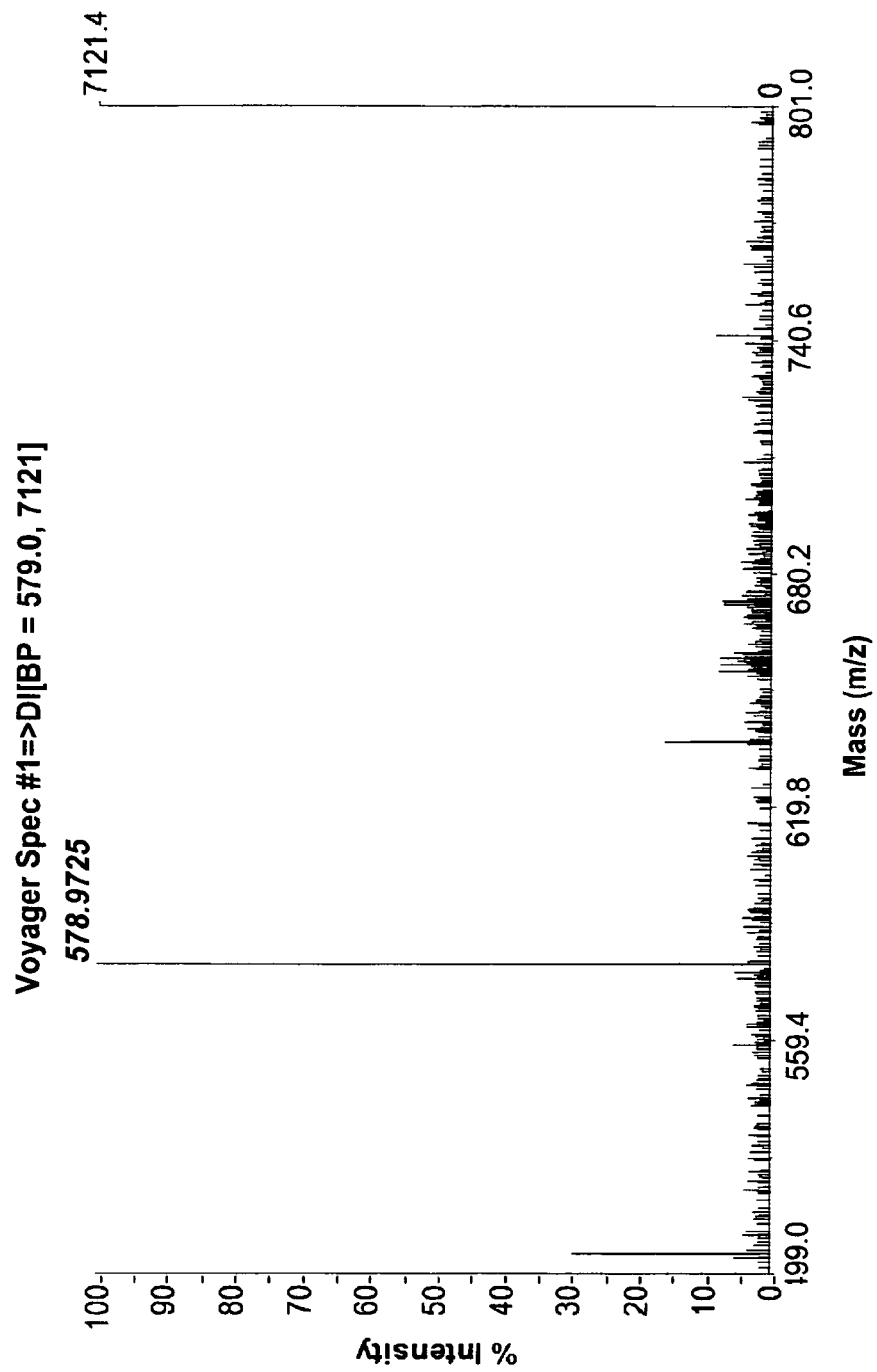

Example 107: Solid-Phase Synthesis of a RNA Phosphorothioate Tetramer, (R$_P$)-Ammonium 2'-O-methyluridin-3'-yl uridin-5'-yl phosphorothioate [(R$_P$)-9u$_M$u] via Route A This compound was obtained by using "D-2 (30 μmol)" instead of "L-2 (30 μmol)" in a similar manner to Example 106. The yield of (R$_P$)-9u$_M$u was 94% (R$_P$:S$_P$=95:5). Retention time: 9.3 min ((S$_P$)-9U$_M$u: 10.3 min); MS (MALDI TOF-MS) m/z Calcd for C$_{19}$H$_{24}$N$_4$O$_{13}$PS [M-H]$^-$ 579.08, found 578.97. The UPLC profile is shown in FIG. 34.

Example 108: Solid-phase synthesis of a RNA Phosphorothioate Tetramer, (S$_P$)-Ammonium 2'-deoxy-2'-fluorouridin-3'-yl uridin-5'-yl phosphorothioate [(S$_P$)-10u$_F$u] via Route A

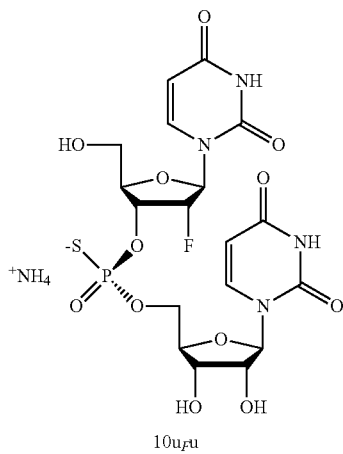

10u$_F$u

Figure 35A:
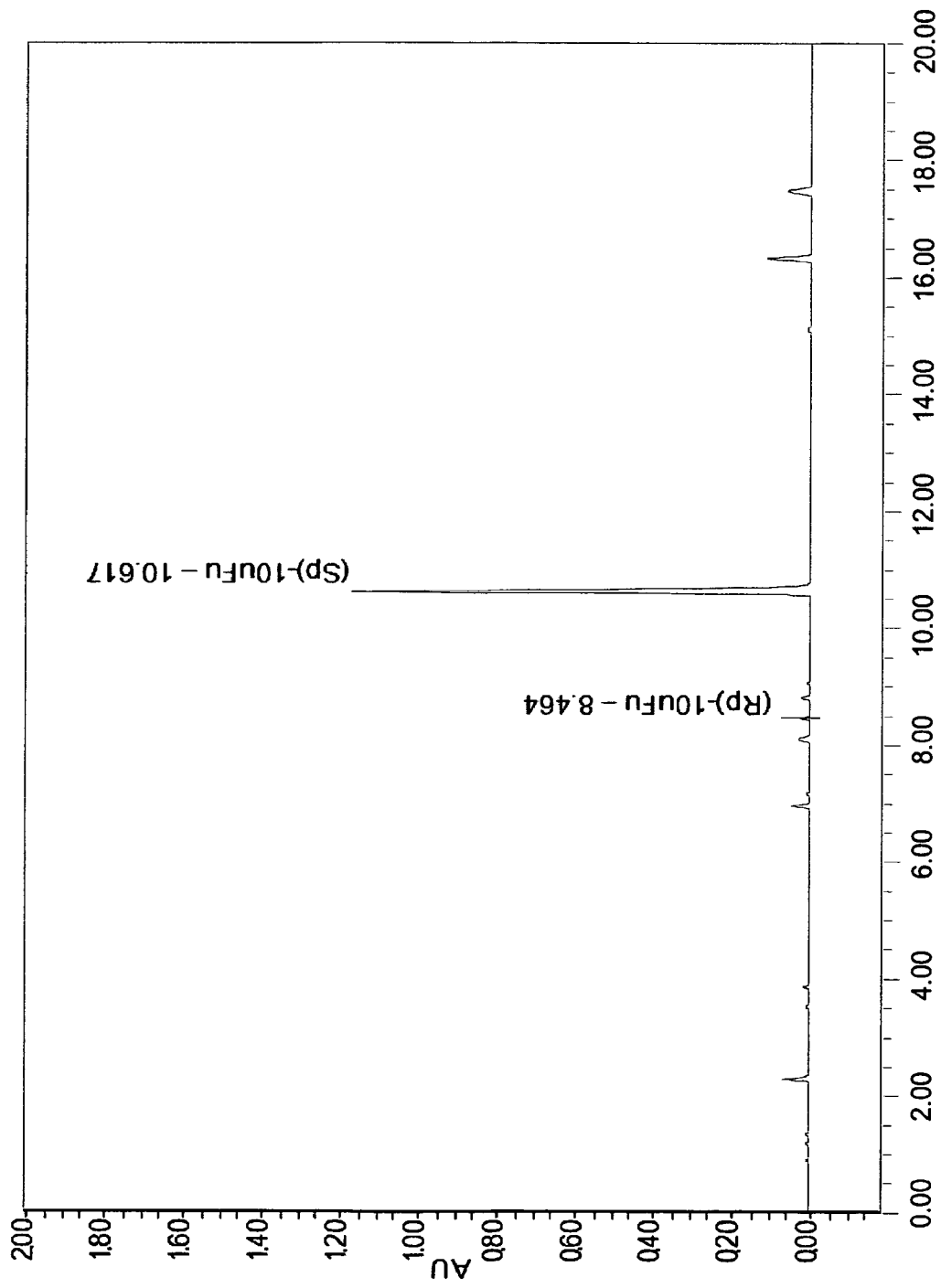
Figure 35B:
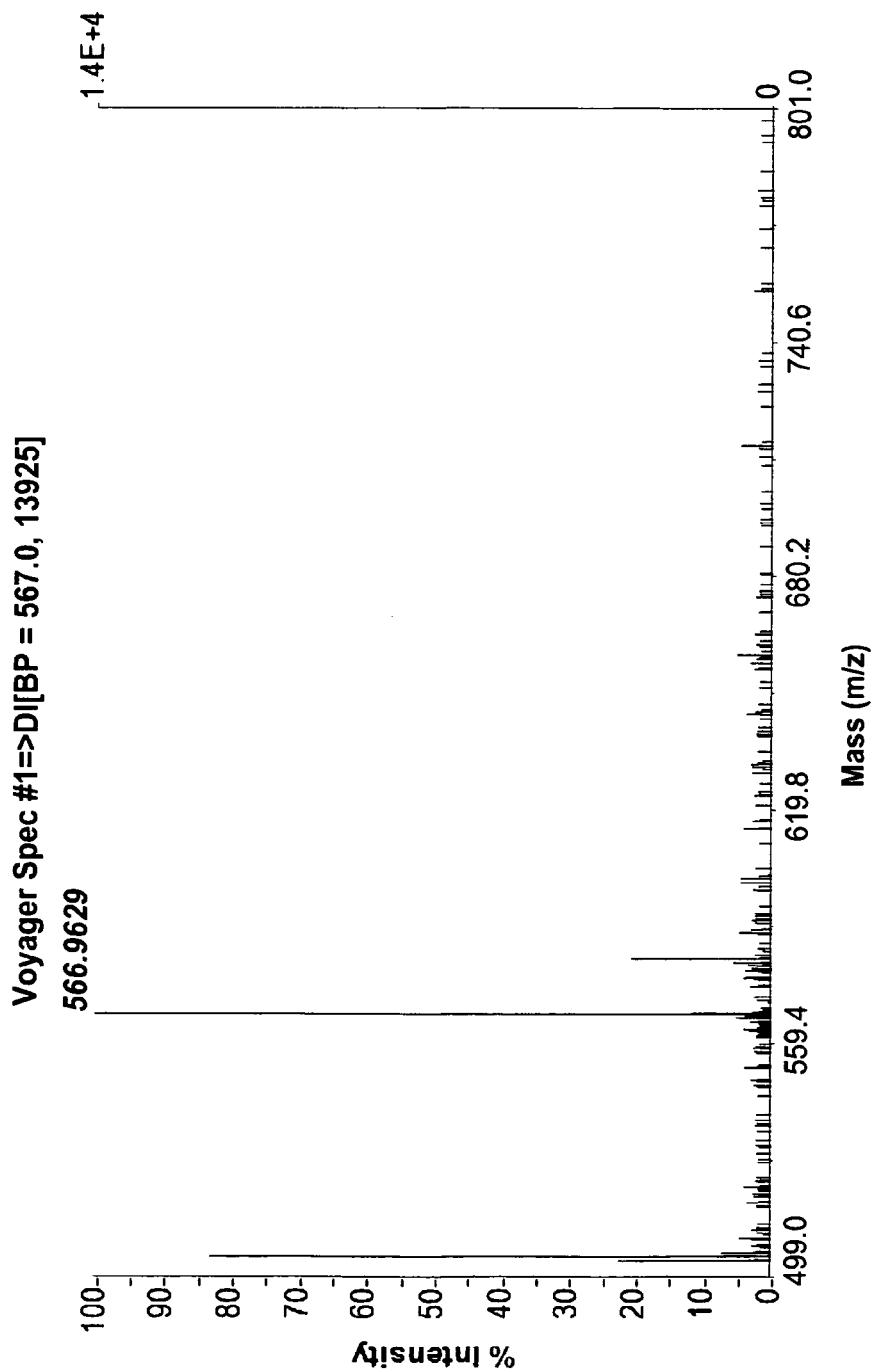

This compound was obtained by using "8-diazabicyclo[5.4.0]undec-7-enium N$^3$-benzoyl-5'-O-(4,4'-dimethoxytrityl)-2'-deoxy-2'-fluorouridin-3'-yl phosphonate (25 μmol)" instead of "8-diazabicyclo[5.4.0]undec-7-enium N$^3$-benzoyl-5'-O-(4,4'-dimethoxytrityl)-2'-O-methyluridin-3'-yl phosphonate (25 μmol)" in a similar manner to Example 106. The yield of (S$_P$)-10u$_F$u was 93% (R$_P$:S$_P$=1:99). Retention time: 10.6 min ((R$_P$)-10u$_F$u: 8.5 min); MS (MALDI TOF-MS) m/z Calcd for C$_{18}$H$_{21}$FN$_4$O$_{12}$PS [M-H]$^-$ 567.06, found 566.96. The UPLC profile is shown in FIG. 35.

Figure 36A:
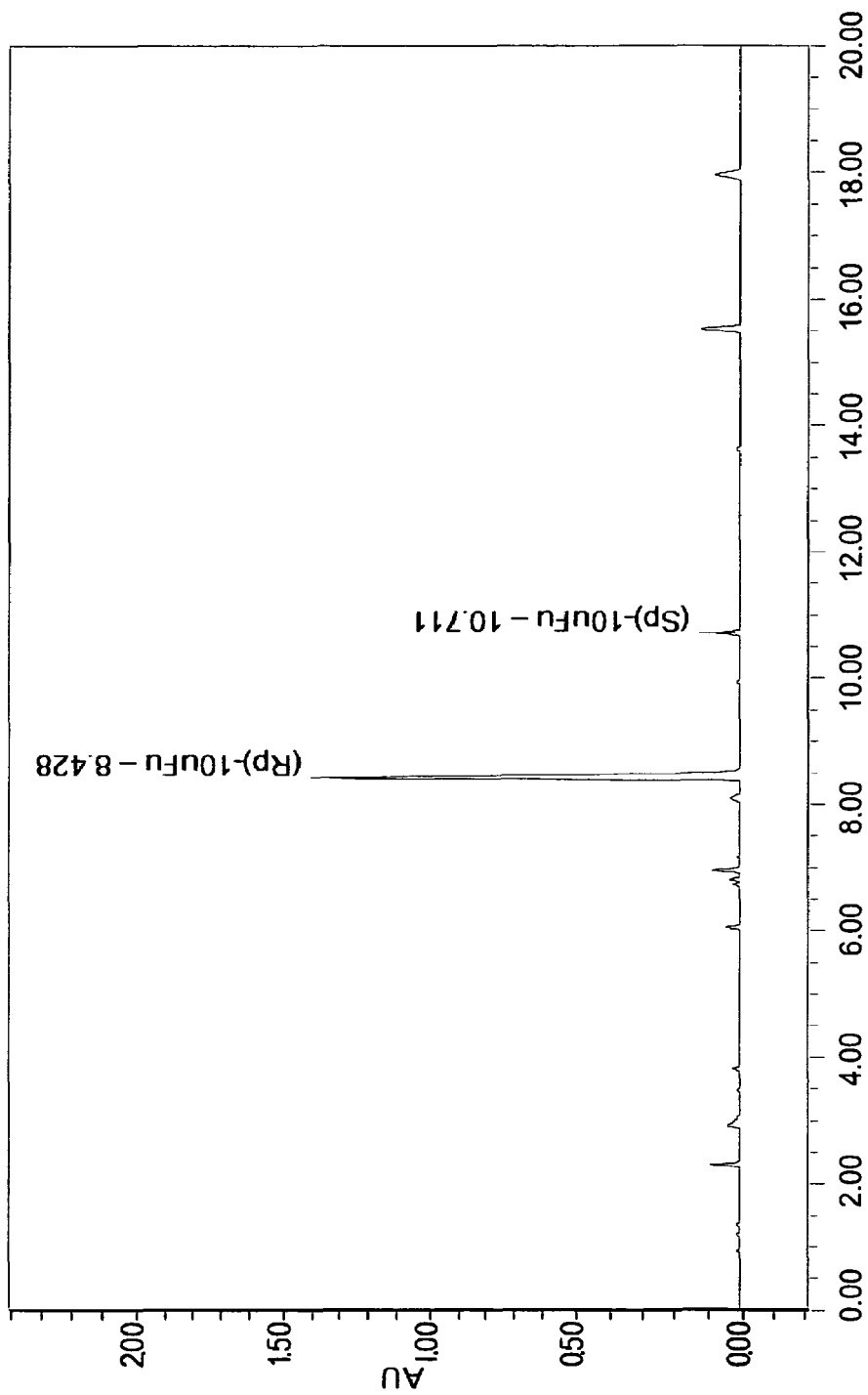
Figure 36B:
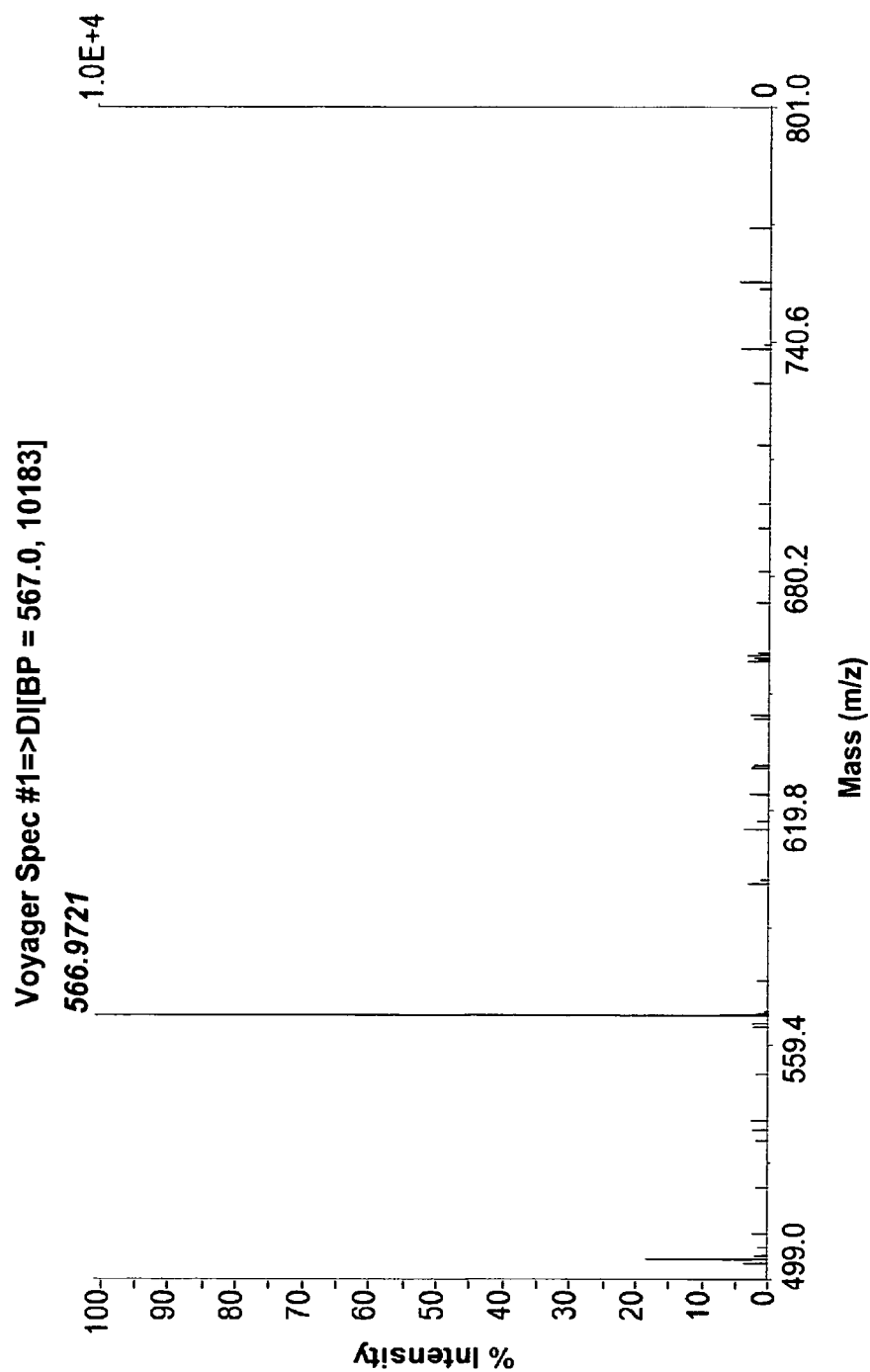

Example 109: Solid-Phase Synthesis of a RNA Phosphorothioate Tetramer, (R$_P$)-Ammonium 2'-deoxy-2'-fluorouridin-3'-yl uridin-5'-yl phosphorothioate [(R$_P$)-10u$_F$u] via Route A This compound was obtained by using "D-2 (30 μmol)" instead of "L-2 (30 μmol)" in a similar manner to Example 108. The yield of (R$_P$)-10u$_F$u was 92% yield, R$_P$:S$_P$=96:4. Retention time: 8.4 min ((S$_P$)-10u$_F$u: 10.7 min); MS (MALDI TOF-MS) m/z Calcd for C$_{18}$H$_{21}$FN$_4$O$_{12}$PS [M-H]$^-$ 567.06, found 566.97. The UPLC profile is shown in FIG. 36.

Example 110: Solution-Phase Synthesis of Unnatural Nucleobase (S$_P$)-Ammonium 1-(3-nitropyrrol-1-yl)-2-deoxyribofuranos-3-yl thymidin-5'-yl phosphorothioate [(S$_P$)-11 nt] via Route A

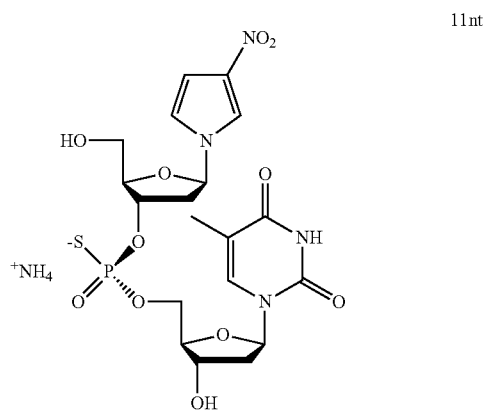

11nt

Figure 37A:
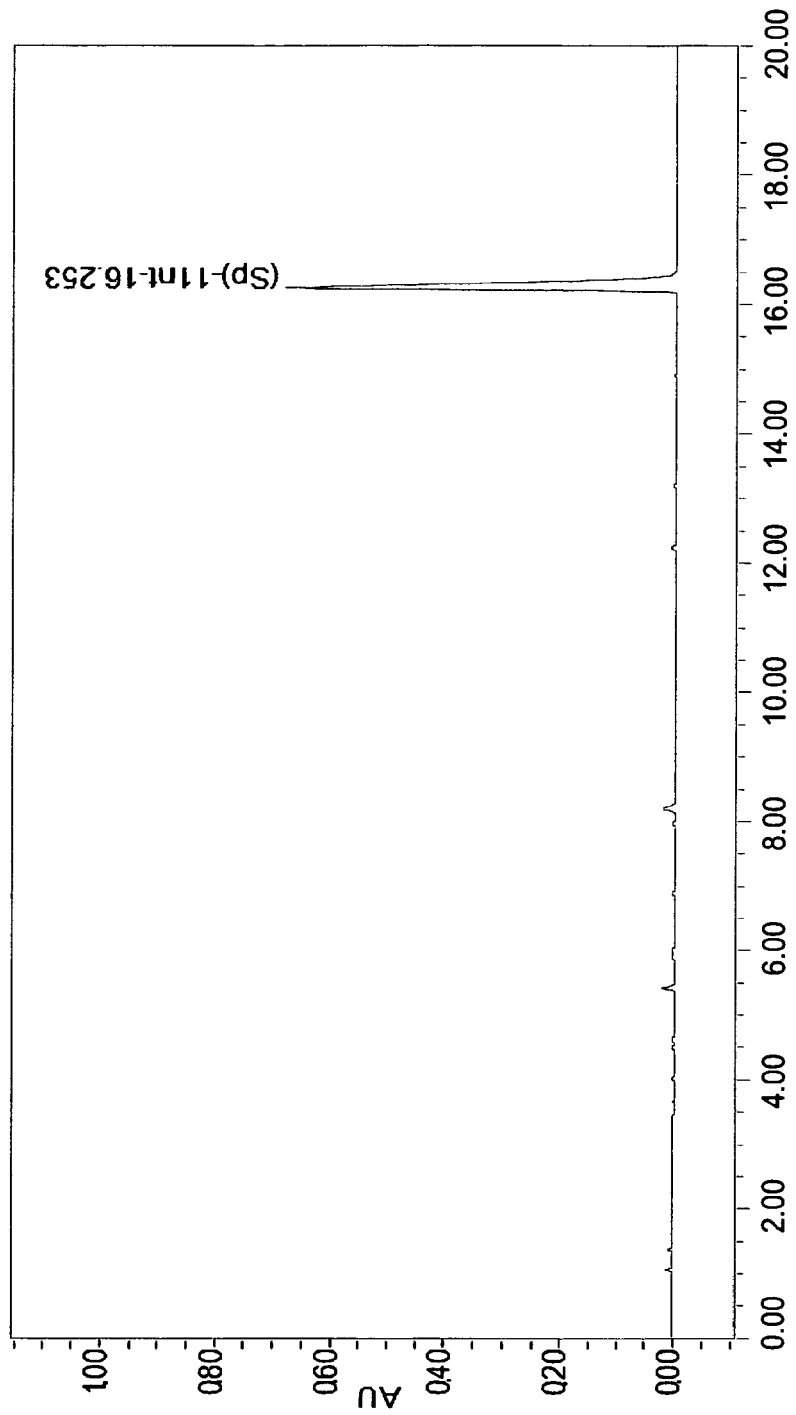
Figure 37B:
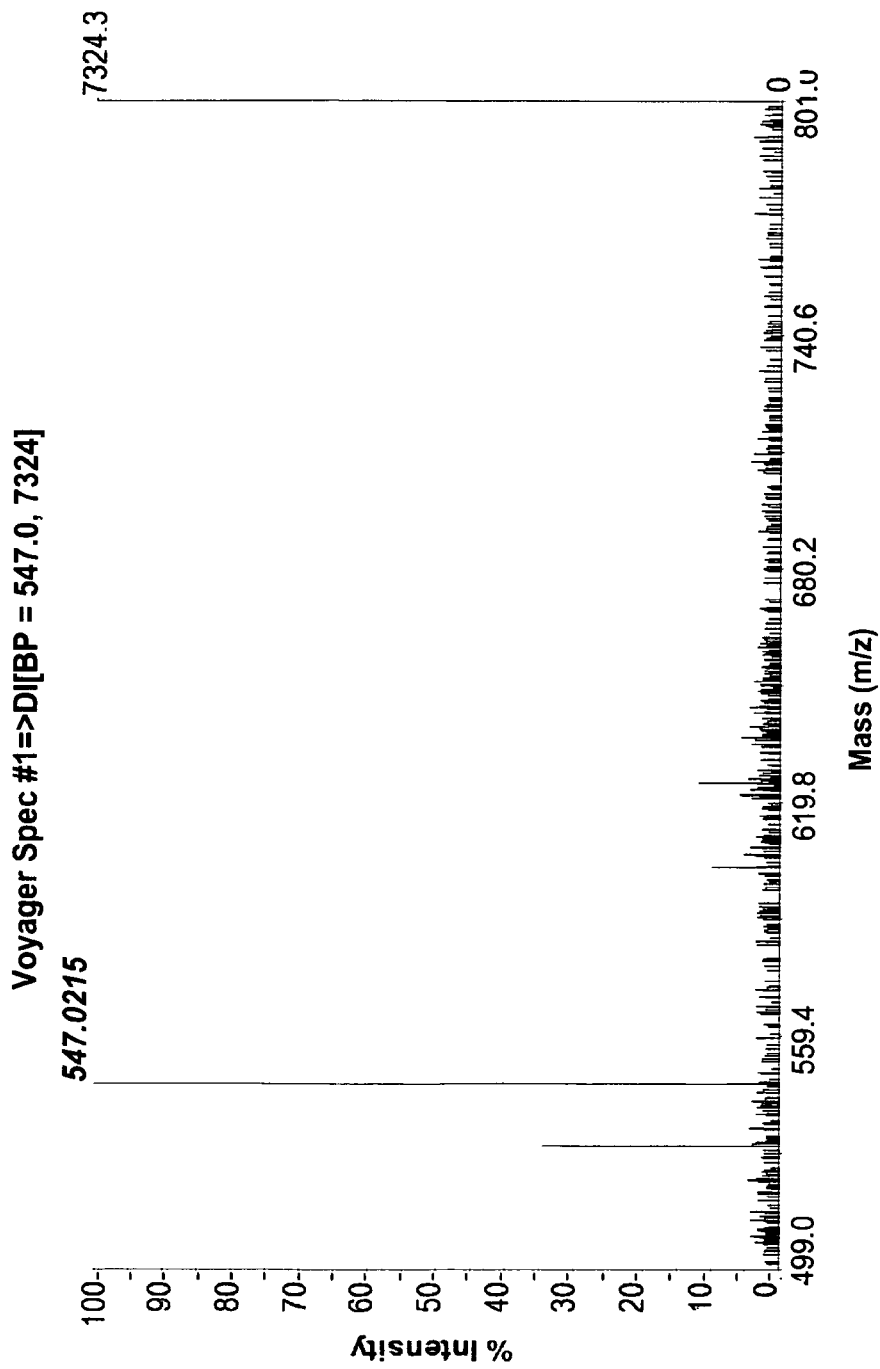

This compound was obtained by using "8-diazabicyclo[5.4.0]undec-7-enium 5-O-(4,4'-dimethoxytrityl)-1-(3-nitropyrrol-1-yl)-2-deoxyribofuranos-3-yl phosphonate (25 μmol)" instead of "8-diazabicyclo[5.4.0]undec-7-enium N$^3$-benzoyl-5'-O-(4,4'-dimethoxytrityl)thymidin-3'-yl phosphonate (25 μmol)" in a similar manner to Example 78. The yield of the product was determined by a UV absorbance measurement at 260 nm with the molar extinction coefficient of an approximate value for natural CT dimer (15200). The yield of (S$_P$)-11nt was 98% yield. Retention time: 16.3 min. (R$_P$)-11nt could not be resolved; MS (MALDI TOF-MS) m/z Calcd for Cl$_9$H$_{24}$N$_4$O$_{11}$PS [M-H]$^-$ 547.09, found 547.02. The UPLC profile is shown in FIG. 37.

Figure 38A:
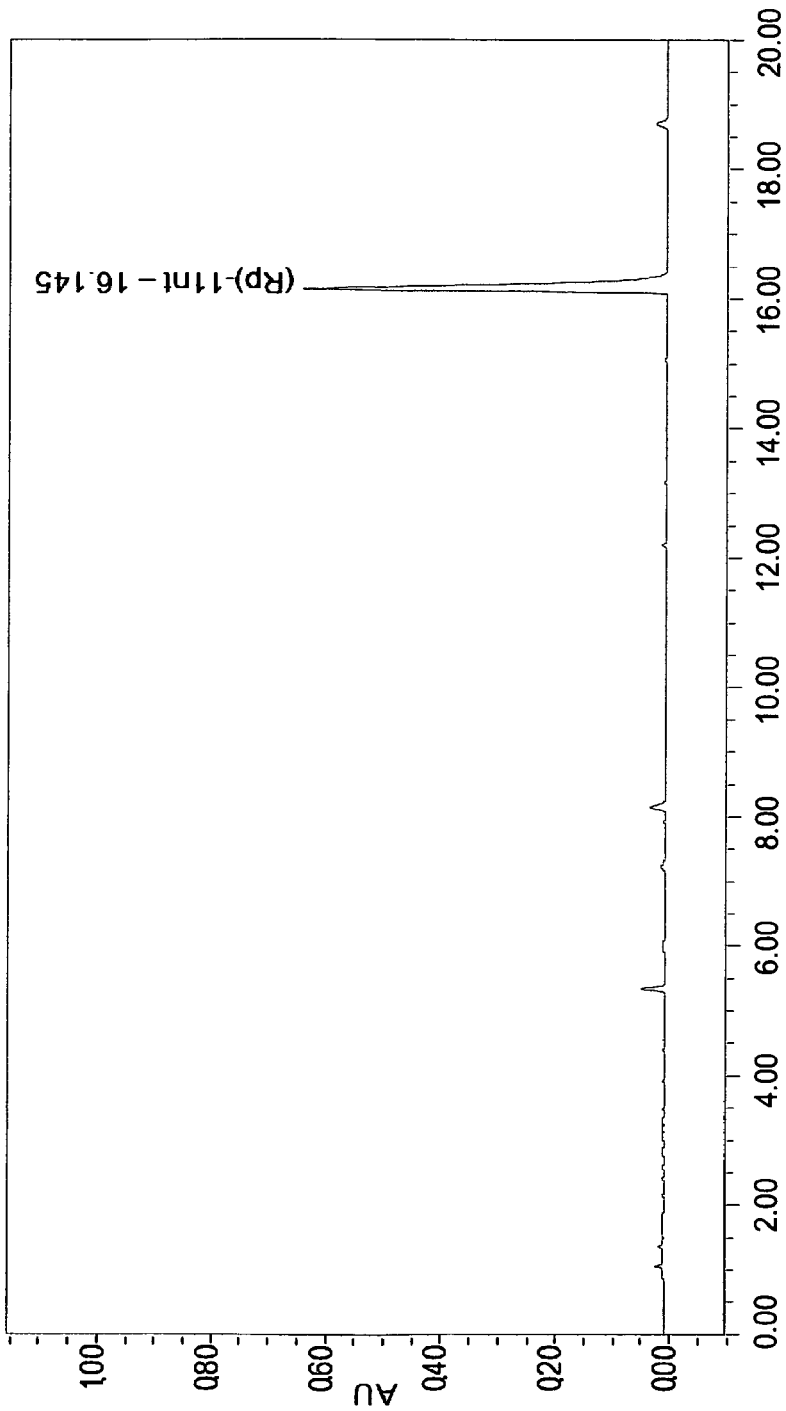
Figure 38B:
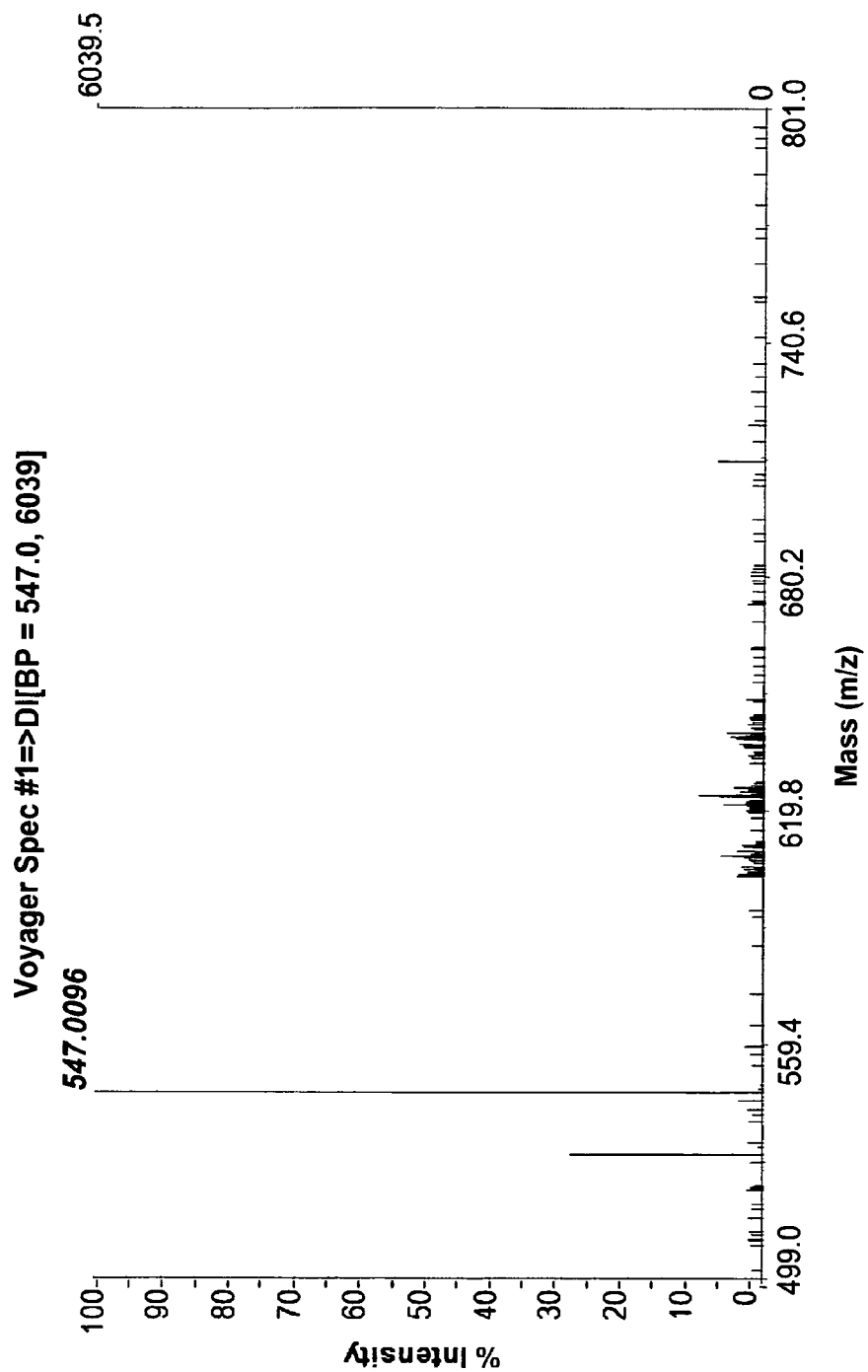

Example 111: Solution-phase synthesis of unnatural nucleobase (R$_P$)-Ammonium 1-(3-nitropyrrol-1-yl)-2-deoxyribofuranos-3-yl thymidin-5'-yl phosphorothioate [(R$_P$)-11nt] via Route A This compound was obtained by using "D-2 (30 μmol)" instead of "L-2 (30 μmol)" in a similar manner to Example 110. The yield of the product was determined by a UV absorbance measurement at 260 nm with the molar extinction coefficient of an approximate value for natural CT dimer (15200). The yield of (R$_P$)-11nt was 97% yield. Retention time: 16.1 min. (S$_P$)-11nt could not be resolved; MS (MALDI TOF-MS) m/z Calcd for C$_{19}$H$_{24}$N$_4$O$_{11}$PS [M-H]$^-$ 547.09, found 547.01. The UPLC profile is shown in FIG. 38.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

The invention claimed is:

1. A method for the synthesis of a nucleic acid comprising a chiral X-phosphonate moiety comprising:
    reacting a molecule comprising an achiral H-phosphonate moiety, a chiral reagent, and a nucleoside comprising a 5'-OH moiety to form a condensed intermediate; and
    converting the condensed intermediate to the nucleic acid comprising a chiral X-phosphonate moiety, wherein:
    the nucleic acid comprises a modified sugar, wherein the modified sugar contains one or more substituents at the 2'-position selected from the group consisting of F, $CF_3$, CN, $N_3$, NO, $NO_2$, O-, S-, or N-alkyl; O-, S-, or N-alkenyl; O-, S-, or N-alkynyl; or O-alkyl-O-alkyl, O-alkyl-N-alkyl or N-alkyl-O-alkyl wherein the alkyl, alkenyl and alkynyl may be substituted or unsubstituted $C_1$-$C_{10}$ alkyl or $C_2$-$C_{10}$ alkenyl and alkynyl;
    each instance of X is independently alkyl, alkoxy, aryl, alkylthio, acyl, —$NR^fR^f$, alkenyloxy, alkynyloxy, alkenylthio, alkynylthio, —$S^-Z^+$, —$Se^-Z^+$, or —$BH_3^-Z^+$;
    each instance of $R^f$ is independently hydrogen, alkyl, alkenyl, alkynyl, or aryl;
    $Z^+$ is ammonium ion, alkylammonium ion, heteroaromatic iminium ion, or heterocyclic iminium ion, any of which is primary, secondary, tertiary or quaternary, or $Z^+$ is a monovalent metal ion.

2. The method of claim 1, wherein a substituent at the 2'-position of the modified sugar is O-alkyl-O-alkyl, wherein alkyl is substituted or unsubstituted $C_1$-$C_{10}$ alkyl.

3. The method of claim 2, wherein a substituent at the 2'-position of the modified sugar is —$O(CH_2)_nOCH_3$, wherein n is from 1 to about 10.

4. The method of claim 3, wherein n is 1.

5. The method of claim 2, wherein a substituent at the 2'-position of the modified sugar is O-methoxyethyl.

6. The method of claim 1, wherein a substituent at the 2'-position of the modified sugar is F.

7. The method of claim 1, wherein a substituent at the 2'-position of the modified sugar is O-alkyl, wherein alkyl is substituted or unsubstituted $C_1$-$C_{10}$ alkyl.

8. The method of claim 1, wherein the nucleic acid comprises one or more natural sugars of DNA or RNA.

9. The method of claim 1, wherein the step of reacting the molecule comprising an achiral H-phosphonate moiety and the nucleoside comprising a 5'-OH moiety to form a condensed intermediate is a one-pot reaction.

10. The method of claim 1, wherein the nucleic acid comprising a chiral X— phosphonate moiety is a compound of Formula 1:

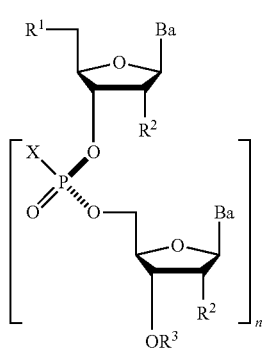

Formula 1 wherein $R^1$ is —OH, —SH, —$NR^dR^d$, —$N_3$, halogen, hydrogen, alkyl, alkenyl, alkynyl, alkyl-$Y^1$—, alkenyl-$Y^1$—, alkynyl-$Y^1$—, aryl-$Y^1$—, heteroaryl-$Y^1$—, —$P(O)(R^e)_2$, —$HP(O)(R^e)$, —$OR^a$ or —$SR^c$;
$Y^1$ is O, $NR^d$, S, or Se;
$R^a$ is a blocking moiety;
$R^e$ is a blocking group;
each instance of $R^d$ is independently hydrogen, alkyl, alkenyl, alkynyl, aryl, acyl, substituted silyl, carbamate, —$P(O)(R^e)_2$, or —$HP(O)(R^e)$;
each instance of $R^e$ is independently hydrogen, alkyl, aryl, alkenyl, alkynyl, alkyl-$Y^2$—, alkenyl-$Y^2$—, alkynyl-$Y^2$—, aryl-$Y^2$—, or heteroaryl-$Y^2$—, or a cation which is $Na^{+1}$, $Li^{+1}$, or $K^{+1}$;
$Y^2$ is O, NH, N-alkyl, N-alkenyl, N-alkynyl, N-aryl, N-acyl, N-silyl, N-carbamate, or S;
each instance of $R^2$ is independently hydrogen, —OH, —SH, —$NR^dR^d$, —$N_3$, halogen, alkyl, alkenyl, alkynyl, alkyl-$Y^1$—, alkenyl-$Y^1$—, alkynyl-$Y^1$—, aryl-$Y^1$—, heteroaryl-$Y^1$—, —$OR^b$, or —$SR^c$, wherein $R^b$ is a blocking moiety;
$R^3$ is hydrogen, a blocking group, a linking moiety connected to a solid support or a linking moiety connected to a nucleic acid; and
n is an integer of 1 to about 200.

11. The method of claim 10, wherein:
    each instance of $R^d$ is independently hydrogen, alkyl, alkenyl, alkynyl, aryl, acyl, or substituted silyl;
    each instance of $R^e$ is independently hydrogen, alkyl, aryl, alkenyl, alkynyl, alkyl-$Y^2$—, alkenyl-$Y^2$—, alkynyl-$Y^2$—, aryl-$Y^2$—, or heteroaryl-$Y^2$; and
    $Y^2$ is O, NH, N-alkyl, N-alkenyl, N-alkynyl, N-aryl, N-acyl, N-silyl, N-carbamate, or S.

12. The method of claim 10, wherein n is about 10 to about 200.

13. The method of claim 10, wherein each X-phosphonate moiety of the compound of Formula 1 is more than 98% diastereomerically pure as determined by $^{31}P$ NMR spectroscopy or reverse-phase HPLC.

14. The method of claim 1, wherein the chiral reagent is a compound of Formula 3:

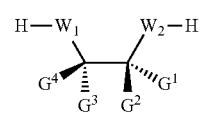

Formula 3 wherein:
$W_1$ and $W_2$ are independently —$NG^5$-, —O—, or —S—;
$G^1$, $G^2$, $G^3$, $G^4$, and $G^5$ are independently hydrogen, alkyl, aralkyl, cycloalkyl, cycloalkylalkyl, heterocyclyl, hetaryl, or aryl, or two of $G^1$, $G^2$, $G^3$, $G^4$, and $G^5$ are taken together to form $G^6$ a saturated, partially unsaturated or unsaturated carbocyclic or heteroatom-containing ring of up to about 20 ring atoms which is monocyclic or polycyclic, fused or unfused, and wherein no more than four of $G^1$, $G^2$, $G^3$, $G^4$, and $G^5$ are taken together to form are $G^6$.

15. The method of claim 14, wherein $G^5$ and one of $G^3$ and $G^4$ are taken together to form $G^6$.

16. The method of claim 14, wherein the chiral reagent is the compound of Formula 3 wherein $W_1$ is $NG^5$ and $W_2$ is O.

17. The method of claim 1, wherein the chiral reagent is Formula O, Formula P, Formula Q or Formula R:
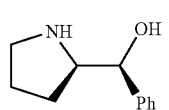  Formula O
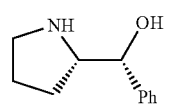  Formula P
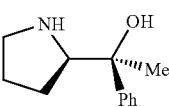  Formula Q
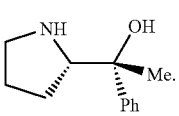  Formula R
* * * * *